(12) United States Patent
Porco, Jr. et al.

(10) Patent No.: US 11,427,595 B2
(45) Date of Patent: Aug. 30, 2022

(54) COMPOSITIONS AND METHODS FOR INHIBITING VIRAL INFECTION

(71) Applicants: Trustees of Boston University, Boston, MA (US); SRI International, Menlo Park, CA (US)

(72) Inventors: John A. Porco, Jr., Brookline, MA (US); Wenhan Zhang, Allston, MA (US); Tony Tianyi Wang, Centreville, VA (US); Shufeng Liu, Harrisonburg, VA (US)

(73) Assignees: TRUSTEES OF BOSTON UNIVERSITY, Boston, MA (US); SRI INTERNATIONAL, Menlo Park, CA (US)

( * ) Notice: Subject to any disclaimer, the term of this patent is extended or adjusted under 35 U.S.C. 154(b) by 0 days.

(21) Appl. No.: 16/660,285

(22) Filed: Oct. 22, 2019

(65) Prior Publication Data
US 2020/0123170 A1    Apr. 23, 2020

Related U.S. Application Data

(60) Provisional application No. 62/748,691, filed on Oct. 22, 2018.

(51) Int. Cl.
| | | |
|---|---|---|
| C07D 491/048 | (2006.01) | |
| C07D 491/147 | (2006.01) | |
| C07D 491/153 | (2006.01) | |
| C07D 498/14 | (2006.01) | |
| A61K 45/06 | (2006.01) | |
| A61P 31/18 | (2006.01) | |

(52) U.S. Cl.
CPC .......... *C07D 491/048* (2013.01); *A61P 31/18* (2018.01); *C07D 491/147* (2013.01); *C07D 491/153* (2013.01); *C07D 498/14* (2013.01); *A61K 45/06* (2013.01)

(58) Field of Classification Search
CPC ............ C07D 491/048; C07D 491/147; C07D 498/14
See application file for complete search history.

(56) References Cited

U.S. PATENT DOCUMENTS

| | | | |
|---|---|---|---|
| 6,518,274 B1 | 2/2003 | Gehling et al. | |
| 9,790,203 B2 | 10/2017 | Geneste et al. | |
| 10,047,064 B2 * | 8/2018 | Marion | C07D 307/93 |
| 10,085,988 B1 * | 10/2018 | Wang | A61K 31/519 |
| 2017/0137400 A1 * | 5/2017 | Marion | C07D 413/04 |

FOREIGN PATENT DOCUMENTS

| | | | | |
|---|---|---|---|---|
| WO | WO-9604284 A1 * | 2/1996 | ............ | C07D 491/14 |

OTHER PUBLICATIONS

Wang, Bin-Gui. Biochemical Systematics and Ecology 32 (2004) 1223-1226. (Year: 2004).*
Doveston, Richard G. et al., "Total synthesis of an oxepine natural product,(±)-janoxepin", Organic letters, 14, (4.), 1122-1125, (2012).
Santos, Mario FC et al., "Anti-parasitic guanidine and pyrimidine alkaloids from the marine sponge Monanchora arbuscula", Journal of natural products, 78, (5.), 1101-1112, (2015).
Taylor, Edward C. et al., "6-Trifluoromethanesulfonyloxy-4 (3H)-pyrimidinones as versatile intermediates for the synthesis of 6-functionalized 4 (3H)-pyrimidinones", Tetrahedron letters, 38, (25.), 4343-4346, (1997).
Ham, Sihyun, and David M. Birney., "Imidoylketene: an ab initio study of its conformations and reactions", The Journal of organic chemistry, 61, 12, 3962-3968, (1996).
Alajarín, Mateo et al., "From Ketenimines to Ketenes to Quinolones: Two Consecutive Pseudopericyclic Events", Organic letters, 7, (23.), 5281-5284, (2005).
Abe, Takumi et al., "A copper-catalyzed Ritter-type cascade via iminoketene for the synthesis of quinazolin-4 (3 H)-ones and diazocines", Chemical Communications, 53, (31.), 4362-4365, (2017).
Schoenherr, Heike, and Tim Cernak., "Profound Methyl Effects in Drug Discovery and a Call for New C—H Methylation Reactions", Angewandte Chemie International Edition, 52, (47.), 12256-12267, (2013).
Scholle, Frank et al., "Virus-host cell interactions during hepatitis C virus RNA replication: impact of polyprotein expression on the cellular transcriptome and cell cycle association with viral RNA synthesis", Journal of virology, 78, (3.), 1513-1524, (2004).
Novac, Olivia et al., "Inhibitors of protein synthesis identified by a high throughput multiplexed translation screen", Nucleic acids research, 32, (3.), 902-915, (2004).
Zhong, Jin et al., "Robust hepatitis C virus infection in vitro", Proceedings of the National Academy of Sciences, 102, (26.), 9294-9299, (2005).
Liu, Shufeng et al., "Human apolipoprotein E peptides inhibit hepatitis C virus entry by blocking virus binding", Hepatology, 56, (2.), 484-491, (2012).
Liu, Shufeng et al., "Tight junction proteins claudin-1 and occludin control hepatitis C virus entry and are downregulated during infection to prevent superinfection", Journal of virology, 83, (4.), 2011-2014, (2009).
Kondratowicz, Andrew S. et al., "T-cell immunoglobulin and mucin domain 1 (TIM-1) is a receptor for Zaire Ebolavirus and Lake Victoria Marburgvirus", Proceedings of the National Academy of Sciences, 108, (20.), 8426-8431, (2011).
Jurgeit, Andreas et al., "Niclosamide is a proton carrier and targets acidic endosomes with broad antiviral effects", PLoS pathogens, 8, (10.), e1002976, (2012).

(Continued)

*Primary Examiner* — Erich A Leeser
(74) *Attorney, Agent, or Firm* — Nixon Peabody LLP; Ronald I. Eisenstein; Ravinderjit Braich

(57) ABSTRACT

Described herein are compounds, agents, compositions, and methods related to the treatment of a viral infection (e.g., Hepatitis C viral infection). In particular, the compounds, agents, compositions, and methods described herein inhibit viral entry into a target cell.

13 Claims, 56 Drawing Sheets

Specification includes a Sequence Listing.

(56) References Cited

OTHER PUBLICATIONS

Ebada, Sherif S., et al., "Chemistry and biology of rocaglamides (= flavaglines) and related derivatives from *Aglaia* species (meliaceae)", Progress in the Chemistry of Organic Natural Products, 94, 1-58, (2011).
Ribeiro, N. et al., "Recent Advances in the Biology and Chemistry of the Flavaglines", Bioorg. Med. Chem., 20, 1857, (2012).
Pan, Li, et al., "Rocaglamide, silvestrol and structurally related bioactive compounds from *Aglaia species*", Natural product reports, 31, (7.), 924-939, (2014).
Cai, Xiao-hua et al., "Progress in the Total Synthesis of Rocaglamide", ISRN organic chemistry, 2011, (2011).
Zhao et al., "Recent Advances in the Synthesis of Flavaglines, a Family of Potent Bioactive Natural Compounds Originating from Traditional Chinese Medicine", European Journal of Organic Chemistry, 36, 5908-5916, (2016).
Hwang, Bang Yeon, et al., "Silvestrol and episilvestrol, potential anticancer rocaglate derivatives from Aglaia silvestris", The Journal of organic chemistry, 69, (10.), 3350-3358, (2004).
Cencic, Regina, et al., "Synergistic effect of inhibiting translation initiation in combination with cytotoxic agents in acute myelogenous leukemia cells", Leukemia research, 34, (4.), 535-541, (2010).
Lin, Chen-Ju, et al., "Targeting synthetic lethal interactions between Myc and the eIF4F complex impedes tumorigenesis", Cell reports, 1, (4.), 325-333, (2012).
Sadlish, Heather, et al., "Evidence for a functionally relevant rocaglamide binding site on the eIF4A-RNA complex", ACS chemical biology, 8, (7.), 1519-1527, (2013).
Robert, Francis, et al., "Translation initiation factor eIF4F modifies the dexamethasone response in multiple myeloma", Proceedings of the National Academy of Sciences, 111, (37.), 13421-13426, (2014).
Cencic, Regina, et al., "Antitumor activity and mechanism of action of the cyclopenta [b] benzofuran, silvestrol", PloS one, 4, (4.), e5223, (2009).
Chu, Jennifer, et al., "Translation inhibition by rocaglates is independent of eIF4E phosphorylation status", Molecular cancer therapeutics, 15, (1.), 136-141, (2016).
Iwasaki, Shintaro et al., "Rocaglates convert DEAD-box protein eIF4A into a sequence-selective translational repressor", Nature, 534, (7608.), 558, (2016).
Kraus, George A. et al., "A synthetic approach to rocaglamide via reductive cyclization of. delta.-keto nitriles", The Journal of Organic Chemistry, 54, (1.), 77-83, (1989).
Trost, Barry M. et al., "An unusual oxidative cyclization. A synthesis and absolute stereochemical assignment of (-)-rocaglamide", Journal of the American Chemical Society, 112, (24.), 9022-9024, (1990).
Paz, Bruno Matos et al., "Enantioselective synthesis of cyclopenta [b] benzofurans via an organocatalytic intramolecular double cyclization", Chemical science, 8, (12.), 8086-8093, (2017).
Dobler, Markus R. et al., "Total synthesis of (±)-rocaglamide and some aryl analogues", Tetrahedron Letters, 42, (47.), 8281-8284, (2001).
Thede, Kai et al., "Stereoselective synthesis of (±)-rocaglaol analogues", Organic letters, 6, (24.), 4595-4597, (2004).
Gerard, Baudouin et al., "A biomimetic approach to the rocaglamides employing photogeneration of oxidopyryliums derived from 3-hydroxyflavones", Journal of the American Chemical Society, 126, (42.), 13620-13621, (2004).
Diedrichs, Nicole et al., "A Highly Efficient Synthesis of Rocaglaols by a Novel α-Arylation of Ketones", European journal of organic chemistry, 2005, (9.), 1731-1735, (2005).
Gerard, Baudouin, et al., "Enantioselective photocycloaddition mediated by chiral Brønsted acids: Asymmetric synthesis of the rocaglamides", Journal of the American Chemical Society, 128, (24.), 7754-7755, (2006).

El Sous, Mariana, et al., "Total Synthesis of (-)-Episilvestrol and (-)-Silvestrol", Angewandte Chemie International Edition, 46, (41.), 7835-7838, (2007).
Gerard, Baudouin, et al., "Enantioselective Synthesis of the Complex Rocaglate (-)-Silvestrol", Angewandte Chemie International Edition, 46, (41.), 7831-7834, (2007).
Malona, John A. et al., "Nazarov cyclization initiated by peracid oxidation: the total synthesis of (±)-rocaglamide", Journal of the American Chemical Society, 131, (22.), 7560-7561, (2009).
Lajkiewicz, Neil J. et al., "Enantioselective photocycloaddition of 3-hydroxyflavones: Total syntheses and absolute configuration assignments of (+)-ponapensin and (+)-elliptifoline", Journal of the American Chemical Society, 134, (31.), 13108-13113, (2012).
Stone, Steven D. et al., "Biomimetic kinetic resolution: highly enantio-and diastereoselective transfer hydrogenation of aglain ketones to access flavagline natural products", Journal of the American Chemical Society, 137, (1.), 525-530, (2014).
Wang, Wenyu et al., "Total Syntheses of the Isomeric Aglain Natural Products Foveoglin A and Perviridisin B: Selective Excited-State Intramolecular Proton-Transfer Photocycloaddition", Angewandte Chemie International Edition, 56, (46.), 14479-14482, (2017).
Roche, Stéphane P. et al., "Biomimetic Photocycloaddition of 3-Hydroxyflavones: Synthesis and Evaluation of Rocaglate Derivatives as Inhibitors of Eukaryotic Translation", Angewandte Chemie International Edition, 49, (37.), 6533-6538, (2010).
Rodrigo, Christina M. et al., "Synthesis of rocaglamide hydroxamates and related compounds as eukaryotic translation inhibitors: synthetic and biological studies", Journal of medicinal chemistry, 55, (1.), 558-562, (2011).
Hawkins, Bill C. et al., "Simplified silvestrol analogues with potent cytotoxic activity", ChemMedChem, 9, (7.), 1556-1566, (2014).
Lajkiewicz, Neil J. et al., "Remodeling natural products: chemistry and serine hydrolase activity of a rocaglate-derived 3-lactone", Journal of the American Chemical Society, 136, (6.), 2659-2664, (2014).
Wang, Wenyu et al., "Synthesis of Aza-Rocaglates via ESIPT-Mediated (3+2) Photocycloaddition", Chemistry—A European Journal, 22, (34.), 12006-12010, (2016).
Zhao, Qian et al., "Bioisosteric modification of flavaglines", Tetrahedron Letters, 57, (26.), 2943-2944, (2016).
Bruce, Ian et al., "Synthesis of the carbocyclic analogue of (±)-Rocaglamide", Tetrahedron letters, 40, (22.), 4279-4282, (1999).
Liu, Tao et al., "Synthetic silvestrol analogues as potent and selective protein synthesis inhibitors", Journal of medicinal chemistry, 55, (20.), 8859-8878, (2012).
Liu, Shufeng et al., "A novel class of small molecule compounds that inhibit Hepatitis C virus infection by targeting the prohibitin-cRAF pathway", EBioMedicine, 2, (11.), 1600-1606, (2015).
Calland, Noémie et al., "Polyphenols inhibit hepatitis C virus entry by a new mechanism of action", Journal of virology, 89, (19.), 10053-10063, (2015).
Lin, Liang-Tzung et al., "Saikosaponin b2 is a naturally occurring terpenoid that efficiently inhibits hepatitis C virus entry", Journal of hepatology, 62, (3.), 541-548, (2015).
Kuadkitkan, Atichat et al., "Identification and characterization of prohibitin as a receptor protein mediating DENV-2 entry into insect cells", Virology, 406, (1.), 149-161, (2010).
Wintachai, Phitchayapak et al., "Identification of prohibitin as a Chikungunya virus receptor protein", Journal of medical virology, 84, (11.), 1757-1770, (2012).
Xiao, Fei et al., "Synergy of entry inhibitors with direct-acting antivirals uncovers novel combinations for prevention and treatment of hepatitis C", Gut, 64, (3.), 483-494, (2015).
Romano, Keith P. et al., "The molecular basis of drug resistance against hepatitis C virus NS3/4A protease inhibitors", PLoS pathogens, 8, (7.), e1002832, (2012).
Tong, Xiao et al., "In vivo emergence of a novel mutant L159F/L320F in the NS5B polymerase confers low-level resistance to the HCV polymerase inhibitors mericitabine and sofosbuvir", The Journal of infectious diseases, 209, (5.), 668-675, (2013).
Walker, Andreas et al., "Detection of a genetic footprint of the sofosbuvir resistance-associated substitution S282T after HCV treatment failure", Virology journal, 14, (1.), 106, (2017).

(56) References Cited

OTHER PUBLICATIONS

Qian, Xi-Jing et al., "Entry inhibitors: New advances in HCV treatment", Emerging microbes & infections, 5, (1.), e3, (2016).
He, Shanshan et al., "Development of an Aryloxazole Class of Hepatitis C Virus Inhibitors Targeting the Entry Stage of the Viral Replication Cycle", Journal of medicinal chemistry, 60, (14.), 6364-6383, (2017).
Yueh, Han et al., "A photochemical flow reactor for large scale syntheses of aglain and rocaglate natural product analogues", Bioorganic & medicinal chemistry, 25, (23.), 6197-6202, (2017).
Solanki, Pavankumar V. et al., "An Improved and Efficient Process for the Production of Highly Pure Paliperidone, a Psychotropic Agent, via DBU Catalyzed N-Alkylation", ACS Sustainable Chemistry & Engineering, 1, (2.), 243-248, (2013).
Kim, Tae Woo et al., "Synthesis and antihypertensive activity of pyrimidin-4 (3H)-one derivatives as losartan analogue for new angiotensin II receptor type 1 (AT1) antagonists", Bioorganic & medicinal chemistry letters, 22, (4.), 1649-1654, (2012).
Puig-De-La-Bellacasa et al., "Diverse combinatorial design, synthesis and in vitro evaluation of new HEPT analogues as potential non-nucleoside HIV-1 reverse transcription inhibitors", European Journal of Medicinal Chemistry, 54, (159.), 159-174, (2012).
Davey et al., "Synthesis of the novel anti-leukaemic tetrahydrocyclopenta [b] benzofuran, rocaglamide and related synthetic studies." Journal of the Chemical Society, Perkin Transactions 1 20 (1992): 2657-2666.
Dye et al., "Simplified quantitation of cytotoxicity by integration of specific lysis against effector cell concentration at a constant target cell concentration and measuring the area under the curve." Journal of immunological methods 138.1 (1991): 1-13.
Gotte et al., "Direct-acting antiviral agents for hepatitis C: structural and mechanistic insights." Nature reviews Gastroenterology & hepatology 13.6 (2016): 338.
Kim et al., "An efficient synthesis of risperidone via stille reaction: Antipsychotic, 5-HT 2, and dopamine-D 2-antagonist." Archives of pharmacal research 28.9 (2005): 1019-1022.
King et al., "X-ray crystal structure of rocaglamide, a novel antileulemic 1 H-cyclopenta [b] benzofuran from Aglaia elliptifolia." Journal of the Chemical Society, Chemical Communications 20 (1982): 1150-1151.
Lal et al., "A convenient one-pot entry into novel 2-substituted-6, 7-dihydro-4H-Pyrimido (2, 1-a) isoquinolin-4-ones." Tetrahedron 46.4 (1990): 1323-1330.
Malona et al., "Nazarov cyclization initiated by peracid oxidation: the total synthesis of (±)-rocaglamide." Journal of the American Chemical Society 131.22 (2009): 7560-7561.
Malona et al., "Total synthesis of (±)-rocaglamide via oxidation-initiated nazarov cyclization." The Journal of organic chemistry 77.4 (2012): 1891-1908.
Proksch et al., "Chemistry and biological activity of rocaglamide derivatives and related compounds in *Aglaia* species (Meliaceae)." Current Organic Chemistry 5.9 (2001): 923-938.
Thuaud et al.,"Novel flavaglines displaying improved cytotoxicity." Journal of medicinal chemistry 54.1 (2011): 411-415.
Venkatesan et al., "Substituted 4H-pyrido [1,2-a] pyrimidin-4-one angiotensin II receptor antagonists." Bioorganic & Medicinal Chemistry Letters 4.1 (1994): 183-188.

\* cited by examiner

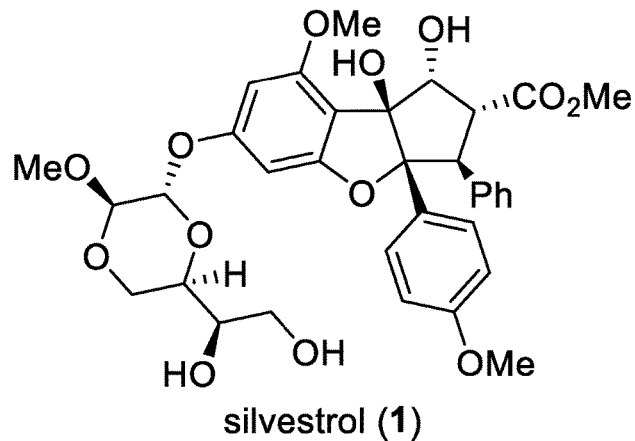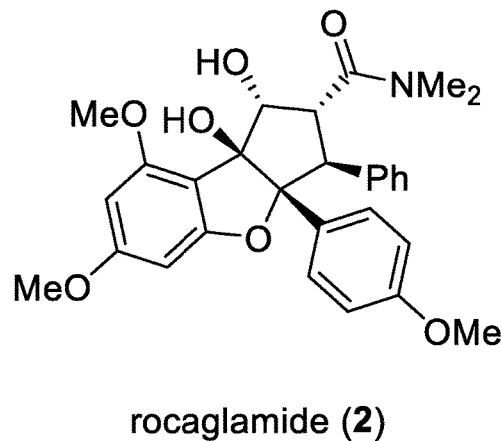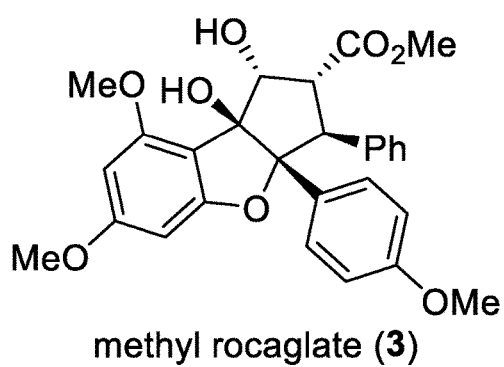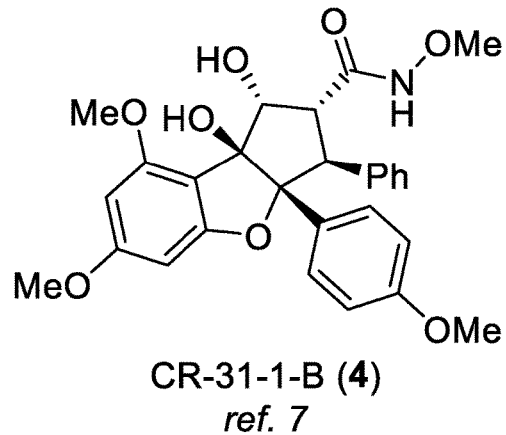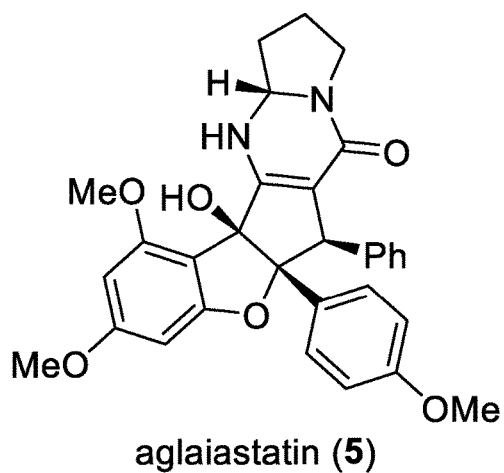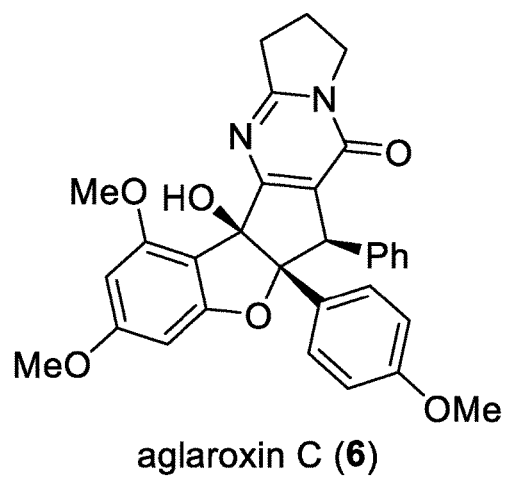
Representative Biologically Active Rocaglate Natural Products and Synthetic Analogues
*FIG. 1*

Retrosynthetic Analysis for Aglaroxin C Analogues

Table 1. Optimization of the Direct Pyrimidinone Formation

| Entry | DMAP (equiv) | amidine (equiv) | Conc. (M) | Temp. (°C) | time (hour) | NMR yield (%) 12a ; 14 ; 15 ; 16 |
|---|---|---|---|---|---|---|
| 1 | 0.2 | 10.0 | 0.2 | 130[a] | 1 | 28 , - , 9 , - |
| 2 | 1.5 | 3.0 | 0.2 | 120 | 12 | 27 , - , 8 , 51 |
| 3 | 0.3 | 3.0 | 0.2 | 120 | 12 | 68 , 4 , 13 , 11 |
| 4 | 0.3 | 1.0 | 0.2 | 120 | 12 | 62 , 13 , 2 , 11[b] |
| 5 | 0.3 | - | 0.2 | 120 | 12 | - , 54 , - , -[c] |
| 6 | 0.3 | 2.0 | 0.025 | 120 | 12 | 81 , 5 , 5 , 8 |
| 7 | 0.3 | 1.8 | 0.025 | 130 | 24 | 55 , 11 , - , 30 |
| 8 | 0.3 | 3.0 | 0.025 | 130 | 0.75 | 90 , - , - , 5[d] |
| 9 | - | 3.0 | 0.025 | 130 | 0.75 | 86 , - , - , 6[e] |

Side Products:
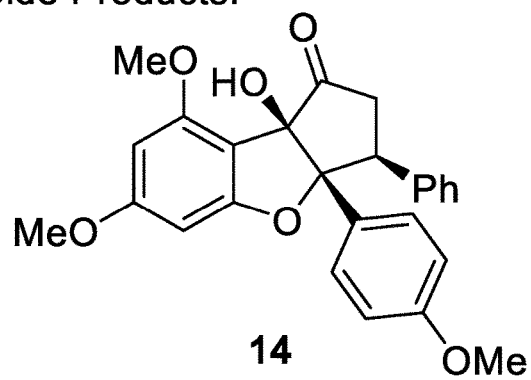
14
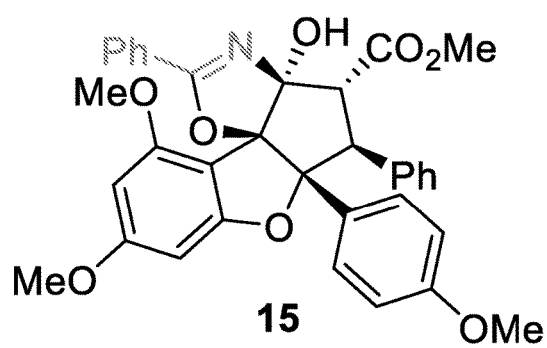
15
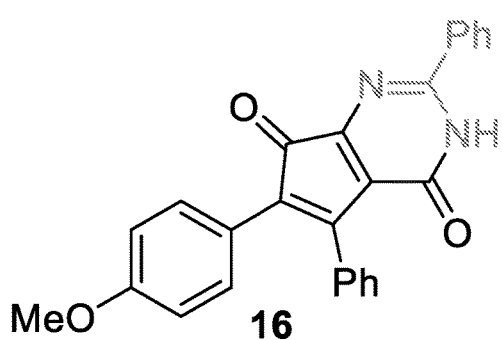
16
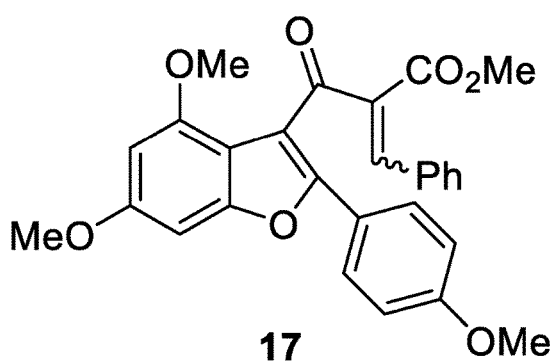
17
*FIG. 4 (continued)*

Table 2. Optimization of Second-Generation Synthesis of Aglaroxin C

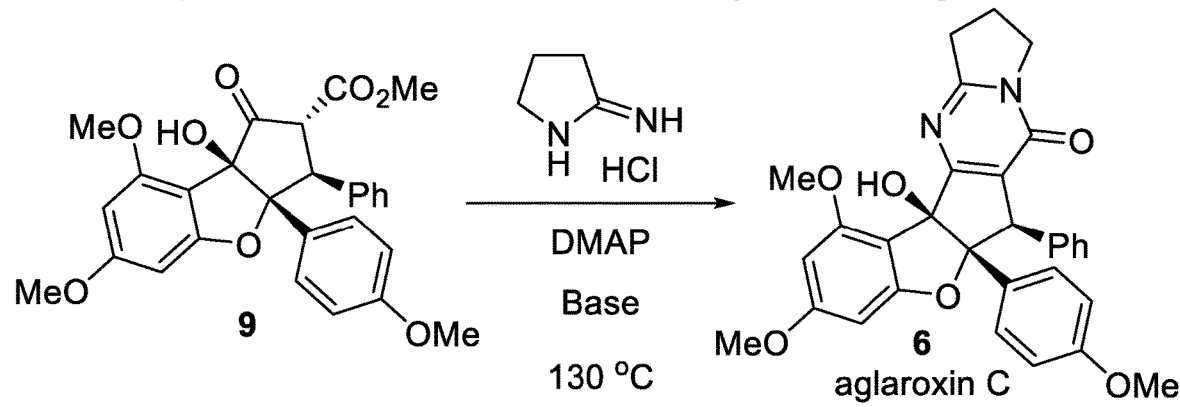

| Entry | base (equiv) | amidine (equiv) | DMAP (equiv) | solvent | NMR yield (%) |
|---|---|---|---|---|---|
| 1 | DBU (4.0) | 2.1 | - | EtOH[a] | -[b] |
| 2 | MeONa (11.6) | 10.0 | 0.1 | toluene[a] | -[b] |
| 3 | MeONa (0.75) | 1.5 | 0.1 | toluene[a] | -[b] |
| 4 | MeONa (9.8) | 10.0 | 1.5 | toluene[a] | 19 |
| 5 | MeONa (4.9) | 5.0 | 1.5 | toluene[c] | -[d] |
| 6 | MeONa (2.95) | 3.0 | 0.4 | xylene[e] | 86[f] |

[a]0.025 M concentration, reflux 12 h; [b]no conversion; [c]0.2 M concentration, reflux 12 h; [d]complex reaction; only isolated the fragmentation products; [e]0.025 M concentration, 130 °C 1 h; [f]76% isolated yield for aglaroxin C; 9% decarboxylated product also obtained.

*FIG. 6*

Table 3. Synthese of Aglaroxin C Analogues Using Direct Pyrimidinone Formation[a]

| | aplaviroc C (6) | 12e | 12a | 12ah | 12ae | 12al | 12aj | 12l | 12o | 12s |
|---|---|---|---|---|---|---|---|---|---|---|
| $EC_{50}^{b}$ (μM) | 1.3 | 2.5 | 0.42 | n.d.[f] | 0.2 | 9.2 | n.d.[f] | 0.52 | 0.24 | 0.40 |
| $CC_{50}^{c}$ (μM) | 12 | 7.5 | 8.1 | n.d.[f] | 7.3 | 37 | n.d.[f] | n.d.[f] | 10 | n.d.[f] |
| $AUC_{0.2-20}^{d}$ cytotoxicity | 110 | 124 | 125 | N/A | 123 | 83 | N/A | 71 | 130 | 90 |
| $AUC_{0.2-20}^{e}$ EC/CC | 2.3 | 1.8 | 2.3 | N/A | 2.0 | 2.1 | N/A | 4.7 | 3.2 | 3.3 |

*FIG. 8 (continued)*

Table 5. Chirality-Based Biological Profiles of Lead Compounds[a]

(+)-12l R = para-Me
(+)-12s R = meta-OMe (-)-12l R = para-Me
(-)-12s R = meta-OMe

| compound | (±)-12l | (+)-12l | (-)-12l | (±)-12s | (+)-12s | (-)-12s |
|---|---|---|---|---|---|---|
| $EC_{50}$[b] (μM) | 0.5 | 0.3 | n.d.[e] | 0.5 | 0.5 | n.d.[e] |
| $CC_{50}$[c] (μM) | n.d.[d] | 10 | n.d.[e] | n.d.[d] | 7.0 | n.d.[e] |

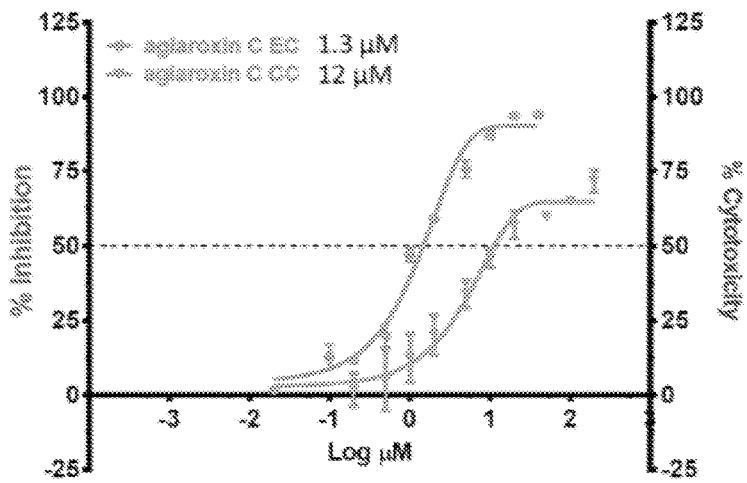
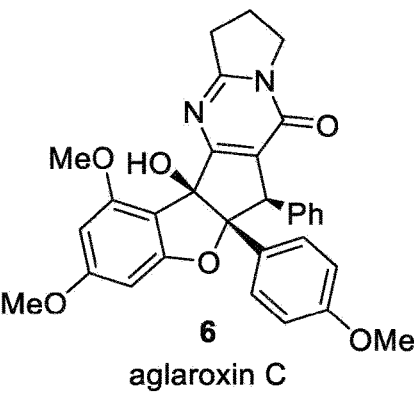
*FIG. 20*
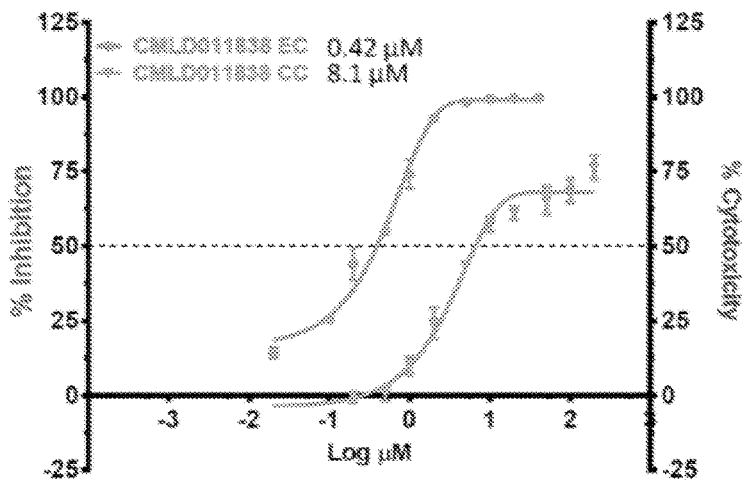
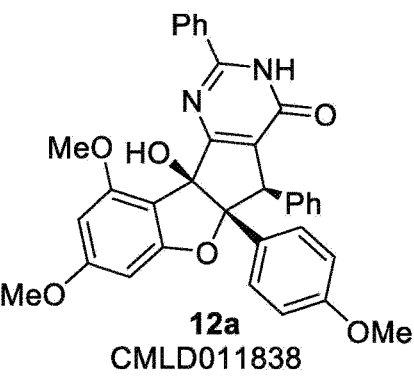
*FIG. 21*
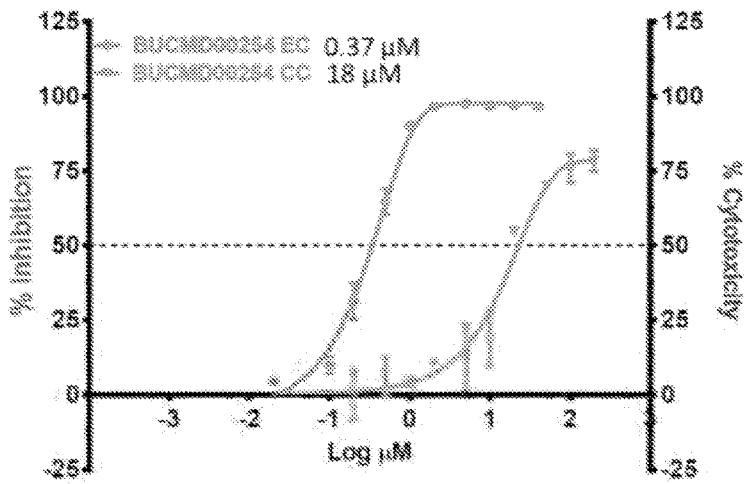
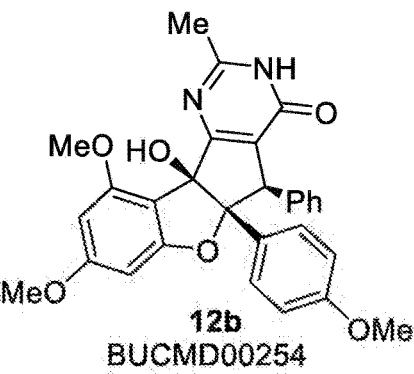
*FIG. 22*

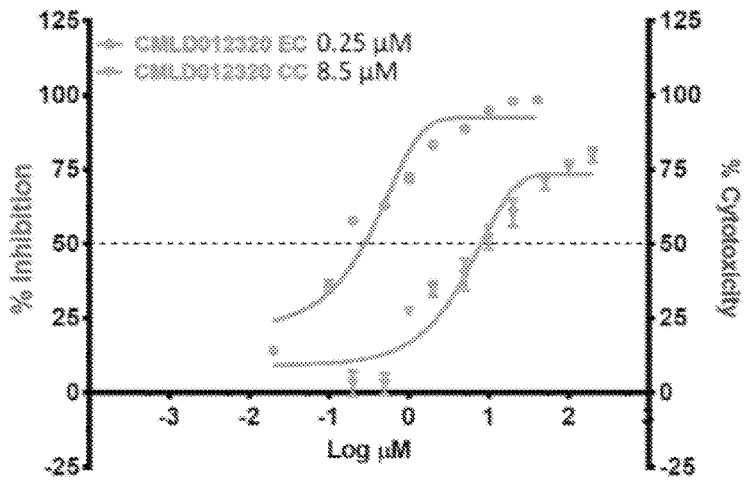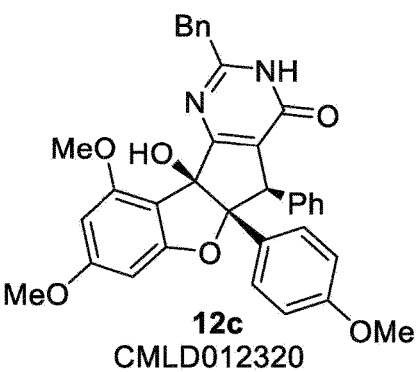
*FIG. 23*
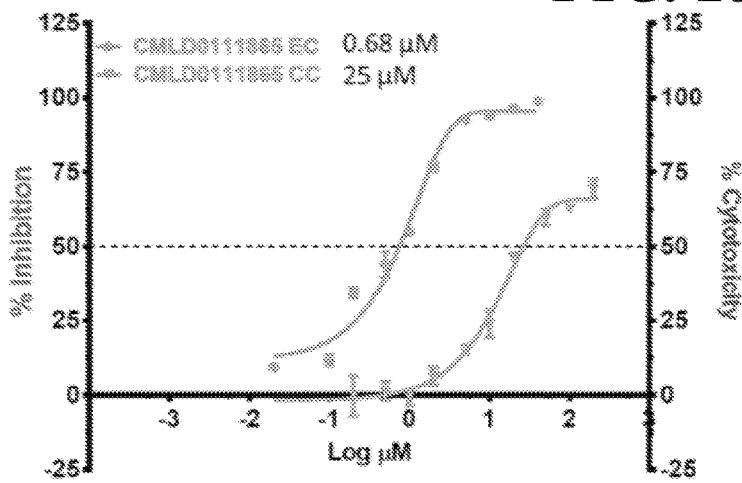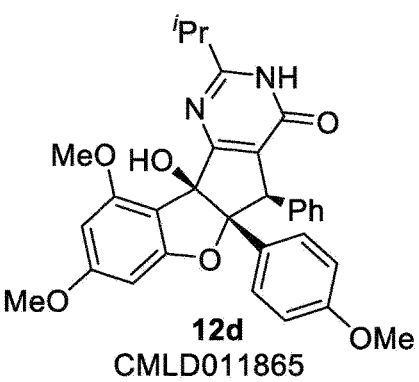
*FIG. 24*
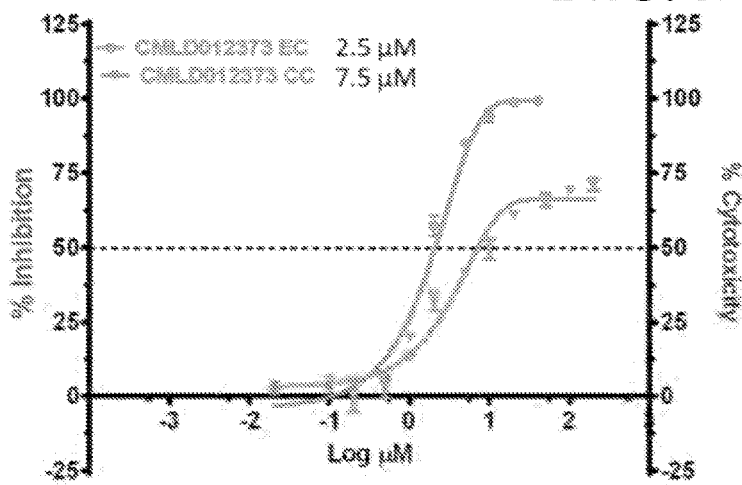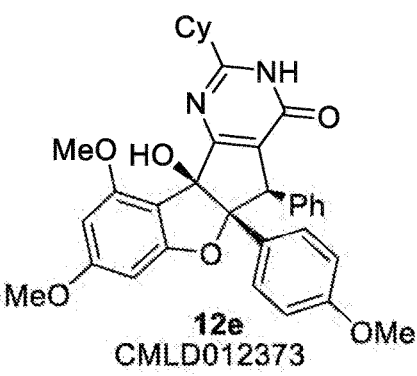
*FIG. 25*

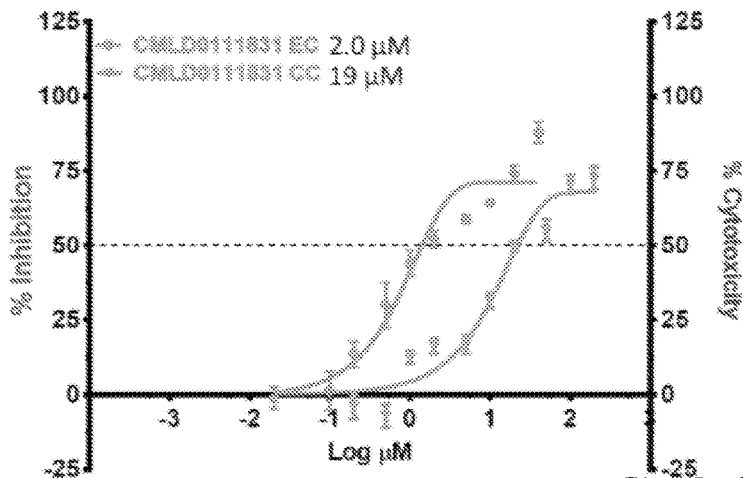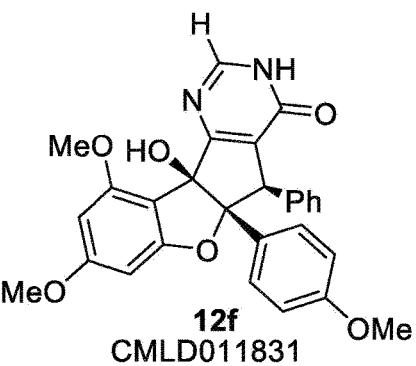
FIG. 26
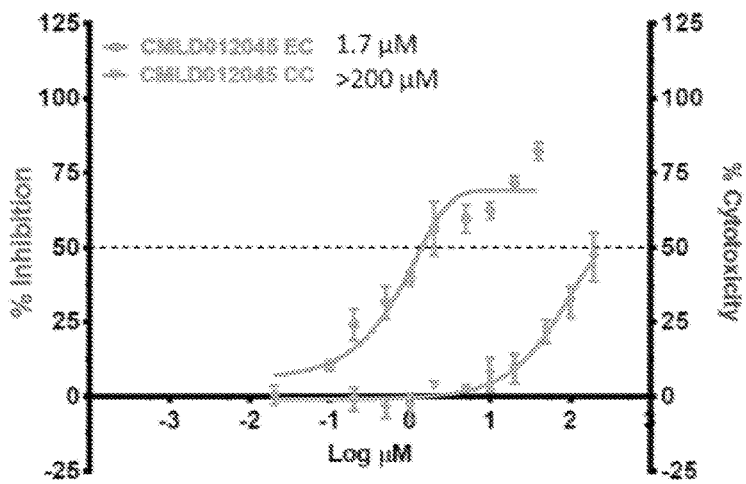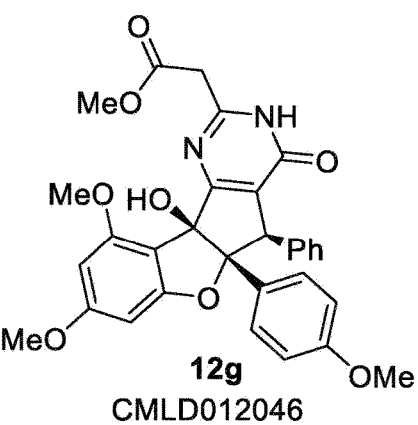
FIG. 27
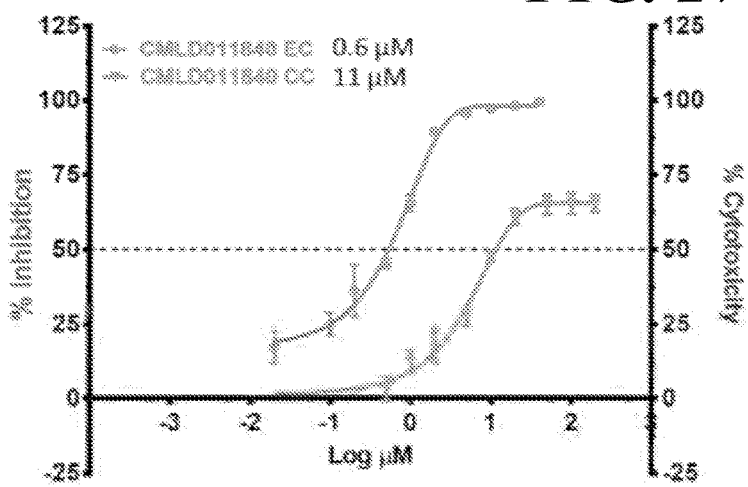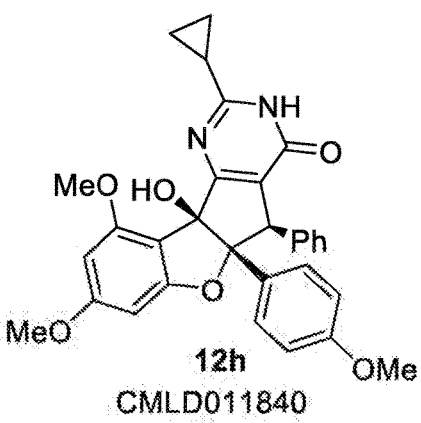
FIG. 28

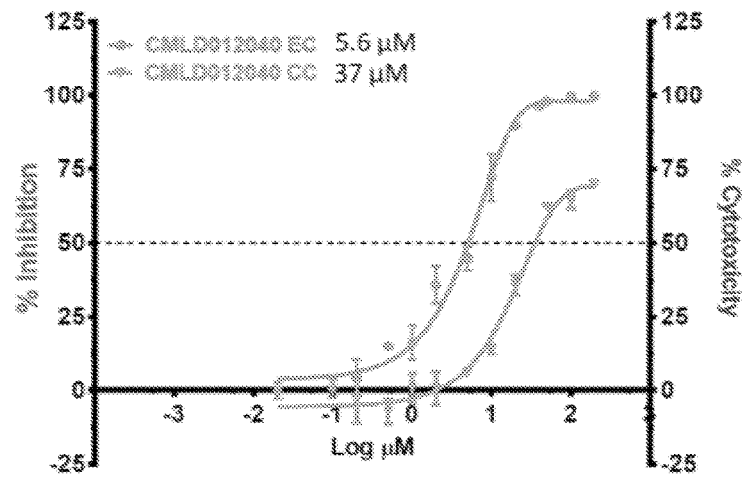
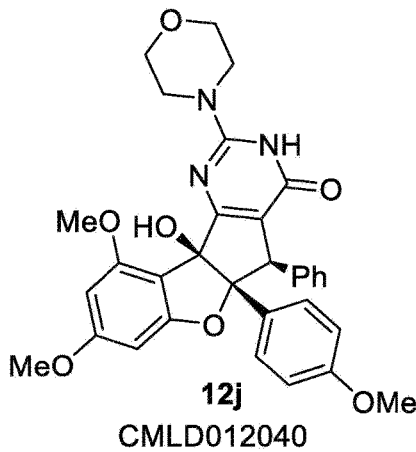
FIG. 29
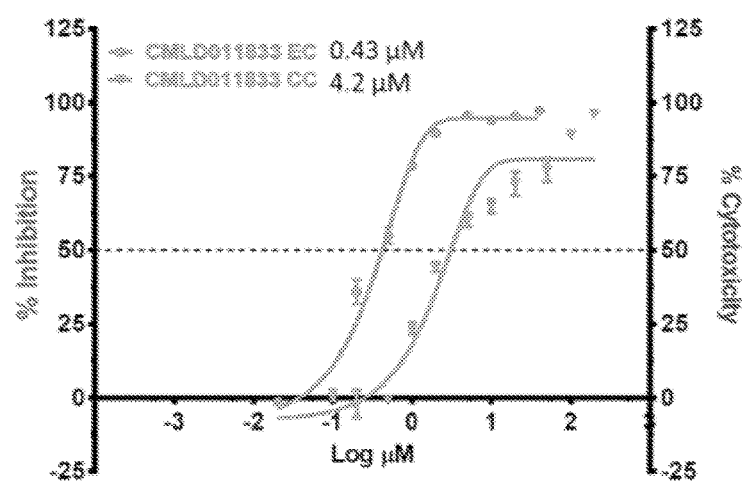
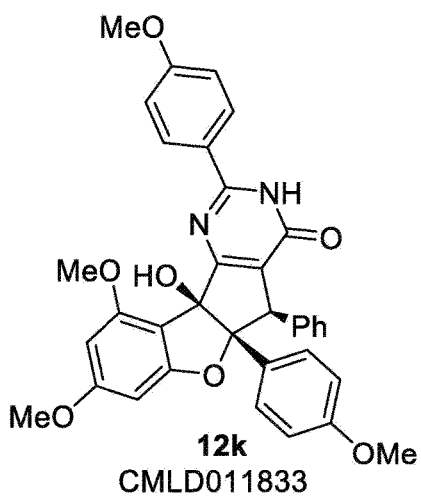
FIG. 30
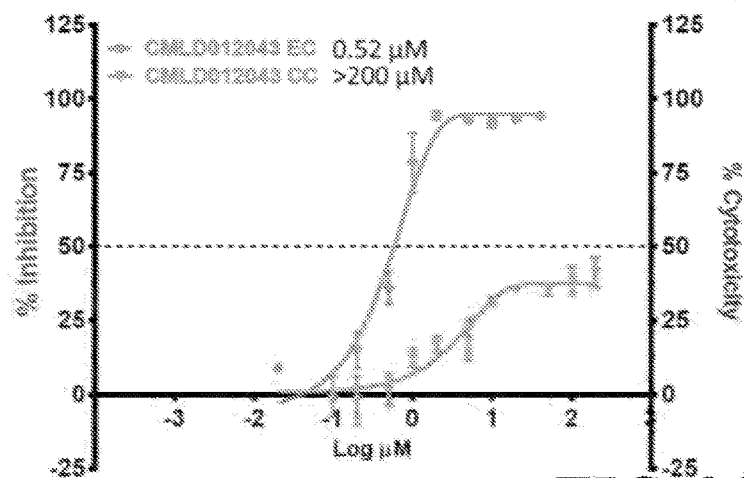
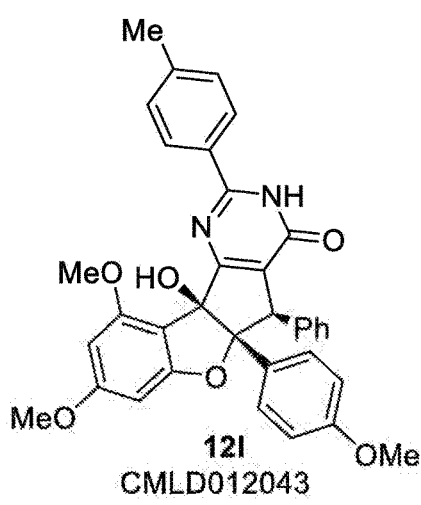
FIG. 31

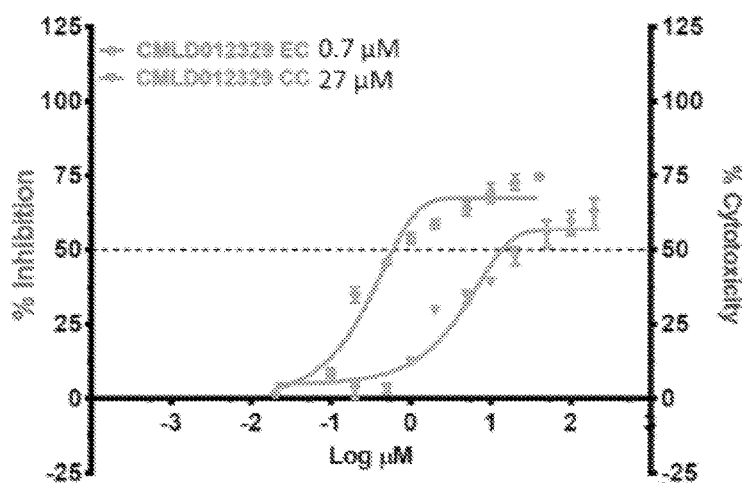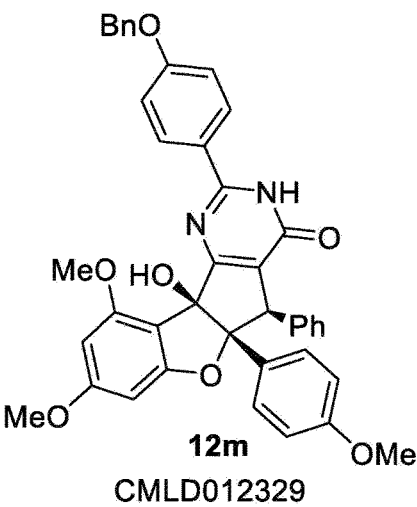
FIG. 32
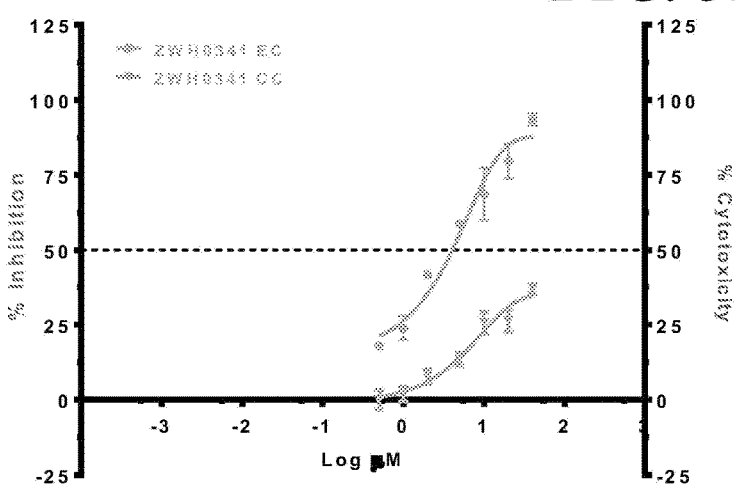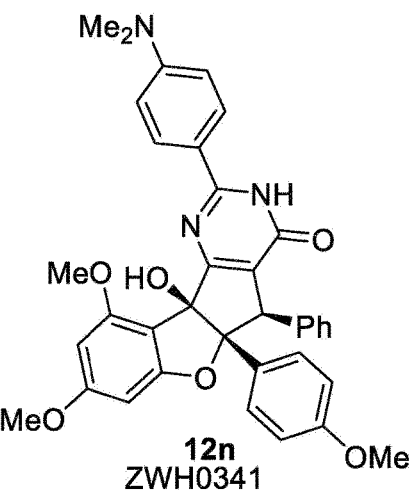
FIG. 33
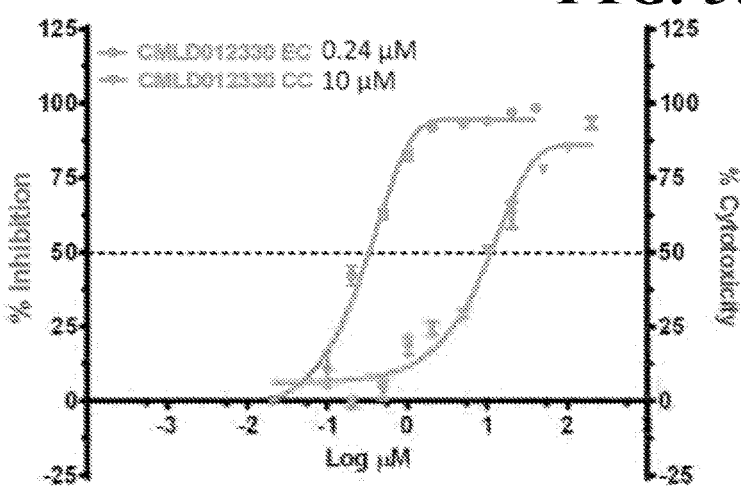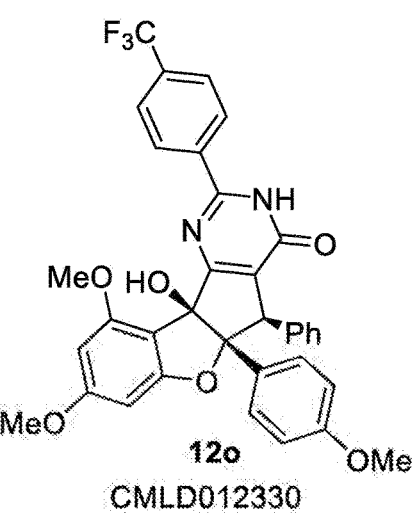
FIG. 34

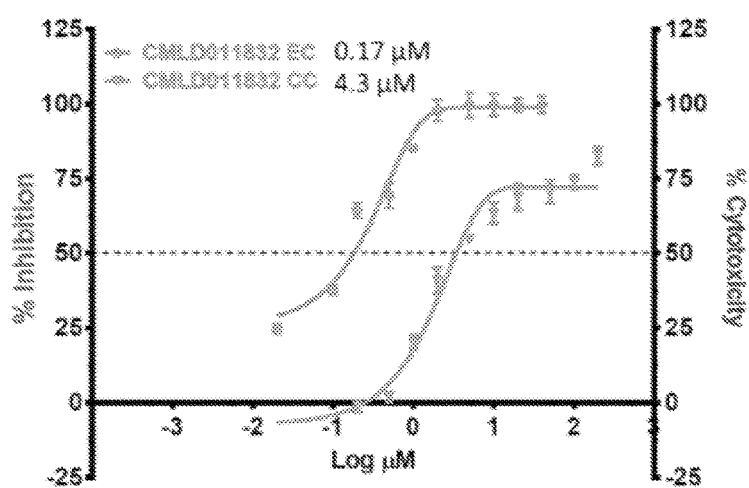
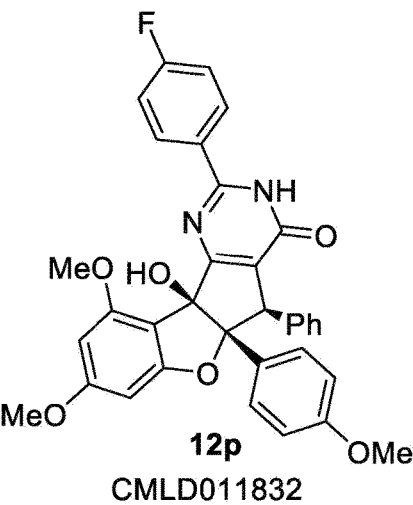
FIG. 35
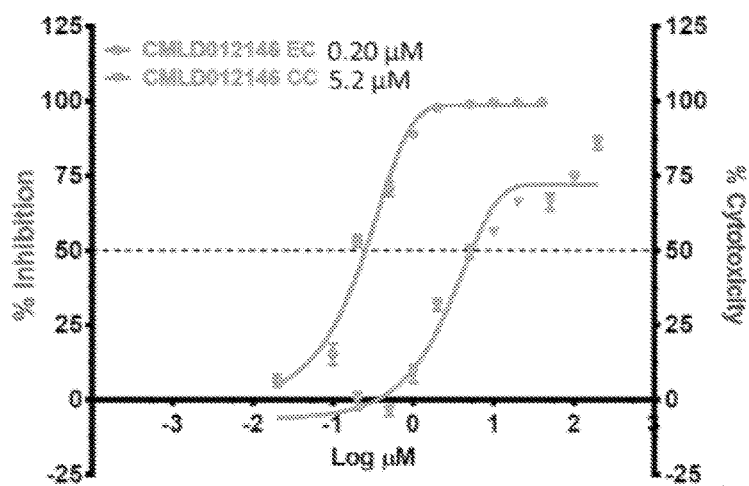
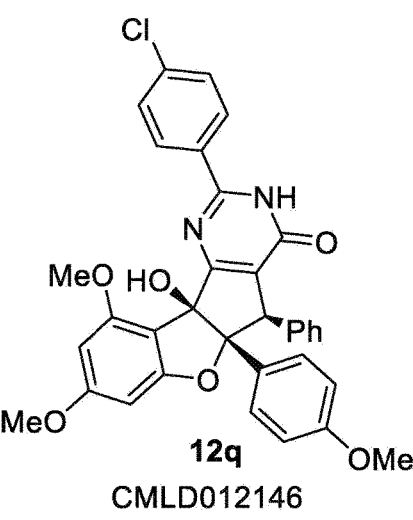
FIG. 36
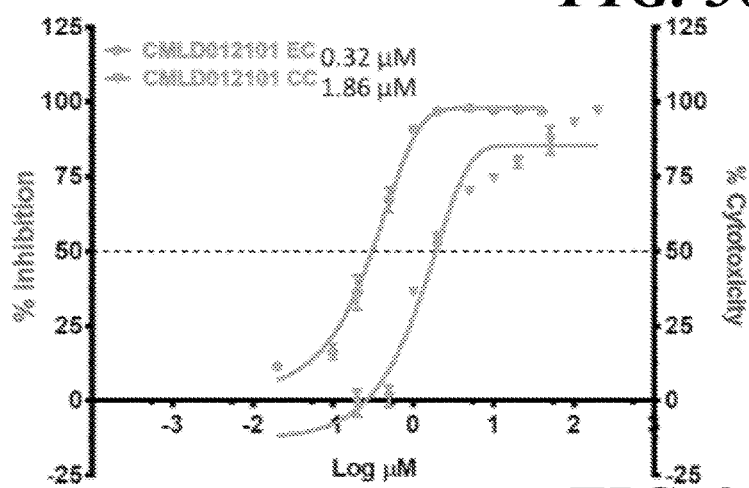
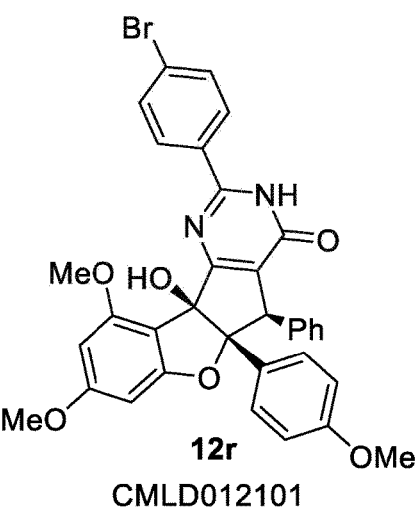
FIG. 37

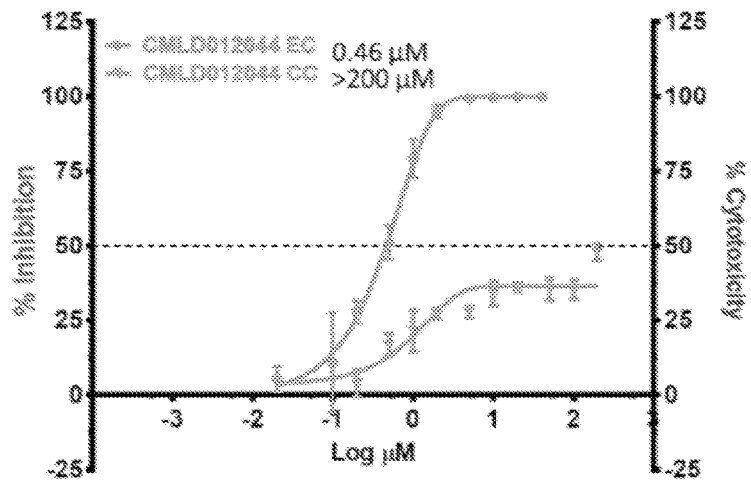
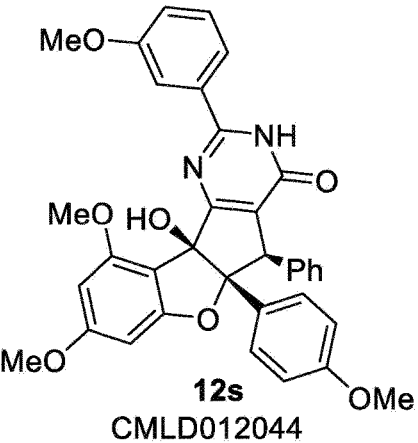
FIG. 38
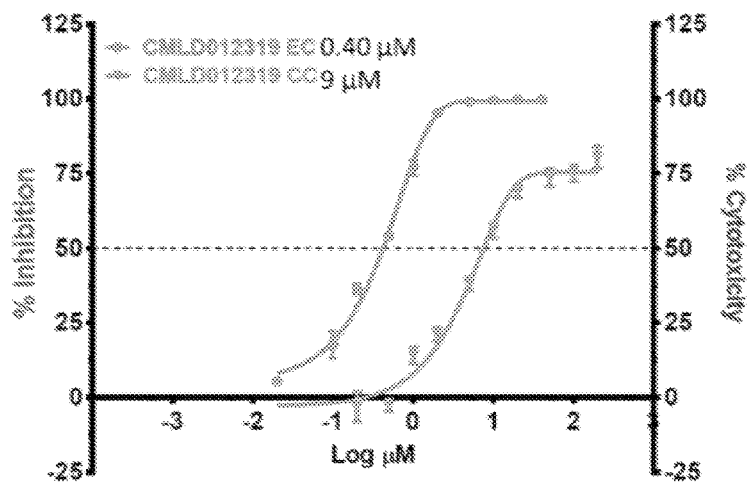
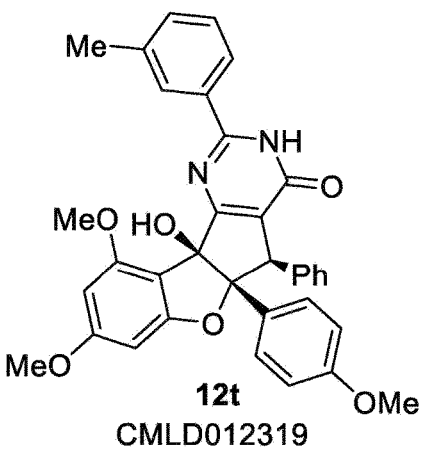
FIG. 39
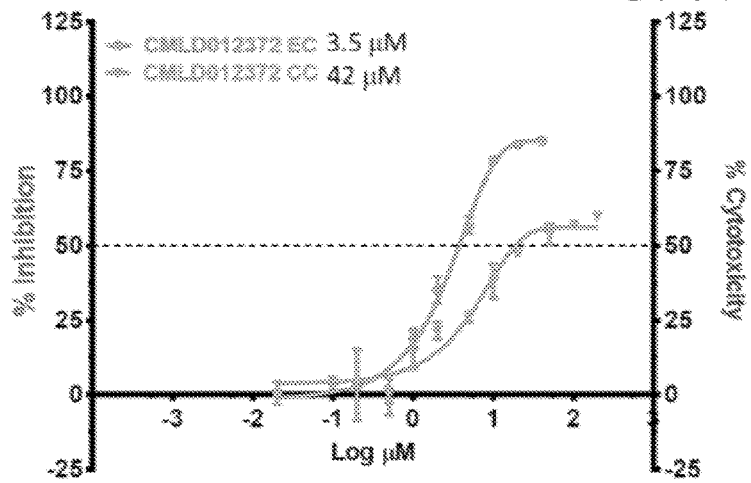
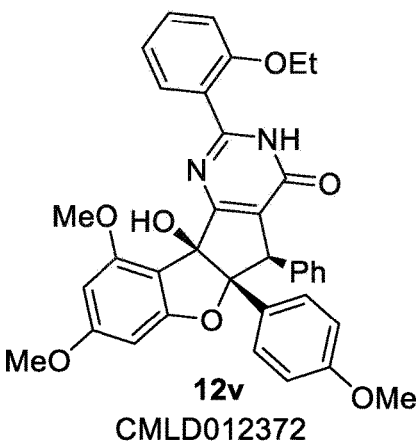
FIG. 40

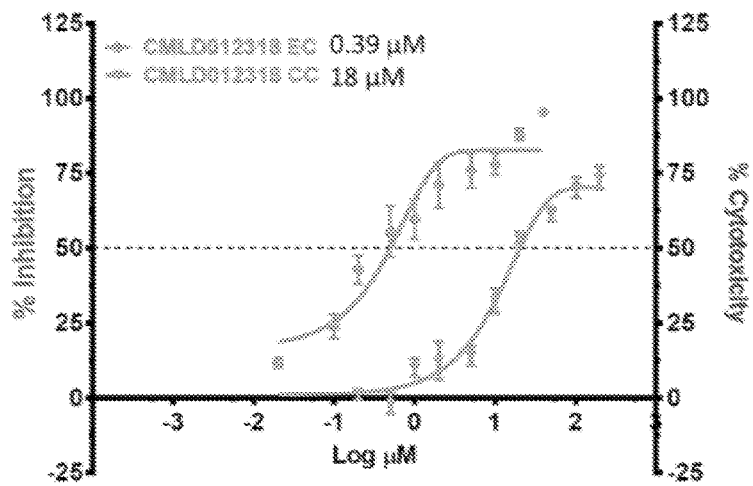
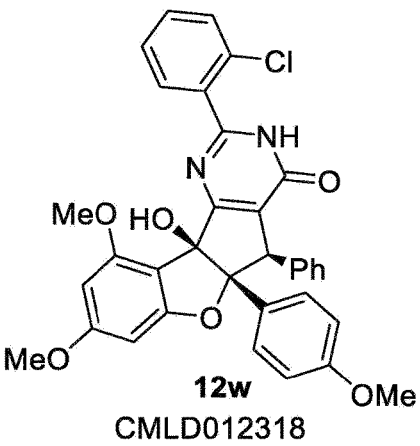
FIG. 41
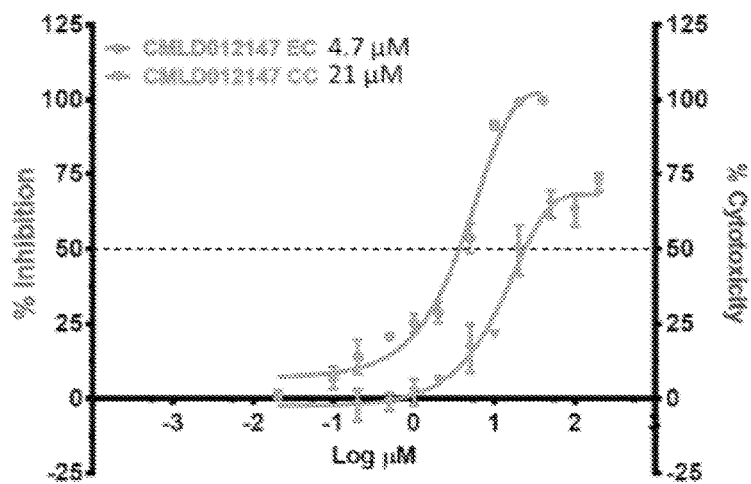
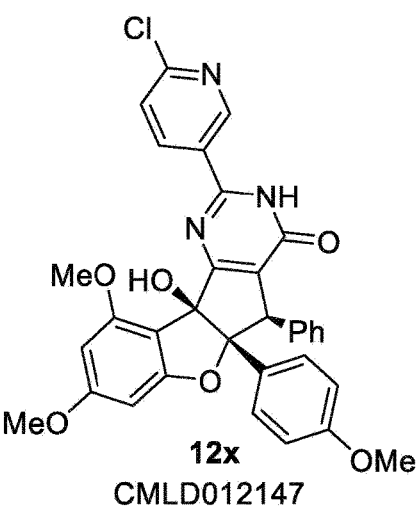
FIG. 42
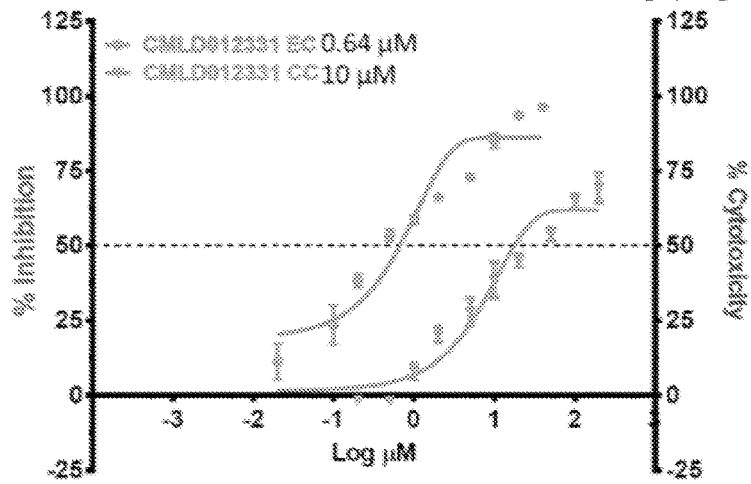
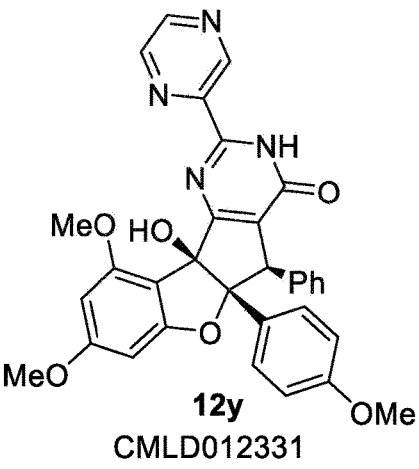
FIG. 43

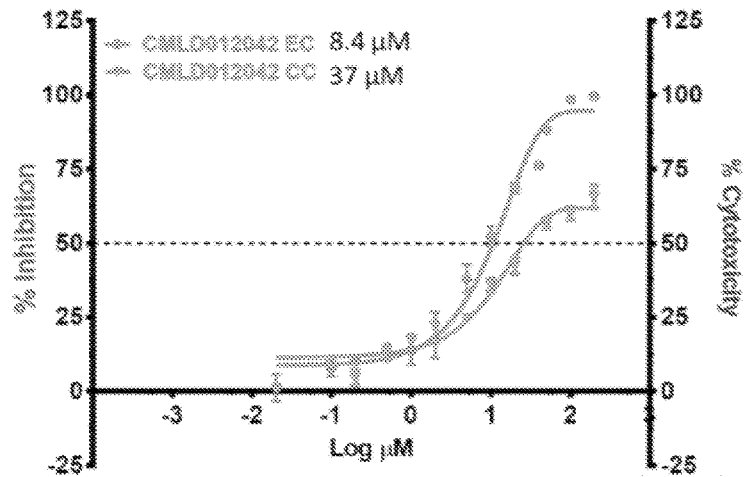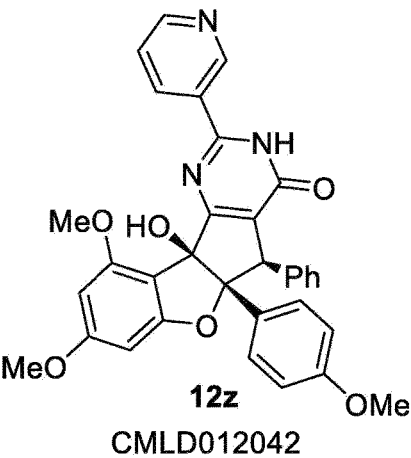
FIG. 44
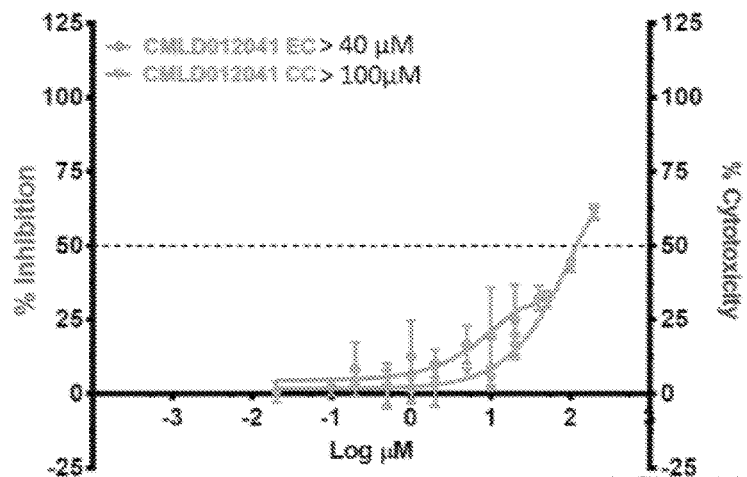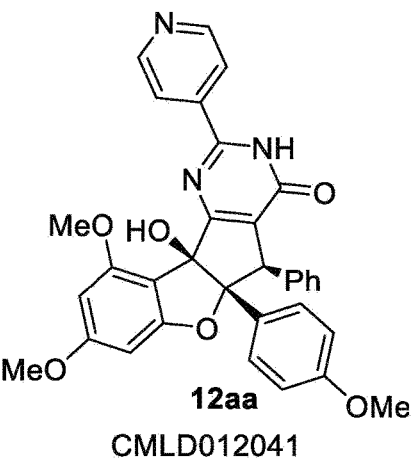
FIG. 45
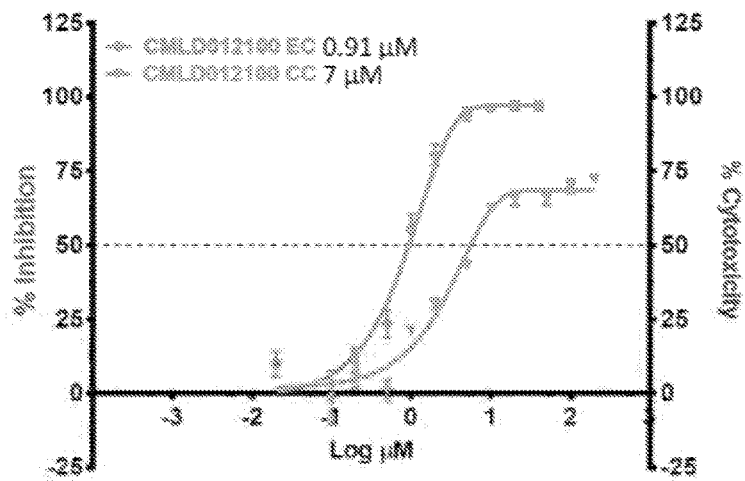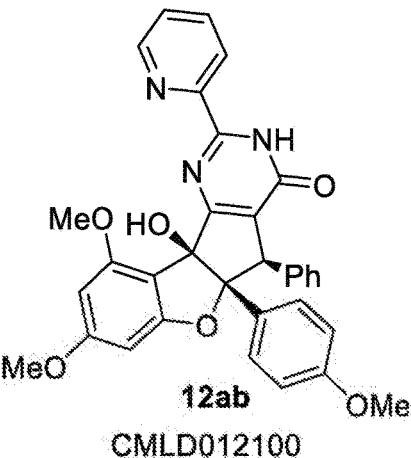
FIG. 46

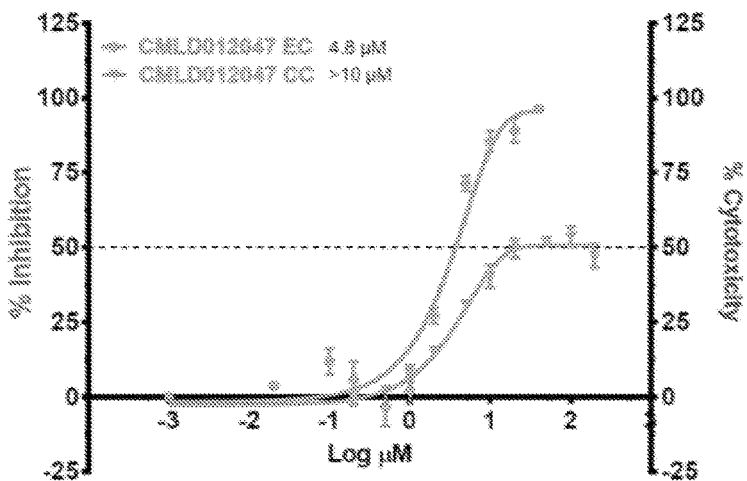
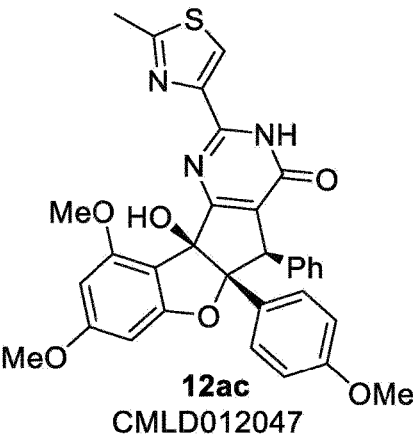
FIG. 47
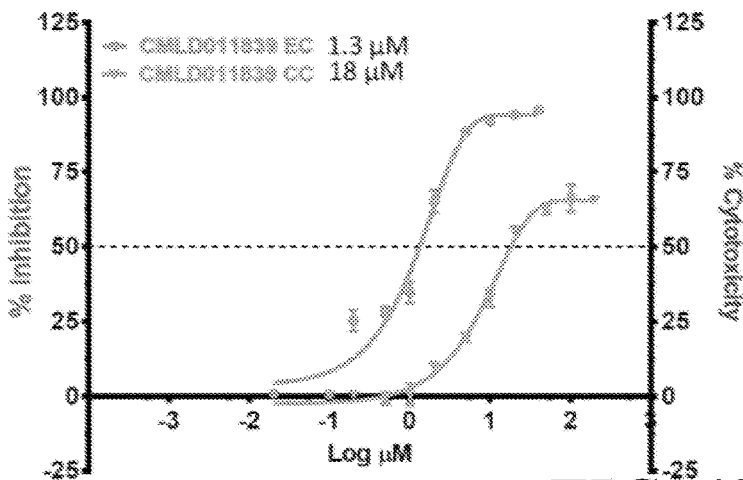
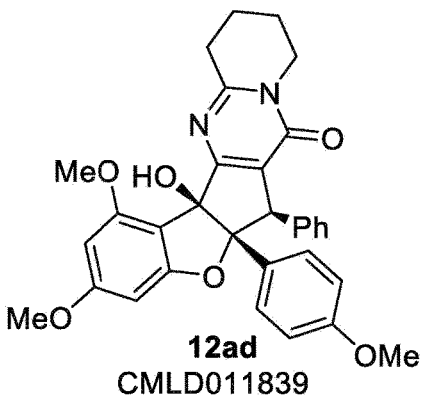
FIG. 48
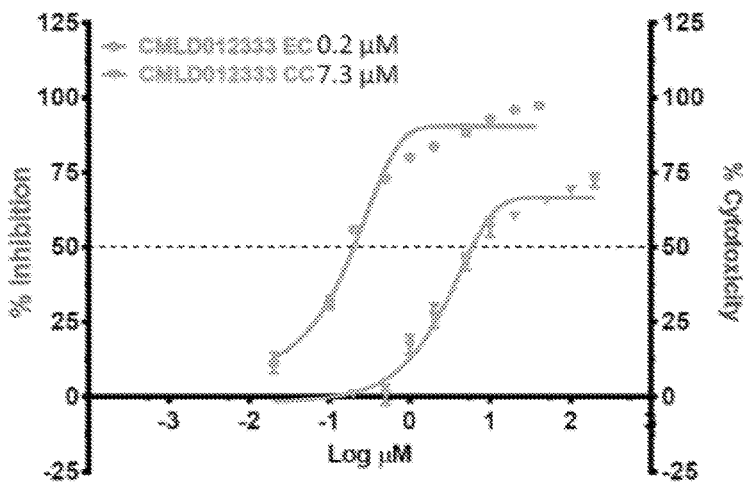
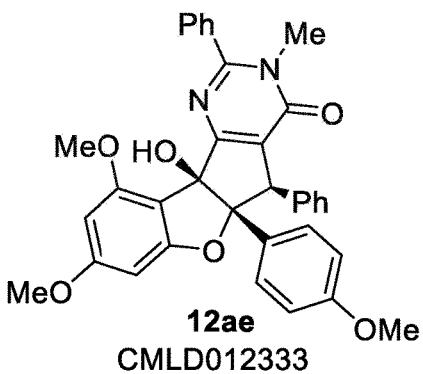
FIG. 49

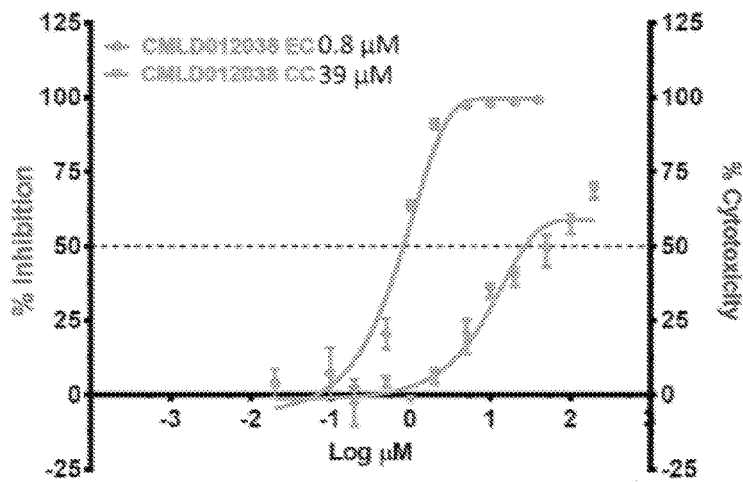
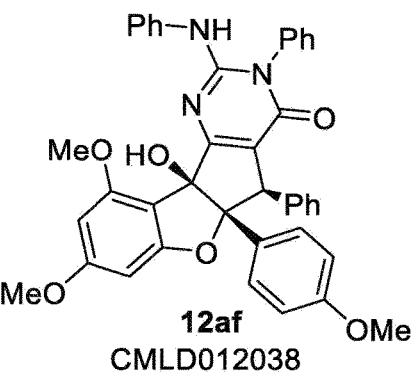
FIG. 50
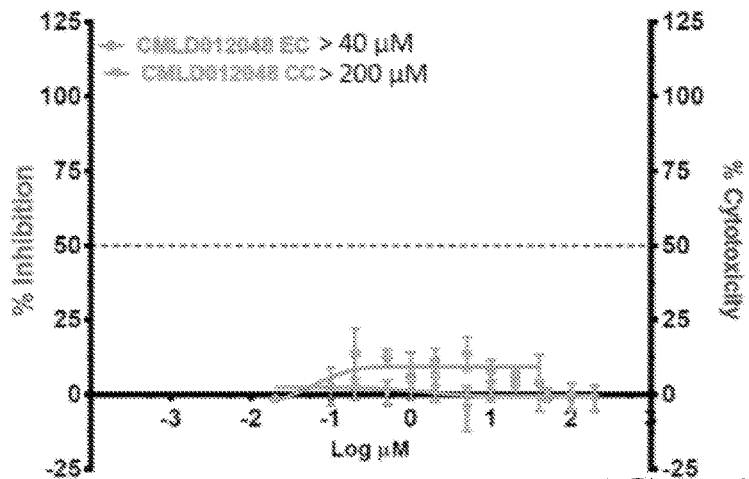
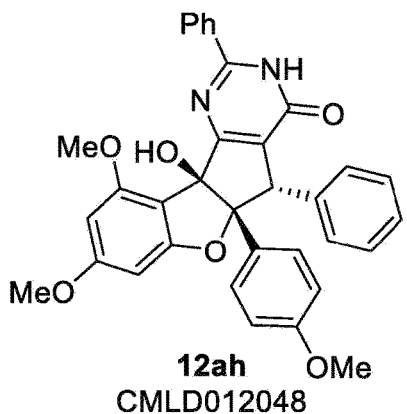
FIG. 51
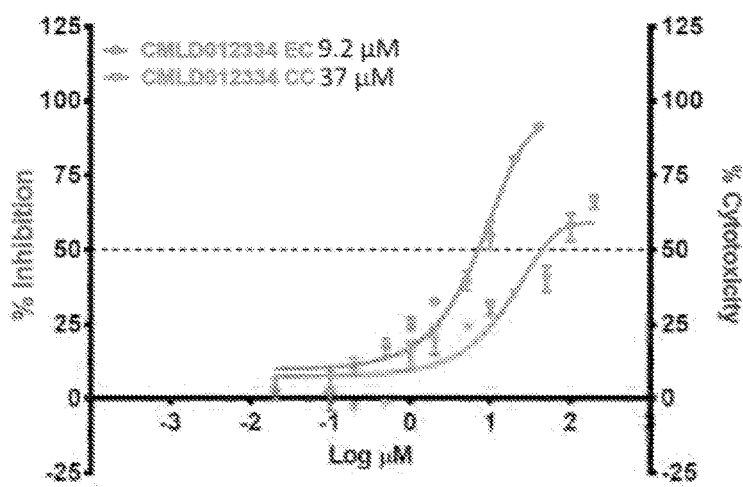
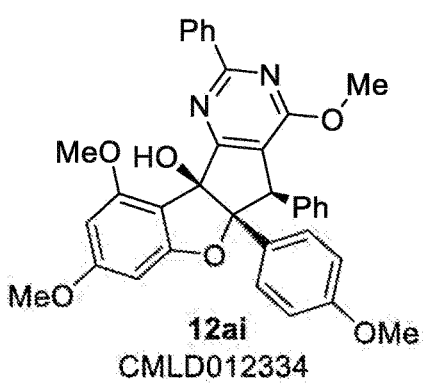
FIG. 52

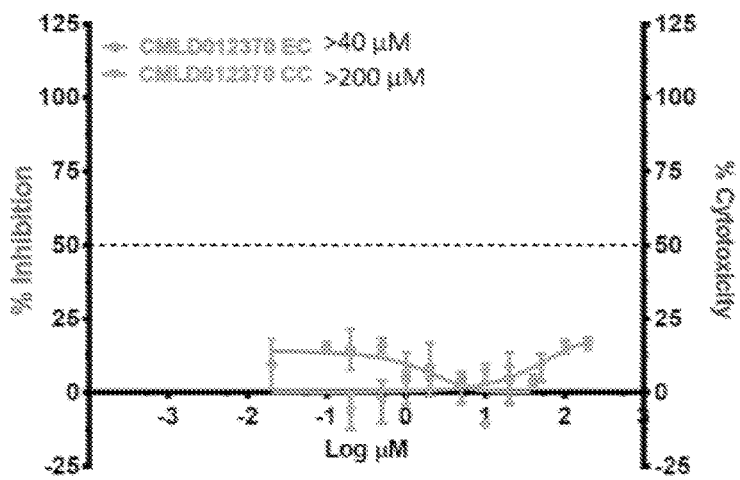
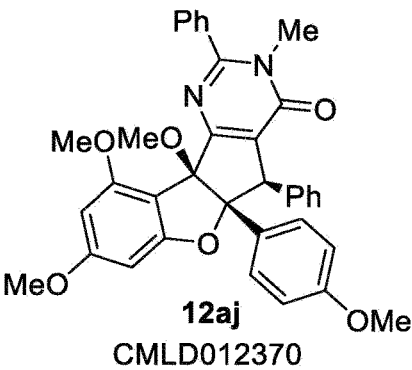
FIG. 53
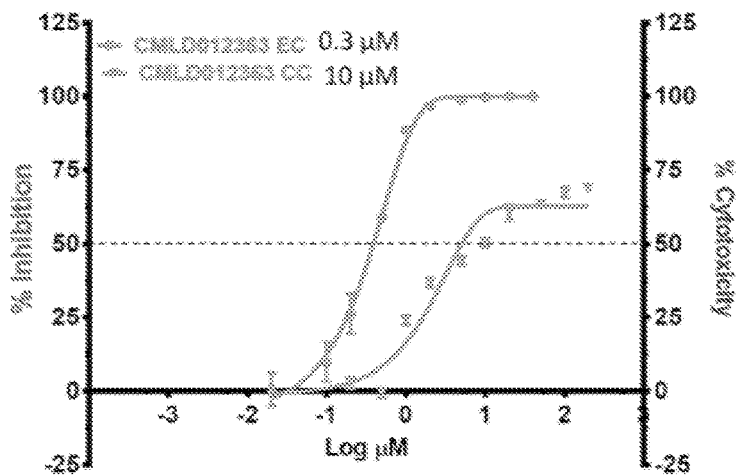
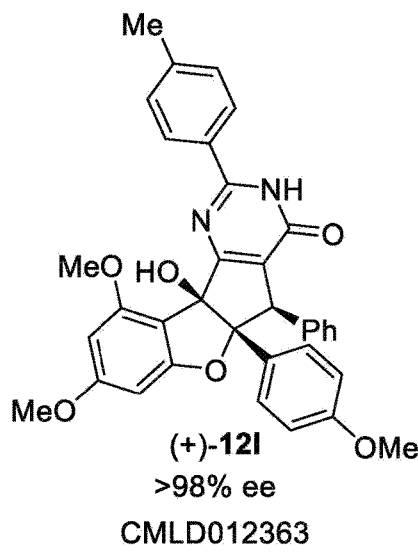
FIG. 54
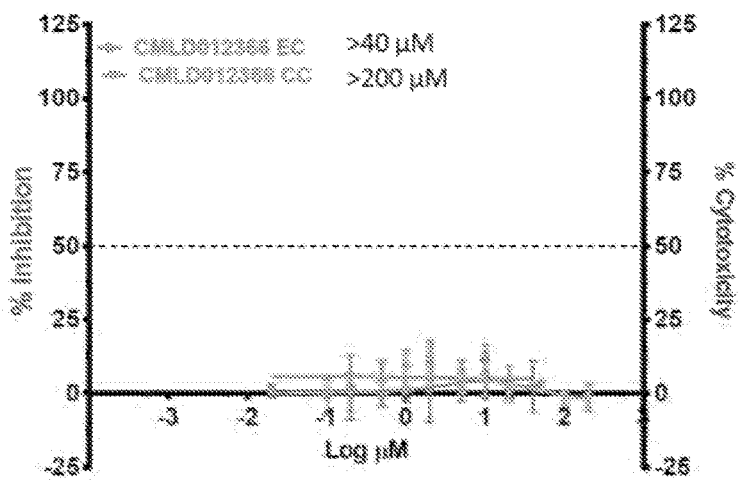
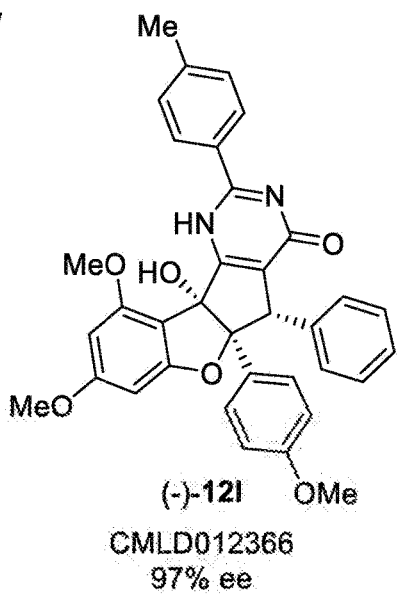
FIG. 55

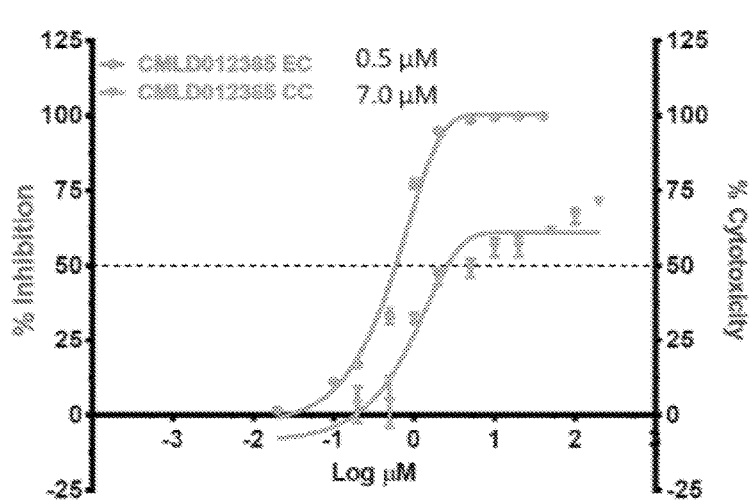
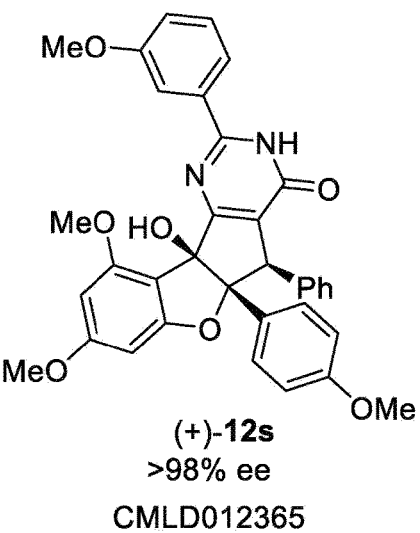
FIG. 56
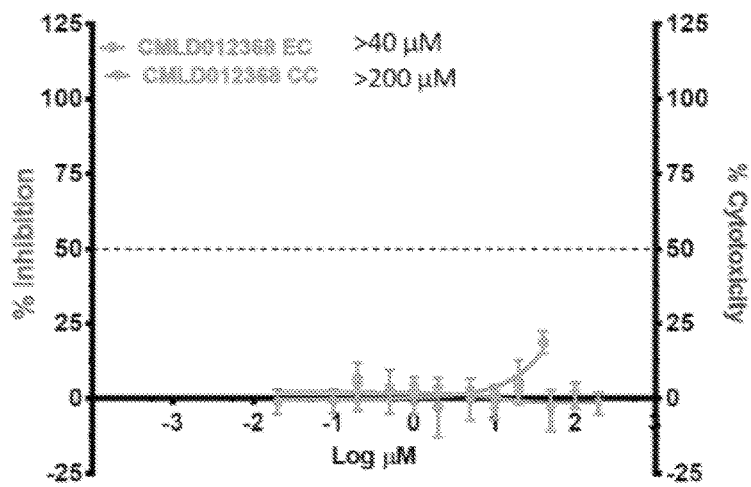
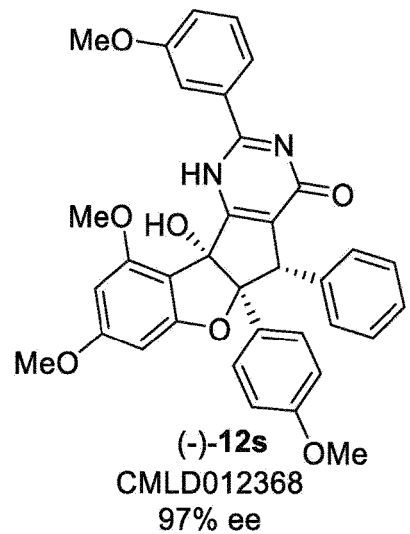
FIG. 57

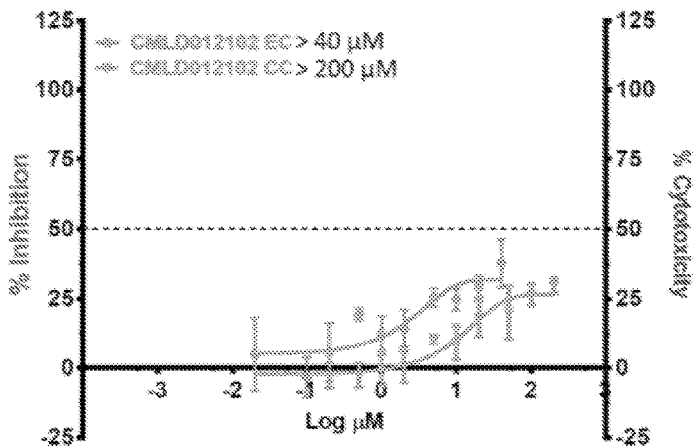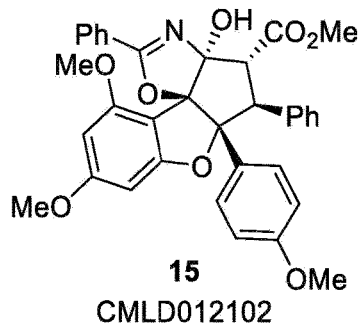
FIG. 58
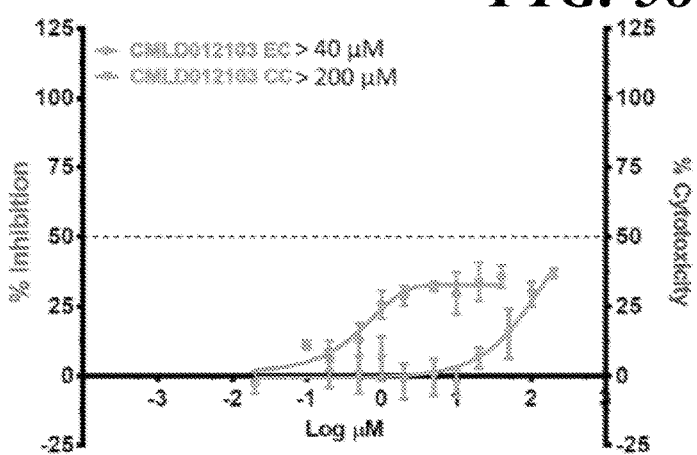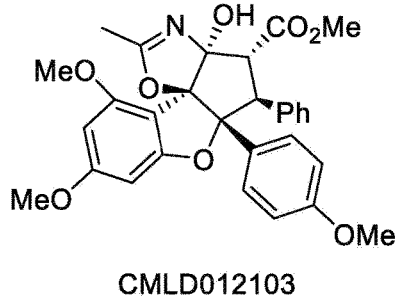
FIG. 59
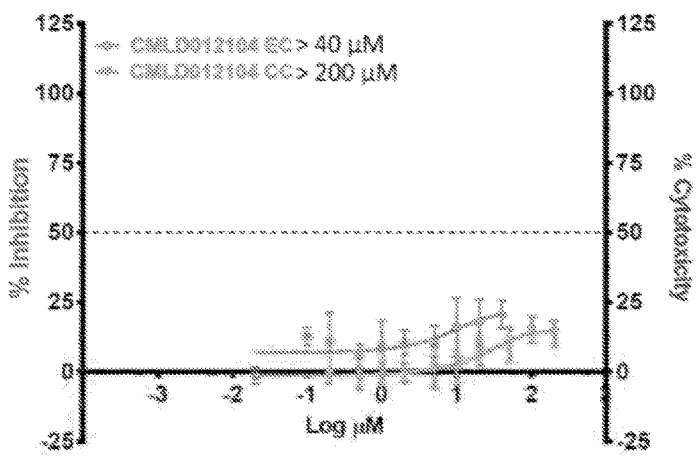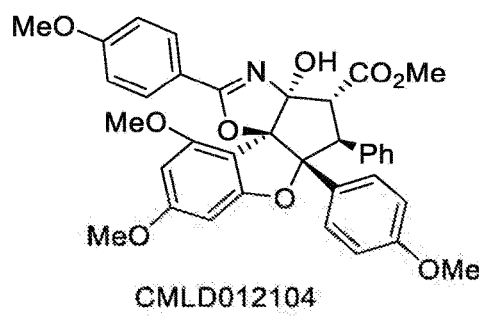
FIG. 60

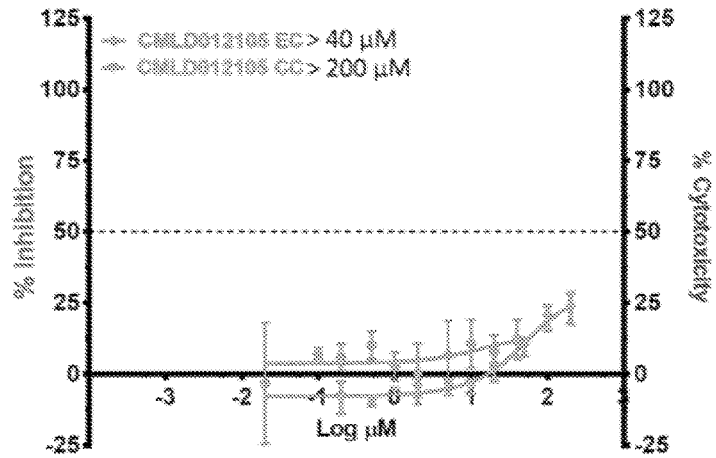
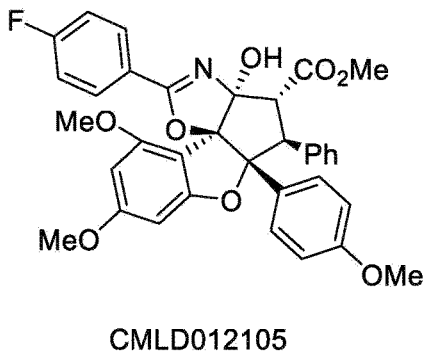
FIG. 61
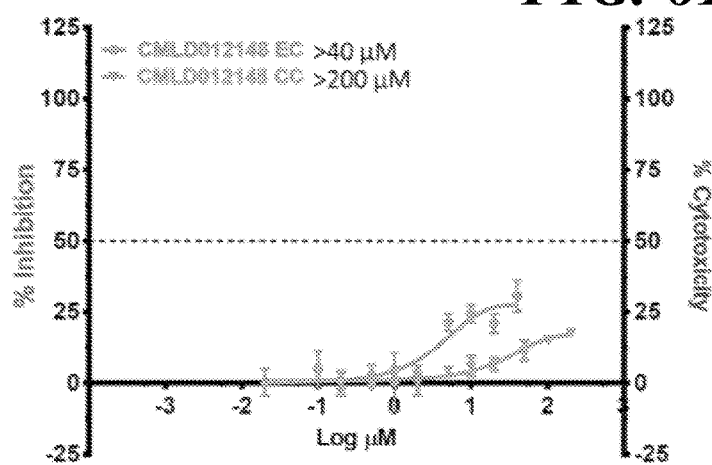
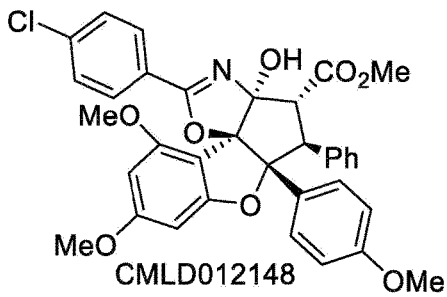
FIG. 62
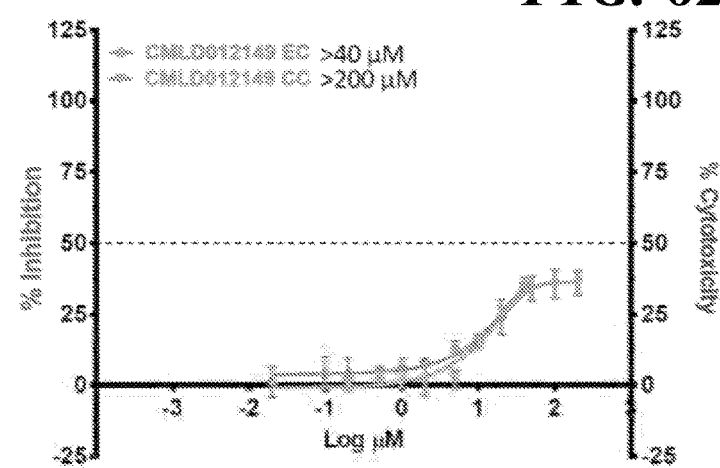
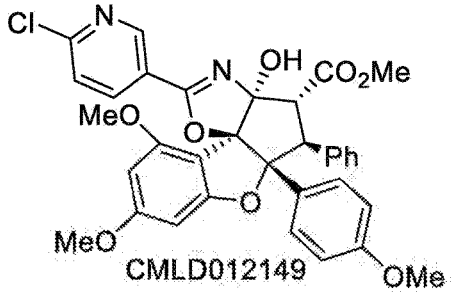
FIG. 63

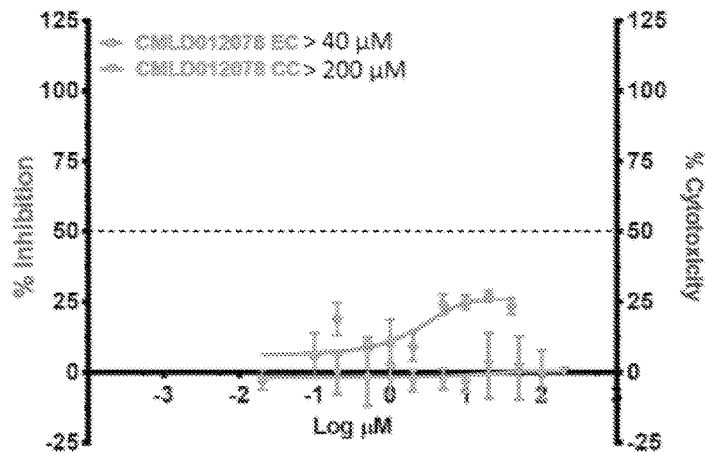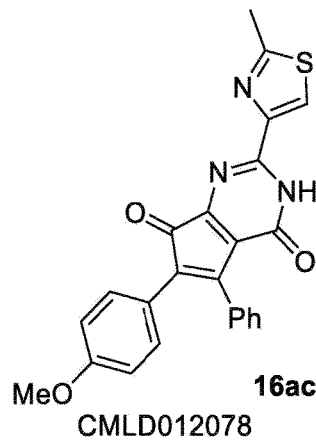
FIG. 64
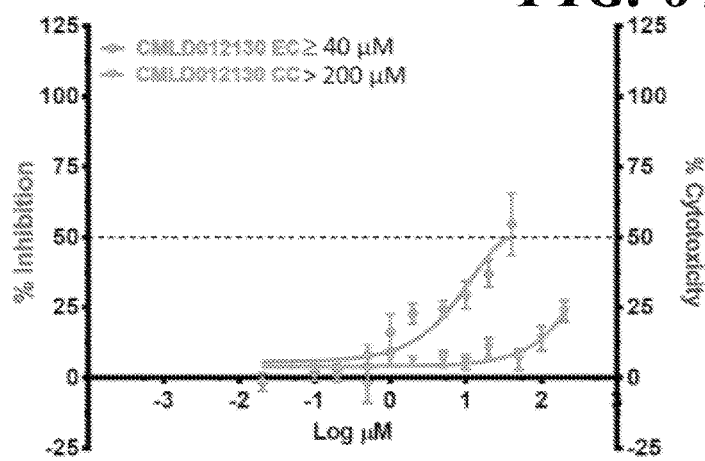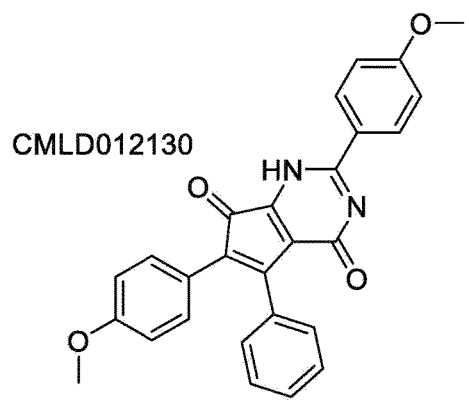
FIG. 65
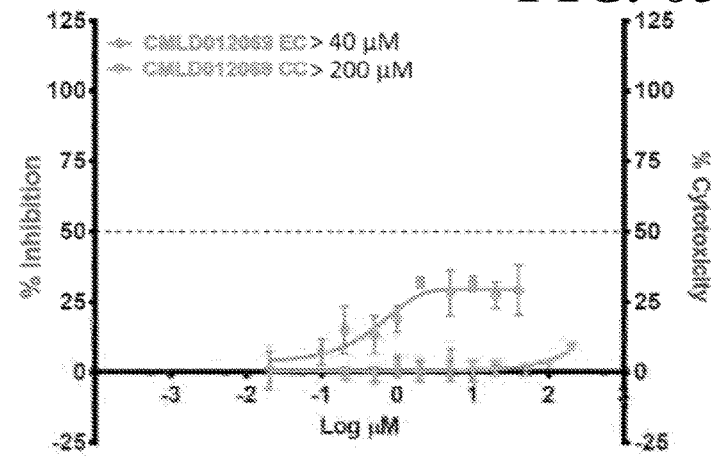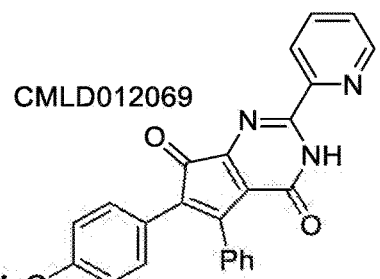
FIG. 66

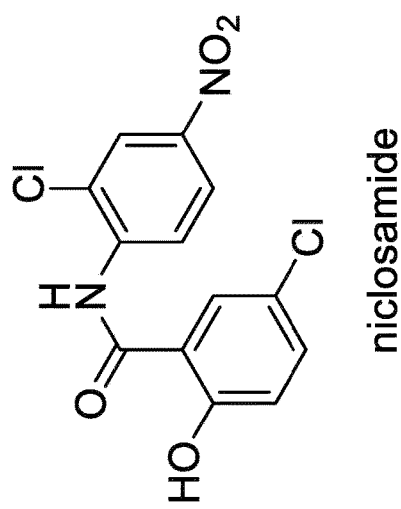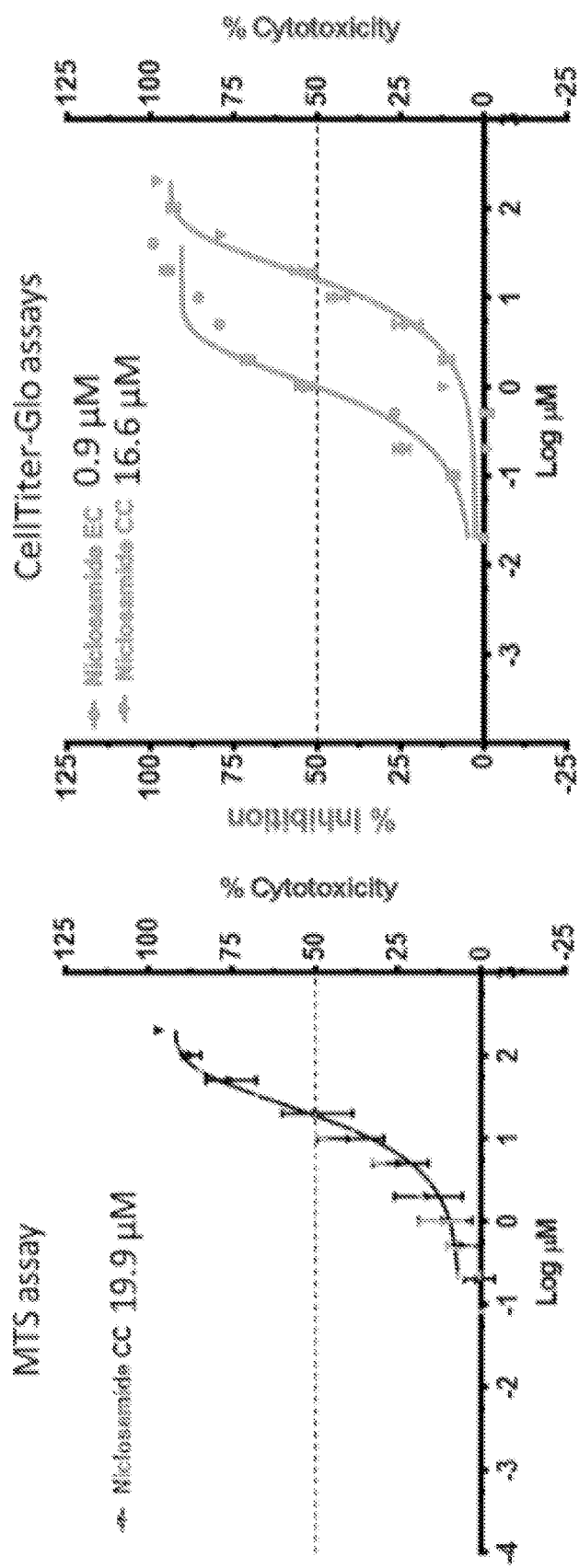
FIG. 68

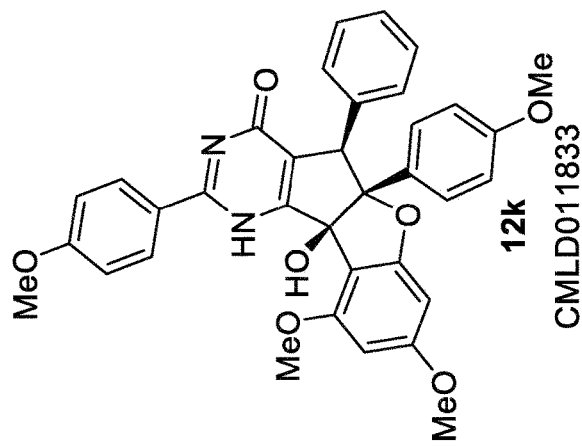
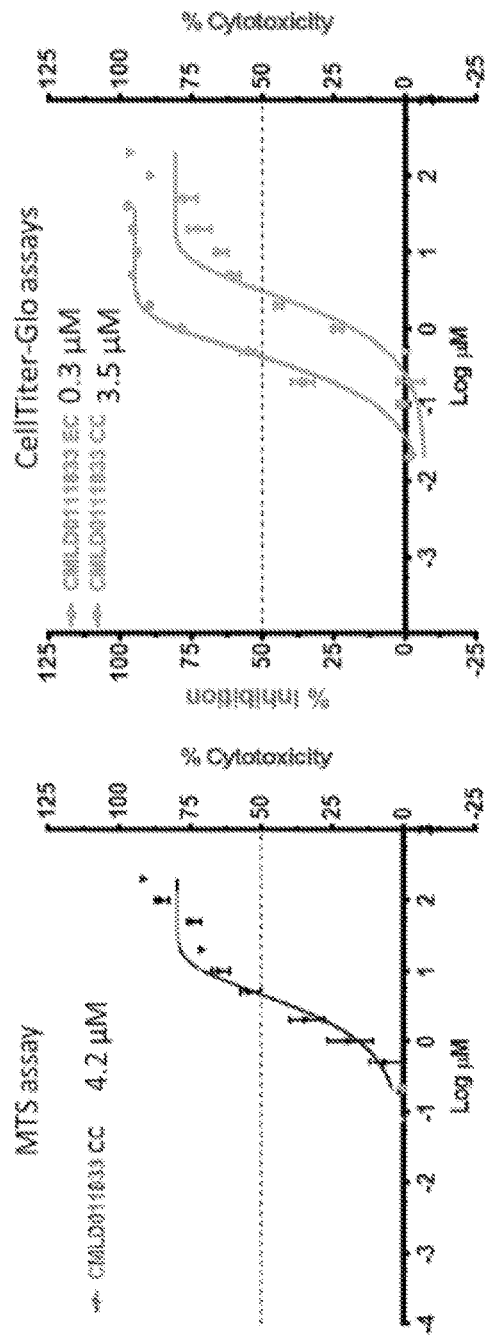
FIG. 69

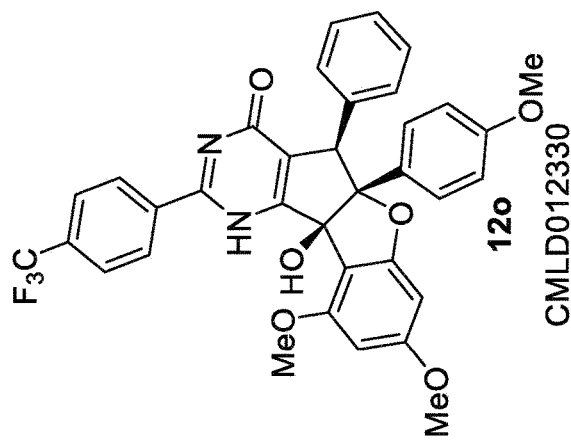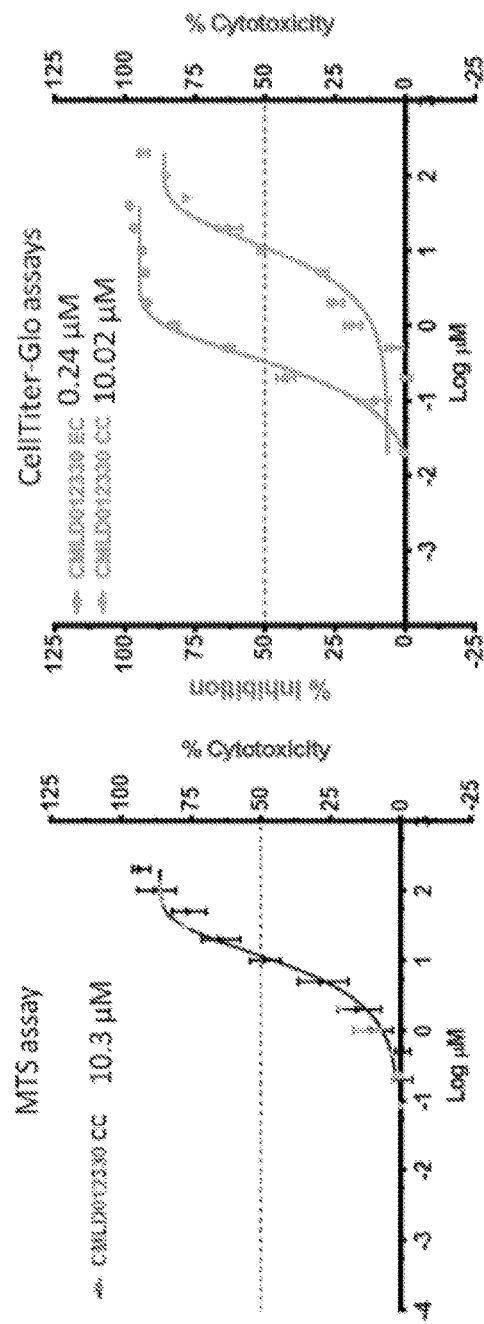
FIG. 70

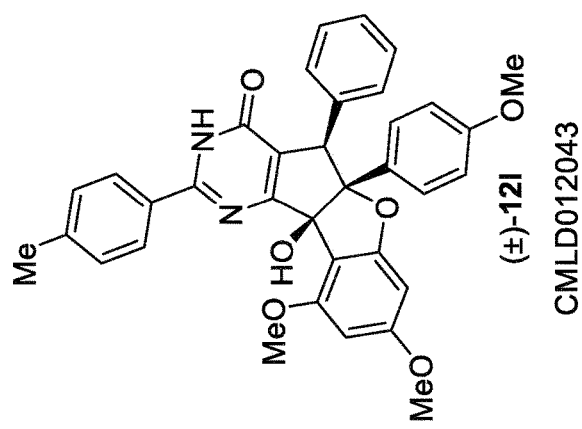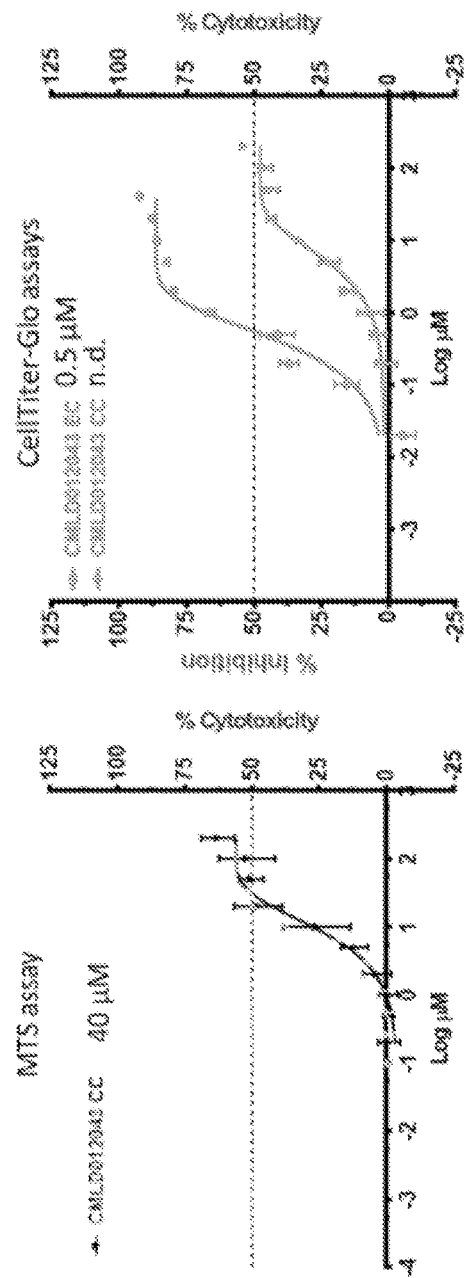
FIG. 71

Synthetic Pathways

COMPOSITIONS AND METHODS FOR INHIBITING VIRAL INFECTION

CROSS-REFERENCE TO RELATED APPLICATIONS

This application claims benefit under 35 U.S.C. § 119(e) of U.S. Provisional Application No. 62/748,691 filed Oct. 22, 2018, the contents of which are incorporated herein by reference in their entirety.

GOVERNMENT SUPPORT

This invention was made with government support under Contract No. R01DK088787 and R35 GM-118173 awarded by the National Institute of Health and under an intramural fund by the U.S. Food and Drug Administration. The government has certain rights in the invention.

SEQUENCE LISTING

The instant application contains a Sequence Listing which has been filed electronically in ASCII format and is hereby incorporated by reference in its entirety. Said ASCII copy, created on Oct. 28, 2019, is named 701586_093740USPT-_SL.txt and is 26,911 bytes in size.

TECHNICAL FIELD

The technology described herein relates to compositions and methods for inhibiting viral infections and uses thereof.

BACKGROUND

Viruses are small infectious agents that enter specific living cells either by endocytosis or direct injection of DNA and multiply, causing disease. One example, the Hepatitis C Virus (HCV), is a widespread viral pathogen affecting nearly 143 million carriers world-wide. Chronic HCV infection is the cause of severe liver disease including liver cancer and cirrhosis. HCV resistance to direct-acting antiviral agents (DAAs) has become a challenge for those infected by the virus. Resistance to current HCV treatments can be lethal and lead to significant liver damage. Unlike Hepatitis A and B, there is currently no way to prevent hepatitis C infection.

SUMMARY

In general, the inventions described herein relate to rocaglate compositions, methods for making rocaglates, as well as their usage as therapeutic agents. For example, a concise synthesis of aglaroxin C analogues utilizing a highly regioselective pyrimidinone condensation is described as well as the use of these compounds for inhibiting a Hepatitis C viral infection.

In a first aspect the disclosure is a compound having the structure of Formula (I), (II), or (III)

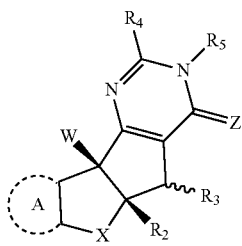

(I)

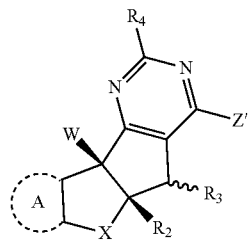

(II)

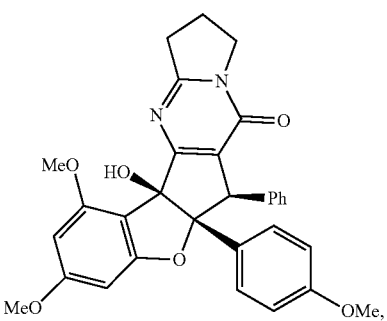

(III)

or stereoisomers, tautomers, or pharmaceutically acceptable salts thereof; wherein:

X is O, S, $CR^BR^E$ or $NR^E$; wherein $R^B$ and $R^E$ independently are H, alkyl, aryl, heteroaryl, heteroalkyl, cycloalkyl, acyl, or allyl;

W is F or —$YR^A$, wherein Y is O, NH or S, and $R^A$ is H, alkyl, aryl, heteroaryl, heteroalkyl, cycloalkyl, acyl, NH(alkyl), $NH_2$ or NH(aryl);

A is a heteroaryl or aryl;

$R_2$ is aryl or heteroaryl;

$R_3$ is H, phenyl, alkyl, heteroalkyl, aryl, heteroaryl, aldehyde, ester, alkenyl, amide or —$CO_2H$; wherein when $R_3$ is not H; $R_3$ is syn to $R_2$ or $R_3$ is trans to $R_2$;

$R_4$ is H, alkyl, aryl, heteroaryl, heteroalkyl, cycloalkyl, acyl halide, CN, NH(alkyl), NH(aryl), NH(CN), $CO_2$(alkyl) or NH—NH(alkyl);

Z is O, NH, S, Se, N(alkyl) or N(aryl), $CR^CR^F$; wherein $R^C$ and $R^F$ independently are H, alkyl, aryl, heteroaryl, heteroalkyl, cycloalkyl, acyl, allyl or CN;

$R_5$ is H, alkyl, alkenyl, alkynyl, aryl, heteroaryl, cycloalkyl heteroalkyl;

Z' is a halide or -$TR_5$'; wherein T is O, S, NH, or $CH_2$ and $R_5$' is H, alkyl, alkenyl, alkynyl aryl, heteroaryl, cycloalkyl, heteroalkyl, acyl or sulfate;

D is a $C_{1-5}$ alkylene, $C_{1-5}$ heteroalkylene, heteroaryl or aryl, wherein when D is a three carbon alkylene the compound does not have the structure of formula ((−)-6)).

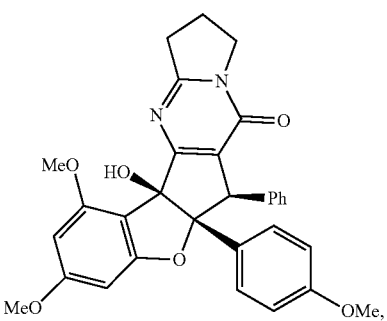

((−)-6)

and;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6. Optionally the compound has the structure of formula 12l or 12s:

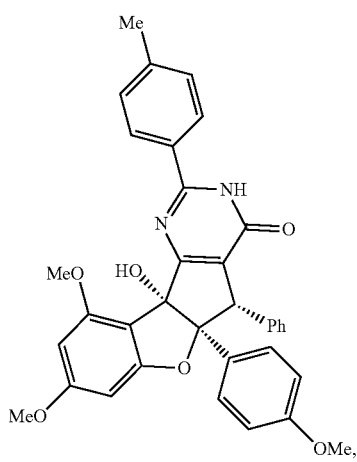

((-)-12l)

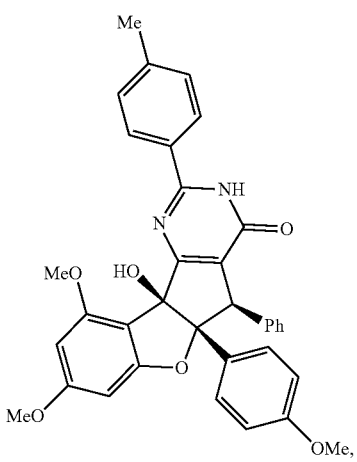

((+)-12l)

-continued

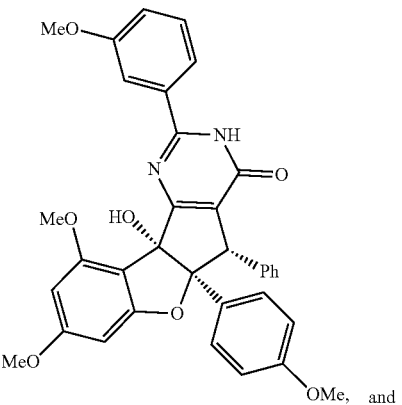

((-)-12s)

and

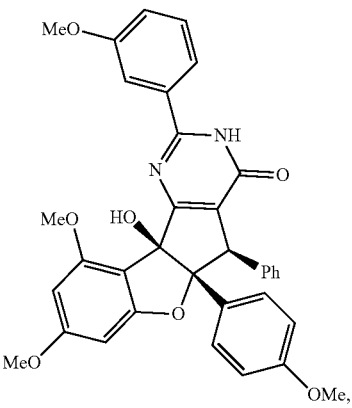

((+)-12s)

In a second aspect, the disclosure is a method for preparing the compounds according to the first aspect and compound ((−)-6)). The method comprising providing a first compound and a second compound in a solution, and reacting the first compound with the second compound. The first compound has the structure of (VI), (VII) or a salt thereof, and the second compound has the structure of (VIII), (IX) or a salt thereof. The structures of (VI), (VII), (VIII) and (IX) are;

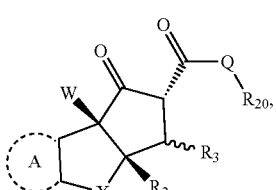

(VI)

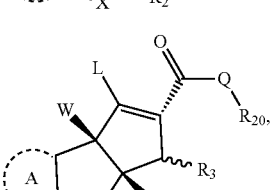

(VII)

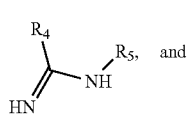

(VIII)

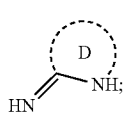

(IX)

wherein Q is $OR^G$ or $NR^HR^I$, wherein $R^G$, $R^H$ and $R^I$ are independently H or an alkyl, and wherein L is a leaving group.

In a third aspect, the disclosure is a pharmaceutical composition comprising a compound according to the first aspect and a pharmaceutically acceptable carrier, diluent, or excipient.

In a fourth aspect, the disclosure is a pharmaceutical composition comprising a compound made by the method according the second aspect.

In a fourth aspect, the disclosure is a method of inhibiting a viral infection in a subject in need thereof. The method comprises administering to the subject a therapeutically effective amount of the compound according to the first aspect or the pharmaceutical composition according to the third aspect. Optionally, the viral infection is caused by a Flavivirdae family virus or an alphavirus. Optionally, the viral infection is caused by a virus selected from the group consisting of: Hepatitis C virus (HCV), Chikungunya virus (alphavirus), Dengue virus, Zika virus, yellow fever virus, Japanese encephalitis virus, West Nile virus, tick-borne encephalitis virus, and Omsk Hemorrhagic Fever Virus (OHFV). Optionally, the administration involves oral delivery or direct injection. Optionally, the method further comprises administering one or more additional agents. Optionally, the agent is an antiviral agent.

In a fifth aspect, the disclosure is a method of inhibiting a Hepatitis C viral infection in a subject in need thereof. The method comprising administering to the subject a therapeutically effective amount of the compound according to the first aspect or the pharmaceutical composition according to the third aspect. Optionally, the subject is a human. Optionally, the administration method is oral or direct injection. Optionally the method further comprises administering one or more additional agents. Optionally, the agent is an antiviral agent. Optionally, the agent is selected from the group consisting of: a small molecule, an antibody, a peptide, a genome editing system, and a nucleic acid. Optionally, the agent is selected from the group consisting of: ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, pegylated interferon, pegylated interferon alpha-2b, interferon alpha-2a, elbasvir, and grazoprevir. Optionally, the agent is sofosbuvir.

In a sixth aspect, the disclosure is a method of inhibiting viral entry into a cell, the method comprising: contacting a cell with at least one compound according to the first aspect. Optionally, the method further comprises contacting the cell with an additional agent. Optionally, the agent is an antiviral agent. Optionally the agent is sofosbuvir. Optionally the compound inhibits prohibitin or glycoprotein fusion with the cell. Optionally, the cell is contacted with 12l or 12s. Optionally, the cell is contacted with both 12l and 12s. Optionally, the cell is a hepatocyte. Optionally, the virus is Hepatitis C virus, Dengue virus, or Chikungunya virus.

In a seventh aspect, the disclosure is a method of inhibiting prohibitin or glycoprotein fusion with a cell, the method comprising: contacting the cell with an effective amount of at least one compound according to the first aspect. Optionally, the method further comprises contacting the cell with an additional agent. Optionally, the agent is an antiviral agent. Optionally, the agent is sofosbuvir. Optionally the compound inhibits prohibitin or glycoprotein fusion with the cell. Optionally, the cell is contacted with 12l or 12s. Optionally, the cell is contacted with both 12l and 12s. Optionally, the cell is a hepatocyte. Optionally, the virus is Hepatitis C virus, Dengue virus, or Chikungunya virus.

The above summary is not intended to represent every embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The patent or application file contains at least one drawing executed in color. Copies of this patent application publication with color drawings will be provided by the Office upon request and payment of the necessary fee.

FIG. 1 demonstrates representative biologically active rocaglates products and synthetic analogues.

FIG. 6 shows Table 2: optimization of pyrimidinone formation using the amidine salt.

FIG. 11A shows a schematic representation of the bicistronic reporter FF/HCV/Ren mRNA used to monitor translation. In this system, Firefly luciferase (FLuc) translation is cap-dependent whereas *Renilla* luciferase (RLuc) expression HCV-IRES dependent. FIG. 11B shows the assessment of cap or HCV dependent translation of FF/HCV/Ren mRNA in the presence of 1 μM of the indicated compounds in Krebs-2 extracts. Results are presented relative to values obtained in the presence of DMSO ad expressed as mean±error of two biological replicates.

FIG. 12A shows that Huh7.5.1 cells were infected by the indicated pseudovirus in the presence of compounds (1 μM) for 3 hours. After an additional 48-hour infection, cells were lysed for luciferase assay. Relative infectivity was calculated by normalizing against the values obtained from cells treated with DMSO (arbitrarily set to 1.0) (mean±SD*P<0.05). FIG. 12B is the same as in FIG. 12A except (+)-12l and 12s were added at 2 μM. FIG. 12C shows Huh7.5.1 cells which were infected by Dengue virus (serotype 2, Thailand 16681 strain, MOI 0.1) treated with 2 μM compounds for 3 hours. 48 hours post-infection, RNA was isolated for quantitative RT-PCR analysis. Viral RNA levels were normalized against GAPDH levels. Date presented are representatives of two independent experiments. FIG. 12D shows (+)-6, (+)-12l, and (±)-12s inhibited HCV infection when added together with the virus. Details on this time-of-addition experiment can be found in EXAMPLES 2 and 6-7.

Figure 16A:
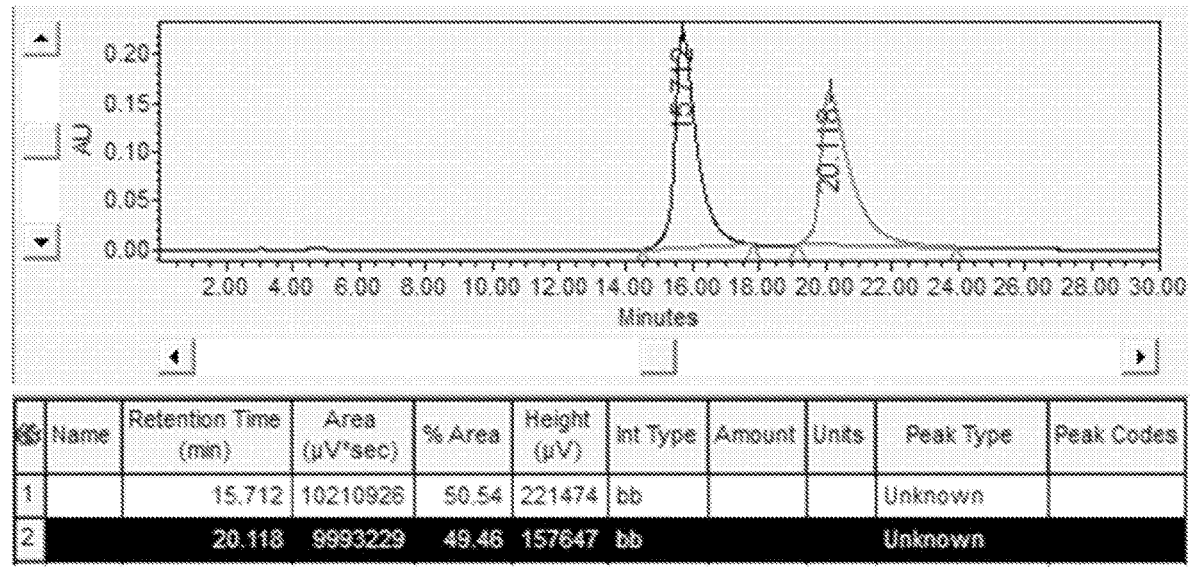
FIG. 16A-16C shows chiral HPLC traces for (+)-, (−)-, and (+)-tosyl enol rocaglates.
Figure 16B:
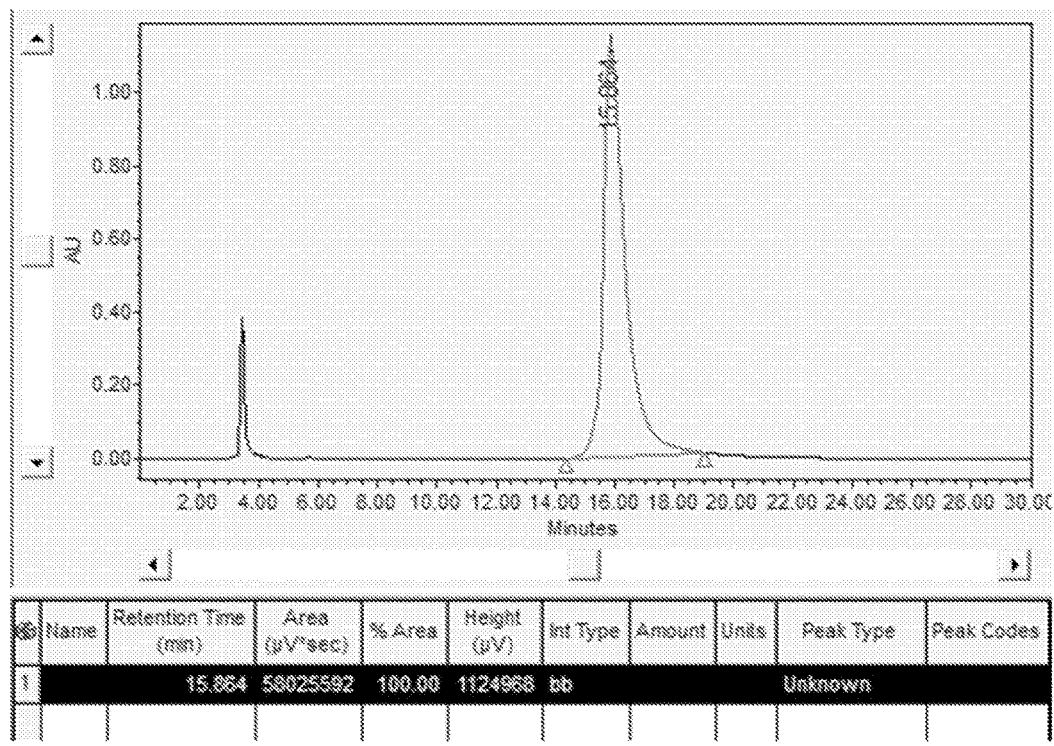
Figure 16C:
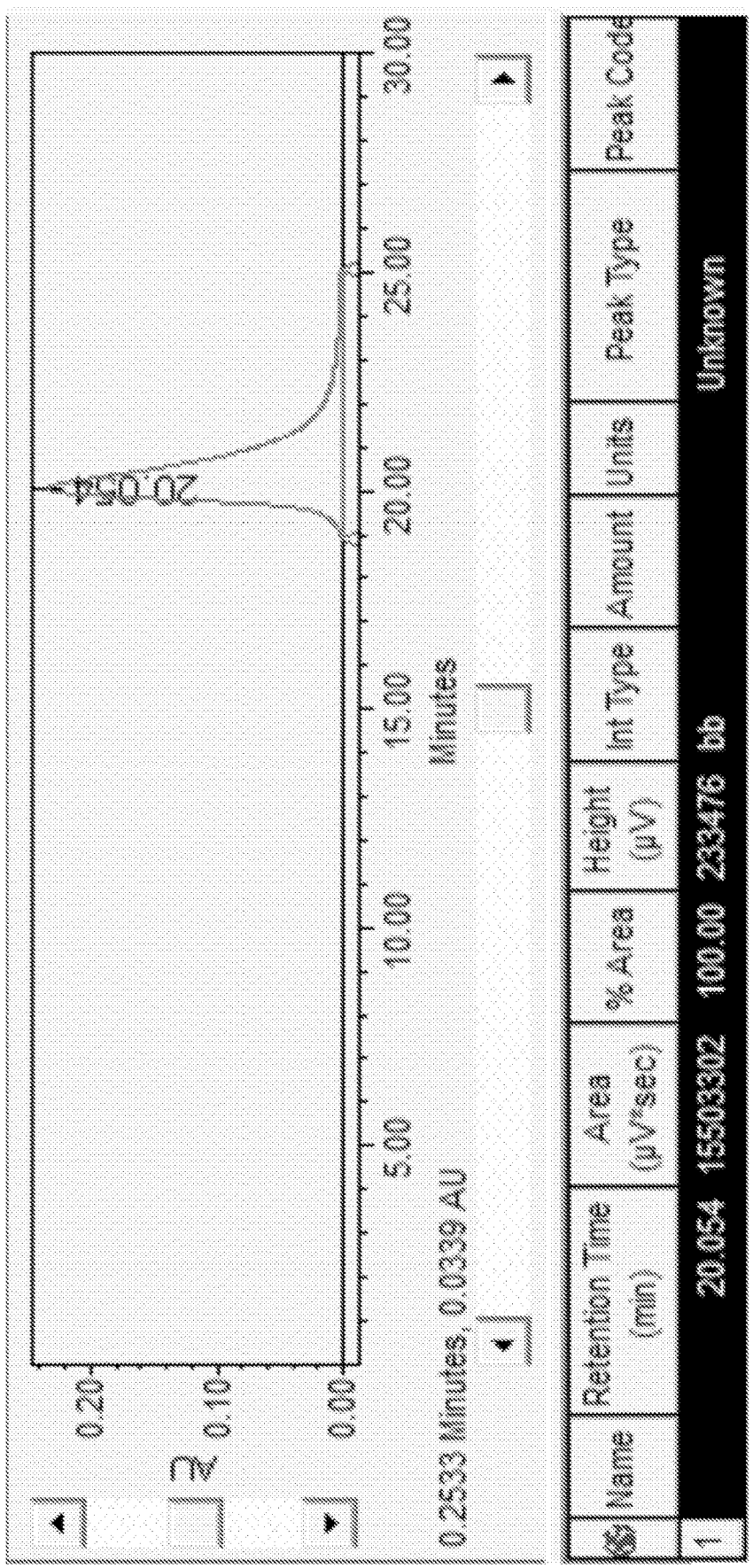

A WelkO column was used with an isocratic mobile phase of 40% isopropanol in hexanes at a flow rate of 1.0 mL/min for 30 min. (+)-tosyl enol rocaglate is shown in FIG. 16A. (−)-tosyl enol rocaglate $[α]_D 26=−223.220°$ (c=0.05, CH2Cl2) is shown in FIG. 16B. (+)-tosyl enol rocaglate $[α]_D 26=206.091°$ (c=0.05, CH2Cl2) is shown in FIG. 16C.

Figure 17A:
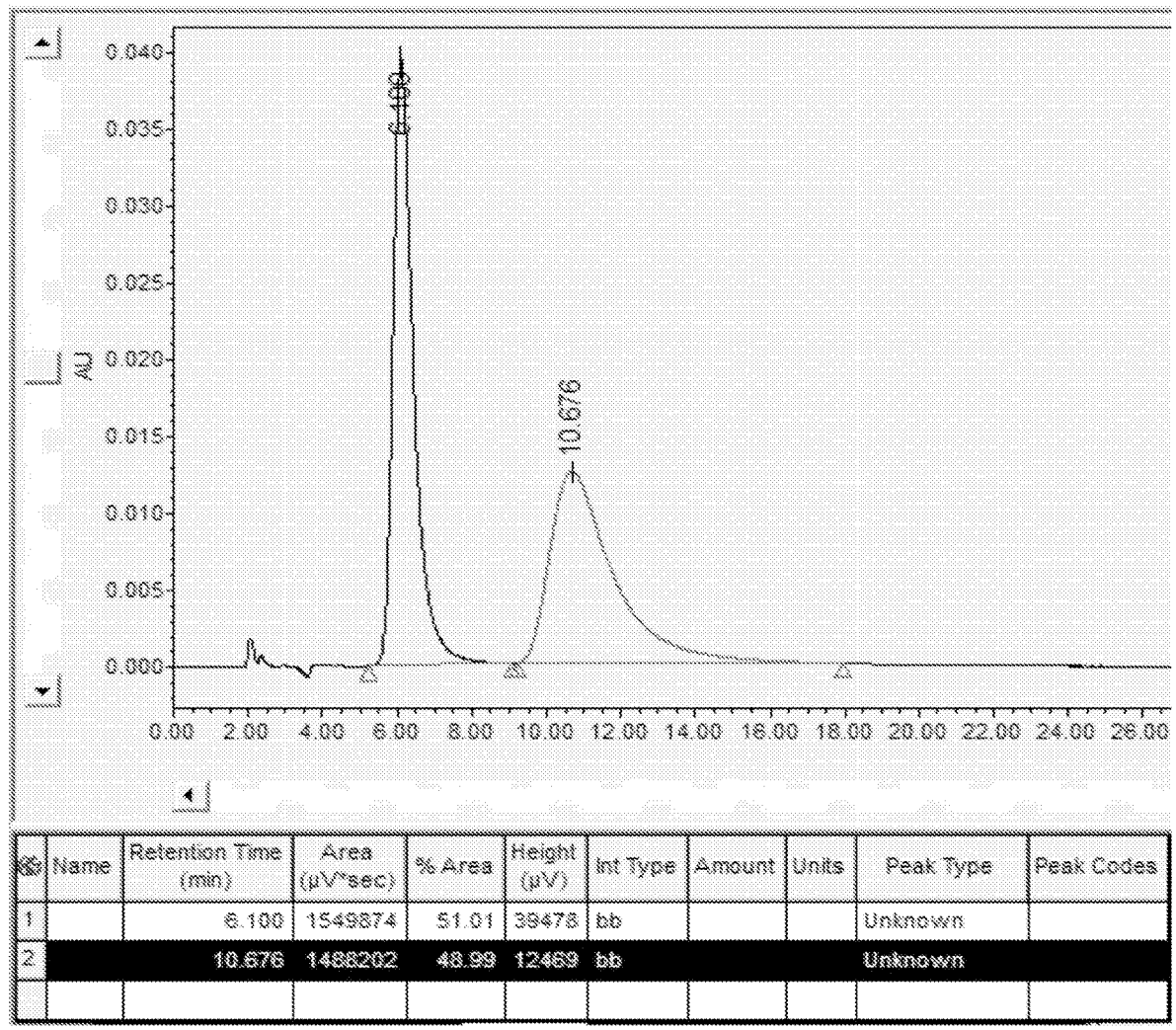
Figure 17B:
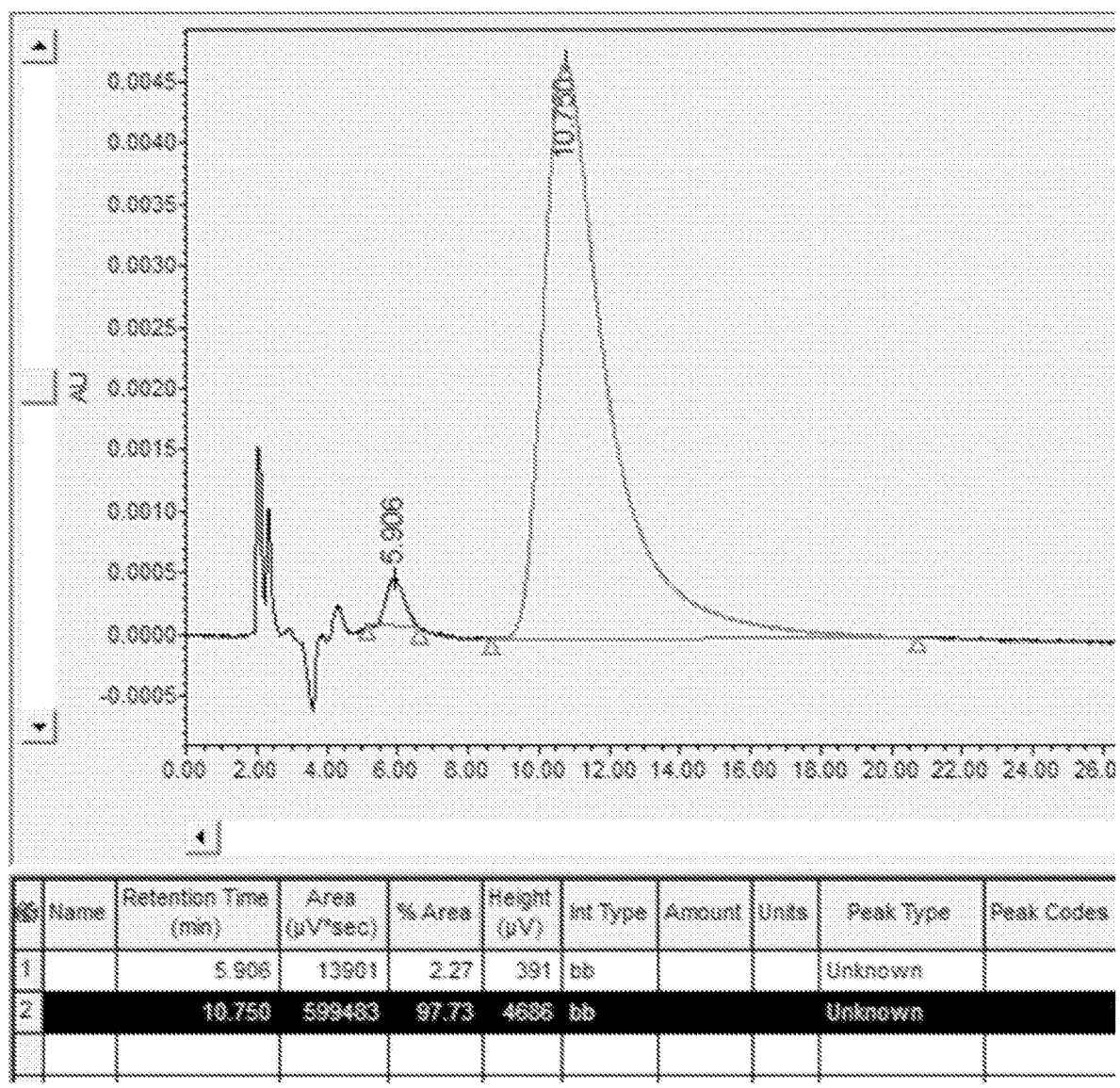
Figure 17C:
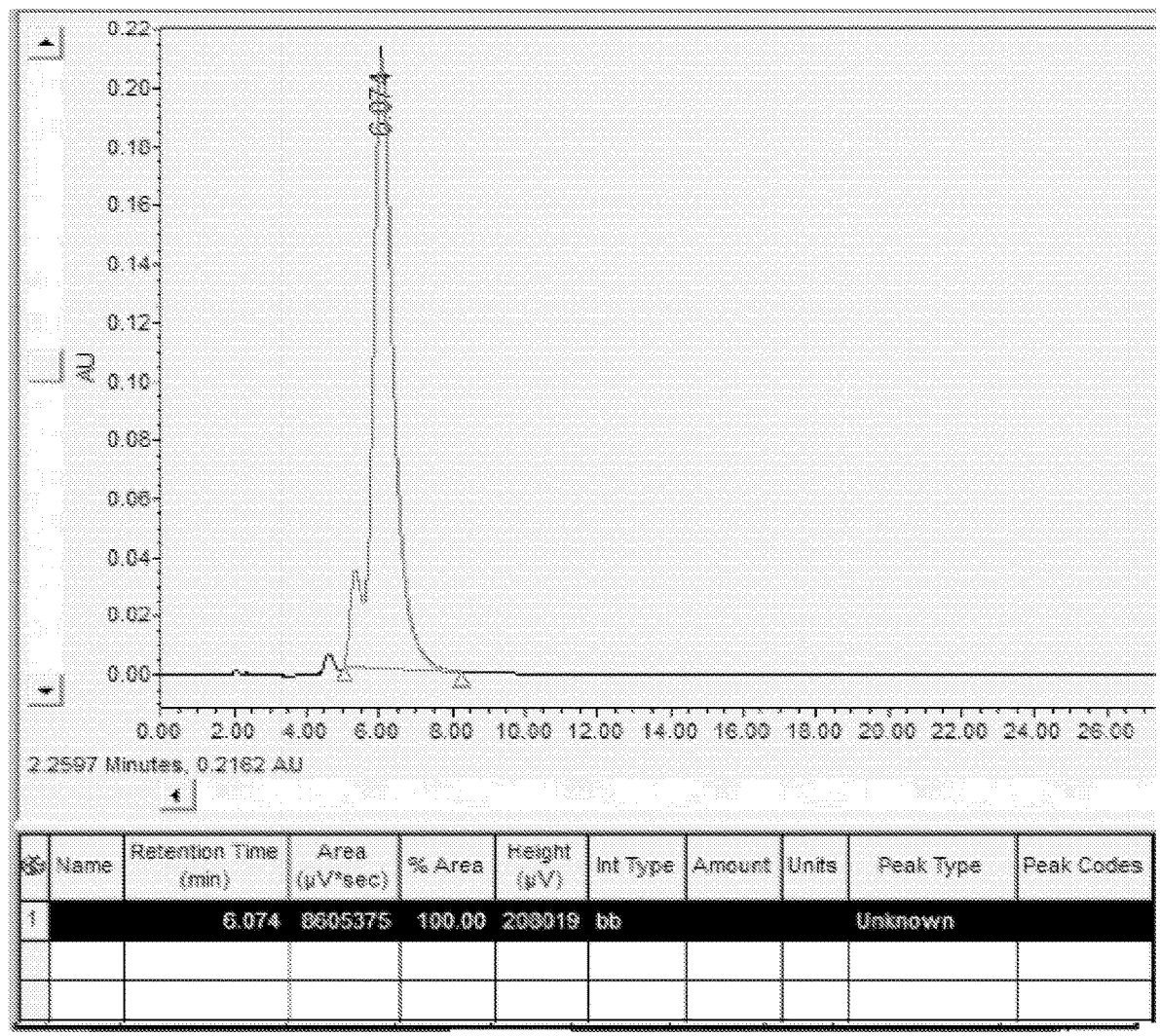
Figure 18A:
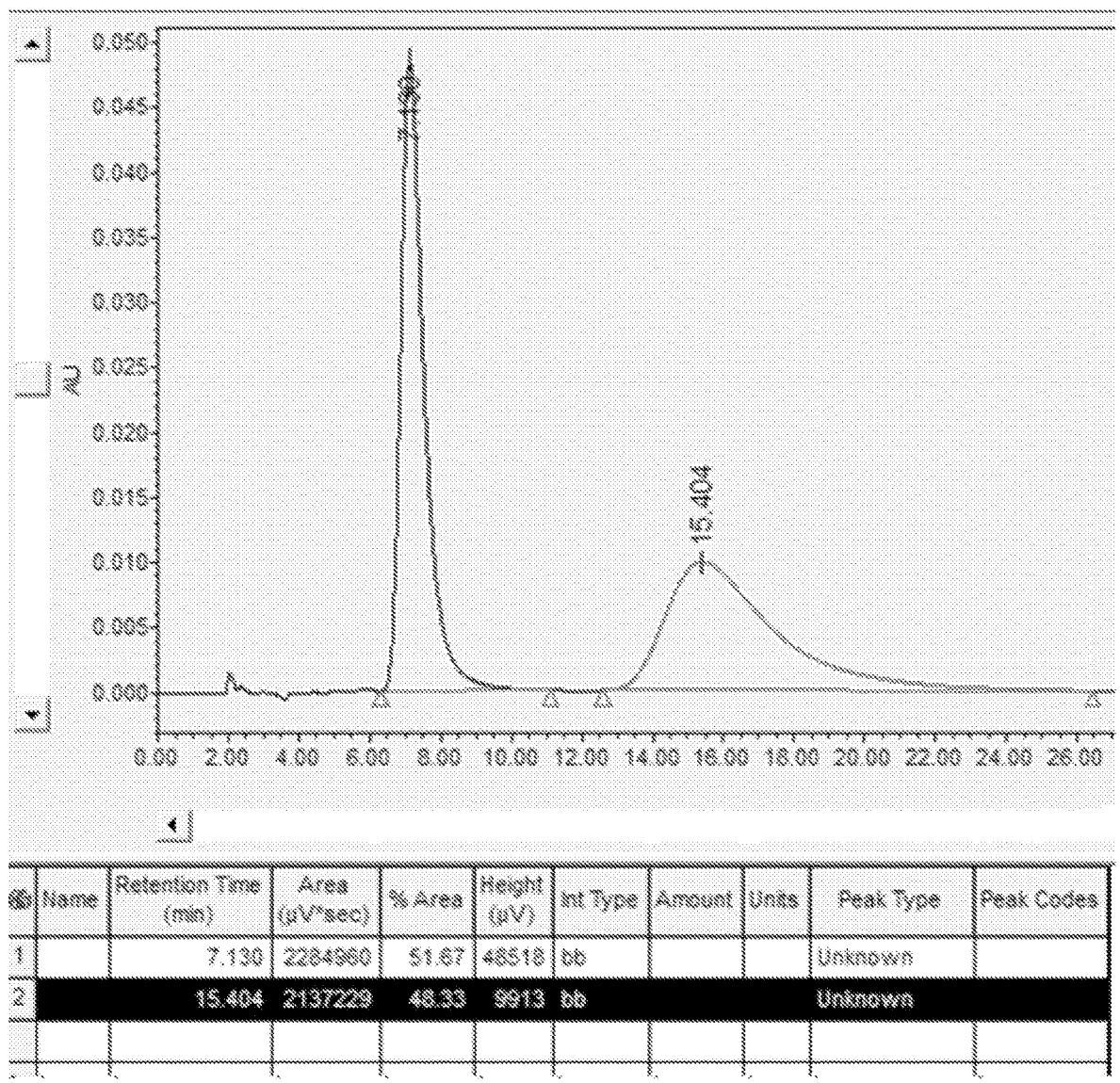
Figure 18B:
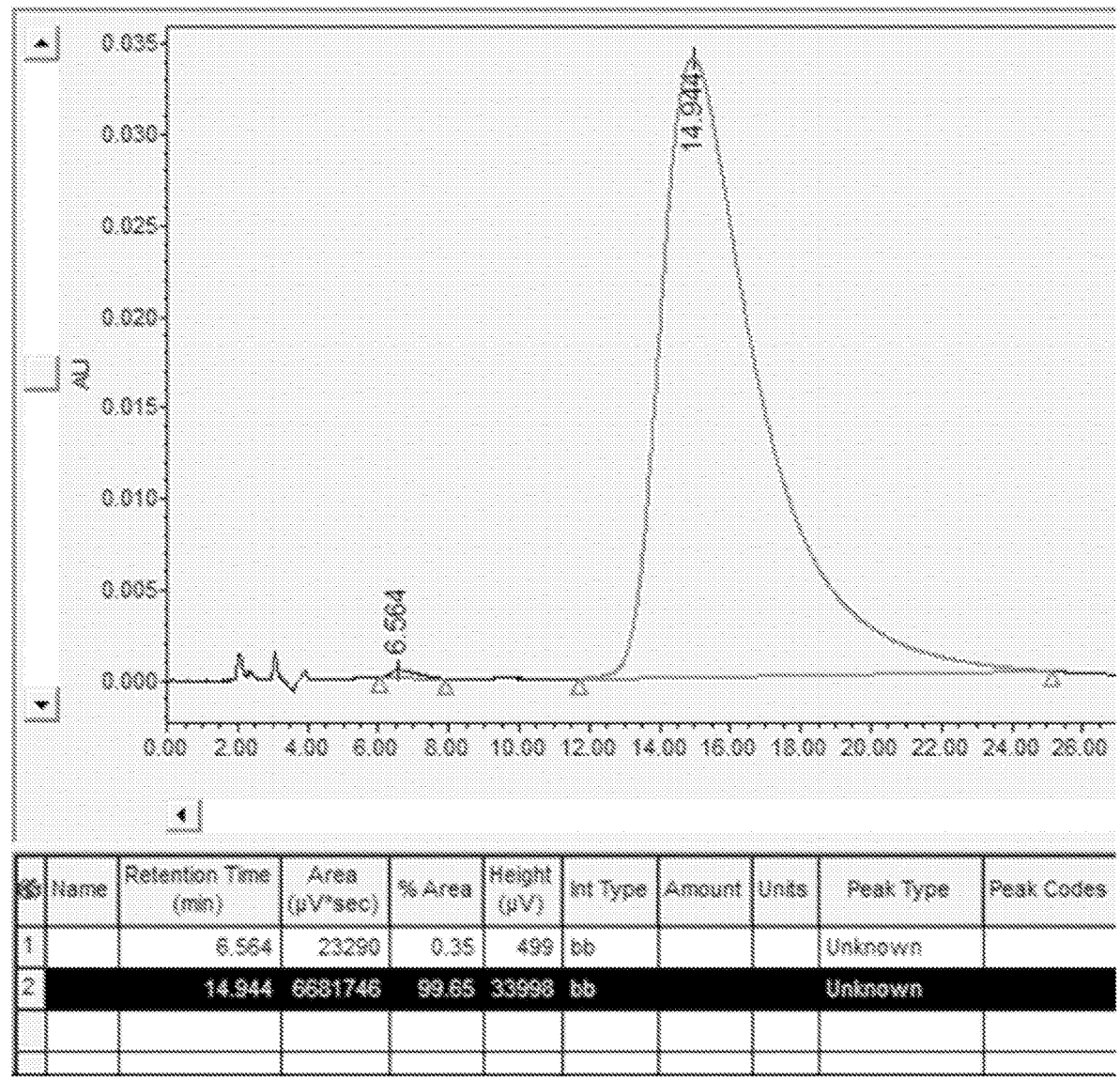
Figure 18C:
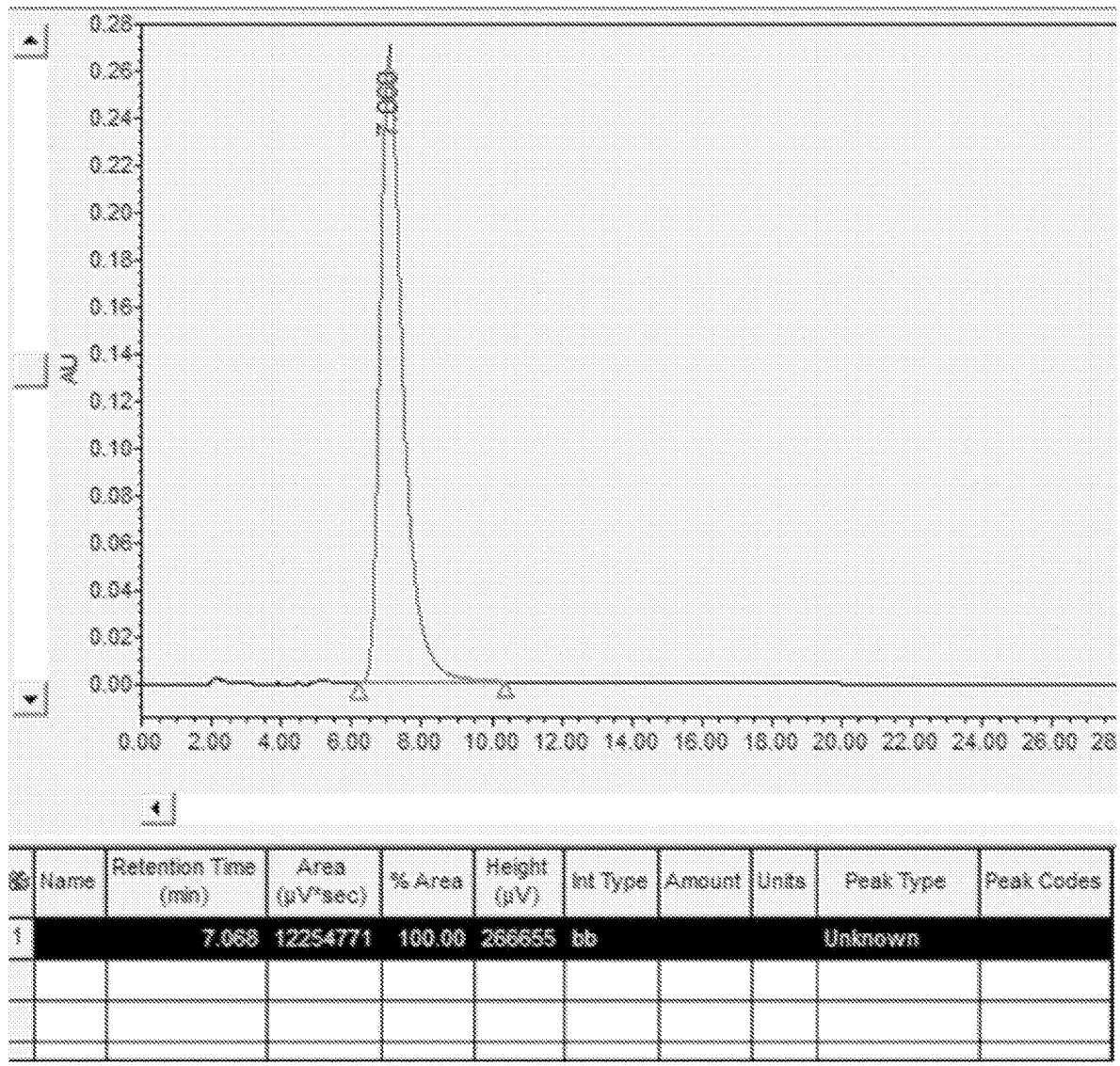

FIG. 17A-FIG. 17C shows chiral HPLC traces for (+)-, (−)-, and (+)-CMLD012043 (12l). A ChiralCel OD column was used with an isocratic mobile phase of 20% isopropanol in hexanes at a flow rate of 1.0 mL/min for 30 min. (+)-CMLD012043 (12l) is shown in FIG. 17A. (−)-CMLD012043 (12l) $[α]_D 26=−59.55°$ (c=0.02, CH2Cl2) is shown in FIG. 17B. Minor solvent residue at 5.9 min. (+)-CMLD012043 (12l) $[α]_D 26=75.200°$ (c=0.02, CH$_2$Cl$_2$). is shown in FIG. 17C. Minor solvent residue is shown at 5.9 min FIG. 18A-18C shows chiral HPLC traces for (+)-, (−)-, and (+)-CMLD012044 (12s). A ChiralCel OD column was used with an isocratic mobile phase of 20% isopropanol in hexanes at a flow rate of 1.0 mL/min for 30 min. (+)-CMLD012044 (12s) is shown in FIG. 18A. (−)-CMLD012044 (12s) $[α]D26=−61.796°$ (c=0.02, CH2Cl2) is shown in FIG. 18B. (+)-CMLD012044 (12s) $[α]D26=74.913°$ (c=0.02, CH2Cl2) is shown in FIG. 18C.

Figure 19:
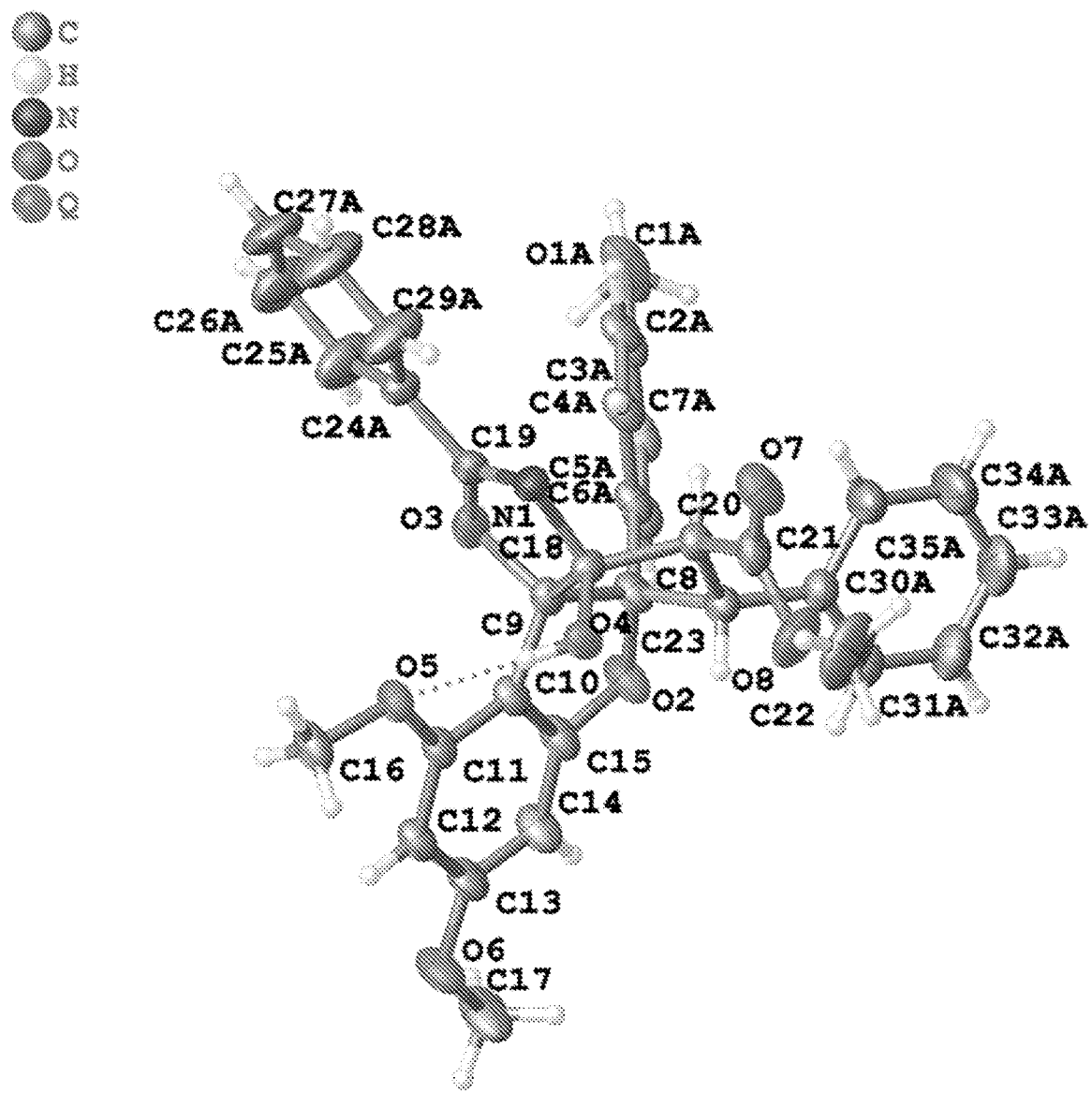

FIG. 19 demonstrates an X-ray crystal structure for oxazoline 15.

FIG. 20-FIG. 57 shows structures of compounds and dose-response curves of said compounds according some embodiments as follows: FIG. 20 aglaroxin C 6. FIG. 21 compound 12a.

FIG. 22 compound 12b. FIG. 23 compound 12c. FIG. 24 compound 12d. FIG. 25 compound 12e.

FIG. 26 compound 12f. FIG. 27 compound 12g. FIG. 28 compound 12h. FIG. 29 compound 12k.

FIG. 30 compound 12k. FIG. 31 compound 12l. FIG. 32 compound 12m. FIG. 33 compound 12n.

FIG. 34 compound 12o. FIG. 35 compound 12p. FIG. 36 compound 12q. FIG. 37 compound 12r.

FIG. 38 compound 12s. FIG. 39 compound 12t. FIG. 40 compound 12v. FIG. 41 compound 12w.

FIG. 42 compound 12x. FIG. 43 compound 12y. FIG. 44 compound 12z. FIG. 45 compound 12aa.

FIG. 46 compound 12ab. FIG. 47 compound 12ac. FIG. 48 compound 12ad. FIG. 49 compound 12a.

FIG. 50 compound 12af. FIG. 51 compound 12ah. FIG. 52 compound 12ai. FIG. 53 compound 12aj.

FIG. 54 compound (+)-12l. FIG. 55 compound (−)-12l. FIG. 56 compound (+)-12s. FIG. 57 compound (−)-12s.

Figure 67:
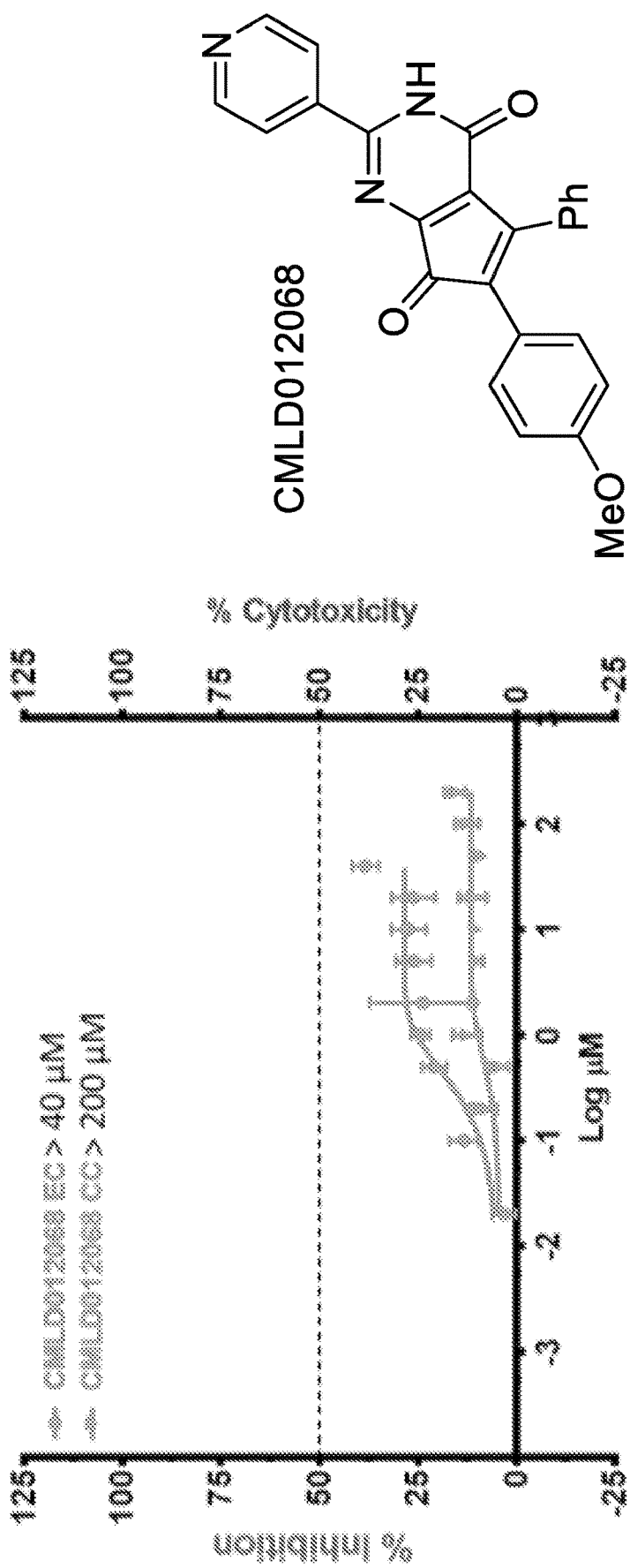

FIG. 58-FIG. 67 shows dose-response curves for isolated side products as follows: FIG. 58 compound 15. FIG. 59 compound CMLD012103. FIG. 60 compound CMLD012104. FIG. 61 compound CMLD012105. FIG. 62 compound CMLD012148. FIG. 63 compound CMLD012149. FIG. 64 compound CMLD012078. FIG. 65 compound CMLD012130. FIG. 66 compound CMLD012069. FIG. 67 compound CMLD012068.

FIG. 68-FIG. 71 shows a comparison between MTS and CellTiter-GLO™ cell viability assays for the following compounds: FIG. 68 shows niclosamide. FIG. 69 shows compound 12k. FIG. 70 shows compound 12o. FIG. 71 shows compound (±)12l.

Figure 72A:
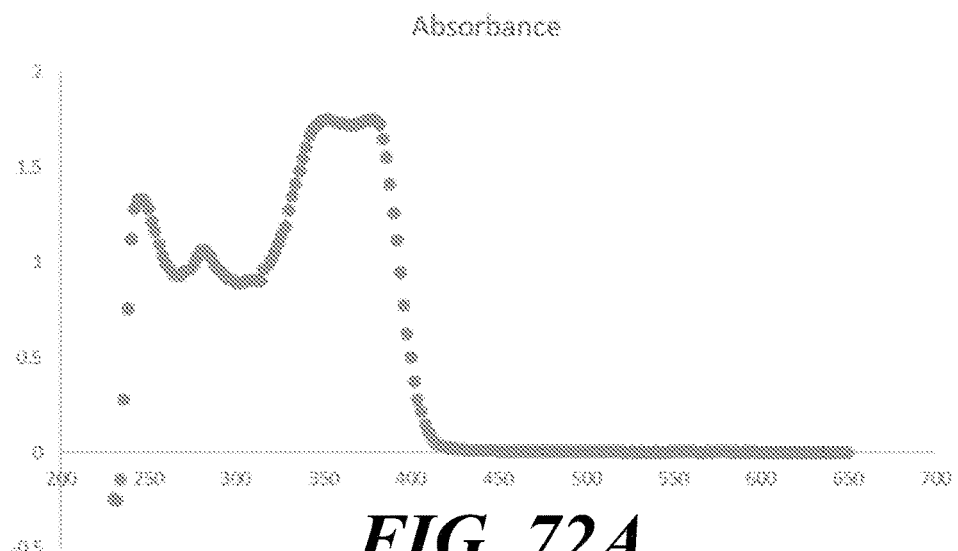
Figure 72B:
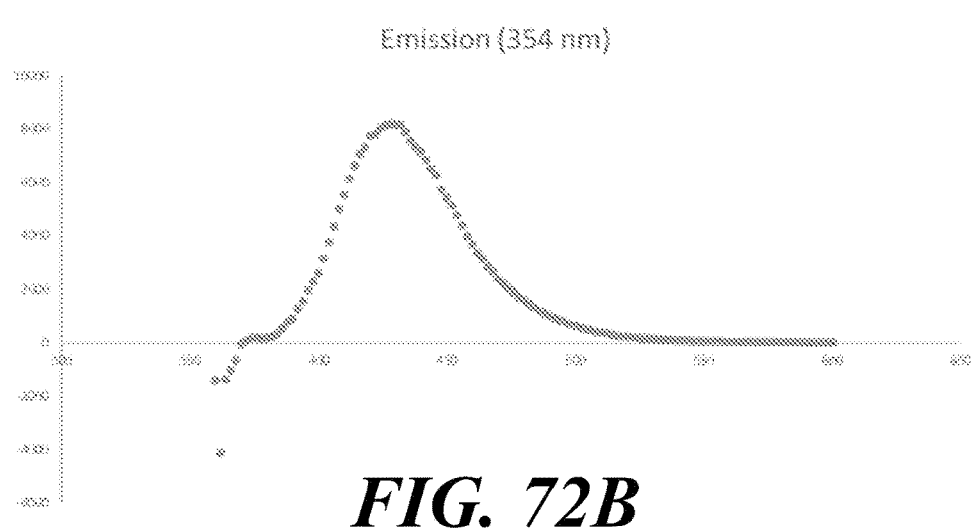
Figure 72C:
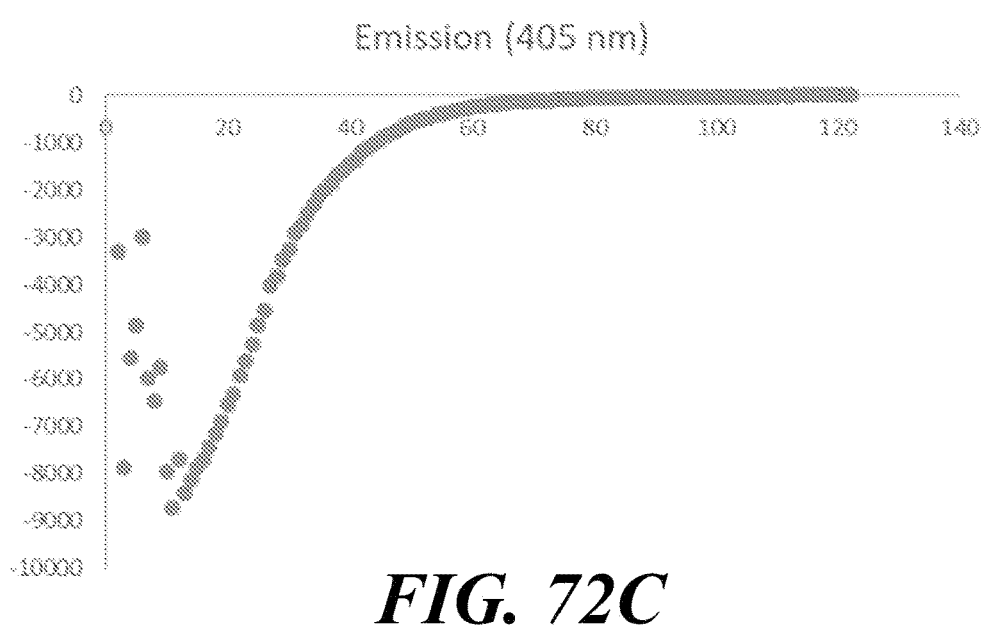

FIG. 72A-72C shows fluorescence emission for the pyrimidinone compound 12n. FIG. 72A shows absorbance. FIG. 72B shows emission at 354 nanometers. FIG. 72C shows emission at 405 nanometers.

Figures 73A, 73B, 73C:
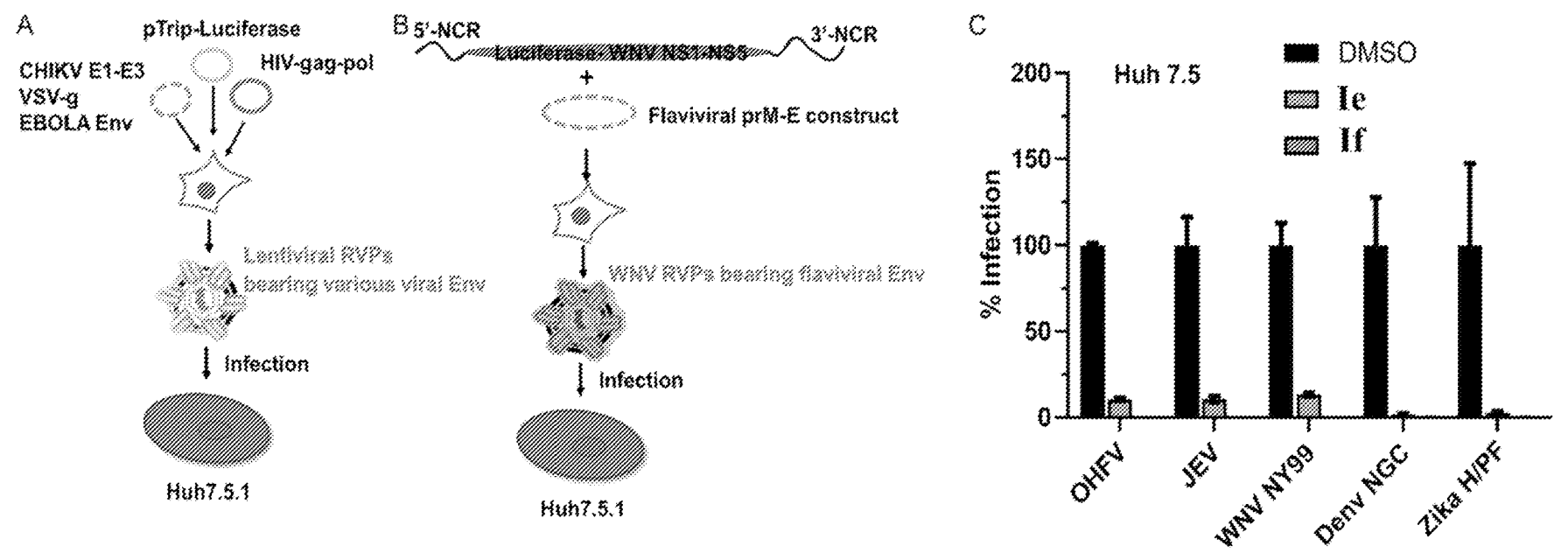

FIG. 73A shows a lentiviral reporter construct (pTrip-luciferase), lentiviral packaging construct (HIV-gag-pol) and an expression plasmid of desired viral envelope protein (e.g., CHIKV E1-E3) were co-transfected into 293T cells to produce lentiviral reporter virus particles whose entry depend on the specific viral Envelope protein. FIG. 73B shows a WNV replication-competent construct expressing the luciferase report gene is co-transfected with a flaviviral prM-Env expression plasmid to generate flaviviral Env-specific RVPs. FIG. 73C demonstrates treatment of Huh 7.5 cells with 4 μM If and Ie for 3 h nearly abolished OHFV, JEV, WNV, Denv, and Zika viral envelope protein-mediated entry. Notably, the bars representing compound 5-treated groups are hardly visible in the graph because the % infections of this group were inhibited to under 1%.

Figure 74:
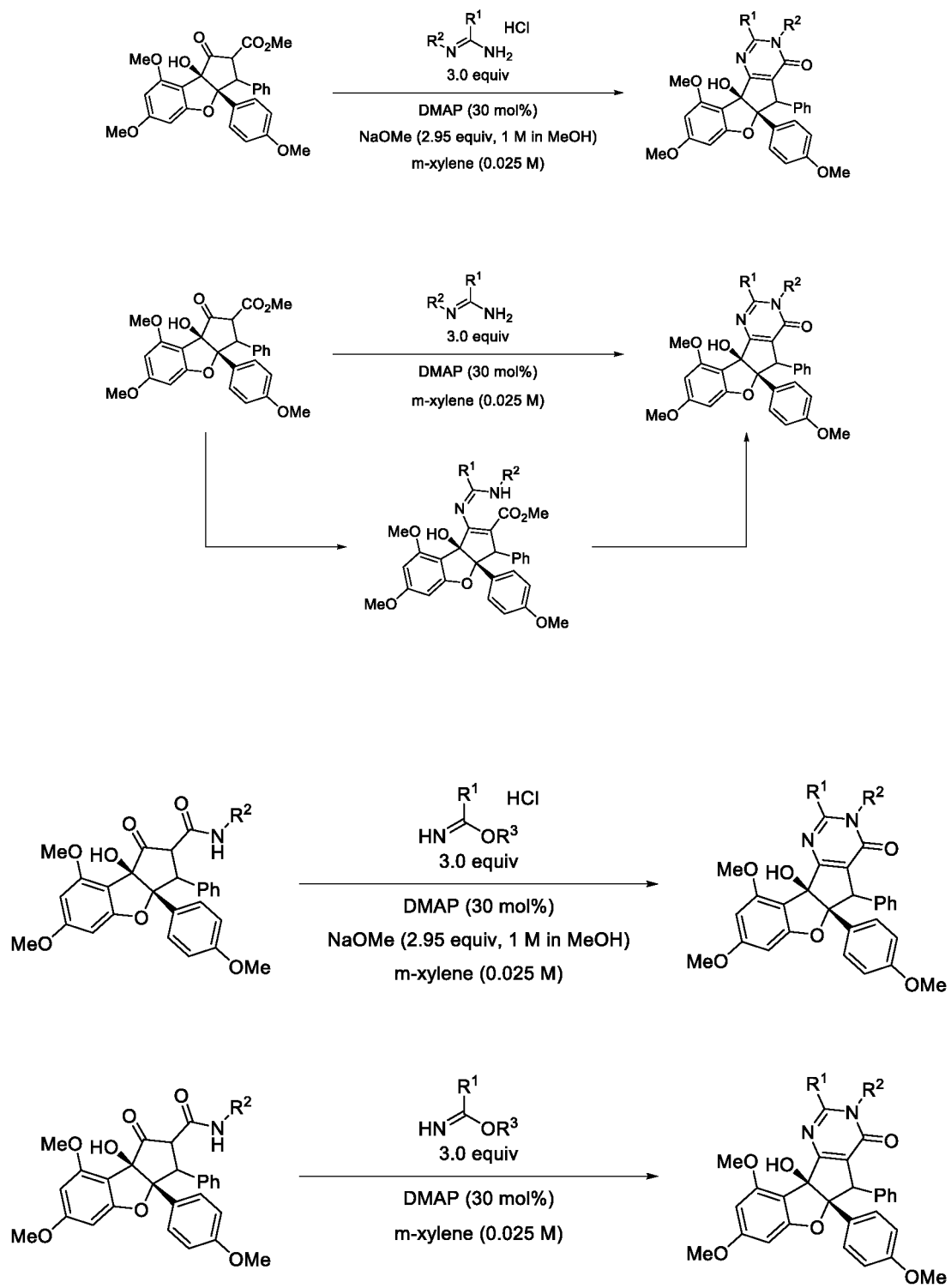

FIG. 74 shows reaction pathways for the preparation of aglaroxin C analogues.

Figure 75:
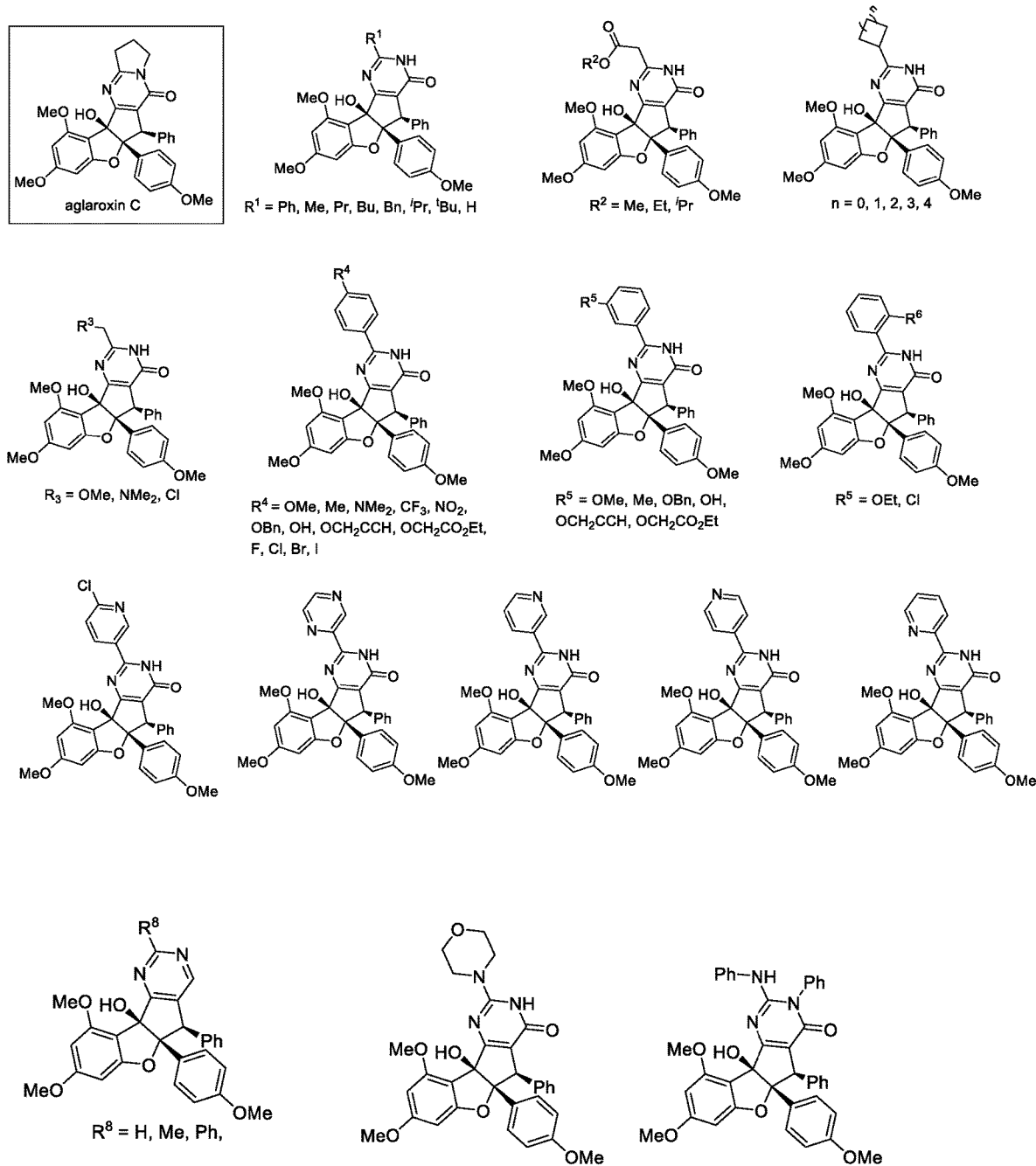
Figure 75:
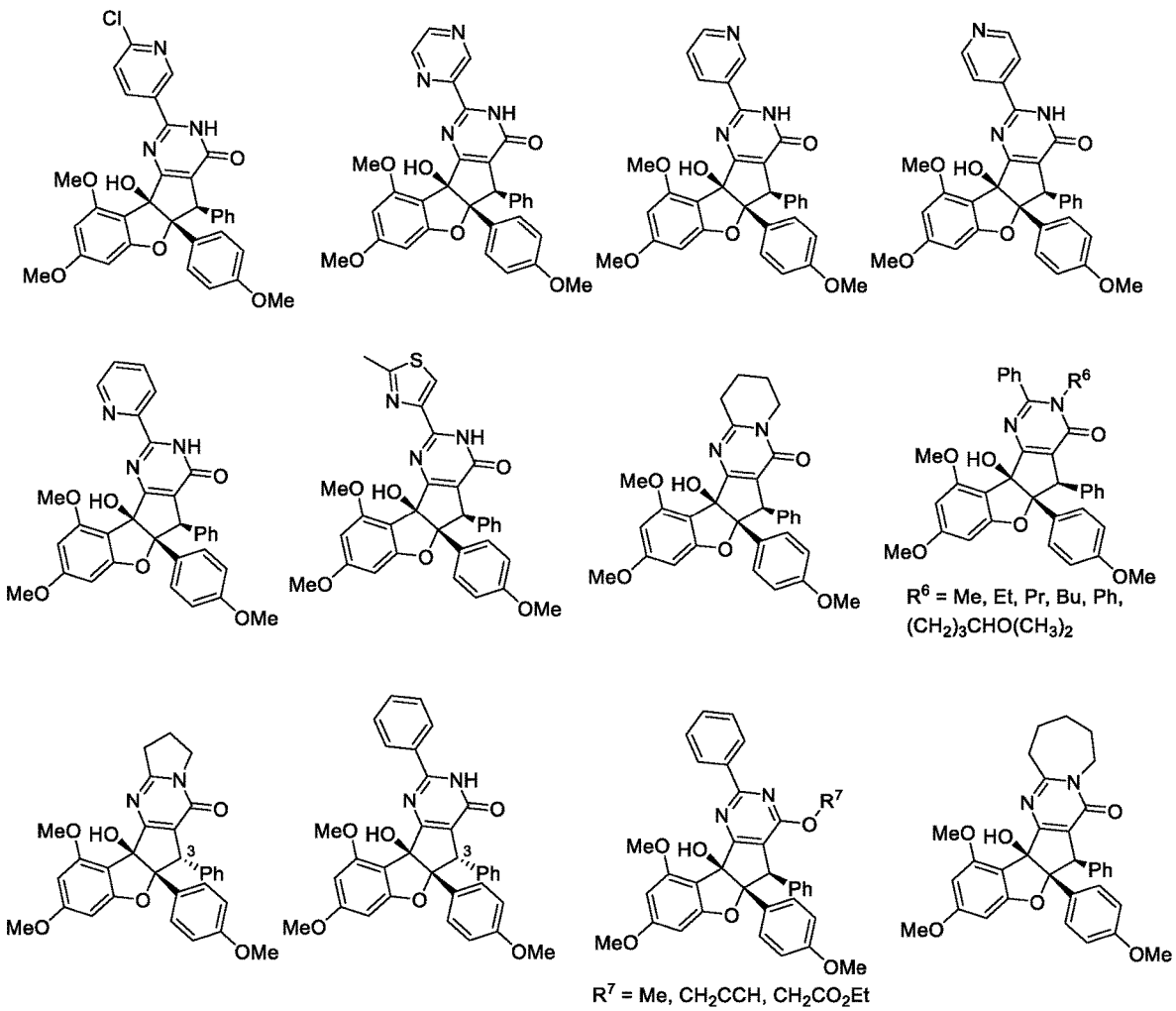

FIG. 75 shows structures of aglaroxin C analogues.

DETAILED DESCRIPTION

As described herein, several novel agents have been developed for the prevention and treatment of viral infections. Specifically, the compounds, compositions and methods described herein prevent viral entry (e.g., the Hepatitis C virus) into cells.

In some embodiments, the disclosure relates to compounds having a structure of the structure of Formula (I), (II), or (III), or stereoisomers, tautomers, or pharmaceutically acceptable salts thereof.

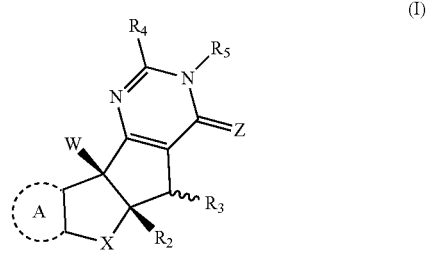

(I)

-continued

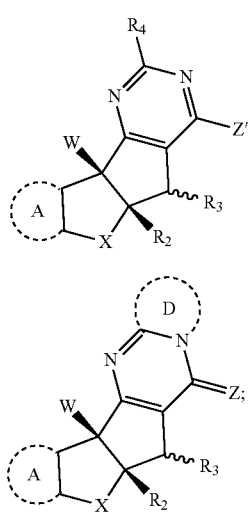

In these structures:

X is O, S, $CR^BR^E$ or $NR^E$; wherein $R^B$ and $R^E$ independently are H, alkyl, aryl, heteroaryl, heteroalkyl, cycloalkyl, acyl, or allyl;

W is F or —$YR^A$, wherein Y is O, NH or S, and $R^A$ is H, alkyl, aryl, heteroaryl, heteroalkyl, cycloalkyl, acyl, NH(alkyl), $NH_2$ or NH(aryl);

A is a heteroaryl or aryl;

$R_2$ is aryl or heteroaryl;

$R_3$ is H, phenyl, alkyl, heteroalkyl, aryl, heteroaryl, aldehyde, ester, alkenyl, amide or —$CO_2H$; wherein when $R_3$ is not H; $R_3$ is syn to $R_2$ or $R_3$ is trans to $R_2$;

$R_4$ is H, alkyl, aryl, heteroaryl, heteroalkyl, cycloalkyl, acyl halide, CN, NH(alkyl), NH(CN) or NH—NH(alkyl);

Z is O, NH, S, Se, N(alkyl) or N(aryl), $CR^CR^F$; wherein $R^C$ and $R^F$ independently are H, alkyl, aryl, heteroaryl, heteroalkyl, cycloalkyl, acyl, allyl or CN;

$R_5$ is H, alkyl, alkenyl, alkynyl, aryl, heteroaryl, cycloalkyl heteroalkyl;

Z' is a halide or -$TR_5$'; wherein T is O, S, NH, or $CH_2$ and $R_5$' is H, alkyl, alkenyl, alkynyl aryl, heteroaryl, cycloalkyl, heteroalkyl, acyl or sulfate;

D is a $C_{1-5}$ alkylene, $C_{1-5}$ heteroalkylene, heteroaryl or aryl, wherein, in some embodiments, when D is a three carbon alkylene the compound does not have the structure of formula ((–)-6),

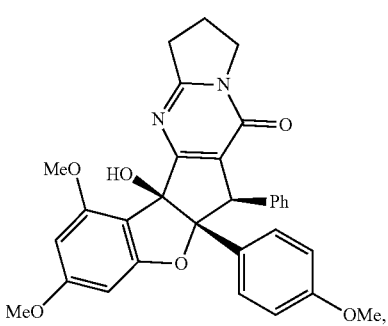

and;
wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo; "m" and "p" are 1, 2, 3, 4, 5 or 6. In some embodiments, $R_3$ is syn to $R_2$.

As used herein, a "stereoisomer" refers to each of two or more compounds differing only in the spatial arrangement of their atom.

As used herein, "tautomers" refers to two molecules with the same molecular formula but different connectivity, for example, a keto-enol pair. For example, in some embodiments, compounds having the structure of (I) and (II) are keto-enol pairs, such as when Z═O and $R_5$ is H in (I), and Z'═OH in (II); and all other groups in (I) and (II) are the same and have the same stereochemistry, then (I) is the keto pair of the enol (II).

The compound in some embodiments can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric (chiral) centers and can therefore exist in different enantiomeric and diastereomeric forms. A compound of the invention can be in the form of an optical isomer or a diastereomer. Accordingly, some embodiments encompass compounds and their uses as described herein in the form of their optical isomers, diastereoisomers and mixtures thereof, including a racemic mixture. Optical isomers of the compounds according to some embodiments can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein the term "aryl", whether alone or as part of a substituent group, refers to an unsubstituted carboxylic aromatic ring comprising between 6 to 14 carbon atoms. Suitable examples include, but are not limited to, phenyl, and naphthyl.

As used herein, "cycloalkyl" refers to a stable non-aromatic monocyclic or polycyclic hydrocarbon radical consisting solely of carbon and hydrogen atoms, which may include fused or bridged ring systems, having from three to fifteen carbon atoms, is some embodiments having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

As used herein, "heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

As used herein, the term "heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. In some embodiments, the heteroaryl radical may be a stable 5-12 membered ring, a stable 5-10 membered ring, a stable 5-9 membered ring, a stable 5-8 membered ring, a stable 5-7 membered ring, or a stable 6-membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (e.g. thienyl).

As used herein the term "acyl" refers to a group of the Formula —C(O)C$_n$ wherein C$_n$ represent a straight or branched alkyl chain wherein n can be 1, 2, 3, 4, 5, 6, 7, 8, 9 or 10. Where an "acetyl" refers to the methyl derivative, —C(O)CH$_3$.

As used herein a "ester" refers to a group of the formula —C(O)—OC$_n$ wherein C$_n$ represent a straight or branched alkyl chain wherein n can be 1, 2, 3, 4, 5, 6, 7, 8, 9 or 10. For example a chemical compound derived from an acid in which at least one —OH (hydroxyl) group is replaced by an —O-alkyl (alkoxy) group.

As used herein the term "alkyl", whether alone or as part of a substituent group, refers to a saturated C$_1$-C$_n$ carbon chain, wherein the carbon chain may be straight or branched; wherein n can be 2, 3, 4, 5, 6, 7, 8, 9 or 10. Suitable examples include, but are not limited to methyl, ethyl, propyl, isopropyl, butyl, isobutyl, sec-butyl, t-butyl, n-pentyl and n-hexyl.

As used herein the term "alkenyl", whether alone or as part of a substituent group, refers to a C$_2$-C$_n$ carbon chain, wherein the carbon chain may be straight or branched, wherein the carbon chain contains at least one carbon-carbon double bond, and wherein n can be 3, 4, 5, 6, 7, 8, 9, or 10.

As used herein the term "alkynyl", whether alone or as part of a substituent group, refers to a C$_2$-C$_n$ wherein the carbon chain may be straight or branched, wherein the carbon chain contains at least one carbon-carbon triple bond, and wherein n can be 3, 4, 5, 6, 7, 8, 9, or 10.

The groups of the present disclosure can be unsubstituted or substituted, as herein defined. In addition, the substituted groups can be substituted with one or more groups such as a C$_1$-C$_6$ alkyl, C$_{1-4}$ alkyl, —O—C$_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), —$SO_2$—($C_{1-4}$ alkyl), halogen, aryl, heteroaryl, and the like.

With reference to substituents, the term "independently" means that when more than one of such substituents is possible, such substituents may be the same or different from each other.

"Amino" refers to a —$NH_2$ substituent.

"Aminocarbonyl" or "Amido" refers to the —C(O)$NH_2$ substituent.

"Carboxyl" refers to the —$CO_2H$ substituent.

"Carbonyl" refers to a —C(O)—, —(CO)— or —C(=O)— group. All notations are used interchangeably within the specification.

"Cyano" refers to the —C≡N substituent.

"Hydroxy" or "hydroxyl" refers to the —OH substituent.

"Oxo" refers to a =O substituent

"Thio" or "thiol" refer to a -SH substituent.

Compound words have the meaning of the individual functional groups or fragments as would be understood in the art. For example, "hydroxyalkyl" refers to the -(alkyl)-OH substituent, "thioalkyl" refers to the -(alkyl)-SH substituent, "cyanoalkylene" refers to the -(alkylene)C≡N substituent; "hydroxyalkylene" refers to the -(alkylene)OH substituent; "arylmethoxy" refers to a methoxy substituted aryl group.

In some embodiments, the ring D has the structure of formula X;

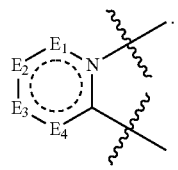

(X)

In structure (X): $E_1$ is N, C(O), NH or $CR_{110}$; $E_2$ is N, C(O), NH or $CR_{111}$; $E_3$ is N, C(O), NH or $CR_{112}$; and $E_4$ is N, C(O), NH or $CR_{113}$. Also in structure (X): $R_{110}$, $R_{111}$, $R_{112}$ and $R_{113}$ independently are H, halogen, CN, $C_1$-$C_8$(alkyl), ($C_1$-$C_8$)haloalkyl, ($C_2$-$C_8$)alkenyl, ($C_2$-$C_8$)alkynyl, $OR^T$, $NR^TR^U$, [($C_1$-$C_8$)alkylene]$OR^T$, [($C_1$-$C_8$)alkylene]$NHR^T$, [($C_1$-$C_8$)alkylene]$NR^TR^U$, C(O)$R^T$, C(O)$NHR^T$, C(O)$NR^TR^U$, C(O)[($C_1$-$C_8$)alkylene]$NHR^T$, C(O)[($C_1$-$C_8$)alkylene]$NR^TR^U$, $CO_2R^T$, C(S)$NHR^T$, C(S)$NR^TR^U$, $SR^T$, S(O)$R^T$, $SO_2R^T$, $SO_2NHR^T$, $SO_2NR^TR^U$, NHC(O)$R^T$, $NR^TC(O)R^U$, NHC(O)$NHR^T$, NHC(O)$NR^TR^U$, $NR^TC(O)NHR^U$, $NR^TC(O)NR^UR^V$, P(O)(OH)(O$R^T$), P(O)(O$R^T$)(O$R^U$), tosylate, aryl, heteroaryl, cycloalkyl or heterocyclyl; $R^T$, $R^U$ and $R^V$ independently are H, —OH, aryl, ($C_1$-$C_8$) alkyl, [($C_1$-$C_8$)alkyl]aryl ($C_1$-$C_8$)alkoxy, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or $R^T$ and $R^U$ together with the nitrogen atom to which they are attached form a heterocyclyl ring.

In some embodiments, the ring D has the structure of formula XI;

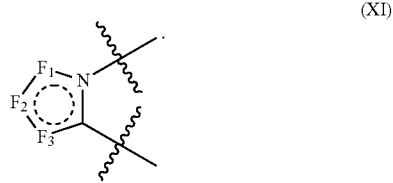

(XI)

In structure (XI) $F_1$, $F_2$ and $F_3$ are independently $CR_{114}$, N, $NR_{115}$, O or S. Also in structure (XI): $R_{114}$ and $R_{115}$ are independently H, CN, halogen, $OR^W$, $SR^W$, ($C_1$-$C_8$)alkyl, C(O)O($C_1$-$C_8$)alkyl, C(O)($C_1$-$C_8$)alkyl, $SO_2$($C_1$-$C_8$)alkyl, $SO_2NR^WR^X$, C(O)$NR^WR^X$, $NR^WR^X$ or $NR^WC(O)R^X$; $R^{RW}$ and $R^{SX}$, independently are H, —OH, aryl, ($C_1$-$C_8$) alkyl, [($C_1$-$C_8$)alkyl]aryl ($C_1$-$C_8$)alkoxy, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or the $R^W$ and $R^X$ together with the nitrogen atom to which they are attached of $NR^WR^X$ or $NR^WC(O)R^X$, optionally form a heterocyclyl ring.

In some embodiments, the ring A has the structure of formula (IV);

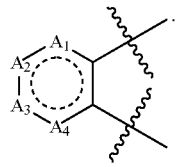

(IV)

In structure (IV): $A_2$ is N, C(O), NH or $CR_{11}$; $A_3$ is N, C(O), NH or $CR_{12}$; and $A_4$ is N, C(O), NH or $CR_{13}$. Also in structure (IV), $R_{10}$, $R_{11}$, $R_{12}$ and $R_{13}$ independently are H, halogen, CN, $C_1$-$C_8$(alkyl), ($C_1$-$C_8$)haloalkyl, ($C_2$-$C_8$)alkenyl, ($C_2$-$C_8$)alkynyl, $OR^O$, $NR^OR^P$, [($C_1$-$C_8$)alkylene] $OR^O$, [($C_1$-$C_8$)alkylene]$NHR^O$, [($C_1$-$C_8$)alkylene]$NR^OR^P$, C(O)$R^O$, C(O)$NHR^O$, C(O)$NR^OR^P$, C(O)[($C_1$-$C_8$)alkylene] $NHR^O$, C(O)[($C_1$-$C_8$)alkylene]$NR^OR^P$, $CO_2R^O$, C(S) $NHR^O$, C(S)$NR^OR^P$, $SR^O$, S(O)$R^O$, $SO_2R^O$, $SO_2NHR^O$, $SO_2NR^OR^P$, NHC(O)$R^O$, $NR^OC(O)R^P$, NHC(O)$NHR^O$, NHC(O)$NR^OR^P$, $NR^OC(O)NHR^P$, $NR^OC(O)NR^PR^Q$, P(O) (OH)(O$R^O$), P(O)(O$R^O$)(O$R^P$), tosylate, aryl, heteroaryl, cycloalkyl or heterocyclyl; $R^O$, $R^P$ and $R^Q$ independently are H, —OH, aryl, ($C_1$-$C_8$)alkyl, [($C_1$-$C_8$)alkyl]aryl ($C_1$-$C_8$) alkoxy, ($C_1$-$C_8$)haloalkyl, cycloalkyl, heterocyclyl, [($C_1$-$C_8$) alkylene]heterocyclyl, [($C_1$-$C_8$)alkylene]aryl or heteroaryl; or $R^O$ and $R^P$ together with the nitrogen atom to which they are attached form a heterocyclyl ring; wherein any vicinal $R_{10}$, $R_{11}$, $R_{12}$, and $R_{13}$ together with the carbons to which they are attached optionally form an aryl or heteroaryl ring. In some embodiments, of structure (IV) $R_{10}$, $R_{11}$, $R_{12}$ or $R_{13}$ is a heteroalkyl. In some embodiments, of structure (IV) $A_1$ is $CR_{11}$ with $R_{11}$ being OMe, $A_2$ is $CR_{12}$ with $R_{12}$ being H, $A_3$ is $CR_{13}$ with $R_{13}$ being OMe and $A_4$ is $CR_{14}$ with $R_{14}$ being H.

As used herein, vicinal refers to any two functional groups bonded to two adjacent carbon atoms such as in a 1,2-relationship. For example, when $A_1$ is $CR_{11}$ and $A_2$ is $CR_{12}$, $R_{11}$ and $R_{12}$ are vicinal; when $A_2$ is $CR_{12}$ and $A_3$ is $CR_{13}$, $R_{12}$ and $R_{13}$ are vicinal; and when $A_3$ is $CR_{13}$ and $A_4$ is $CR_{14}$, $R_{13}$ and $R_{14}$ are vicinal. It is understood that in embodiments wherein any vicinal $R_{10}$, $R_{11}$, $R_{12}$, and $R_{13}$ together with the carbons to which they are attached optionally for a ring, the ring can be the ring with a structure corresponding to the formal loss of $H_2$ from the vicinal groups. For example, where $A_2$ is $CR_{12}$ and $R_{12}$ is —$NH_2$, and $A_3$ is $CR_{13}$ and $R_{13}$ is phenyl, the structure can optionally include the fragment (XII):

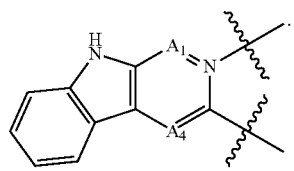
(XII)

In some embodiments, the ring A has the structure of formula (V);

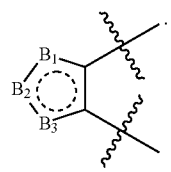
(V)

In structure (V): $B_1$, $B_2$ and $B_3$ are independently $CR_{14}$, N, $NR_{15}$, O or S. Also in structure (V) $R_{14}$ and $R_{15}$ are independently H, CN, halogen, $OR^R$, $SR^R$, $(C_1-C_8)$alkyl, $C(O)O(C_1-C_8)$alkyl, $C(O)(C_1-C_8)$alkyl, $SO_2(C_1-C_8)$alkyl, $SO_2NR^RR^S$, $C(O)NR^RR^S$, $NR^RR^S$ or $NR^RC(O)R^S$; $R^R$ and $R^S$, independently are H, —OH, aryl, $(C_1-C_8)$alkyl, $[(C_1-C_8)$alkyl]aryl $(C_1-C_8)$alkoxy, $(C_1-C_8)$haloalkyl, cycloalkyl, heterocyclyl, $[(C_1-C_8)$alkylene]heterocyclyl, $[(C_1-C_8)$alkylene]aryl or heteroaryl; or the $R^R$ and $R^S$ together with the nitrogen atom to which they are attached of $NR^RR^S$ or $NR^RC(O)R^S$, optionally form a heterocyclyl ring. In some embodiments, at least one of $B_1$, $B_2$ and $B_3$ is $CR_{14}$, or $NR_{15}$ and $R_{14}$ or $R_{15}$ is a heteroalkyl. In some embodiments, at least one of $B_1$, $B_2$ and $B_3$ is or $NR_{15}$ and the remaining two of $B_1$, $B_2$ and $B_3$ are N.

In some embodiments, the compound has a structure (I) including ring A having the structure (IV) or (V), and: W is —OH, —$NH_2$, —SH, —OMe, —$NH(CH_2)_2OMe$, or —$OCH_2C≡CH$; X is O, S, $CH_2$, or NH; Z is O, S, $CH_2$, NH, or N—C≡N; $R_2$ is aryl; $R_3$ is H, phenyl, heteroalkyl, aryl, heteroaryl, or amide; $R_5$ is H, phenyl, alkyl, Me, or heteroalkyl, and $R_4$ is H, alkyl, aryl, heteroaryl, heteroalkyl, cycloalkyl. In some embodiments, the compound has a structure (I) including ring A and: W is OH; X is O; Z is O; $R_2$ is an aryl; $R_3$ is a phenyl; $R_2$ is syn relative to $R_3$; $R_5$ is H or alkyl; and $R_4$ is alkyl or aryl.

In some embodiments, the compound has a structure (II) including ring A having the structure (IV) or (V), and: W is —OH, —$NH_2$, —SH, —OMe, —$NH(CH_2)_2OMe$, or —$OCH_2C≡CH$; X is O, S, $CH_2$, or NH; Z' is OH, SH, $NH_2$, —$NH(CH_2)_2OMe$ or —$OCH_2C≡CH$; $R_2$ is aryl; $R_3$ is H, phenyl, heteroaryl, aryl, heteroaryl, or amide; and $R_4$ is H, alkyl, aryl, heteroaryl, heteroalkyl, cycloalkyl. In some embodiments, the compound has a structure (II) including ring A and: W is OH; X is O; Z' is O; $R_2$ is an aryl; $R_3$ is a phenyl; $R_2$ is syn relative to $R_3$; and $R_4$ is alkyl or aryl.

In some embodiments, the compound is selected from the compounds having the following listed structures:

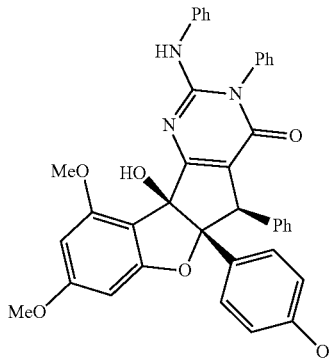
(12af)

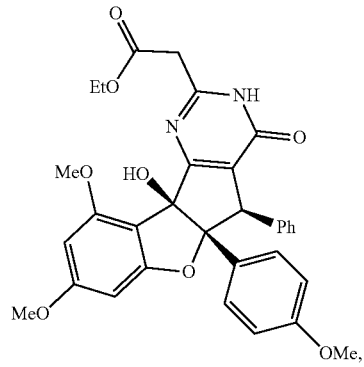
(CMLD012046)

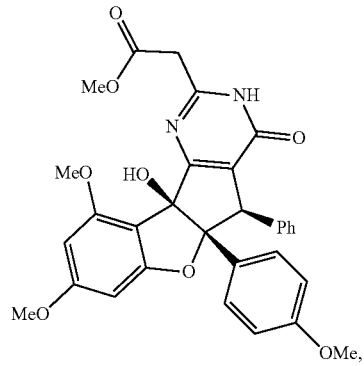
(12g)

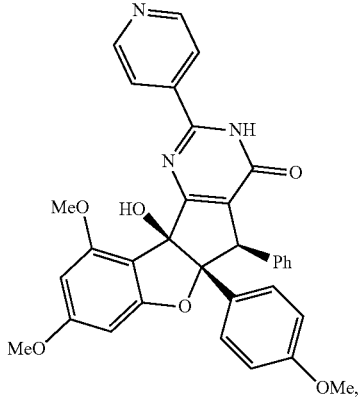
(12aa)

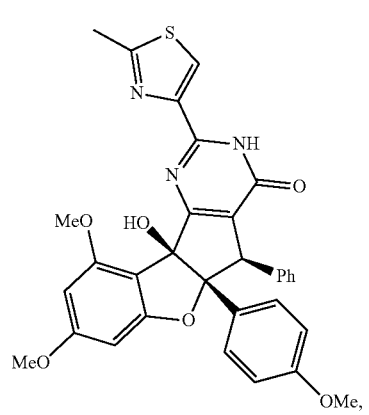
(12ac)
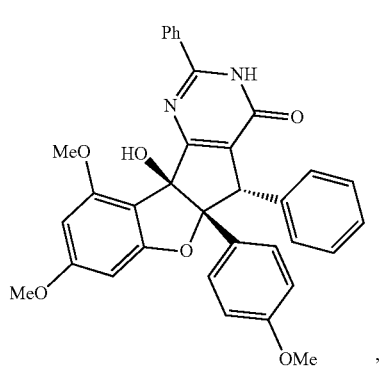
(12ah)
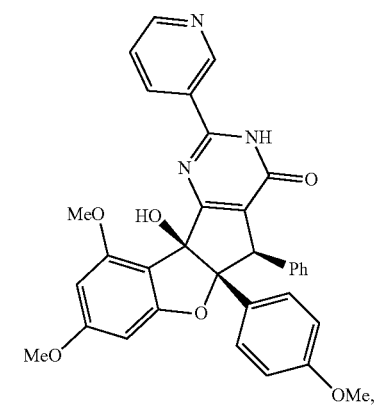
(12z)
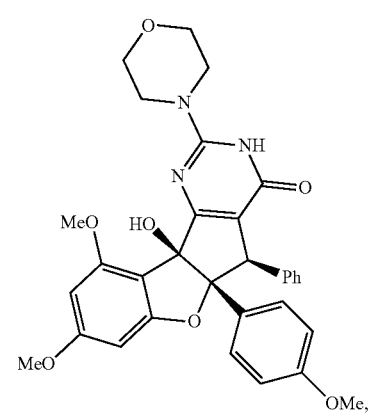
(12j)
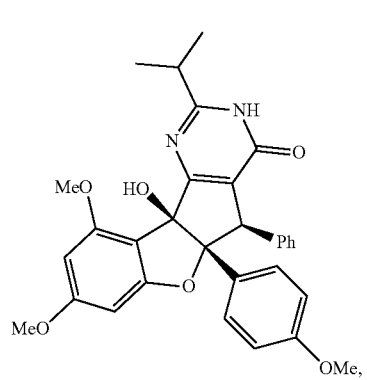
(12d)
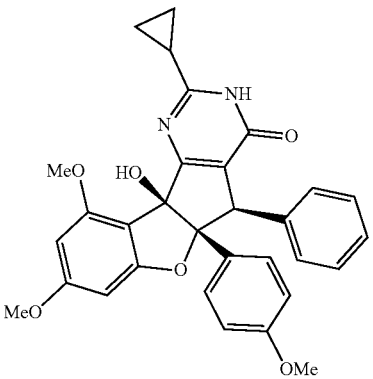
(12h)
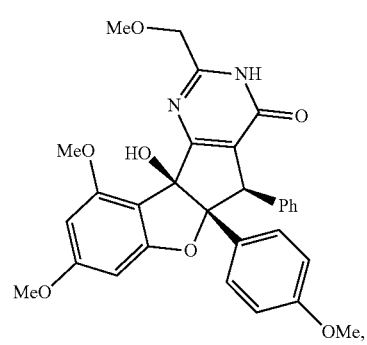
(12i)
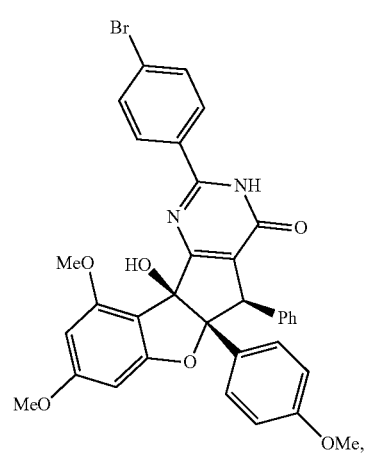
(12r)

-continued
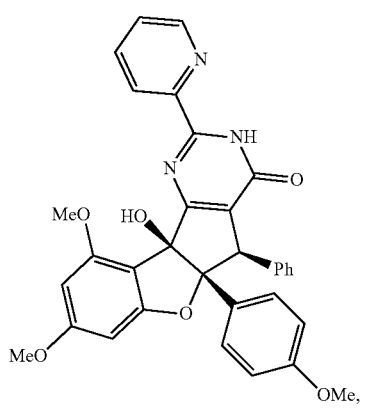
(12ab)
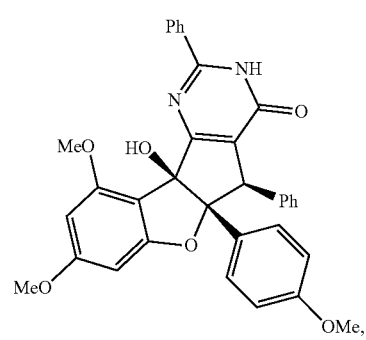
(12a)
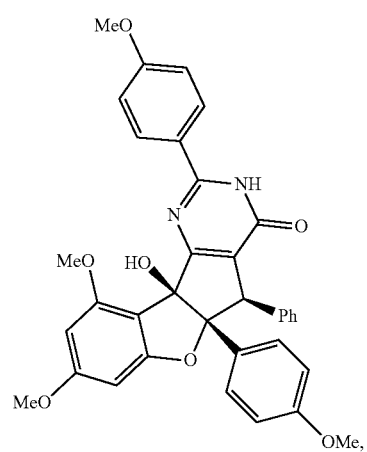
(12k)
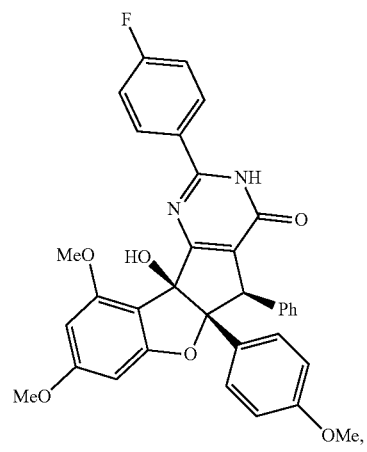
(12p)
-continued
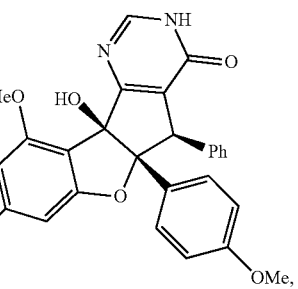
(12f)
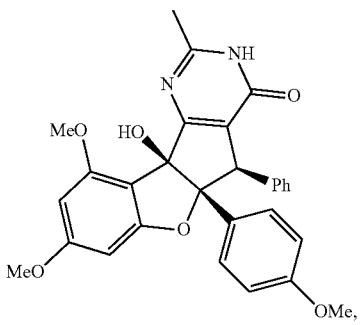
(12b)
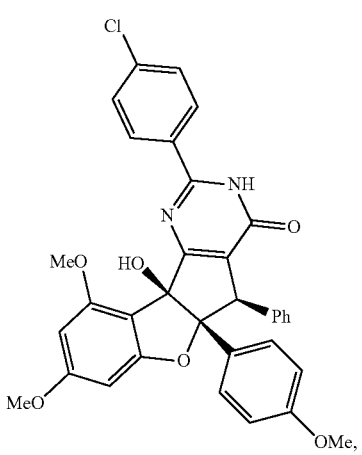
(12q)
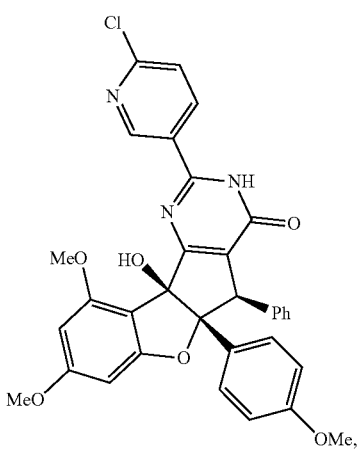
(12x)

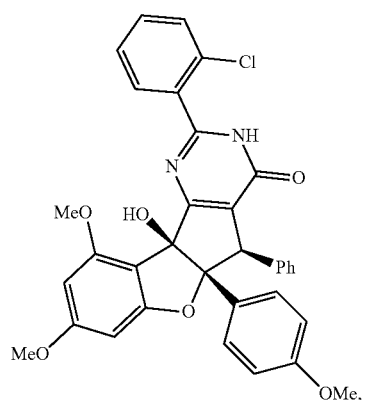
(12w)
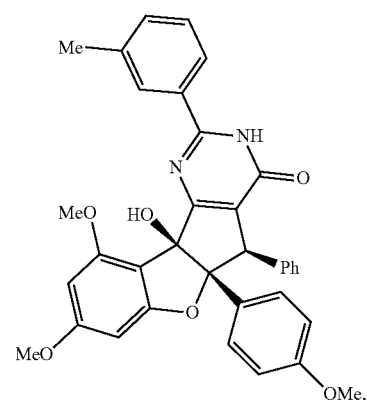
(12t)
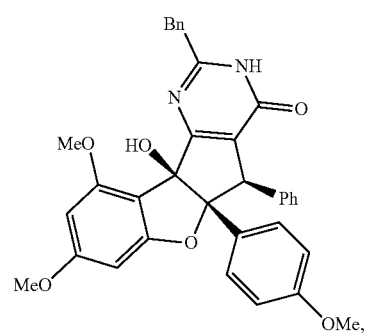
(12c)
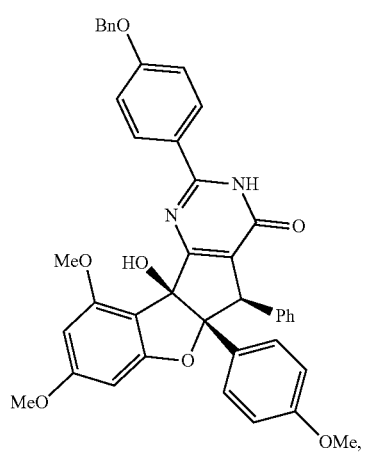
(12m)
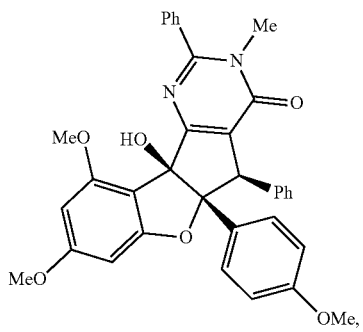
(12ae)
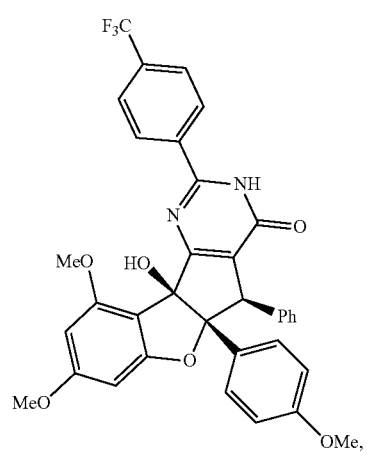
(12o)
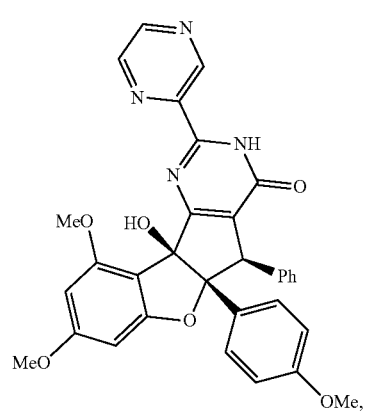
(12y)
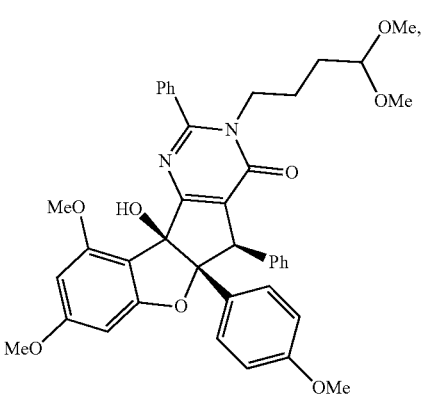
(CMLD012332)

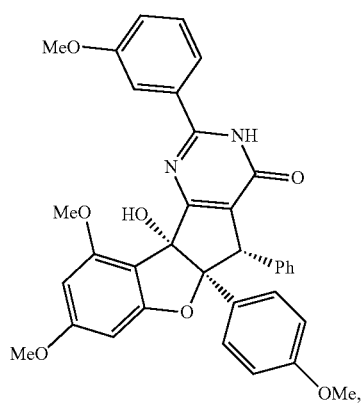
((-)-12s)
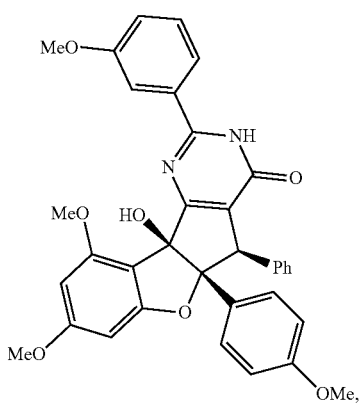
((+)-12s)
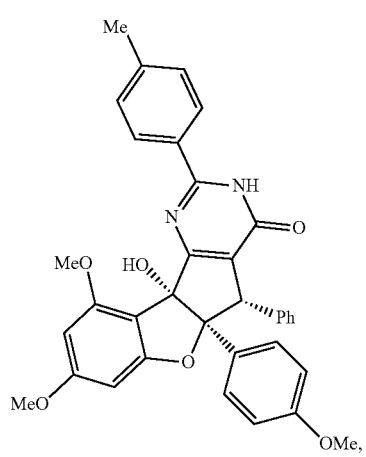
((-)-12l)
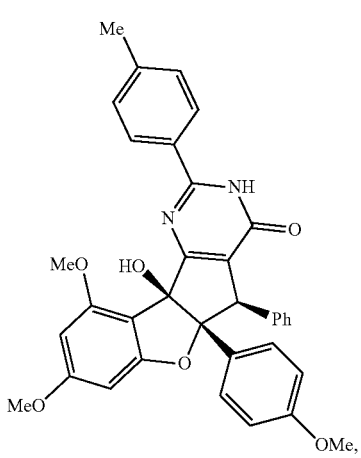
((+)-12l)
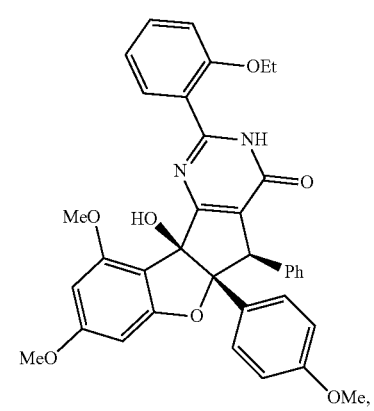
(12v)
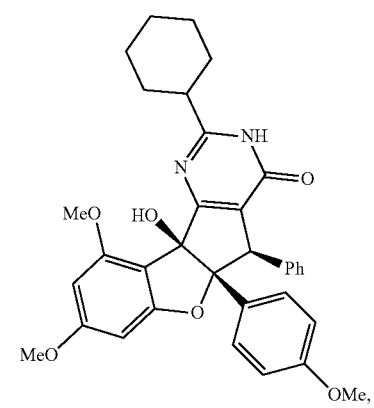
(12e)
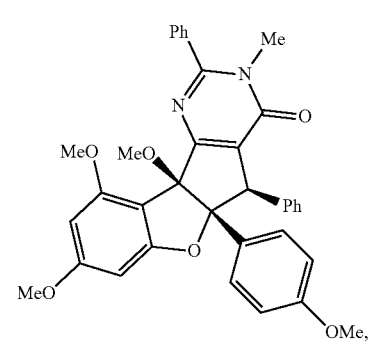
(12aj)

-continued
(12ak)
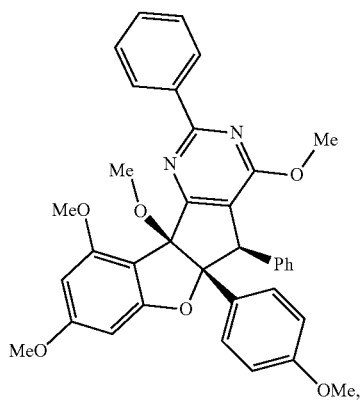
(CMLD012982)
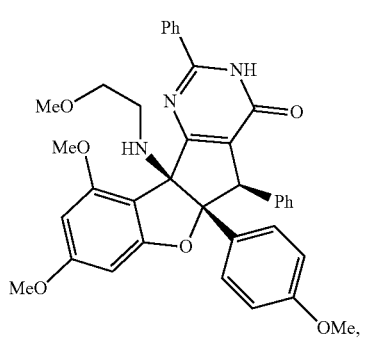
(CMLD012982′)
(12ap)
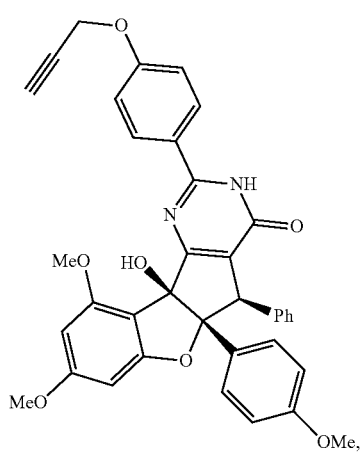
(12ao)
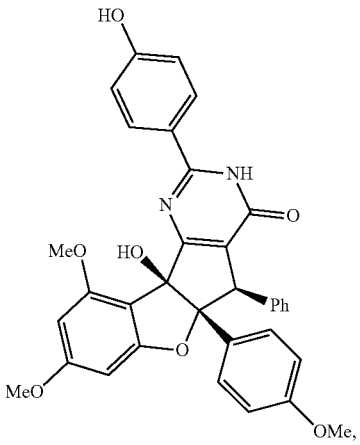
(12n)
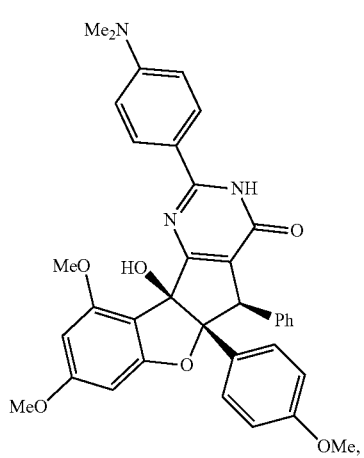
(Ia)
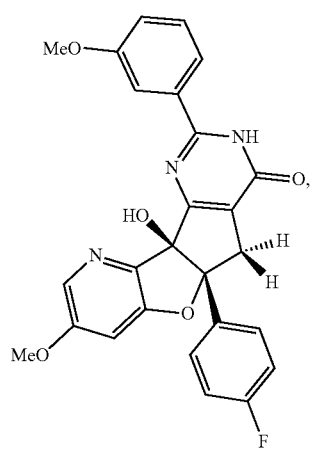

(Ic)
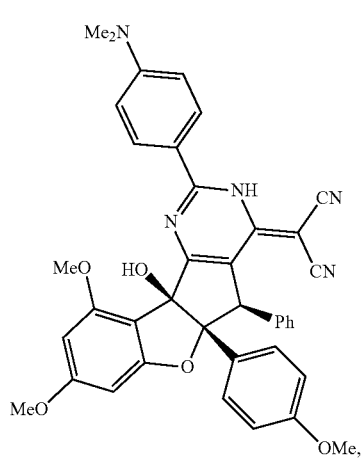
(Id)
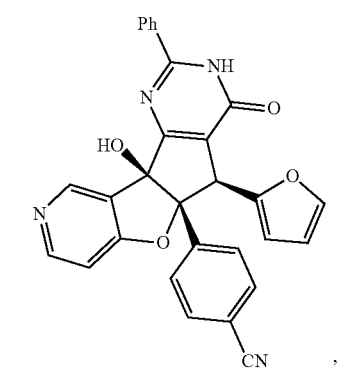
(Ie)
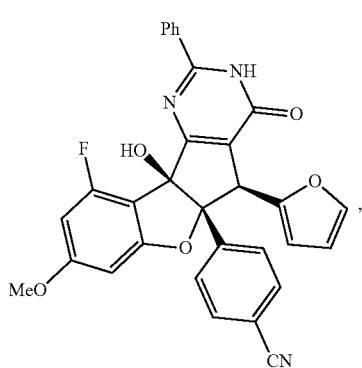
(If)
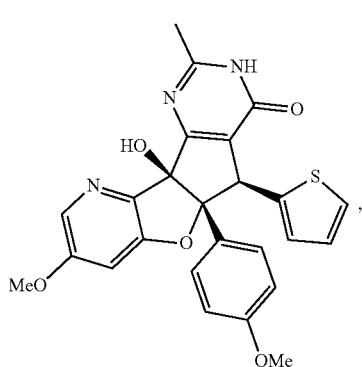
(Ig)
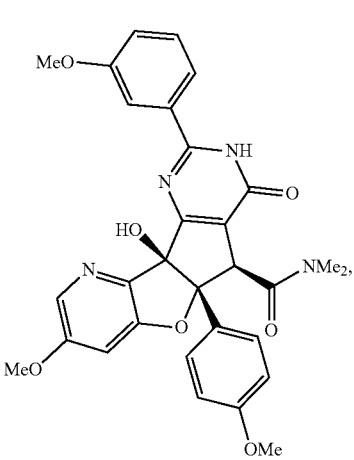
(Ih)
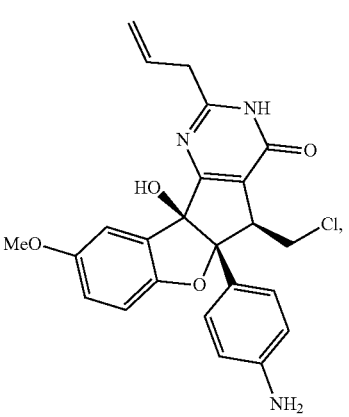
(Ii)
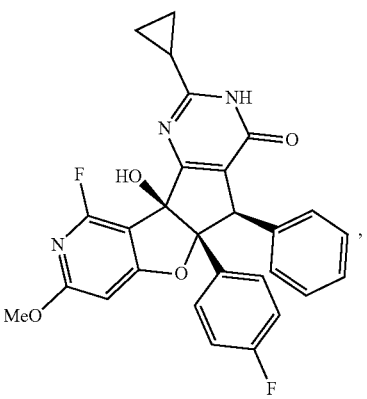
(Ij)
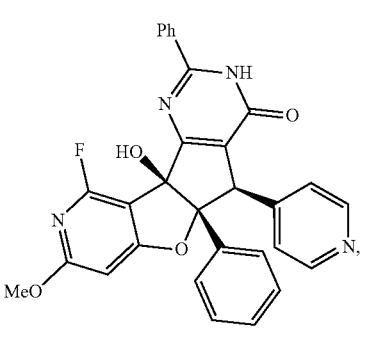

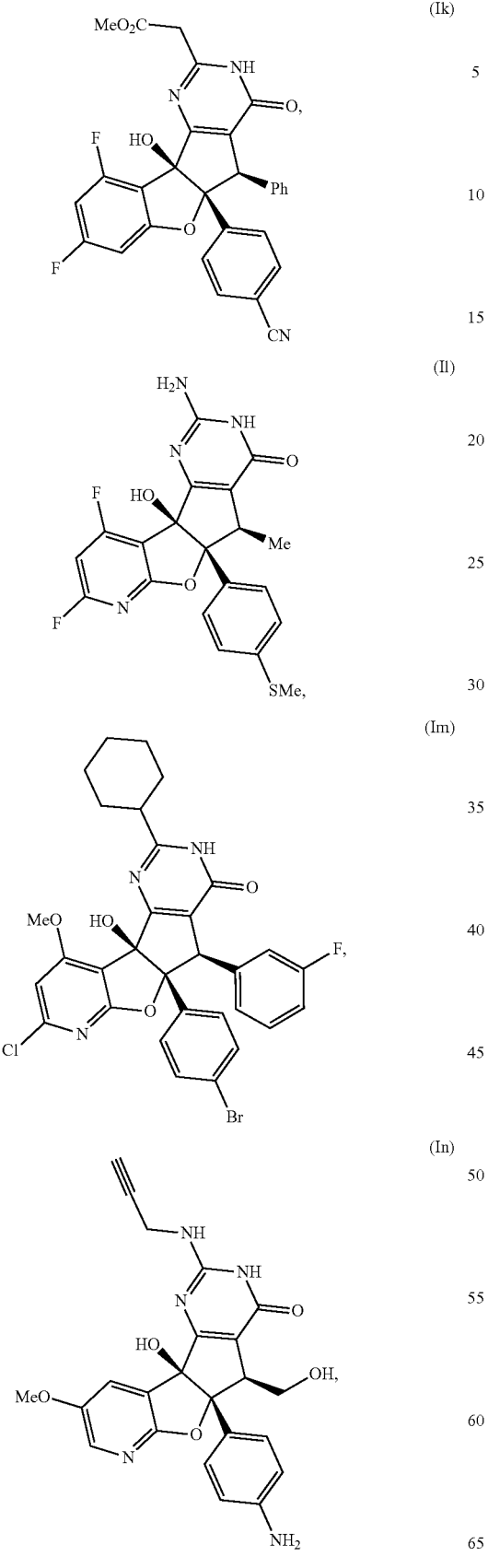
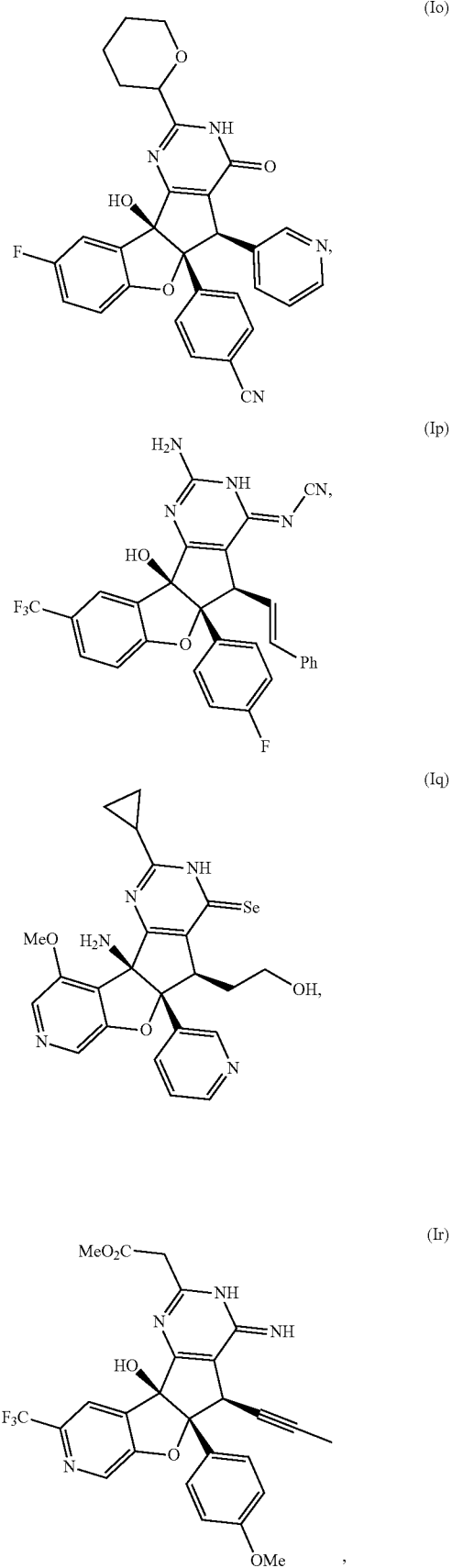

-continued
(Is)
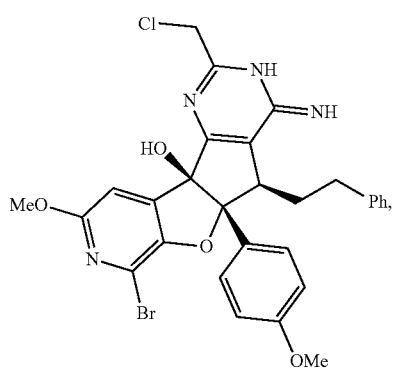
(It)
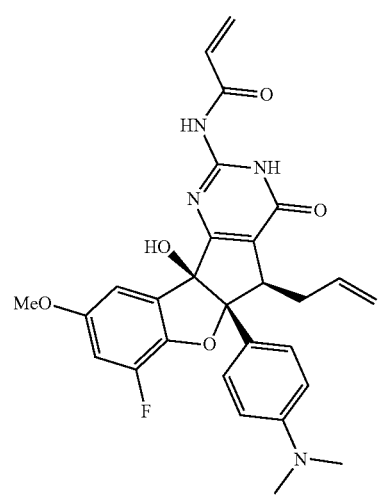
(12am)
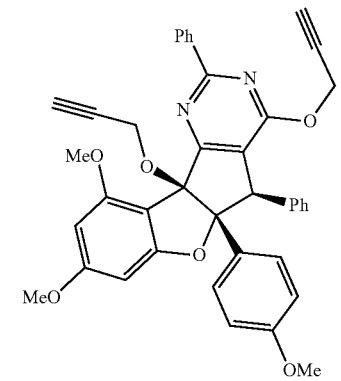
(12an)
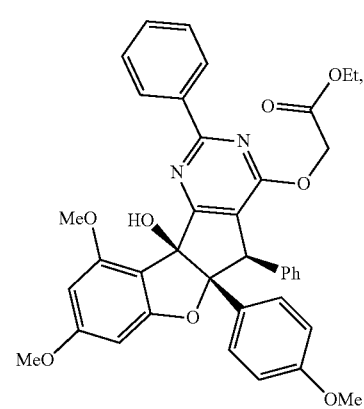
-continued
(12al)
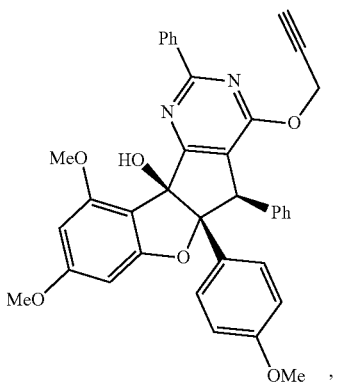
(12ai)
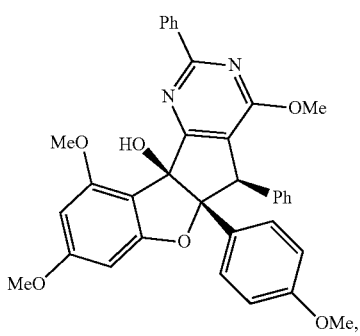
(12ad)
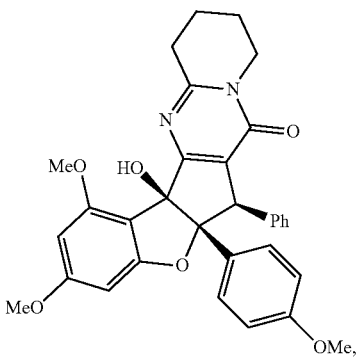
((+)-6)
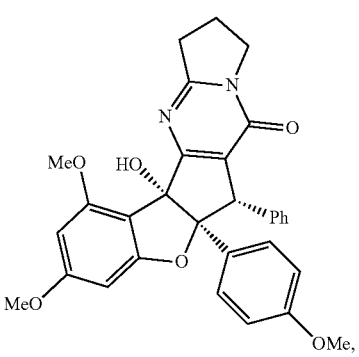

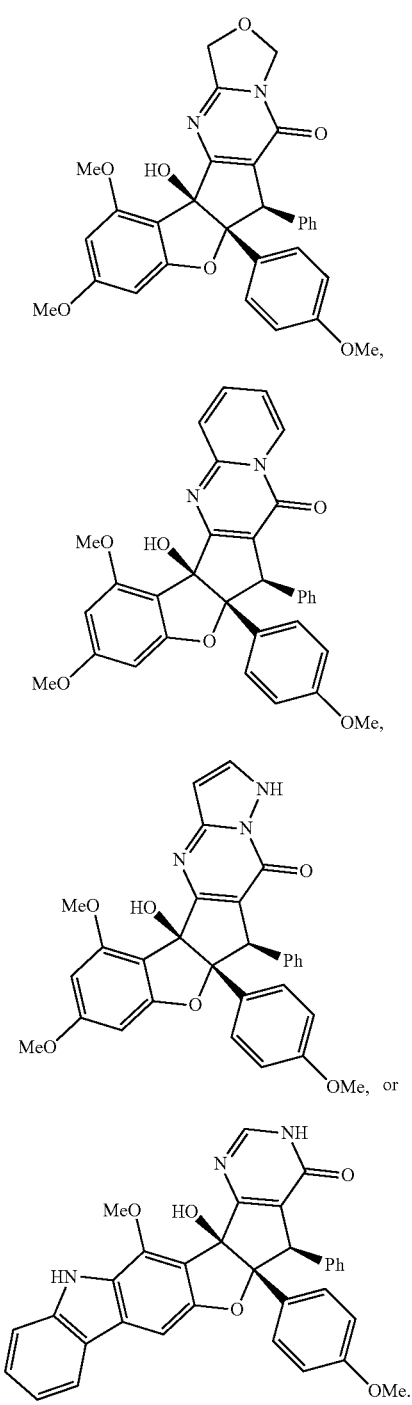

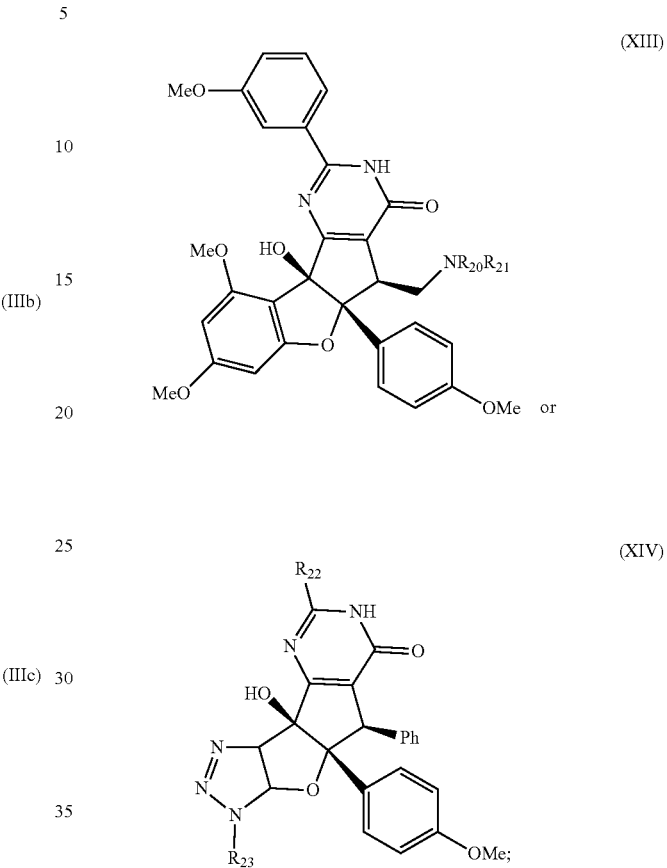

compound 12ap. Or, as an other example, or compound 12a which can be propargylated to form compound 12an (See EXAMPLES). In some embodiments, the compound is:

wherein $R_{20}$, $R_{21}$, $R_{22}$, $R_{23}$ and $R_{24}$ independently are H, halogen, CN, $C_1$-$C_8$(alkyl), ($C_1$-$C_8$)haloalkyl, ($C_2$-$C_8$)alkenyl, ($C_2$-$C_8$)alkynyl, $OR^d$, $NR^dR^e$, [($C_1$-$C_8$)alkylene]$OR^d$, [($C_1$-$C_8$)alkylene]$NHR^d$, [($C_1$-$C_8$)alkylene]$NR^dR^e$, $C(O)R^d$, $C(O)NHR^d$, $C(O)NR^dR^e$, $C(O)[(C_1$-$C_8)$alkylene]$NHR^d$, $C(O)[(C_1$-$C_8)$alkylene]$NR^dR^e$, $CO_2R^d$, $C(S)NHR^d$, $C(S)NR^dR^e$, $SR^d$, $S(O)R^d$, $SO_2R^d$, $SO_2NHR^d$, $SO_2NR^dR^e$, $NHC(O)R^d$, $NR^dC(O)R^e$, $NHC(O)NHR^d$, $NHC(O)NR^dR^e$, $NR^dC(O)NHR^e$, $NR^dC(O)NR^eR^f$, $P(O)(OH)(OR^d)$, $P(O)(OR^d)(OR^e)$, tosylate, aryl, heteroaryl, cycloalkyl or heterocyclyl; $R^d$, $R^e$ and $R^f$ independently are H, —OH, aryl, ($C_1$-$C_8$) alkyl, [($C_1$-$C_8$)alkyl]aryl ($C_1$-$C_8$)alkoxy, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or $R^d$ and $R^U$ together with the nitrogen atom to which they are attached form a heterocyclyl ring.

It is understood that these listed compounds represent a subset of some possible structures and other embodiments will include derivatives of these. For example, such compounds can include additional functional groups, or fewer functional groups while still having the core structure shown by (I), (II) or (III). In some embodiments, the compounds having core structures (I), (II) or (III) can be used as pre-cursors to other compounds having the same core structure. For example, compound 12m which can be hydrogenated (loss of a functional group) to compound 12ao, which can be a propargylated (addition of a functional group) to Some embodiments relate to a method for preparing a compound having the formula (I), (II) or (III'), wherein the compounds (I), (II) are as previously described herein and where compound (III') is as previously described for structure (III) but can also include aglaroxin C ((−)-6)). In some embodiments, the method comprises providing a first compound and a second compound in a solution, and reacting the first compound with the second compound. The first compound has the structure of (VI), (VII) or a salt thereof, and the second compound has the structure of (VIII), (IX) or a salt thereof. The structures of (VI), (VII), (VIII) and (IX) are;

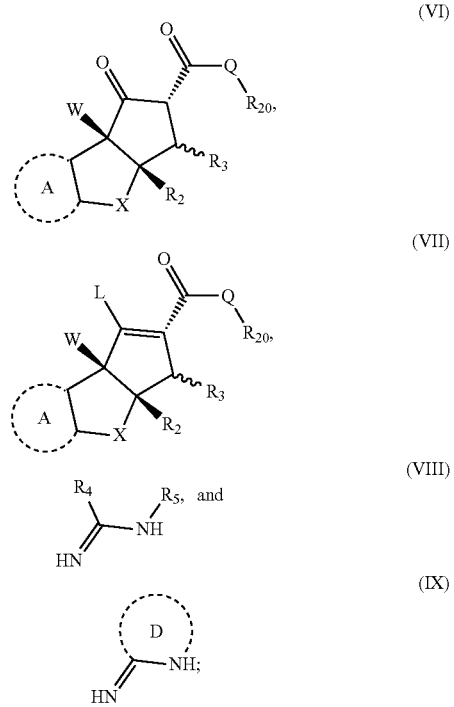

wherein Q is OR$^G$ or NR$^H$R$^I$, wherein R$^G$, R$^H$ and R$^I$ are independently H or an alkyl, and wherein L is a leaving group. In some embodiments, the leaving group L is OH, OTs, OAc, OTf, or OMs; where OT$_s$ is p-toluenesulfonate, OT$_f$ is trifluoromethanesulfonate and OM$_s$ is methanesulfonate.

In some embodiments, the solution comprises an inert solvent. For example, the solvent can include one or more organic solvent selected from ethers (e.g. diethyl ether, t-butyl ethers), cyclic ethers such as tetrahydrofuran (THF), dimethylformamide (DMF), acetonitrile, alkanes (e.g. pentane, hexane), and aromatic solvents (e.g. toluene, xylene). In some embodiments, the solvent is xylene.

In some embodiments, the first compound and the second compound, are combined and heated to a temperature above about 50° C. for at least 2 minutes and less than 2 hours. In some embodiments, the first compound and the second compound are combined and heated in a temperature range between a high and low temperature, wherein the low temperature is selected to be about 50, 60, 70, 80, 90, 100, 110, 120 or 130° C.; and the high temperature is selected to be not more than about 150, 140, 130, 120, 110 or 100° C. In some embodiments, the temperatures are selected to be between about 100 and 150° C. In some embodiments, the temperature is maintained at the temperature range between the low and high temperature selected for at least 2, 5, 10, 20, 30, 40, 50, 60 minutes and not more than about 24 hours, 6 hours, 120, 110, 100, 90, 80, 70, or 60 minutes. In some embodiments, the temperature is maintained for a time in a range of about 30 min and 60 min.

In some embodiments, the second compound is provided in a molar amount greater than the molar amount of the first compound. In some embodiments, the second compound is provided in as at least 1.5, 2, 3, 4, 5, 6, 7, 8 or 10 molar equivalents as compared to the second compound.

In some embodiments, the first or the second compound is provided as a salt. In some embodiments, the second compound is provided as a HCl salt.

In some embodiments, the first and second compound are combined in the presence of a base. In some embodiments, the base has a pKa in a range of greater than about 8 and less than about 16, such as between about 9 and about 14. In some embodiments, the base is 1,8-diazabicyclo[5.4.0]undec-7-ene (DBU) or an alkoxy base such as MeONa. In some embodiments, the base is added in a molar amount that is greater than the first compound. In some embodiments, the base is added in at least about 1.5, 2, 3, 4, 5, 6, 7, 8, 9, or 10 equivalents as compared to the first compound.

In some embodiments, a catalyst is combined with the first and second compound. In some embodiments, the catalysts is 4-dimethylaminopyridine (DMAP). In some embodiments, the catalyst is added in 1.5 equivalents or less with respect to the first compound. In some embodiments, the catalyst is added in a range between about 0 (e.g., no-catalyst) and up to about 1.5 equivalents, such as between about 0.1 and about 1.0, or between about 0.2 and about 0.6.

In some embodiments, the concentration of the first compound which is combined with the second compound is less than about 0.1 M, such as less than about 0.09, 0.08, 0.07, 0.06, 0.05, 0.04 or 0.03M. In some embodiments, the concentration of the first compound is between about 0.01 and about 0.03 M.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

As used herein, the terms "treat," "treatment," or "treating," refer to therapeutic treatments, wherein the object is to reverse, alleviate, inhibit, slow down or stop the progression or severity of a condition associated with a viral infection, e.g., HCV infection. The term "treating" includes reducing or alleviating at least one adverse effect or symptom of a viral infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). Symptoms and clinical markers of a viral infection are further described herein below.

As used herein, the term "prevent" or "preventing" refers to the prevention of at least one symptom associated with a viral infection, or complete prevention of a viral infection, or the lessening of the severity of a viral infection (e.g., preventing the progression of a viral infection) in a subject, and/or delaying one or more symptoms of a viral infection, and/or delaying the onset of a viral infection and/or symptoms following exposure to a virus.

As used herein, the term "administering" refers to the placement of a therapeutic (e.g., a compound or agent that inhibits viral entry of HCV), or composition or pharmaceutical composition thereof as disclosed herein into a subject by a method or route which results in at least partial delivery of the agent to the subject. Compositions and pharmaceutical compositions comprising therapeutics (e.g., a compound or agent that inhibits viral entry of HCV) as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., HCV infection. A subject can be male or female.

A subject can be one who has been previously diagnosed with or identified as suffering from or having a disease or disorder in need of treatment (e.g., HCV infection) or one or more complications related to such a disease or disorder, and optionally, have already undergone treatment for the disease or disorder or the one or more complications related to the disease or disorder. A subject can be resistant to at least one treatment for the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, an "agent" refers to e.g., a molecule, protein, peptide, antibody, or nucleic acid, that inhibits activity of a polypeptide or polynucleotide, or binds to, partially or totally blocks stimulation, decreases, prevents, delays activation, inactivates, desensitizes, or down regulates the activity of the polypeptide or the polynucleotide. Agents that inhibit HCV entry, e.g., inhibit binding of a viral polypeptide to a host receptor, inhibit expression, e.g., translation, post-translational processing, stability, degradation, dissociation, or localization of a polypeptide, or transcription, post transcriptional processing, stability or degradation of a polynucleotide or bind to, partially or totally block stimulation, nucleotide binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, gene editing system, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans.

As used herein, an "inhibitor" refers to any agent, compound, or composition that reduces the levels or activity of a virus (e.g., HCV).

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a viral infection or prior to receiving a given treatment, or a biological sample that has not been contacted with an agent disclosed herein).

As used herein, an "appropriate control" refers to an untreated, otherwise identical cell or population (e.g., a subject who was not administered an agent described herein, or was administered by only a subset of agents described herein, as compared to a non-control cell).

The term "statistically significant" or "significantly" refers to statistical significance and generally means a two-standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Pathogenic Viruses

In one aspect, described herein is a method of preventing and treating a viral infection. In another aspect, described herein is a method of inhibiting a hepatitis C viral (HCV) infection in a subject in need thereof, the method comprises: administering to the subject a therapeutically effective amount of any one or more of the compounds described herein or any one or more of the pharmaceutical compositions described herein.

As used herein, a "viral infection" refers to any infection caused by a virus (e.g., Hepatitis C). A viral infection as described herein can be caused by any virus type currently known, or yet to be discovered that results in a pathogenic disease.

Viruses are small infectious agents which generally contain a nucleic acid core and a protein coat, but are not independently living organisms. Viruses can also take the form of infectious nucleic acids lacking a protein. A virus cannot replicate in the absence of a living host cell. Viruses enter specific living cells either by endocytosis or direct injection of DNA and multiply, causing disease. The multiplied virus can then be released and infect additional cells. Some viruses are DNA-containing viruses and others are RNA-containing viruses.

Specific examples of viruses that have been found in humans include but are not limited to: Hepadnaviridae (Hepatitis C virus); Filoviridae (e.g., Ebola viruses); Chikungunya virus (alphavirus), vesicular stomatitis virus, Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted); Norwalk and related viruses, and astroviruses.

Hepatitis C is a liver disease caused by the hepatitis C virus (HCV). HCV can cause both acute and chronic forms of the disease. The symptoms can range in severity from mild illness to serious lifelong liver damage, and even death. HCV is also the leading cause of liver cancer and HCV has been reported to affect over 71 million people world-wide. HCV is transmitted through sexual transmission, contact with blood comprising the HCV, transfusion of unscreened blood, drug use and needle sticks. The virus is not spread through food, water, casual contact, or breast milk.

Specifically, the Hepatitis C virus is a blood borne pathogen. HCV is a member of the genus Hepacivirus and comprises a viral envelope, and single stranded RNA. The hepatitis C viral envelope comprises host lipoproteins (e.g., Apolipoproteins B, E, and C) and viral glycoproteins such as E1 and E2. E2 protrudes from the membrane of the HCV envelope. These glycoproteins allow for HCV entry into host cells and interaction with the host immune system. In particular, the E2 glycoprotein can be shielded from host immune system detection, as the E2 protein has a hypervariable region 1 that prevents CD81 from latching onto the virus. Additional, non-structural proteins that are comprised within the HCV include core protein, NS1, NS2, NS3, NS4A, NS5A, and NS5B (viral RNA-dependent RNA polymerase). Amino acid sequences of these proteins are known in the art. These proteins are involved in many facets of viral replication within the host and preventing immune detection and destruction of the virus by the host.

There are several genotypes and subtypes of HCV known in the art. The methods and compositions described herein can be used to treat HCV infection by any one of the HCV genotypes.

Generally, pathogenic viruses can comprise viral envelopes that cover the viral protective protein capsids. These envelopes can be derived from, e.g., portions of the host cell membranes (phospholipids, surface molecules, and proteins), but can include some viral glycoproteins. The surface molecules and proteins of the virus can mediate fusion of viral and target cell membranes to initiate infection.

Furthermore, the host cell can also comprise receptors that bind to the virus and allow for viral fusion, contributing to viral pathogenesis. One example, is the scaffolding protein, prohibitin (or PHB), which is encoded by the PHB gene (SEQ ID NO: 1). Prohibitins have multiple functions which include mitochondrial function, mitochondrial morphology, and transcriptional modulation of mammalian cells. Nucleic acid and amino acid sequences for prohibitin are known in the art (SEQ ID NO: 2). Additional non-limiting examples of host molecules that can initiate viral and host cell fusion can include: CD81, LDL receptor, SR-BI, DC-SIGN, Claudin-1, and Occludin.

In another aspect, described herein is a method of inhibiting viral entry into a cell, the method comprises: contacting a cell with at least one compound or pharmaceutical composition described herein.

In another aspect, described herein is a method of inhibiting prohibitin or glycoprotein fusion with a cell, the method comprising: contacting the cell with an effective amount of at least one compound or pharmaceutical composition described herein.

In one embodiment of any of the aspects, the compounds and agents described herein inhibit viral envelope or glycoprotein fusion with the cell. In another embodiment, the compounds and agents described herein inhibit HCV fusion with prohibitin on a target cell.

As used herein, the terms "fusion to a target cell" or "viral entry" are used interchangeably to refer to the event when a virus contacts a portion or fragment of a cell membrane (e.g., a target cell) and merges the viral envelope (e.g., HCV) with the cell membrane permitting formation of a fusion pore. The formation of the fusion pore allows for exchange between the viral capsid and the target or host cell cytosol. Following fusion to a target cell, a virus can begin to replicate using the proteins already within the host cell.

Described herein is a method of identifying and screening for a compound or agent that inhibits viral entry into a target cell (e.g., HCV). Fusion and viral entry can be determined by any assay known in the art (e.g., a cell-cell fusion assay or time of addition assay).

Methods of Treating a Viral Infection

The compounds and agents, or compositions and pharmaceutical compositions described herein can be used to treat a subject having a viral infection, or prevent a subject from having a viral infection. Thus, provided herein are methods for treating and/or preventing a viral infection in a subject. Methods include administering to a subject in need thereof (e.g., a subject having or at risk of having a viral infection) an agent that inhibits viral entry.

In another aspect, the compounds, agents, or compositions or pharmaceutical compositions thereof described herein can be used to treat or prevent an HCV infection.

In one aspect, described herein is a method of treating or preventing a viral infection comprising administering to a subject having or at risk of having a viral infection any compound, composition thereof, or pharmaceutical composition thereof that inhibits HCV entry into a cell.

In one embodiment of any of the aspects, the virus causes hepatitis C.

In another embodiment, the subject has not been previously diagnosed as having a viral infection.

In another aspect, described herein is a method of treating a viral infection comprising (a) diagnosing a subject as having a viral infection, and (b) administering to a subject having a viral infection a compound or agent, or composition or pharmaceutical composition thereof, that inhibits the entry of HCV into a cell. In one embodiment, the viral infection is HCV infection.

In another aspect, described herein is a method of treating a viral infection comprising (a) receiving the results of an assay that diagnoses a subject as having a viral infection, and (b) administering to a subject having a viral infection a compound or agent, or composition or pharmaceutical composition thereof, that inhibits viral entry of HCV.

In another aspect, described herein is a method of treating a Hepatitis C viral (HCV) infection comprising (a) receiving the results of an assay that diagnoses a subject as having a HCV infection, and (b) administering to a subject having a HCV infection a compound or agent, or composition or pharmaceutical composition thereof, that inhibits viral entry of HCV.

In particular, the methods and compositions described herein can be used to treat or prevent a hepatitis C infection.

A skilled clinician can diagnose a subject as having a viral infection via detection of symptoms of a viral infection, such as, fatigue, loss of immune function, vomiting, diarrhea, headaches, gastrointestinal upset, nausea, weight loss, etc. However, some subjects can remain asymptomatic and/or carry the virus or the disease. Further, viral infections can further be diagnosed via clinical tests of a biological sample from a subject, e.g., blood, saliva, spinal fluid, synovial fluid, or tissue biopsy. Clinical tests are known in the art and include, but are not limited to, antibody tests, viral antigen detection tests, viral culture, and viral DNA/RNA detection tests. Clinical tests useful in diagnosing a viral infection are further reviewed in, e.g., U.S. Pat. Nos. 6,432,633; and 5,173,399, the contents of which are incorporated herein by reference in their entireties. HCV, for example, is typically diagnosed by testing for anti-HCV antibodies with a serological test and further testing for HCV RNA. If necessary, a liver biopsy may also be taken to assess the level of liver damage (e.g., fibrosis or cirrhosis of the liver) in the subject. Major symptoms associated with HCV include but are not limited to: fever, fatigue, decreased appetite, nausea, vomiting, abdominal pain, dark urine, grey-colored feces, joint pain and jaundice (yellowing of skin and the whites of the eyes).

Risk factors for having or developing a viral infection include exposure to the virus, exposure or contact with a subject infected with a virus, exposure to contaminated surfaces contacted with a virus, contact with a biological sample or bodily fluid from a subject infected by a virus, sexual intercourse with a subject infected by a virus, needle sharing, blood transfusions, drug use, and any other risk factor known in the art to transmit a virus from one subject to another. Risk factors for a subject can be evaluated, e.g., by a skilled clinician or by the subject. Generally, subjects with a Hepatitis C viral infection are injecting drug users (IDUs), recipients of blood products, and sometimes patients on hemodialysis.

Current therapeutics used to treat viral infections include anti-viral agents. Non-limiting examples of antivirals and therapeutics used to treat an infection (e.g., an HCV infection) include ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, PEGylated interferon, PEGylated interferon alpha-2b, interferon alpha-2a, elbasvir, and grazoprevir. However, there are currently no vaccines or compounds available to prevent HCV before or after exposure to the virus.

Target Cells:

Various aspects described herein are directed to inhibiting viral entry into a target cell. As used herein, "a target cell" refers to a cell within the host subject that is contacted by a virus, or becomes physically attached to a virus via viral fusion (e.g., the merging of viral membrane and the target cell membrane), as described herein. Viral fusion is mediated via transmembrane proteins on the target cell and the virus, and allows for the passage of genetic material from the virus to the target cell. Thus, a target cell is a cell that can be physically attached (e.g., fused) to e.g., a glycoprotein, glycoprotein fragment, or glycoprotein envelope spike of a virus. The target cell express cells surface proteins or receptors that facilitate the fusion of a viral envelope protein to its extracellular surface.

Exemplary cell surface proteins and receptors expressed on a target cell that can bind and attach to a viral envelope include, but are not limited to, prohibitins, cluster of differentiation 81 (CD81), scavenger receptor class B type I (SR-BI), low density lipoprotein receptor (LDL-R), claudin-1 (CLDN 1), tight junction proteins, occludin (OCLN), epidermal growth factor receptor (EGFR), ephrin receptor A2 (EphA2), transferrin receptor (TfR1), cholesterol transporter Niemann-Pick Cl-like 1 (NPC1L1), cluster of differentiation 4 (CD4), CC chemokine receptor 4 (CC4), CC chemokine receptor 5, C-X-C chemokine receptor type 4 (CXCR4), CC chemokine receptor 3 (CC3), nicotinic acetylcholine receptor (nAChR), the neuronal cell adhesion molecule (NCAM), and the p75 neurotrophin receptor (p75NTR), phosphate transporter 2 (Pit2), malonyl CoA-acyl carrier protein transacylase (MCAT), feline leukemia virus subgroup C receptor-related proteins (FLVCRs), xenotropic and polytropic retrovirus receptor 1 (XPR1), TVA, TVB, biliverdin reductase (BLVR), and hyaluronidase-2 (HYAL2).

Viral entry of HCV and interacting host proteins are further described in, for example, Zhe-Zhu et al. *World J. Gasteroenterol.* (2014), which incorporated herein by reference in its entirety.

One skilled in the art can identify a target cell by determining if a cell expresses any of the cell surface proteins or receptors via, e.g., fluorescent microscopy to visualize the cell surface protein or receptors, or via sorting for cells expressing these cell surface proteins or receptors via fluorescence activated cell sorting (FACS) using standard protocols for sorting by cell surface proteins. One can additionally, e.g., perform time of addition or viral fusion assays to determine if a virus can attach and fuse a cell, thus identifying a target cell.

In one embodiment of any of the aspects, the target cell is a hepatocyte. In another embodiment, the target cell is a leukocyte, fibroblast, blood cell, vascular cell, endothelial cells, epithelial cell, nerve cell, biliary ductal cell, Küpffer cell, endothelial cell, Ito cell, oval cell, lymphocyte, parenchymal cell, stem cell, or any other cell known in the art.

A target cell can be a human cell or mammalian cell, for example, a canine, avian, feline, equine, bovine, porcine, primate, rodent, or bat cell.

Compounds and Agents

The agents described herein can also be polypeptides that block viral entry to a target cell. In some embodiments, the virus is HCV. As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

In some embodiments, viral entry into a cell (e.g., a target cell) and the viral proteins (e.g., E1 or E2) is decreased in a cell's genome using any genome editing system including, but not limited to, zinc finger nucleases, TALENS, meganucleases, and CRISPR/Cas systems that prevent the fusion of the HCV virus to a target cell.

The agents described herein can further be an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides as described herein are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect.

In addition to antisense oligonucleotides, RNAi can be used to prevent Env fusion. The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA.

Pharmaceutical Salts

In one aspect, provided herein is a composition or pharmaceutical composition comprising any of the compounds or agents described herein. In one embodiment, the composition further comprises a pharmaceutically acceptable carrier.

Compounds of Formula (I), (II), (III) or (III') agents described herein, or derivatives thereof can also include pharmaceutically acceptable salts thereof. As used herein, the term "pharmaceutically-acceptable salts" refers to the conventional nontoxic salts or quaternary ammonium salts of small molecules as disclosed herein, e.g., from non-toxic organic or inorganic acids. These salts can be prepared in situ in the administration vehicle or the dosage form manufacturing process, or by separately reacting a small molecule in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Prodrugs

In some embodiments, prodrugs of compounds of Formula (I), (II), (III) or (III') also fall within the scope of the invention. As used herein, a "prodrug" refers to a compound that can be converted via some chemical or physiological process (e.g., enzymatic processes and metabolic hydrolysis) to a compound of Formula (I), (II), (III) or (III'). Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, *APHA Acad. Pharm. Sci.* 40 (1977); Bioreversible Carriers in Drug in Drug Design, Theory and Application, E. B. Roche, ed., *APHA Acad. Pharm. Sci.* (1987); Design of Prodrugs, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", Des. *Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., *"Prodrugs", Br. J Clin. Pharmac.* 28: 497-507 (1989), and Sofia et al. "Nucleotide prodrugs for the treatment of HCV infection", *Adv Pharmacol.* 67:39-73, (2013), contents of all of which are herein incorporated by reference in their entireties.

Compositions

In one aspect, described herein is a composition comprising any of the compounds described herein. Another aspect herein provides a composition comprising any of the agents described herein. In one embodiment, the composition further comprises a pharmaceutically acceptable carrier.

In another aspect, described herein is a pharmaceutical composition comprising any of the compounds described herein. Yet another aspect herein provides a pharmaceutical composition comprising any of the agents described herein.

For administering to a subject, compounds of Formula (I), (II), (III) or (III') can be incorporated into pharmaceutical composition. As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Amount of the compound of Formula (I), (II), (III) or (III') in the pharmaceutical composition can be based on weight, moles, or volume. In some embodiments, the pharmaceutical composition comprises at least 0.0001% of the compound of Formula (I), (II), (III) or (III'). In some embodiments, the pharmaceutical composition comprises at least 0.1% of the compound of Formula (I), (II), (III) or (III'). In some embodiments, the pharmaceutical composition comprises at least 0.5% of the compound of Formula (I), (II), (III) or (III'). In some embodiments, the pharmaceutical composition comprises at least 1% of the compound of Formula (I), (II), (III) or (III'). In some embodiments, the pharmaceutical composition comprises at least 2% of the compound of Formula (I), (II), (III) or (III'). In some embodiments, the pharmaceutical composition comprises at least 3% of the compound of Formula (I), (II), (III) or (III'). In some embodiments, the pharmaceutical composition comprises at least 4% of the compound of Formula (I), (II), (III) or (III'). In some embodiments, the pharmaceutical composition comprises at least 5% of the compound of Formula (I), (II), (III) or (III'). In some embodiments, the pharmaceutical composition comprises at least 10% of the compound of Formula (I), (II), (III) or (III'). In some embodiments, the pharmaceutical composition comprises 0.01%-99% of the compound of Formula (I), (II), (III) or (III'). In some embodiments, the pharmaceutical composition comprises 0.05%-90% of the compound of Formula (I), (II), (III) or (III'). In some embodiments, the pharmaceutical composition comprises 0.1%-85% of the compound of Formula (I), (II), (III) or (III'). In some embodiments, the pharmaceutical composition comprises 0.5%-80% of the compound of Formula (I), (II), (III) or (III'). In some embodiments, the pharmaceutical composition comprises 1%-75% of the compound of Formula (I), (II), (III) or (III'). In some embodiments, the pharmaceutical composition comprises 2%-70% of the compound of Formula (I), (II), (III) or (III'). In some embodiments, the pharmaceutical composition comprises 3%-65% of the compound of Formula (I), (II), (III) or (III'). In some embodiments, the pharmaceutical composition comprises 4%-60% of the compound of Formula (I), (II), (III) or (III'). In some embodiments, the pharmaceutical composition comprises 5%-50% of the compound of Formula (I), (II), (III) or (III').

Generally, a pharmaceutical composition of the invention comprises a therapeutically effective amount of a compound of Formula (I), (II), (III) or (III'). In some embodiments, the pharmaceutical composition comprises a compound of Formula (I), (II), (III) or (III') at a concentration of about 0.01 μM to 300 μM, or about 0.1 μM to 150 μM, or about 1 μM to 50 μM, or about 1 μM to 25 μM. The dosage can vary within this range depending upon the dosage form employed and the route of administration utilized.

It will also be appreciated that certain of the compound of Formula (I), (II), (III) or (III') can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of Formula (I), (II), (III) or (III') which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. The terms "physiologically tolerable carriers" and "biocompatible delivery vehicles" are used interchangeably. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the compound of Formula (I), (II), (III) or (III') together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the compound of Formula (I), (II), (III) or (III'), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compound of Formula (I), (II), (III) or (III') are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

The compound of Formula (I), (II), (III) or (III') can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compound of Formula (I), (II), (III) or (III') can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

Injectable preparations, for example, sterile injectable aqueous or oleaginous suspensions, can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable formulations.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compound of Formula (I), (II), (III) or (III') with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or non-aqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Administration and Dosing

As used herein, the term "administering" refers to the placement of a therapeutic (e.g., a compound, composition, pharmaceutical composition, or an agent described herein) into a subject by a method or route which results in at least partial localization of the composition at a desired site such that desired effect is produced. A therapeutic (e.g., a compound, composition, pharmaceutical composition, or an agent described herein) described herein can be administered by any appropriate route known in the art including, but not limited to, oral or parenteral routes, including intravenous, intramuscular, parenteral, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are orally administered. Without limitations, oral administration can be in the form of solutions, suspensions, tablets pills, capsules, sustained-release formulations, oral rinses, powders and the like.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In jurisdictions that forbid the patenting of methods that are practiced on the human body, the meaning of "administering" of a therapeutic to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of therapeutic includes both methods practiced on the human body and also the foregoing activities.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The term "effective amount" is used interchangeably with the term "therapeutically effective amount" or "amount sufficient" and refers to the amount of at least one therapeutic (e.g., a compound, composition, pharmaceutical composition, or an agent described herein) at dosages and for periods of time necessary to achieve the desired therapeutic result, for example, to "attenuate", reduce or stop at least one symptom of a viral infection, e.g., an HCV infection. For example, an effective amount using the methods as disclosed herein would be considered as the amount sufficient to reduce one or more symptoms of an HCV infection by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from HCV infection. Accordingly, the term "effective amount" or "therapeutically effective amount" as used herein refers to the amount of therapeutic (e.g., Formulas (I), (II), (III) or (III') of a pharmaceutical composition to alleviate at least one symptom of a disease. Stated another way, "therapeutically effective amount" of a therapeutic as disclosed herein is the amount of the therapeutic which exerts a beneficial effect on, for example, the symptoms of the disease (e.g., HCV infection). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of a HCV infection or at one related symptom thereof.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of use or administration utilized.

As used herein, the term ED denotes "effective dose" and is used in connection with animal models. The term EC denotes "effective concentration" and is used in connection with in vitro models.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage of a therapeutic (e.g., a compound, composition, pharmaceutical composition, or an agent described herein) may be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 g/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that therapeutic (e.g., a compound, composition, pharmaceutical composition, or an agent described herein) or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the agent or composition is administered continuously (e.g., at constant levels over a period of time). Continuous administration of an agent can be achieved, e.g., by epidermal patches, continuous release formulations, or on-body injectors.

The compound can be administered as a single bolus or multiple boluses, as a continuous infusion, or a combination thereof. For example, the compound can be administered as a single bolus initially, and then administered as a continuous infusion following the bolus. The rate of the infusion can be any desired rate. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another embodiment of any of the aspects, more than one-unit dosage form can be administered simultaneously.

The dosage of the therapeutic as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Efficacy

The efficacy of a therapeutic described herein, e.g., for the treatment of a viral infection, can be determined by the skilled practitioner. However, a treatment is considered "effective treatment," as the term is used herein, if one or more of the signs or symptoms of viral infection (e.g., HCV infection) are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., immune function. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of a viral infection, e.g., an HCV infection, as the case may be. When using an experimental animal model, efficacy of treatment is evidenced when a statistically significant change in a marker is observed, e.g., reduced viral infection.

Anti-Viral Therapies

In some embodiments of any of the aspects, the agent or compositions described herein are used as a monotherapy. In some embodiments of any of the aspects, the methods described herein further comprise administering one or more additional agents to the subject. In some embodiments, the agent is an anti-viral agent. In some embodiments, the agent is selected from the group consisting of: a small molecule, an antibody, a peptide, a genome editing system, and a nucleic acid. In some embodiments, the agent is sofosbuvir.

In another embodiment, the therapeutics described herein can be used in combination with other known agents and therapies for HCV infection. Administered "in combination," as used herein, means that two (or more) different treatments are delivered to the subject during the course of the subject's affliction with the disorder, e.g., the two or more treatments are delivered after the subject has been diagnosed with the disorder (e.g., HCV infection) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery."

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The compounds and agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

Therapeutics currently used to treat or prevent viral infections include but are not limited to: ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, PEGylated interferon, PEGylated interferon alpha-2b, interferon alpha-2a, elbasvir, and grazoprevir.

When administered in combination, the agent or compound described herein and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of diabetes) is lower (e.g., at least 20%, at least 30%, at least 40%, or at least 50% lower) than the amount or dosage of each agent individually required to achieve the same therapeutic effect.

The present invention is further illustrated by the following Examples, which in no way should be construed as further limiting.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the various aspects described herein can be described as in the following numbered paragraphs:

1. A compound having the structure of Formula (I), (II), or (III)

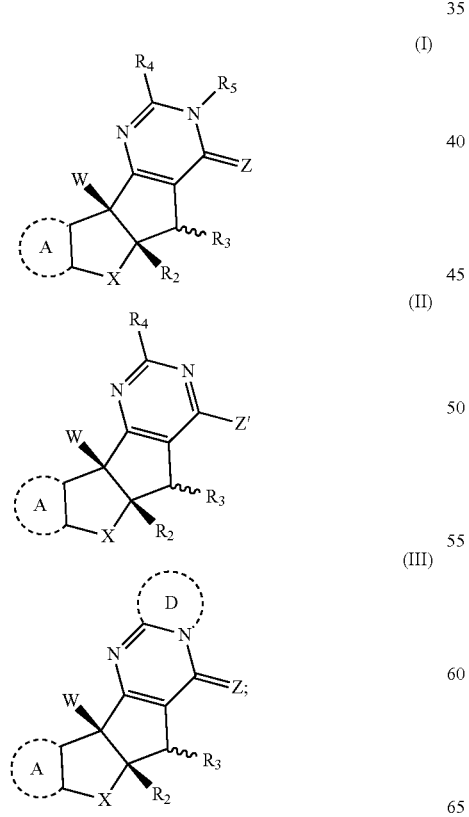

or stereoisomers, tautomers, or pharmaceutically acceptable salts thereof, wherein:

X is O, S, $CR^B R^E$ or $NR^E$; wherein $R^B$ and $R^E$ independently are H, alkyl, aryl, heteroaryl, heteroalkyl, cycloalkyl, acyl, or allyl;

W is F or —$YR^A$, wherein Y is O, NH or S, and $R^A$ is H, alkyl, aryl, heteroaryl, heteroalkyl, cycloalkyl, acyl, NH(alkyl), $NH_2$ or NH(aryl);

A is a heteroaryl or aryl;

$R_2$ is aryl or heteroaryl;

$R_3$ is H, phenyl, alkyl, heteroalkyl, aryl, heteroaryl, aldehyde, ester, alkenyl, amide or —$CO_2H$; wherein when $R_3$ is not H; $R_3$ is syn to $R_2$ or $R_3$ is trans to $R_2$;

$R_4$ is H, alkyl, aryl, heteroaryl, heteroalkyl, cycloalkyl, acyl halide, CN, NH(alkyl), NH(aryl), NH(CN), $CO_2$(alkyl), or NH—NH(alkyl);

Z is O, NH, S, Se, N(alkyl) or N(aryl), $CR^C R^F$; wherein $R^C$ and $R^F$ independently are H, alkyl, aryl, heteroaryl, heteroalkyl, cycloalkyl, acyl, allyl or CN;

$R_5$ is H, alkyl, alkenyl, alkynyl, aryl, heteroaryl, cycloalkyl heteroalkyl;

Z' is a halide or -$TR_5$'; wherein T is O, S, NH, or $CH_2$ and $R_5$' is H, alkyl, alkenyl, alkynyl aryl, heteroaryl, cycloalkyl, heteroalkyl, acyl or sulfate;

D is a $C_{1-5}$ alkylene, $C_{1-5}$ heteroalkylene, heteroaryl or aryl, wherein when D is a three carbon alkylene the compound does not have the structure of formula (IIIa)

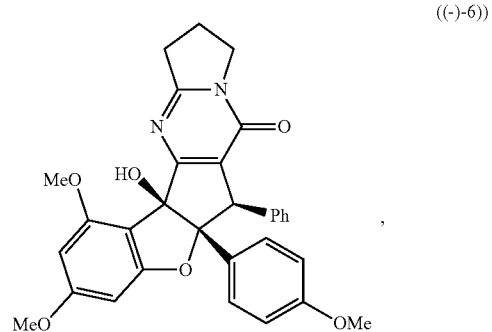 [SMILES: COc1ccc([C@@]23Oc4cc(OC)cc(OC)c4[C@]2(O)c2nc4n(c(=O)c2[C@H]3c2ccccc2)CCC4)cc1 ; ","]

and;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6.

2. The compound according to paragraph 1, wherein D has the structure of formula X;

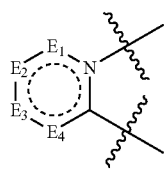

(X)

wherein;

$E_1$ is N, C(O), NH or $CR_{110}$;

$E_2$ is N, C(O), NH or $CR_{111}$;

$E_3$ is N, C(O), NH or $CR_{112}$;

$E_4$ is N, C(O), NH or $CR_{113}$; and $R_{110}$, $R^{111}$, $R_{112}$ and $R_{113}$ independently are H, halogen, CN, $C_1$-$C_8$(alkyl), $(C_1$-$C_8)$haloalkyl, $(C_2$-$C_8)$alkenyl, $(C_2$-$C_8)$alkynyl, $OR^T$, $NR^TR^U$, $[(C_1$-$C_8)$alkylene]$OR^T$, $[(C_1$-$C_8)$alkylene]$NHR^T$, $[(C_1$-$C_8)$alkylene]$NR^TR^U$, $C(O)R^T$, $C(O)NHR^T$, $C(O)NR^TR^U$, $C(O)[(C_1$-$C_8)$alkylene]$NHR^T$, $C(O)[(C_1$-$C_8)$alkylene]$NR^TR^U$, $CO_2R^T$, $C(S)NHR^T$, $C(S)NR^TR^U$, $SR^T$, $S(O)R^T$, $SO_2R^T$, $SO_2NHR^T$, $SO_2NR^TR^U$, $NHC(O)R^T$, $NR^TC(O)R^U$, $NHC(O)NHR^T$, $NHC(O)NR^TR^U$, $NR^TC(O)NHR^U$, $NR^TC(O)NR^UR^V$, $P(O)(OH)(OR^T)$, $P(O)(OR^T)(OR^U)$, tosylate, aryl, heteroaryl, cycloalkyl or heterocyclyl; $R^T$, $R^U$ and $R^V$ independently are H, —OH, aryl, $(C_1$-$C_8)$alkyl, $[(C_1$-$C_8)$alkyl]aryl $(C_1$-$C_8)$alkoxy, $(C_1$-$C_8)$haloalkyl, cycloalkyl, heterocyclyl, $[(C_1$-$C_8)$alkylene]heterocyclyl, $[(C_1$-$C_8)$alkylene]aryl or heteroaryl; or $R^T$ and $R^U$ together with the nitrogen atom to which they are attached form a heterocyclyl ring.

3. The compound according to paragraph 1, wherein D has the structure of formula XI;

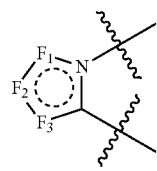

(XI)

wherein;

$F_1$, $F_2$ and $F_3$ are independently $CR_{114}$, N, $NR_{115}$, O or S; wherein $R_{114}$ and $R_{115}$ are independently H, CN, halogen, $OR^W$, $SR^W$, $(C_1$-$C_8)$alkyl, $C(O)O(C_1$-$C_8)$alkyl, $C(O)(C_1$-$C_8)$alkyl, $SO_2(C_1$-$C_8)$alkyl, $SO_2NR^WR^X$, $C(O)NR^WR^X$, $NR^WR^X$ or $NR^WC(O)R^X$;

$R^{RW}$ and $R^{SX}$, independently are H, —OH, aryl, $(C_1$-$C_8)$alkyl, $[(C_1$-$C_8)$alkyl]aryl $(C_1$-$C_8)$alkoxy, $(C_1$-$C_8)$haloalkyl, cycloalkyl, heterocyclyl, $[(C_1$-$C_8)$alkylene]heterocyclyl, $[(C_1$-$C_8)$alkylene]aryl or heteroaryl; or the $R^W$ and $R^X$ together with the nitrogen atom to which they are attached of $NR^WR^X$ or $NR^WC(O)R^X$, optionally form a heterocyclyl ring.

4. The compound according to paragraph 1, wherein A has the structure of formula (IV);

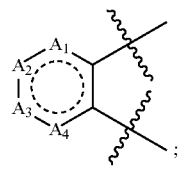

(IV)

wherein;

$A_1$ is N, C(O), NH or $CR_{10}$;

$A_2$ is N, C(O), NH or $CR_{11}$;

$A_3$ is N, C(O), NH or $CR_{12}$;

$A_4$ is N, C(O), NH or $CR_{13}$; and $R_{10}$, $R_{11}$, $R_{12}$ and $R_{13}$ independently are H, halogen, CN, $C_1$-$C_8$(alkyl), $(C_1$-$C_8)$haloalkyl, $(C_2$-$C_8)$alkenyl, $(C_2$-$C_8)$alkynyl, $OR^O$, $NR^OR^P$, $[(C_1$-$C_8)$alkylene]$OR^O$, $[(C_1$-$C_8)$alkylene]$NHR^O$, $[(C_1$-$C_8)$alkylene]$NR^OR^P$, $C(O)R^O$, $C(O)NHR^O$, $C(O)NR^OR^P$, $C(O)[(C_1$-$C_8)$alkylene]$NHR^O$, $C(O)$ $[(C_1$-$C_8)$alkylene]$NR^OR^P$, $CO_2R^O$, $C(S)NHR^O$, $C(S)NR^OR^P$, $SR^O$, $S(O)R^O$, $SO_2R^O$, $SO_2NHR^O$, $SO_2NR^OR^P$, $NHC(O)R^O$, $NR^OC(O)R^P$, $NHC(O)NHR^O$, $NHC(O)NR^OR^P$, $NR^OC(O)NHR^P$, $NR^OC(O)NR^PR^Q$, $P(O)(OH)(OR^O)$, $P(O)(OR^O)(OR^P)$, tosylate, aryl, heteroaryl, cycloalkyl or heterocyclyl; $R^O$, $R^P$ and $R^Q$ independently are H, —OH, aryl, $(C_1$-$C_8)$alkyl, $[(C_1$-$C_8)$alkyl]aryl $(C_1$-$C_8)$alkoxy, $(C_1$-$C_8)$haloalkyl, cycloalkyl, heterocyclyl, $[(C_1$-$C_8)$alkylene]heterocyclyl, $[(C_1$-$C_8)$alkylene]aryl or heteroaryl; or $R^O$ and $R^P$ together with the nitrogen atom to which they are attached form a heterocyclyl ring; wherein any vicinal $R_{10}$, $R_{11}$, $R_{12}$, and $R_{13}$ together with the carbons to which they are attached optionally form an aryl or heteroaryl ring.

5. The compound according to paragraph 4, wherein at least one of $R_{10}$, $R_{11}$, $R_{12}$ or $R_{13}$ is a heteroalkyl.

6. The compound according to paragraph 4, wherein: the compound has the structure of formula (I)

W is OH;

X is O;

Z is O;

$R_2$ is an aryl;

$R_3$ is a phenyl;

$R_2$ is syn relative to $R_3$;

$R_5$ is H or alkyl;

$R_4$ is alkyl or aryl.

7. The compound according to paragraph 4, wherein: the compound has the structure of formula (II);

W is OH;

X is O;

Z' is OH;

$R_2$ is an aryl;

$R_3$ is a phenyl;

$R_2$ is syn relative to $R_3$;

$R_4$ is alkyl or aryl.

8. The compound according to paragraph 1, wherein A has the structure of formula (V);

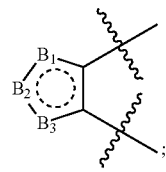

(V)

wherein;

B$_1$, B$_2$ and B$_3$ are independently CR$_{14}$, N, NR$_{15}$, O or S; wherein R$_{14}$ and R$_{15}$ are independently H, CN, halogen, OR$^R$, SR$^R$, (C$_1$-C$_8$)alkyl, C(O)O(C$_1$-C$_8$)alkyl, C(O)(C$_1$-C$_8$)alkyl, SO$_2$(C$_1$-C$_8$)alkyl, SO$_2$NR$^R$R$^S$, C(O)NR$^R$R$^S$, NR$^R$R$^S$ or NR$^R$C(O)R$^S$;

R$^R$ and R$^S$, independently are H, —OH, aryl, (C$_1$-C$_8$) alkyl, [(C$_1$-C$_8$)alkyl]aryl (C$_1$-C$_8$)alkoxy, (C$_1$-C$_8$)haloalkyl, cycloalkyl, heterocyclyl, [(C$_1$-C$_8$)alkylene]heterocyclyl, [(C$_1$-C$_8$)alkylene]aryl or heteroaryl; or the R$^R$ and R$^S$ together with the nitrogen atom to which they are attached of NR$^R$R$^S$ or NR$^R$C(O)R$^S$, optionally form a heterocyclyl ring.

9. The compound according to paragraph 8, wherein at least one of B$_1$, B$_2$ and B$_3$ is CR$_{14}$, or NR$_{15}$ and R$_{14}$ or R$_{15}$ is a heteroalkyl.

10. The compound according to paragraph 8, wherein;
the compound has the structure of formula (I);
W is OH;
X is O;
Z is O;
R$_2$ is an aryl;
R$_3$ is a phenyl;
R$_2$ is syn relative to R$_3$;
R$_5$ is H or alkyl;
R$_4$ is alkyl or aryl.

11. The compound according to paragraph 8, wherein;
the compound has the structure of formula (II);
W is OH;
X is O;
Z' is OH;
R$_2$ is an aryl;
R$_3$ is a phenyl;
R$_2$ is syn relative to R$_3$;
R$_4$ is alkyl or aryl.

12. The compound according to paragraph 1, wherein R$_3$ is syn to R$_2$.

13. The compound according to paragraph 1, wherein the compound is selected from the following compounds;

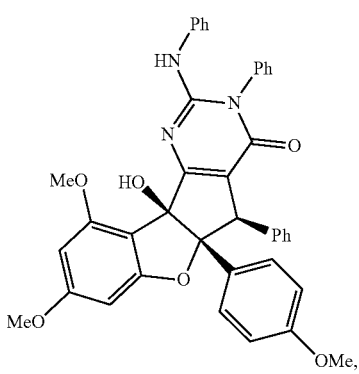
(12af)

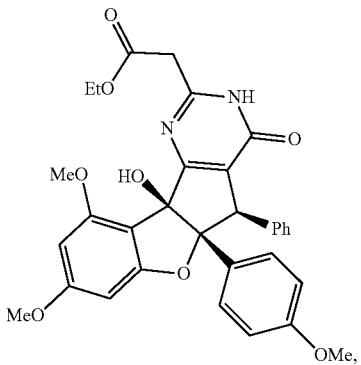
(CMLD012046)

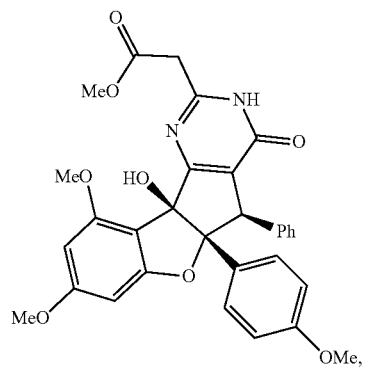
(12g)

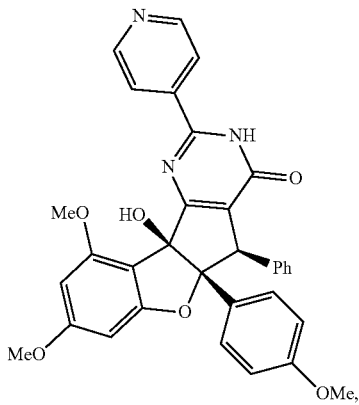
(12aa)

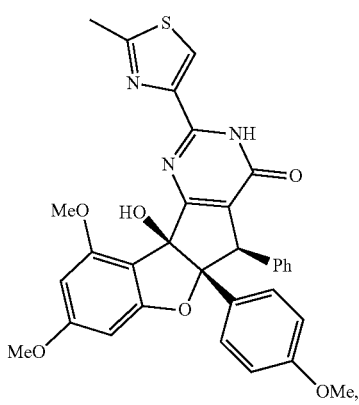
(12ac)

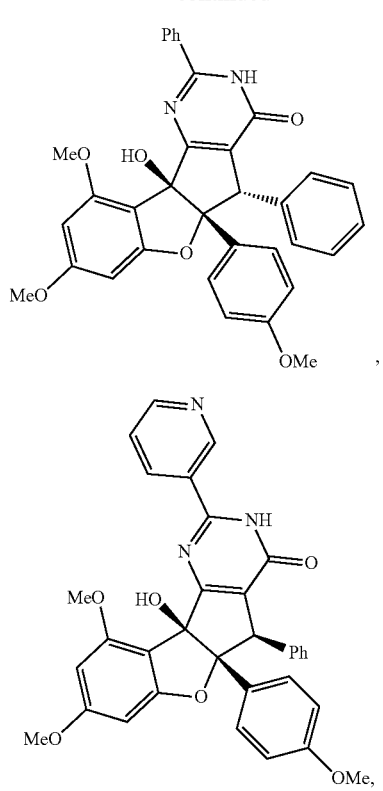
(12ah)
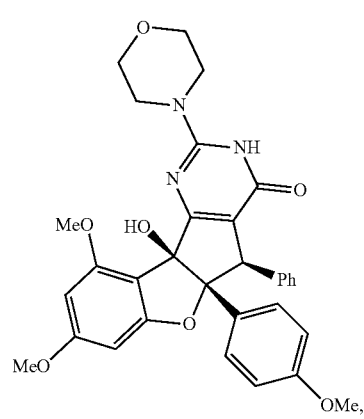
(12z)
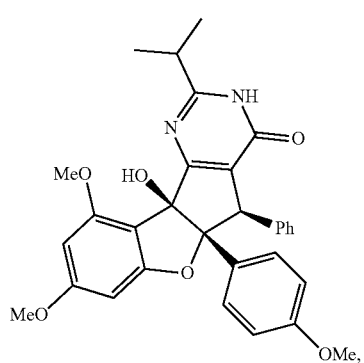
(12j)
(12d)
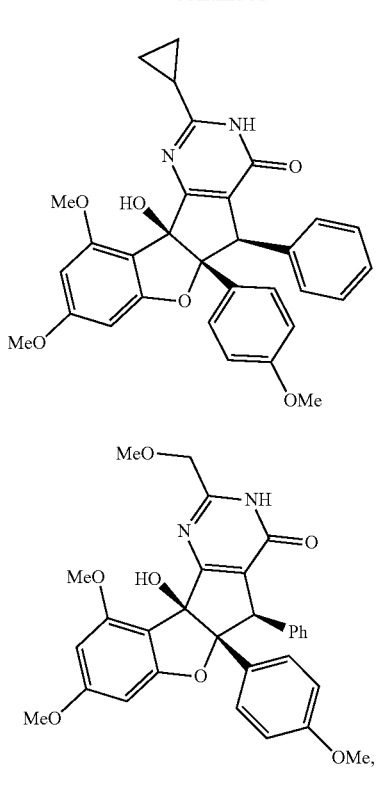
(12h)
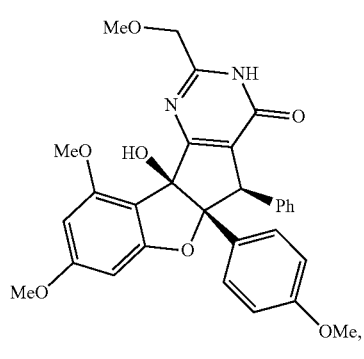
(12i)
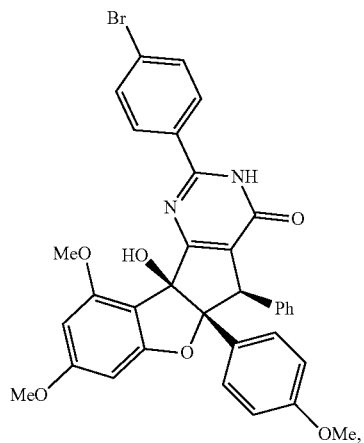
(12r)
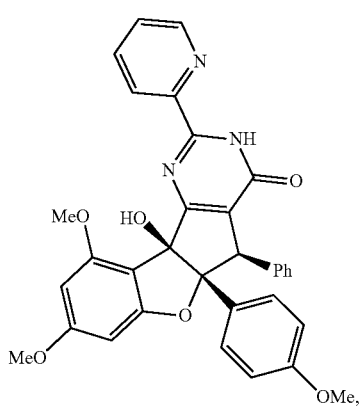
(12ab)

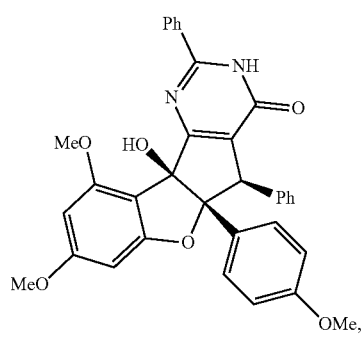
(12a)
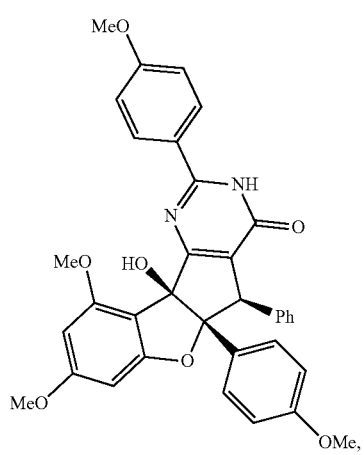
(12k)
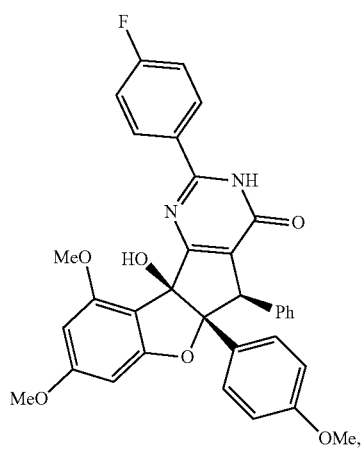
(12p)
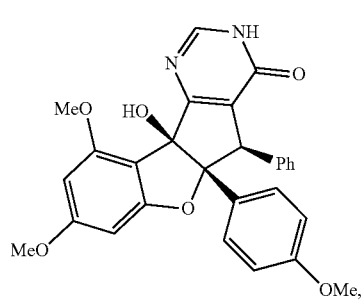
(12f)
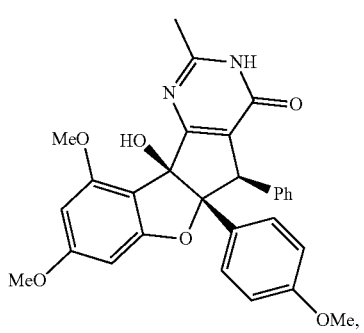
(12b)
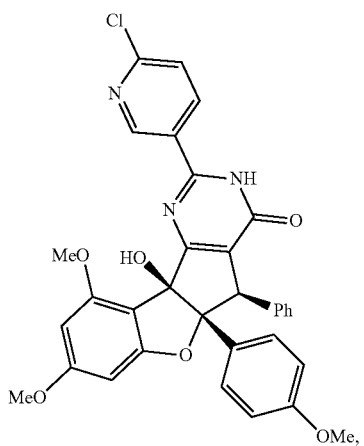
(12q)
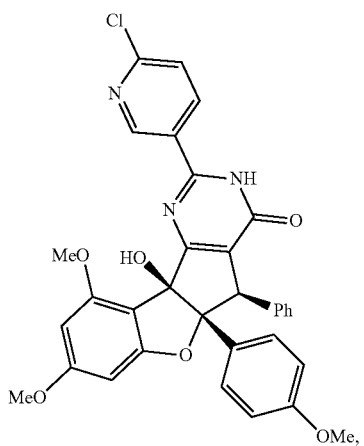
(12x)
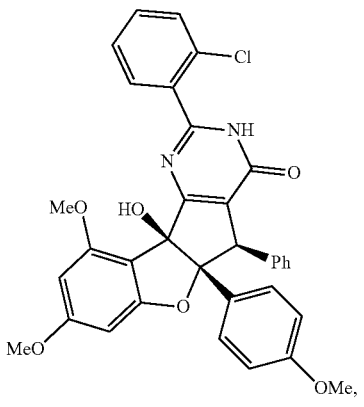
(12w)

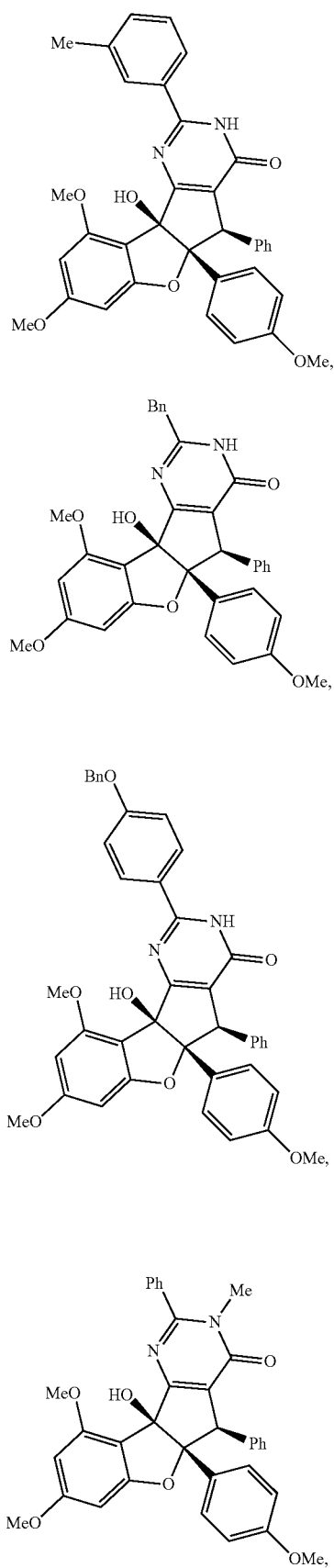
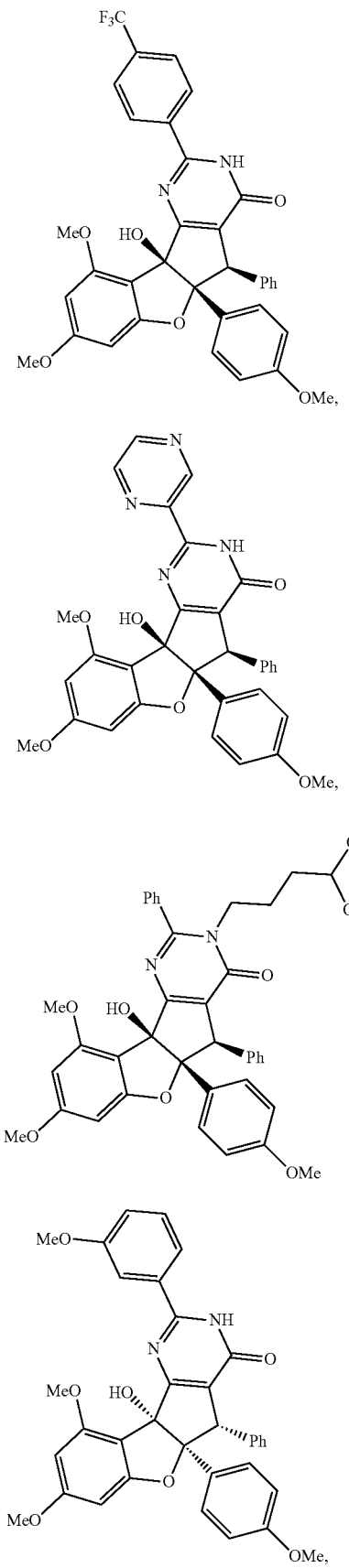

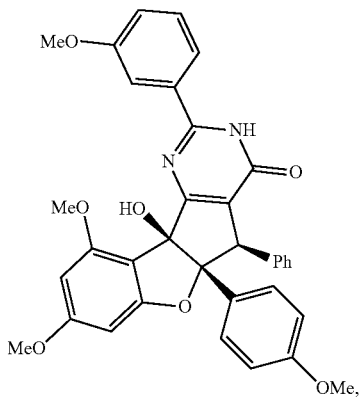
((+)-12s)
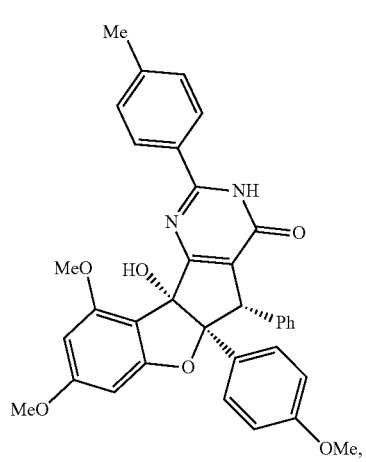
((-)-12l)
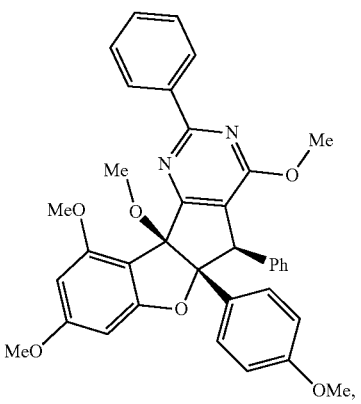
((+)-12l)
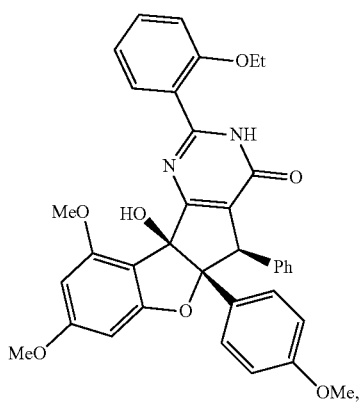
(12v)
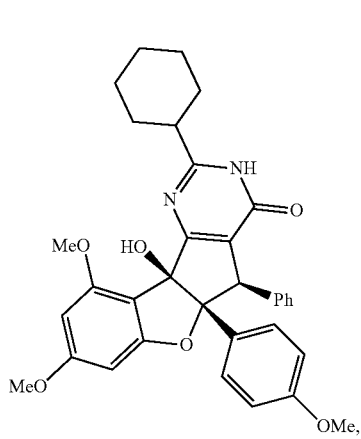
(12e)
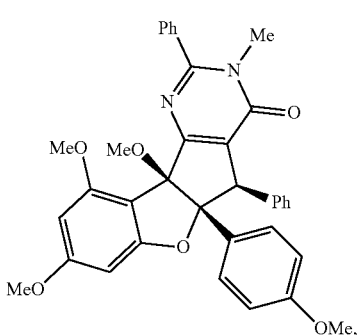
(12aj)
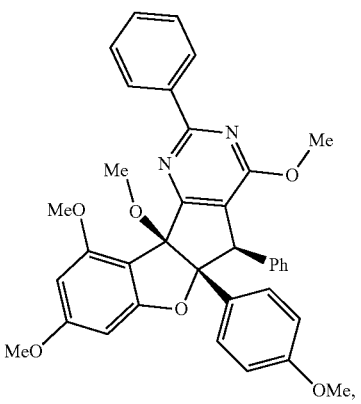
(12ak)

-continued
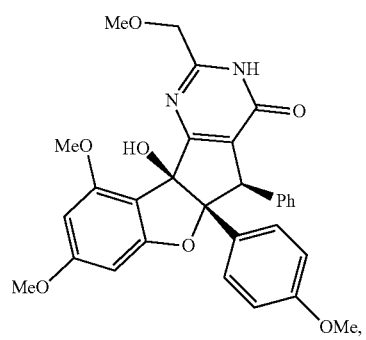
(CMLD012982)
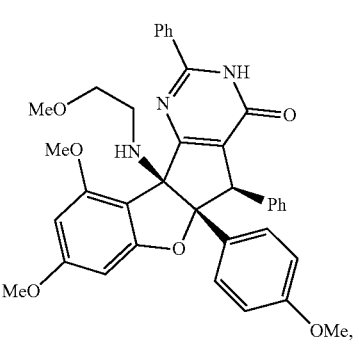
(CMLD012982')
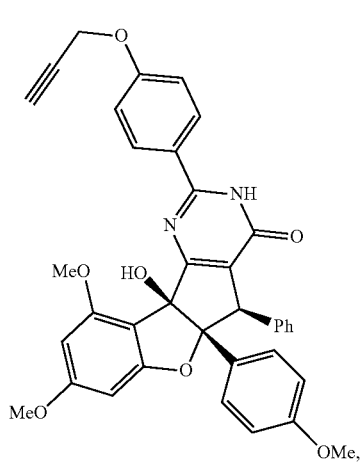
(12ap)
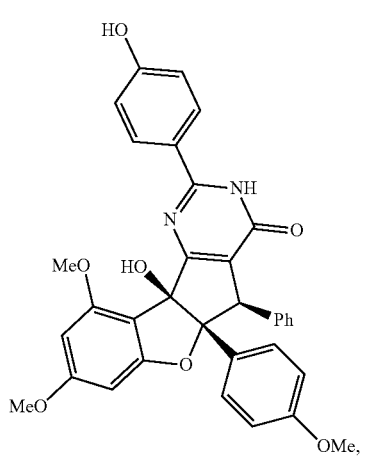
(12ao)
-continued
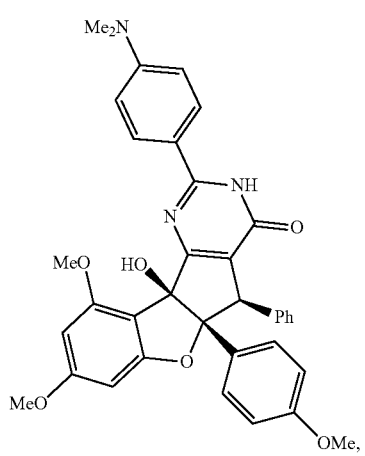
(12n)
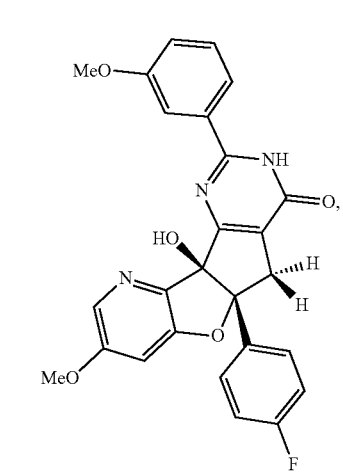
(Ia)
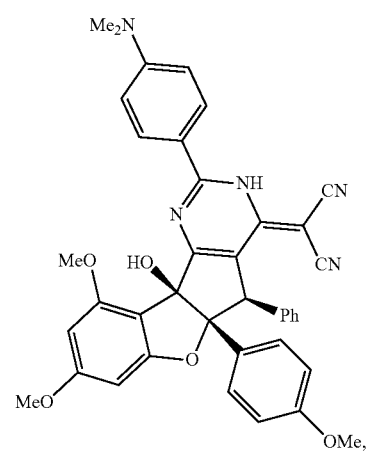
(Ic)

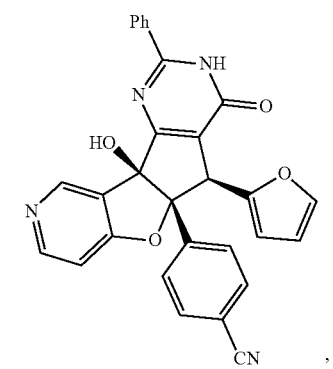
(Id)
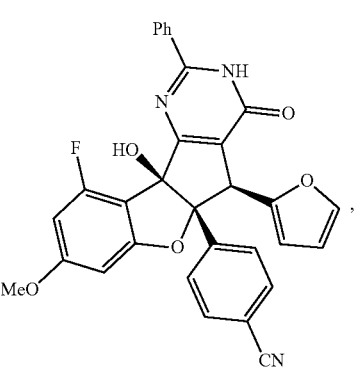
(Ie)
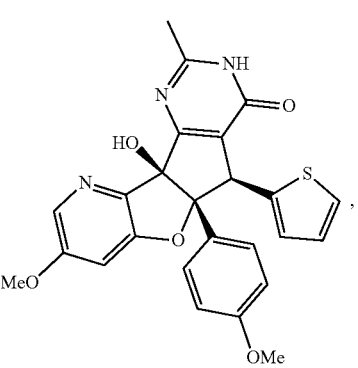
(If)
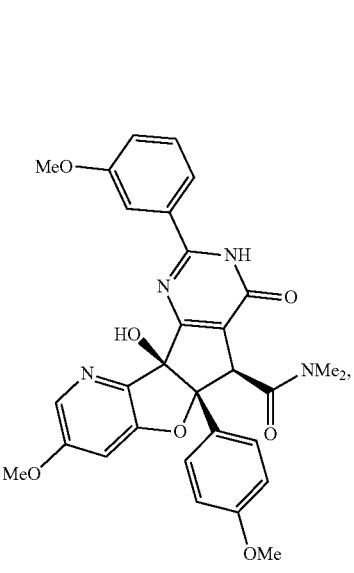
(Ig)
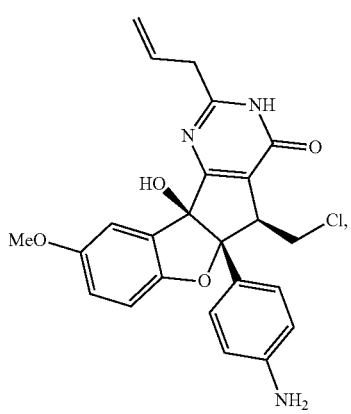
(Ih)
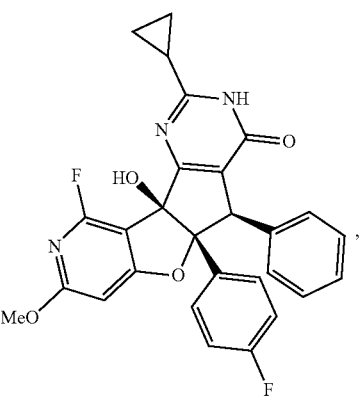
(Ii)
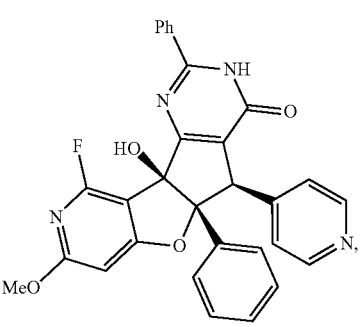
(Ij)
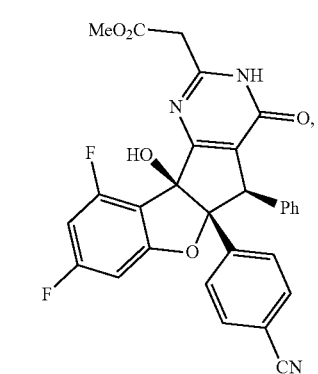
(Ik)

-continued
(Il)
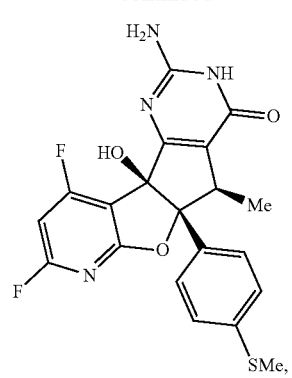
(Im)
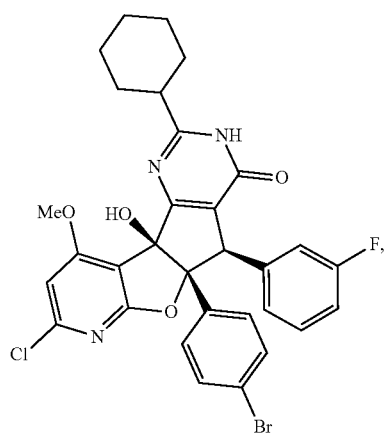
(In)
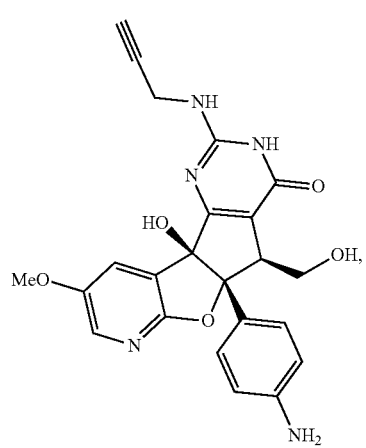
(Io)
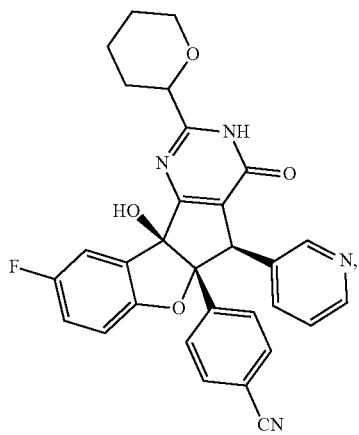
(Ip)
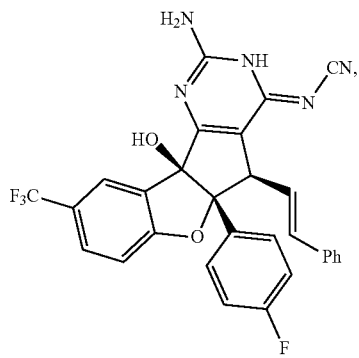
(Iq)
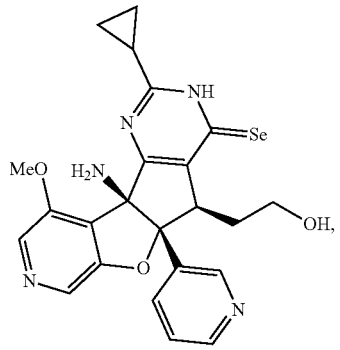
(Ir)
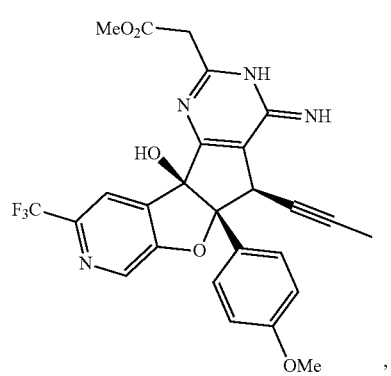

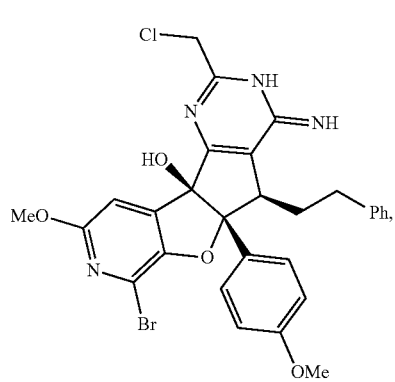
(Is)
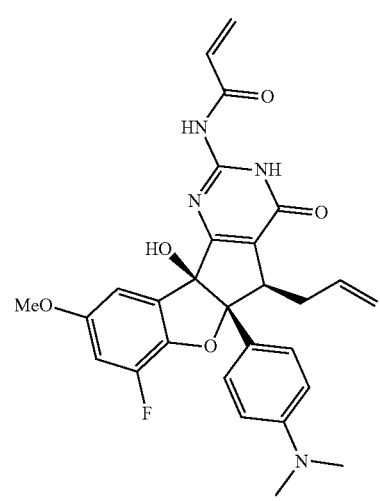
(It)
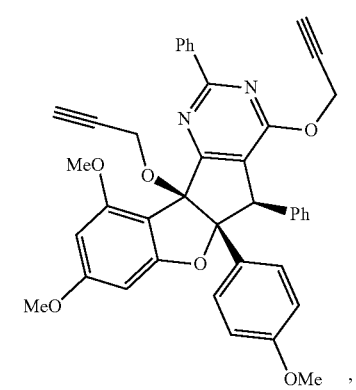
(12am)
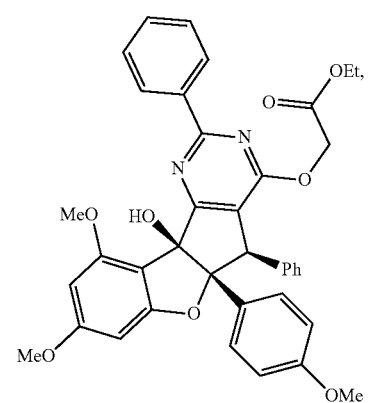
(12an)
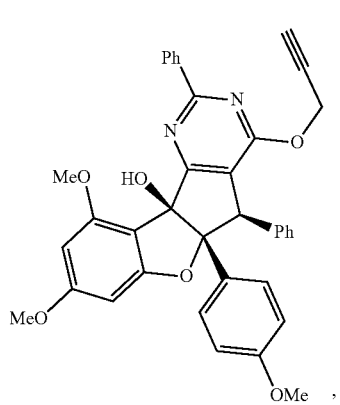
(12al)
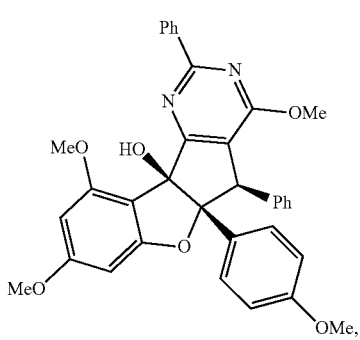
(12ai)
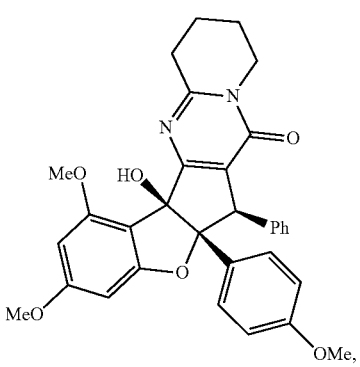
(12ad)
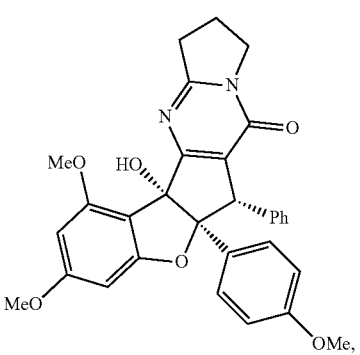
((+)-6)

-continued

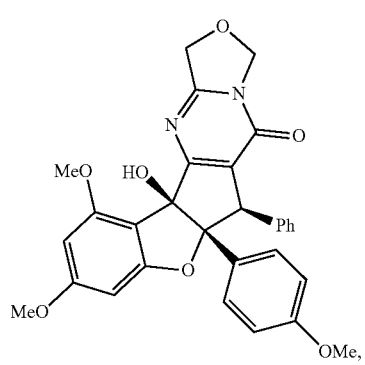
(IIIa)

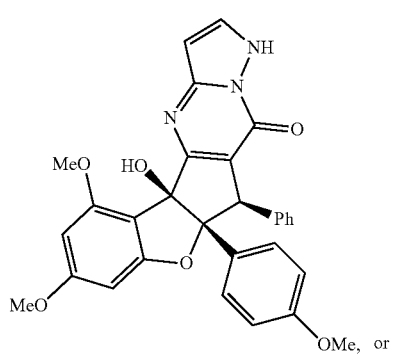
(IIIb)

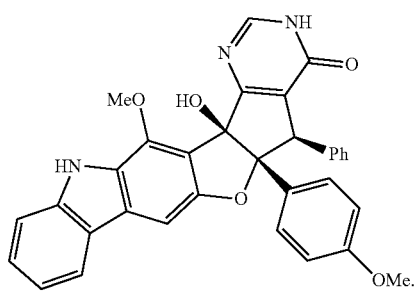
(IIIc)

(IIId)

14. A method for preparing a compound having formula (I), (II) or (III');

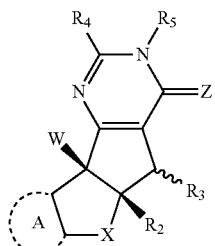
(I)

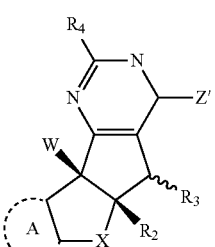
(II)

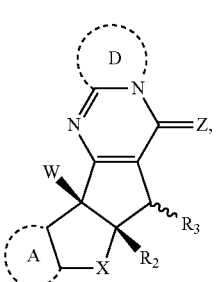
(III')

or stereoisomers, tautomers, or pharmaceutically acceptable salts thereof,
wherein:
X is O, S, $CR^B R^E$ or $NR^E$; wherein $R^B$ and $R^E$ independently are H, alkyl, aryl, heteroaryl, heteroalkyl, cycloalkyl, acyl, or allyl;
W is F or —$YR^A$, wherein Y is O, NH or S, and $R^A$ is H, alkyl, aryl, heteroaryl, heteroalkyl, cycloalkyl, acyl, NH(alkyl), $NH_2$ or NH(aryl);
A is a heteroaryl or aryl;
$R_2$ is aryl or heteroaryl;
$R_3$ is H, phenyl, alkyl, heteroalkyl, aryl, heteroaryl, aldehyde, ester, alkenyl, amide or —$CO_2H$; wherein, when $R_3$ is not H, $R_3$ is syn to $R_2$, or $R_3$ is trans to $R_2$;
$R_4$ is H, alkyl, aryl, heteroaryl, heteroalkyl, cycloalkyl, acyl halide, CN, NH(alkyl), NH(CN) or NH—NH(alkyl);
Z is O, NH, S, Se, N(alkyl) or N(aryl), $CR^C R^F$; wherein $R^C$ and $R^F$ independently are H, alkyl, aryl, heteroaryl, heteroalkyl, cycloalkyl, acyl, allyl or CN;
$R_5$ is H, alkyl, alkenyl, alkynyl, aryl, heteroaryl, cycloalkyl heteroalkyl;
Z' is a halide or -$TR_5'$; wherein T is O, S, NH, or $CH_2$ and $R_5'$ is H, alkyl, alkenyl, alkynyl aryl, heteroaryl, cycloalkyl, heteroalkyl, acyl or sulfate;
D is a $C_{1-5}$ alkylene, $C_{1-5}$ heteroalkylene, heteroaryl or aryl,
and;
wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6;

the method comprising:

providing a first compound and a second compound in a solution, and reacting the first compound with the second compound;

wherein the first compound has the structure of (VI), (VII) or a salt thereof, and the second compound has the structure of (VIII), (IX) or a salt thereof, wherein the structures of (VI), (VII), (VIII) and (IX) are;

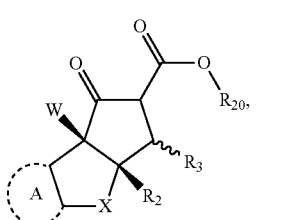

(VI)

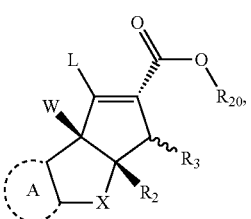

(VII)

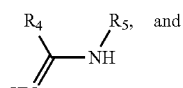

(VIII)

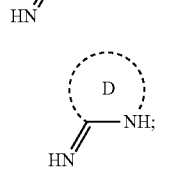

(IX)

wherein Q is $OR^G$ or $NR^HR^I$, wherein $R^G$, $R^H$ and $R^I$ are independently H or an alkyl, and wherein L is a leaving group.

15. The method of paragraph 14, wherein L is OH, $OT_s$, OAc, $OT_f$, or $OM_s$.

16. The method of paragraph 14, wherein the first compound and the second compound, are combined and heated to a temperature above about 50° C. for at least 2 minutes and less than 2 hours.

17. The method of paragraph 14, the second compound is provided in a molar amount greater than the molar amount of the first compound.

18. The method of paragraph 14, wherein the second compound is provided in a concentration less than 2 M.

19. A pharmaceutical composition comprising a compound made by the method of any one of paragraphs 14-18.

20. A pharmaceutical composition comprising a compound according to any one of paragraphs 1-13 and a pharmaceutically acceptable carrier, diluent or excipient.

21. A method of inhibiting a viral infection in a subject in need thereof, the method comprising: administering to the subject a therapeutically effective amount of the compound of any one of paragraphs 1-13 or the pharmaceutical composition of any one of paragraphs 19-20.

22. The method of paragraph 21, wherein the viral infection is caused by a Flavivirdae family virus or an alphavirus.

23. The method of paragraph 21, wherein the viral infection is caused by a virus selected from the group consisting of: Hepatitis C virus (HCV), Hepatitis B virus, Hepatitis A virus, Chikungunya virus, Dengue virus, Zika virus, yellow fever virus, Japanese encephalitis virus, West Nile virus, tick-borne encephalitis virus, and Omsk Hemorrhagic Fever Virus (OHFV).

24. The method of paragraph 21, wherein the subject is a human.

25. The method of paragraph 21, wherein the administering is oral administration or direct injection.

26. The method of paragraph 21, further comprising administering one or more additional agents.

27. The method of paragraph 26, wherein the agent is an antiviral agent.

28. A method of inhibiting a Hepatitis C viral infection in a subject in need thereof, the method comprising: administering to the subject a therapeutically effective amount of the compound of any one of paragraphs 1-13 or the pharmaceutical composition of any one of paragraphs 19-20.

29. The method of paragraph 28, wherein the subject is a human.

30. The method of paragraph 28, wherein the administering is oral or direct injection.

31. The method of paragraph 28, further comprising administering one or more additional agents.

32. The method of paragraph 31, wherein the agent is an antiviral agent.

33. The method of paragraph 31, wherein the agent is selected from the group consisting of: a small molecule, an antibody, a peptide, a genome editing system, and a nucleic acid.

34. The method of any one of paragraphs 28-33, wherein the agent is selected from the group consisting of: ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, pegylated interferon, pegylated interferon alpha-2b, interferon alpha-2a, elbasvir, and grazoprevir.

35. The method of paragraph 32, wherein the antiviral agent is sofosbuvir.

36. A method of inhibiting viral entry into a cell, the method comprising: contacting a cell with at least one compound of any one of paragraphs 1-13.

37. The method of paragraph 36, further comprising contacting the cell with an additional agent.

38. The method of paragraph 37, wherein the agent is an antiviral agent.

39. The method of paragraph 37, wherein the agent is sofosbuvir.

40. The method of paragraph 36, wherein the compound inhibits prohibitin or glycoprotein fusion with the cell.
41. The method of paragraph 36, wherein the cell is contacted with 12l or 12s.
42. The method of paragraph 36, wherein the cell is contacted with both 12l and 12s.
43. The method of any one of paragraphs 36-42, wherein the cell is a hepatocyte.
44. The method of any one of paragraphs 36-43, wherein the virus is Hepatitis C virus, Dengue virus, or Chikungunya virus.
45. A method of inhibiting prohibitin or glycoprotein fusion with a cell, the method comprising: contacting the cell with an effective amount of any one of the compounds of paragraphs 1-13.
46. The method of paragraph 45, further comprising contacting the cell with an additional agent.
47. The method of paragraph 45, wherein the agent is an antiviral agent.
48. The method of paragraph 45, wherein the inhibition of prohibitin or glycoprotein fusion inhibits viral entry.
49. The method of paragraph 45, wherein the cell is a hepatocyte.

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Example 1: Chemical Synthesis Enables Structural Reengineering of Aglaroxin c Leading to Inhibition Bias for HCV Infection As a unique rocaglate (flavagline) natural product, aglaroxin C displays intriguing biological activity by inhibiting HCV viral entry. To further elucidate structure-activity relationships and diversify the pyrimidinone scaffold, a concise syn-thesis of aglaroxin C was characterized utilizing a highly regioselective pyrimidinone condensation. More than forty aglaroxin C analogues were prepared utilizing various amidine condensation partners. Through biological evaluation of analogues, two lead compounds, 12l (CMLD012043) and 12s (CMLD012044), were discovered which show preferential bias for the inhibition of HCV viral entry vs. translation inhibition. Overall, the study demonstrates the power of chemical synthesis to produce natural product variants with both target inhibition bias and improved therapeutic indexes.

Rocaglates (flavagline) natural products were first isolated from the dried roots and stems of *Aglaia elliptifolia* Merr. (family Meliaceae) in 1982. Since then, over thirty rocaglate natural products have been identified with unique structures and intriguing biological activities. For instance, silvestrol (1, FIG. 1) was identified as an excellent translation inhibitor for cancer chemotherapy, whereas other related natural products and analogues (2-4) displayed similar activities. In previous studies, translation inhibition was found to be associated with inhibition of the DEAD box RNA helicase eIF4A. Owing to the interesting structures and biological activities of rocaglates, the synthesis of rocaglates and derivatives as well as investigations of their biology have been previously studied. For example, the enantioselective synthesis of aglaiastatin (5) and aglaroxin C (6) through biomimetic kinetic resolution is known. Subsequent studies revealed that 5 was a promising translation inhibitor. In contrast, 6, containing a fully substituted pyrimidinone core, showed only moderate translation inhibition. In separate studies, it was discovered that 6 inhibited hepatitis C viral (HCV) entry into host cells at a low μM concentration, potentially through inhibition of the prohibitins (PHBs) as viral entry factors. Notably, prohibitins 1 and 2 have been reported as general viral entry factors for other viruses including dengue virus type 2 (DENV-2) and Chikungunya. However, 6 did not induce cytotoxicity by translation inhibition at a concentration that is effective for inhibition of viral entry, providing a promising therapeutic index (TI) for potential treatment of HCV infection.

Figure 14:
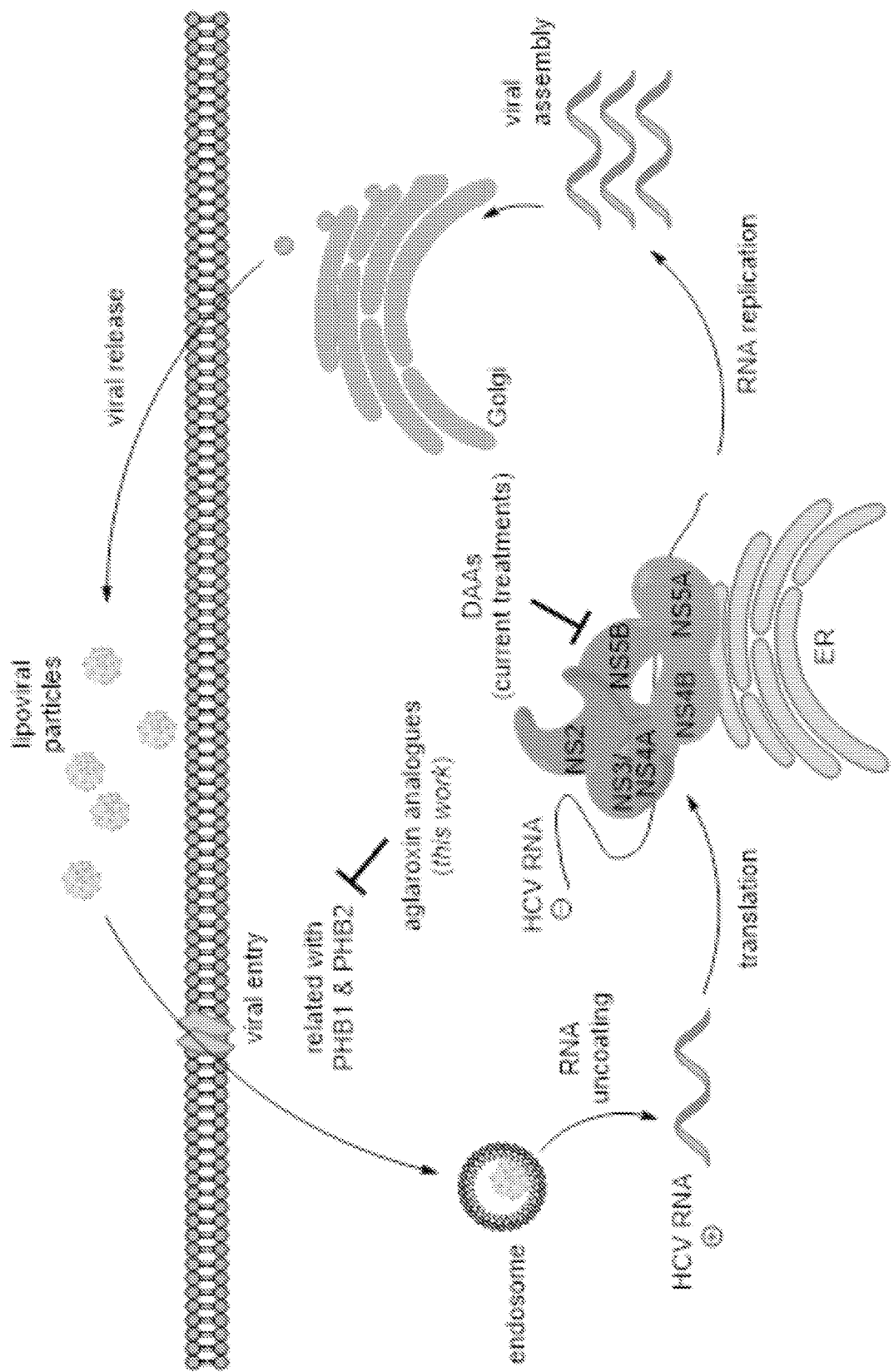
FIG. 14 shows Figure SI1 which is a graphic comparison between aglaroxin analogues as viral entry inhibitor and current DAAs as treatment for HCV.

HCV is a widespread viral pathogen. The recent estimated number of viral carriers is 143 million worldwide, and over 2% of the population in North America has been infected. In addition, chronic HCV infection causes severe liver diseases in carriers, including liver cancer and cirrhosis. In 2015, over a half million people died from diseases due to HCV infection. Recently, direct-acting antiviral agents (DAAs) have become available to cure HCV infection by inhibiting the function of non-structural (NS) viral proteins. However, treatment effects of DAAs vary across different genotypes of HCV, and HCV potentially may develop resistance to these agents. For example, the NS3 protease inhibitor simeprevir only treats genotypes 1 and 4 of HCV, and several signature resistance mutations have been identified against this treatment. Sofosbuvir, a top NS5B inhibitor, failed in HCV treatment which was associated with resistance mutations (FIG. 14). Accordingly, discovery of alternative treatments for HCV is sorely needed. As PHB-mediated cellular signaling pathways are required by all HCV genotypes to infect host cells, it is conceivable that a small molecule such as aglaroxin C (6) may block infection from multiple HCV genotypes. Additionally, targeting the host component for viral entry may create higher genetic barriers against resistance. Lastly, aglaroxin C and analogues may also be valuable for dissecting the mechanisms of HCV entry and may inhibit other viruses sharing the same entry mechanism.

The goal was to reengineer the structure of aglaroxin C (6) to increase activity against HCV entry while minimizing translation inhibition, which may lead to undesired cytotoxicity.

Figure 2:
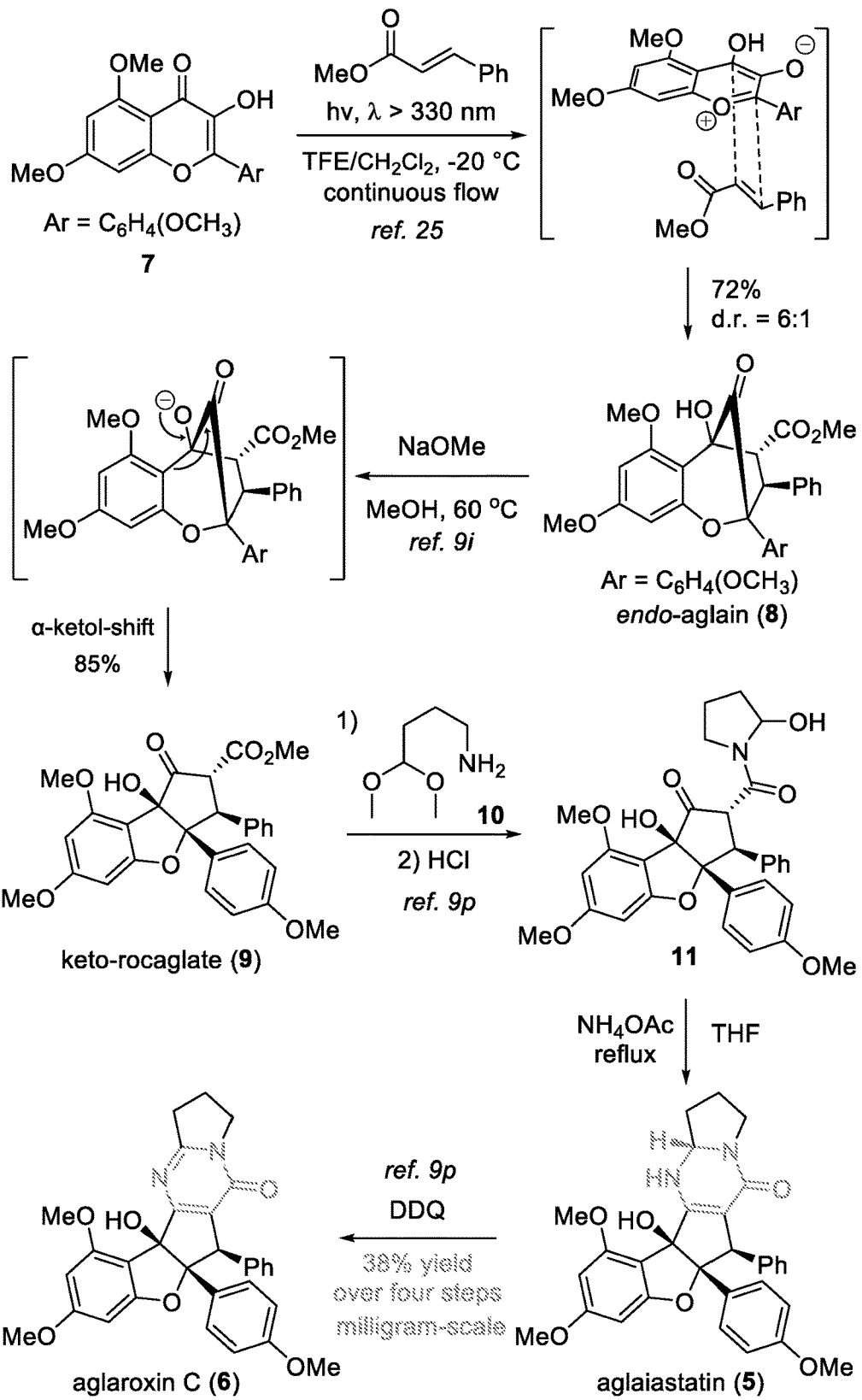
FIG. 2 shows the first-generation synthesis of aglaroxin C using stepwise pyrimidinone formation.

As the oxidation state change between 6 and aglaiastatin (5) led to different biological profiles, it was speculated that the pyrimidinone subunit of 6 may be important for inhibition of HCV viral entry vs. translation inhibition. Our first-generation synthesis of aglaroxin C (6) utilized a key intermediate, keto-rocaglate 9, which was synthesized through the excited state intramolecular proton transfer (ESIPT) [3+2] cycloaddition between 3-hydroxyflavone 7 and methyl cinnamate followed by α-ketol shift of the aglain intermediate 8, FIG. 2. However, the late stage pyrimidinone synthesis in the first-generation synthetic route is not ideal for rapid analog synthesis, affording 6 in low yield on a multi-milligram scale.

A stepwise pyrimidinone synthesis can suffer from poor functional group tolerance in analogues due to the use of both acidic and oxidative conditions. Moreover, use of tethered aminoacetals such as 10 in the ester-amide exchange to produce intermediate 11 considerably narrows the diversity of accessible analogues due to limited availability of such building blocks. Therefore, a streamlined synthesis of aglaroxin analogues was pursued through late stage, one-step pyrimidinone formation FIG. 3.

Results and Discussion

Development of a Direct Pyrimidinone Formation.

Figure 3:
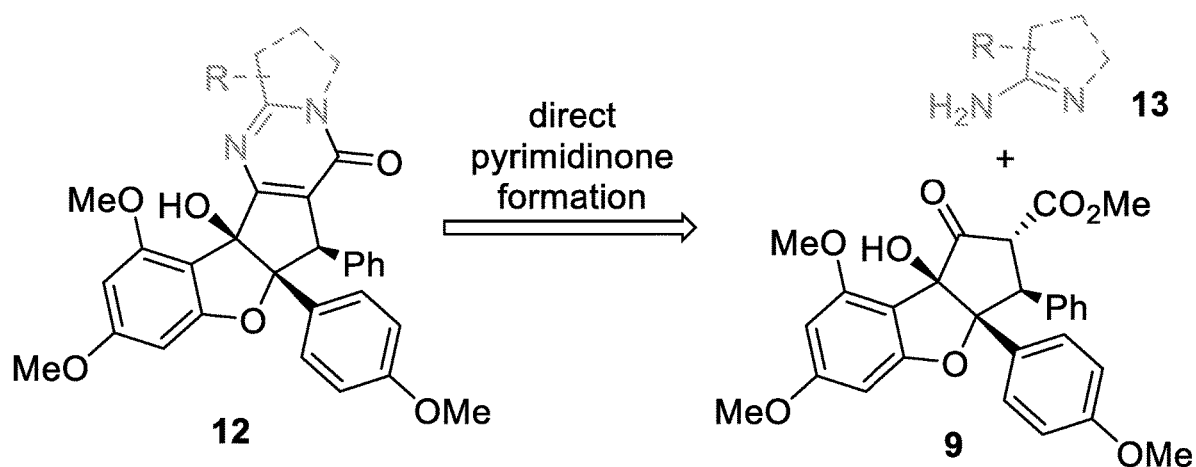
FIG. 3 shows retrosynthetic analysis for aglaroxin C analogues.

The second-generation synthetic route FIG. 3, which relies on condensation of keto-rocaglate (9) with commercially available amidines 13, was expected to flexibly provide analogues (12) for biological experiments. Pyrimidinones have served as biologically important substructures in both drugs and natural products. There are many well-established and practical methods for the synthesis of pyrimidinones and pyrimidines, including the Traube synthesis of purines. Thus, it was considered that late stage construction of the pyrimidinone core of aglaroxin analogues would be useful. However, condensation between the structurally complex substrate 9 and amidines 13 can be challenging. In particular, the highly ionizable tertiary, benzylic alcohol adjacent to the keto ester moiety may provide unexpected reactivity under the reaction conditions.

Figure 4:
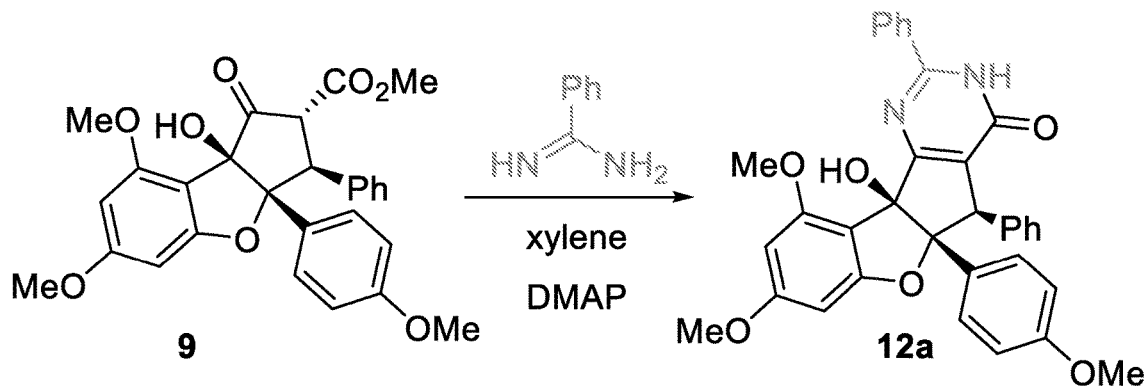
FIG. 4 shows Table 1: optimization of the direct pyrimidinone formation and side products observed.

The initial model study for pyrimidinone formation employed benzamidine as a simplified condensation partner. Microwave conditions, FIG. 4 (Table 1, entry 1), produced minimal amounts of pyrimidinone 12a in an unsatisfactory yield of 28% (determined by 1H NMR analysis) due to low conversion.[9p] Thermal conditions (entry 2) resulted in full consumption of 9, while cyclopentapyrimidinedione 16 and 3,5-dimethoxyphloroglucinol were found as the major identified side products. The formation of fragmentation product 16 was found to correlate with the amount of 4-dimethylaminopyridine (DMAP) employed; reduction to 0.3 equivalents of DMAP minimized production of 16 (entry 3) but also led to formation of an unexpected cyclization product, oxazoline 15. The structure of 15 was confirmed by single crystal X-ray crystal structure analysis. Reduced equivalents of the benzamidine reaction partner resulted in an incomplete reaction, with increased production of decarboxylation product 14 and retro-Nazarov products 17 (entries 4 & 5). Next, it was discovered that diluting the reaction eight-fold improved the yield of 12a (entry 6). Increasing both temperature and reaction time under dilute conditions eliminated the production of 15, but also led to a lower yield of 12a in favor of significant amounts of 16 (entry 7). Gratifyingly, by reducing the reaction time to 45 minutes, a 90% NMR yield of 12a was obtained with minimal fragmentation to 16 (entry 8); ultimately, an 81% isolated yield of 12a was obtained on a 100-mg scale. Interestingly, it was discovered that the model reaction gave the almost identical yield in absence of DMAP under the optimized conditions (entry 9), but better reproducibility was achieved when amidine hydrochloride salt was used with DMAP (vide infra).

Proposed Mechanistic Pathway.

Figure 5:
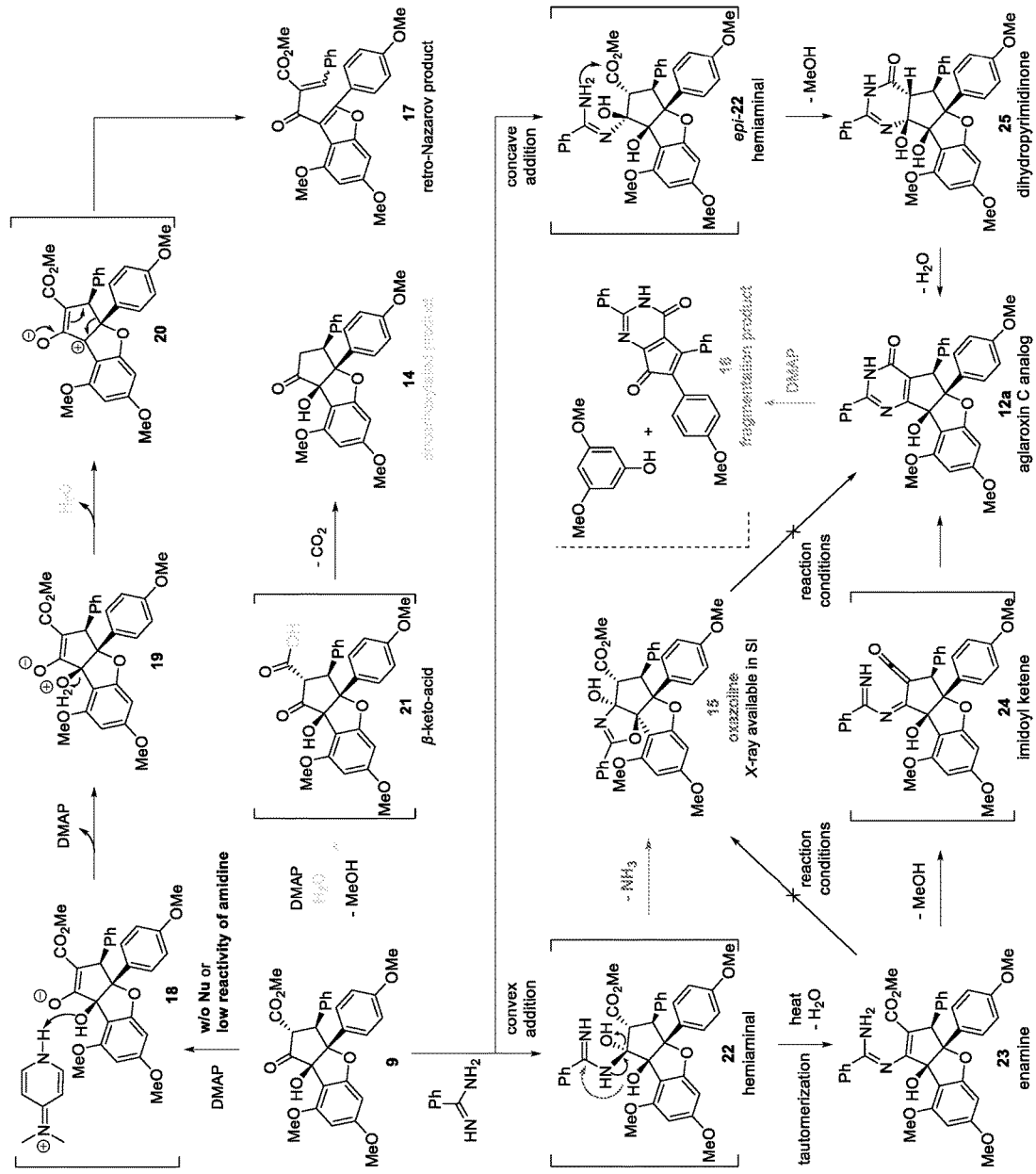
FIG. 5 shows possible mechanistic pathways and products of direct pyrimidinone formation.

According to trends observed during reaction optimization, the mechanistic pathway depicted in FIG. 5 was proposed. It was postulated that water generated from the pyrimidinone condensation may hydrolyze 9 to the β-ketoacid intermediate 21, which undergoes decarboxylation to ketone 14. When no nucleophile was used, 14 and retro-Nazarov product 17 were obtained. Presumably DMAP may promote intramolecular proton transfer to 19 followed by the extrusion of water to afford the retro-Nazarov precursor 20, whereas the formed water triggered decarboxylation of 9 (an alternative mechanism is shown in the SI). In the presence of the amidine, the desired formation of hemiaminals 22 and epi-22 appears to compete with decarboxylation and retro-Nazarov reaction, which can be enhanced through use of increased equivalents of the amidine. Based on the Katrizky mechanism determined for the Traube reaction of β-keto esters and amidines, two possible pathways may be envisioned for the formation of pyrimidinone 12a. In one mechanism, hemiaminal epi-22, generated from disfavored concave-addition of the amidine to 9, may cyclize to dihydropyrimidinone 25 followed by extrusion of water. In contrast, hemiaminal 22, obtained from amidine addition to the convex face of 9, has an anti-relationship between the aminal and ester thereby preventing direct cyclization. Instead, loss of water would produce the observed enamine 23, which then cyclizes to 12a through extrusion of methanol generating imidoyl ketene 24 followed by a 6πr-electrocyclization to pyrimidinone 12a. To support the formation of hemiaminal 22, the oxazoline byproduct 15 was formed through cyclization of the tertiary alcohol of 22 to the amidine carbon followed by extrusion of ammonia. The formation of 22 is also supported by our isolation of enamine 23 from a 250 mg scale reaction, where a 28% yield of 23 was found to precipitate after 10 minutes; it was discovered that 23 can also be synthesized in 60% yield using 9 and benzamidine at 60° C. in toluene. Interestingly, isolated 23 was found to solely produce 12a with no observed formation of 15 when 23 was resubjected to the reaction conditions. It was rationalized that the sp³-hybridized hemiaminal carbon of 22 allows for a conformation necessary for intramolecular cyclization, whereas the sp²-hybridized enamine carbon of 23 prevents a similar cyclization. This conforms to the observation that elevated temperatures facilitate extrusion of water generating enamine 23 and minimize formation of byproduct 15. In contrast, 15 did not generate 12a under the reaction conditions. In a control experiment, DMAP was found to accelerate the fragmentation of 12a into 16 and 3,5-dimethoxyphloroglucinol.

Second-Generation Synthesis of Aglaroxin C.

After determining optimal conditions for direct pyrimidinone formation, these conditions were applied to synthesize aglaroxin C (6). In this case, the requisite pyrrolidin-2-imine was commercially available as an HCl salt, FIG. 6 (Table 2). Initial attempts using stepwise free-basing protocols failed due to the high-water solubility of the amidine; accordingly, in-situ free-basing conditions were performed for optimization studies. Using excess base (entries 1 and 2), no conversion of substrate 9 was observed after refluxing for 12 h. As 9 exists as mixture of enol/keto isomers, presumably excess base favors formation of an unreactive enolate. In contrast, use of excess pyrrolidin-2-imine HCl salt (entry 3) did not induce pyrimidinone formation. It was assumed that DMAP is protonated by the amidine salt which negated its function. When a slight excess of amidine vs. NaOMe (entry 4) was used, 6 was obtained in 19% isolated yield. Consistent with our earlier optimization efforts, use of increased concentration and 12 h reaction time resulted in a complex reaction mixture containing fragmentation products (entry 5). Finally, use of 3.0 equiv. of amidine salt and 2.95 equiv. of NaOMe along with a catalytic amount of DMAP (40 mol %, 130° C.) afforded 6 in 76% isolated yield on a 100-mg scale (entry 6).

Synthesis of Aglaroxin Analogues.

Figure 7:
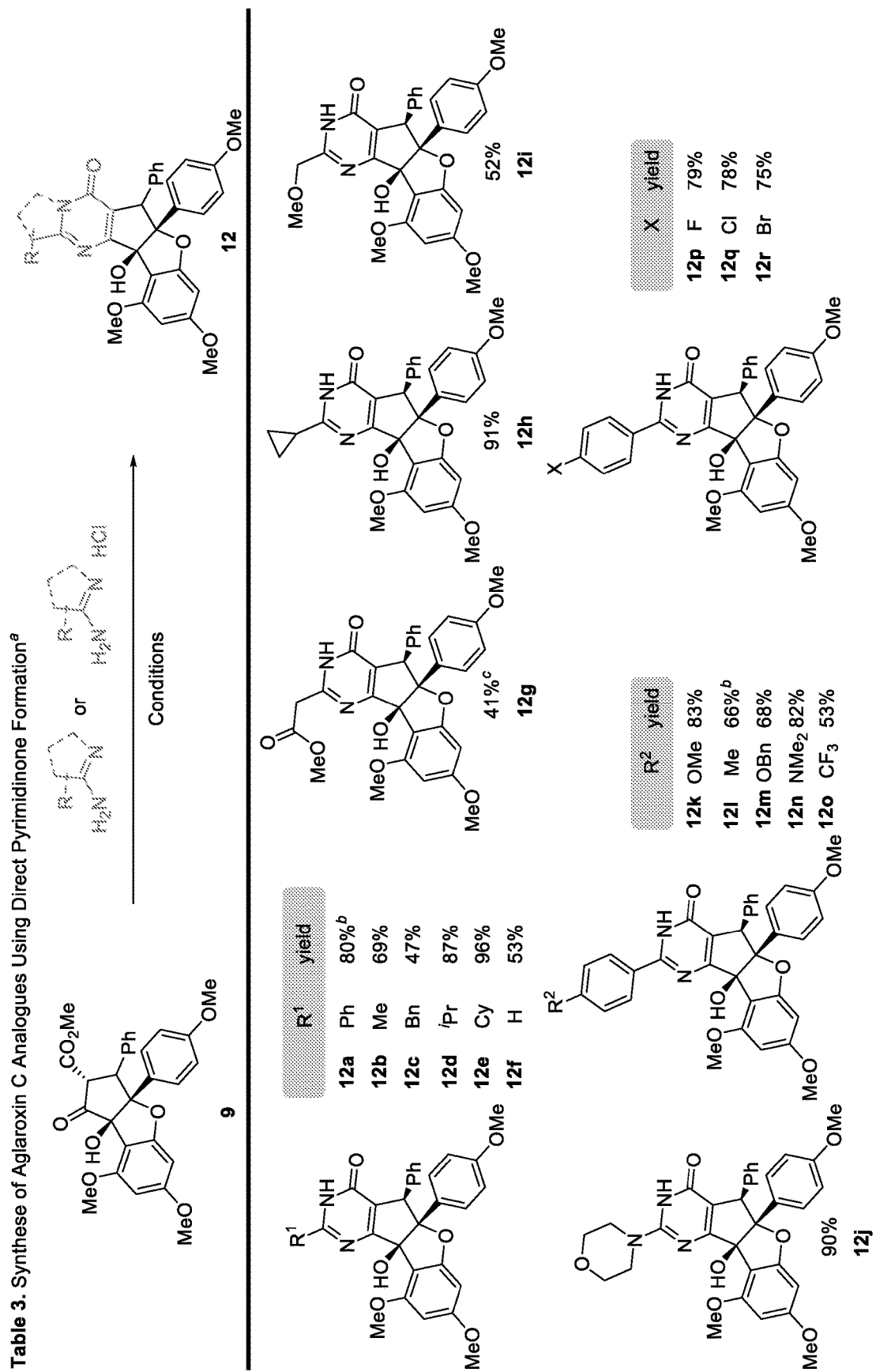
FIG. 7 shows Table 3: synthesis of aglaroxin C analogues using direct pyrimidinone formation with amidines.
Figure 7:
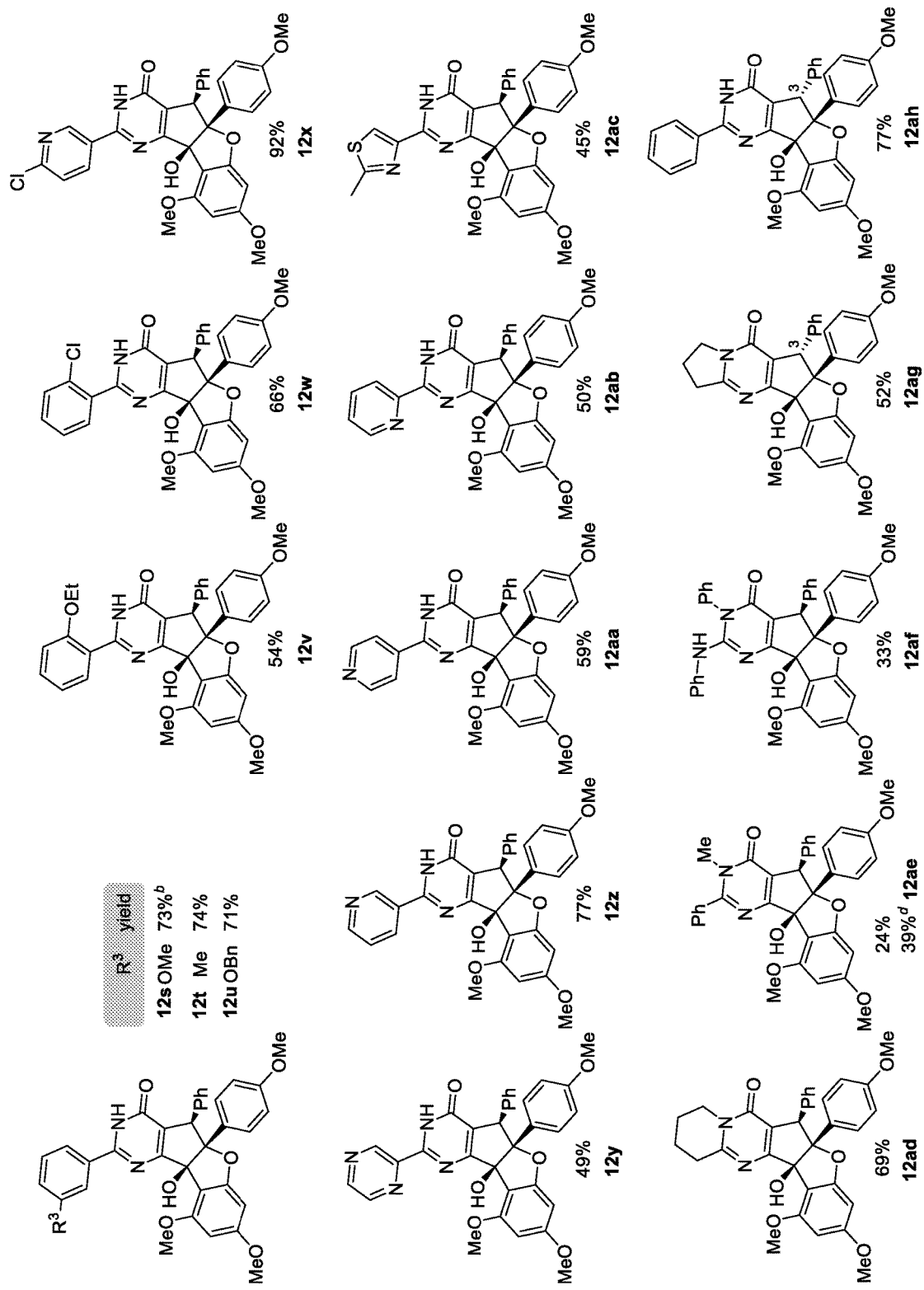

With reliable annulation protocols available using both amidines and amidine salts, a library of aglaroxin analogues were synthesized, FIG. 7 (Table 3). In general, direct pyrimidinone formation was found to tolerate both aromatic and aliphatic amidines. Consistent yields were observed for formation of C-substituted pyrimidinones (12b-12f). For instance, simple aliphatic amidines reacted with 9 to afford such as iso-butanamidine and cyclohexylcarboxamidine afforded the desired products 12d and 12e in excellent yields. Interestingly, condensation of carbomethoxyformamidine with 9 was followed by an unexpected decarboxylation to produce the non-substituted product 12f in 53% yield. Moreover, it was discovered that the pyrimidinone condensation could tolerate various functional groups, including ester 12g (41%), cyclopropane 12h (91%), and methoxyl methylene 12i (52%). Ester exchange was observed when ethyl amidinoacetate was employed, producing compound 12g. Additionally, guanidine-type reaction partners successfully underwent condensation, yielding products such as 12j (90% yield).

Preliminary biological studies of the analog set indicated that C-aryl pyrimidinones consistently possessed good inhibition of HCV infection with low cytotoxicity (vide infra). Accordingly, additional C-aryl pyrimidinone analogues were synthesized with a variety of substitution patterns, with an initial focus on para-substituted aryl benzamidines, FIG. 7 (Table 3, 12k-12r). Generally, condensations tolerated both electron-rich and deficient benzamidines; however, it was discovered that greater amounts of fragmentation products were generated using electron-deficient amidines (cf compounds 12k-12n 66-83% yield) with compound 12o, which was generated in 53% yield along with the corresponding fragmentation products. Compound 12m was further subjected to hydrogenolysis to afford the free phenol which may serve as a potential handle for further modifications. As expected, analogues including para-halides (12p-12r) were synthesized in 70-80% yields. Such compounds may also allow for late stage functionalization via aminations and $S_NAr$ reactions. It was discovered that meta-substituted benzamidines were also workable, affording products (12s-12u) using the standard protocol in reasonable yields (71%-73%). Using the sterically hindered ortho-substituted benzamidines, 12v and 12w were synthesized in moderate yields (54% and 66%). Six C-heteroaryl substituted analogues (12x-12ac) were also synthesized; in these cases, substantial fragmentation of the desired products were observed. Only 12x and 12z were obtained in reasonable yields (92% and 77%, respectively), while compounds 12y and 12aa-12ac were obtained in yields averaging 50%.

As aglaroxin C FIG. 6 (6, Table 2) was synthesized regioselectively using an unsymmetrical amidine, additional unsymmetrical amidines were tested in the pyrimidinone formation. Among all products formed, it was found that the N-substituent was situated exclusively on the nitrogen adjacent to the pyrimidinone carbonyl (12ad-af). During the synthesis of 12ae, a small amount of oxazoline 15 was obtained as the only observable side product. This result supports our mechanistic proposal FIG. 5 wherein the less sterically hindered, unsubstituted nitrogen likely engages in initial hemiaminal formation with 9. Along these lines, 12ac, a ring-expanded analog of 6, was synthesized in 69% yield. Unlike 12ad, adducts 12ae and 12af were synthesized in 24 and 33% yields, respectively; these reactions generated significant amounts of retro-Nazarov and decarboxylated products, suggestive of lower overall reactivities among the N-substituted amidines. The yield of 12ae was optimized to 39% by increasing the reaction concentration to 0.2 M. Finally, using exo-keto-rocaglate as the starting material, compounds 12ah and 12ag, the C-3 epimers of 12a and 6, were synthesized in 77 and 52% yields, respectively.

Figure 8:
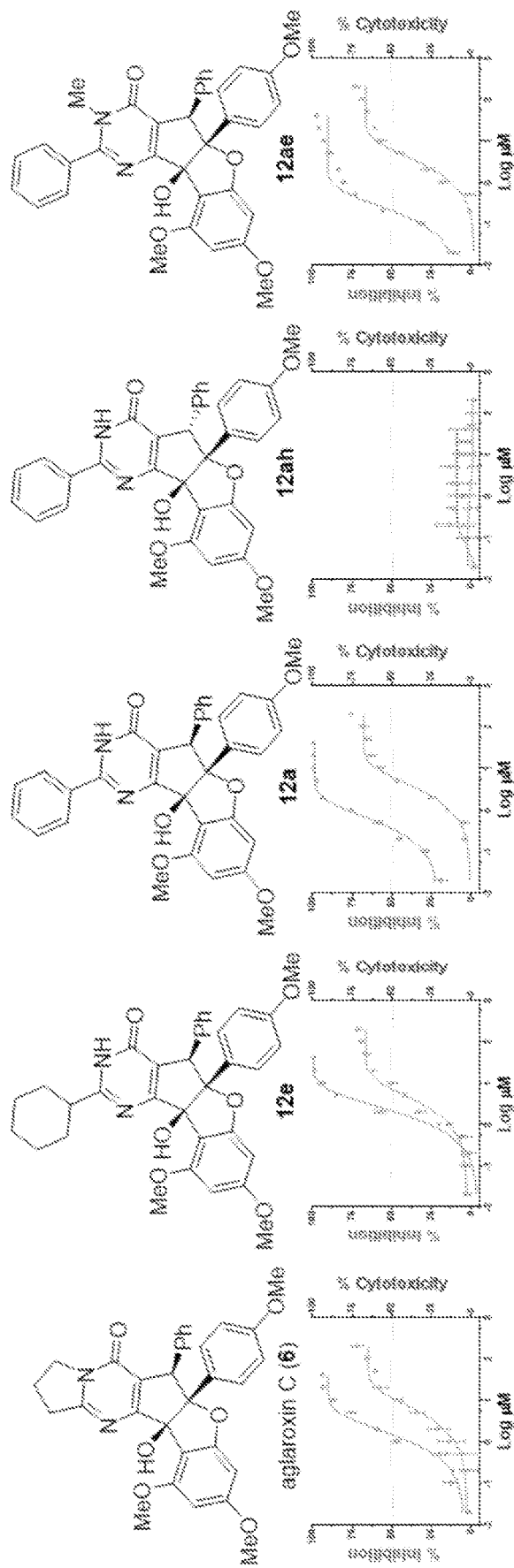
FIG. 8 shows Table 4 demonstrating the structure-activity relationship of aglaroxin C analogues in the HCV infection inhibition assay.
Figure 8:
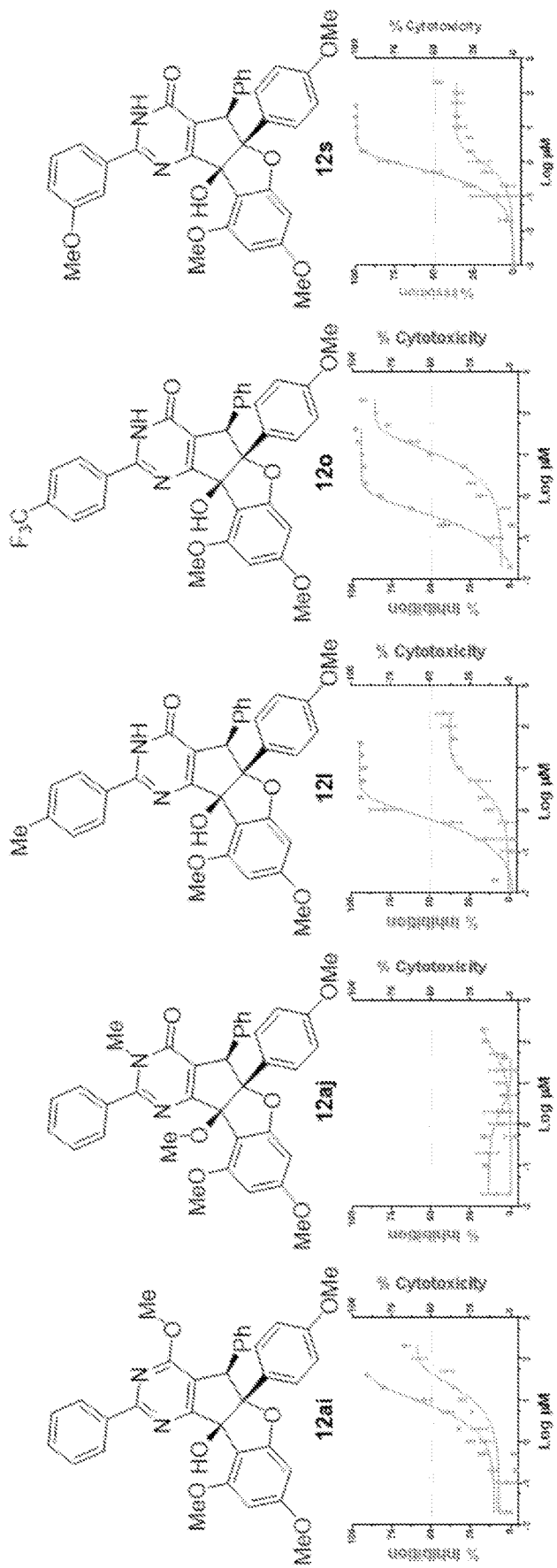

As a comparison to the direct condensation with unsymmetrical amidines, alkylations of 12a were performed to produce compounds 12ai-aj FIG. 8 (Table 4) 12al-an (see Supporting Information). Unfortunately, all attempted alkylations displayed poor chemo- and regioselectivity, favoring the undesired O-alkylation products such as O-methoxypyrimidine 12ai.

Biological Studies

Structure-Activity Relationships.

The library of (±)-aglaroxin analogues and side products against HCV infection were evaluated, and also tested their corresponding cytotoxicity in human hepatic (Huh) 7.5.1 cells. In comparison to aglaroxin C (6), C-alkyl substituted pyrimidinones 12b-d and 12h (Table 3, FIG. 7) exhibited increased inhibition against HCV infection, whereas 12e-g had decreased activities. Nevertheless, the C-aryl substituted products (12a, k-w) showed a promising increase of inhibition of HCV infection with similar or reduced cytotoxicity in comparison to 6. Excitingly, 12l (CMLD012043) and 12s (CMLD012044) showed a three-fold greater inhibition of HCV infection in comparison to 6, while 12l and 12s exhibited relatively low cytotoxicity to Huh-7.5.1 cells (less than 50% cell death at 200 µM). Thus, the two lead compounds (12l and 12s) provided excellent selectivity indexes (SI) in inhibiting HCV infection (vide infra). Notably, among all the C-heteroaryl substituted aglaroxin analogues (12x-12ac), only 12y and 12ab displayed slightly increased inhibition of HCV infection relative to 6. The six-membered ring analog 12ad and guanidine-type adducts 12j and 12af were found to have moderate antiviral activity.

To further understand structure-activity relationships (SAR) among aglaroxin analogues, compounds are highlighted in FIG. 8 (Table 4) along with dose-response curves depicting their effectiveness in both HCV infection and cytotoxicity assays. As a benchmark compound, 6 was found to inhibit HCV infection with an $EC_{50}$ of 1.3 µM and showed a $CC_{50}$ of 12 µM. Of note, $EC_{50}$ and $CC_{50}$ values were calculated according to the fitted sigmoid curves, which are reported as absolute values (indicating the concentration of compounds providing 50% inhibition and 50% cell death, respectively). Next, the $EC_{50}$ of cyclohexyl-(12e) and phenyl-substituted (12a) pyrimidinones were compared and it was discovered that C-aryl substitutions led to improved potency against viral infection (420 nM vs. 2.5 µM). The C-3 epimer (12ah) of 12a was found to be inactive against HCV infection and no cytotoxicity. It is apparent that a syn-relationship of the two aryl rings on the cyclopenta[b] benzofuran core is crucial for HCV inhibition.

Based on the observation that N-methylated isomer 12ae was one-fold more active than 12a ($EC_{50}$ 0.2 µM vs. 0.42 µM) with similar cytotoxicities ($CC_{50}$ 7.3 µM vs. 8.1 µM), methylation was utilized to evaluate other sites for introduction of target identification tags. In contrast to N-methylation, a decrease in inhibition of HCV infection ($EC_{50}$=9.2 µM) was observed with the O-methylated pyrimidine 12ai. The doubly methylated product 12aj was also found inactive and non-toxic. Finally, the impact of substituting the conjugated C-aryl group of the pyrimidinone was studied (cf 12l, 12o, and 12s). Compound 12o, with an electron-withdrawing $CF_3$-group, had higher cytotoxicity ($CC_{50}$=10 µM), and only a one-fold better $EC_{50}$ (0.24 µM) for HCV inhibition than 12l and 12s ($EC_{50}$~0.5 µM). The two lead compounds 12l and 12s displayed improved $EC_{50}$s in the viral infection assay but displayed low cytotoxicity; neither compound reached 50% cell death up to 200 µM concentration (maximum cytotoxicity plateau: 40% and 35% cell death for 12l and 12s, respectively).

Of note, a similar plateauing of cytotoxicity using aglaroxin C (6) and its analogues (12e, 12a, and 12ae) was observed. In contrast, the 4'-trifluoromethylphenyl analog 12o achieved close to 100% cell death. For a more reliable comparison of cytotoxicities among these compounds, the area under the cytotoxicity curve (AUC) was calculated by integration, an alternative method for accurately quantifying low cytotoxicity. In this manner, $AUC_{0.2-200}$ analysis indicates that 12e, 12a, and 12ai share similar cytotoxicities to 6, whereas 12l and 12s exhibit relatively lower cytotoxicities. Extending this analysis to compare the SI among the analogues, the $AUC_{0.2-20}$(EC/CC) ratios were calculated, determining that 12ae, 12l, 12o, and 12s had wider therapeutic windows (0.6 to greater than 2-fold increase in the SI) than 6. Based on the performance of 12l and 12s using these metrics, these two lead compounds were utilized for further biological investigations including mechanism studies.

Figure 9:
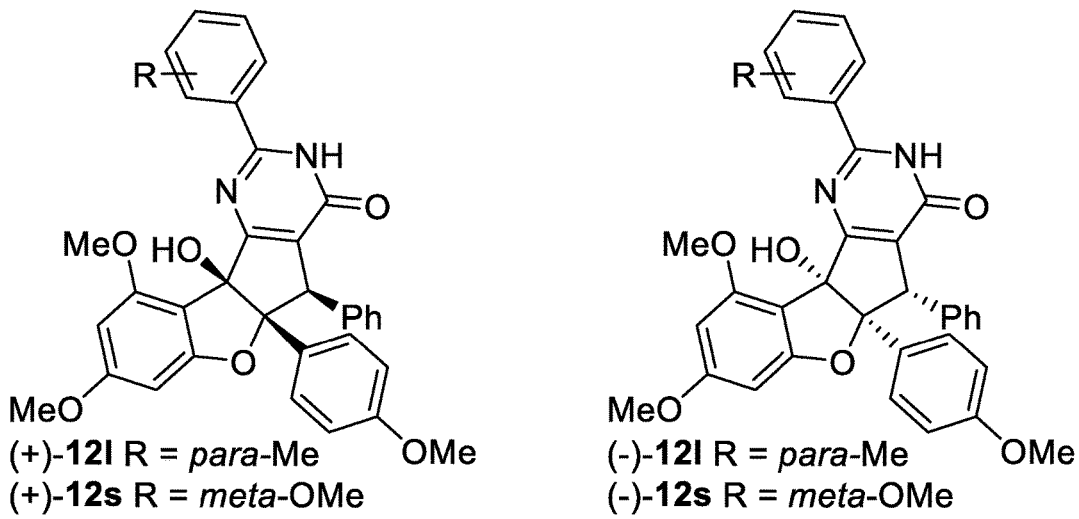
FIG. 9 shows Table 5: chirality-based biological profiles of lead compounds.
Figure 10A:
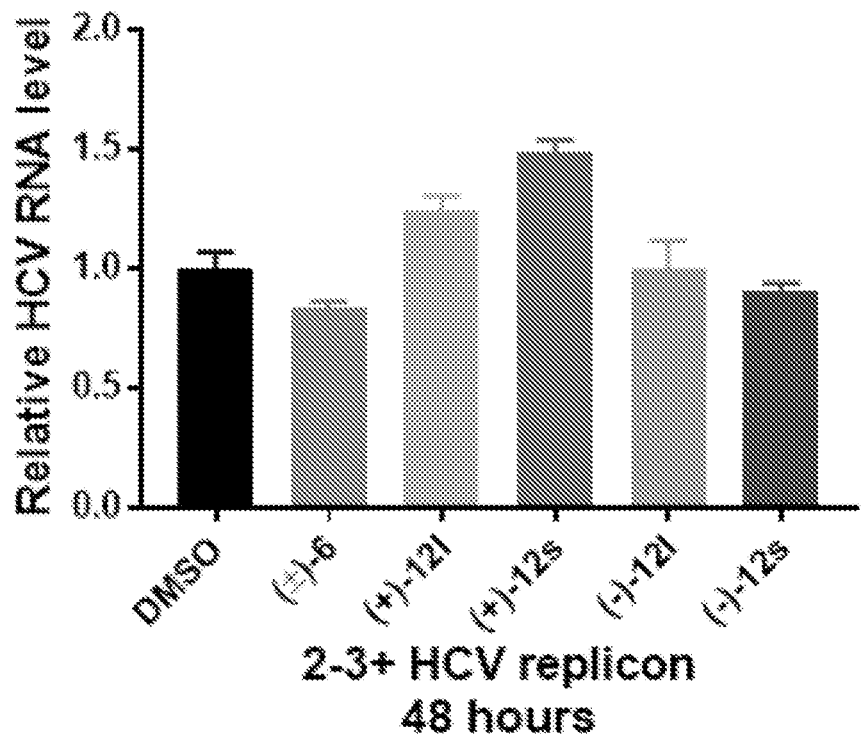
FIG. 10A-10D demonstrates aglaroxin C and analogues (12l and 12s) neither inhibit HCV RNA replication nor protein translation. HCV replicon cell line 2-3+ was treated with the indicated compounds for 3 h. Cells were incubated for an additional 48 hours (FIG. 10A and FIG. 10C) or 72 hours (FIG. 10B and FIG. 10D). Cellular RNA or protein was isolated for quantifications of HCV viral RNA by real-time PCR (FIG. 10A and FIG. 10B) or structural protein NS5 by Western blotting (FIG. 10C and FIG. 10D).
Figure 10B:
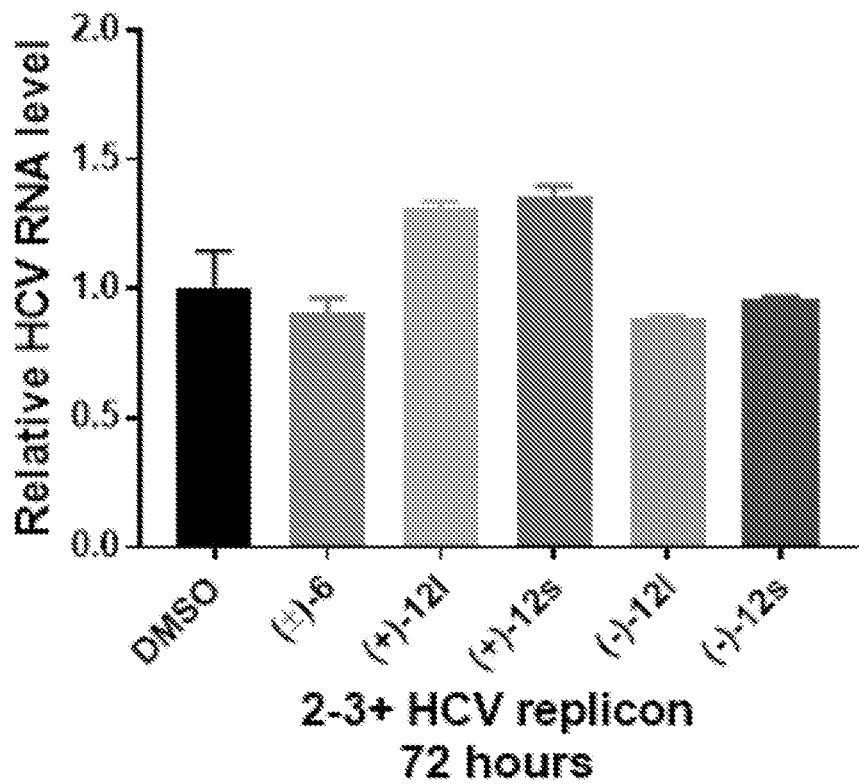
Figure 10C:
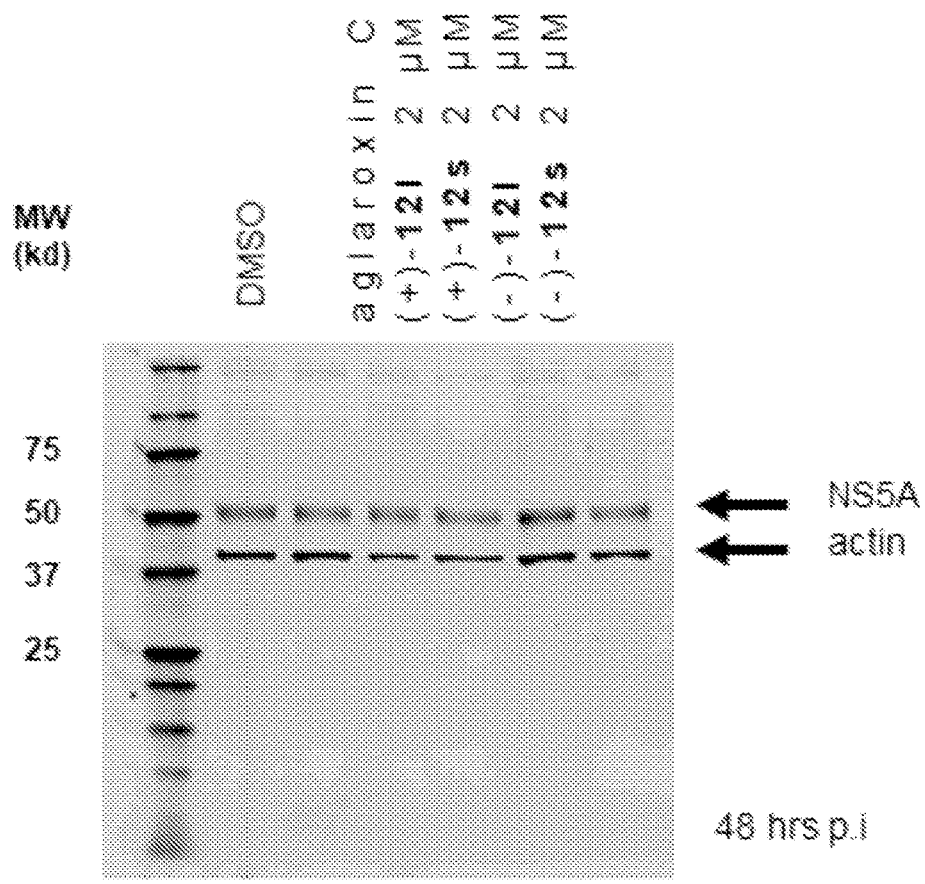
Figure 10D:
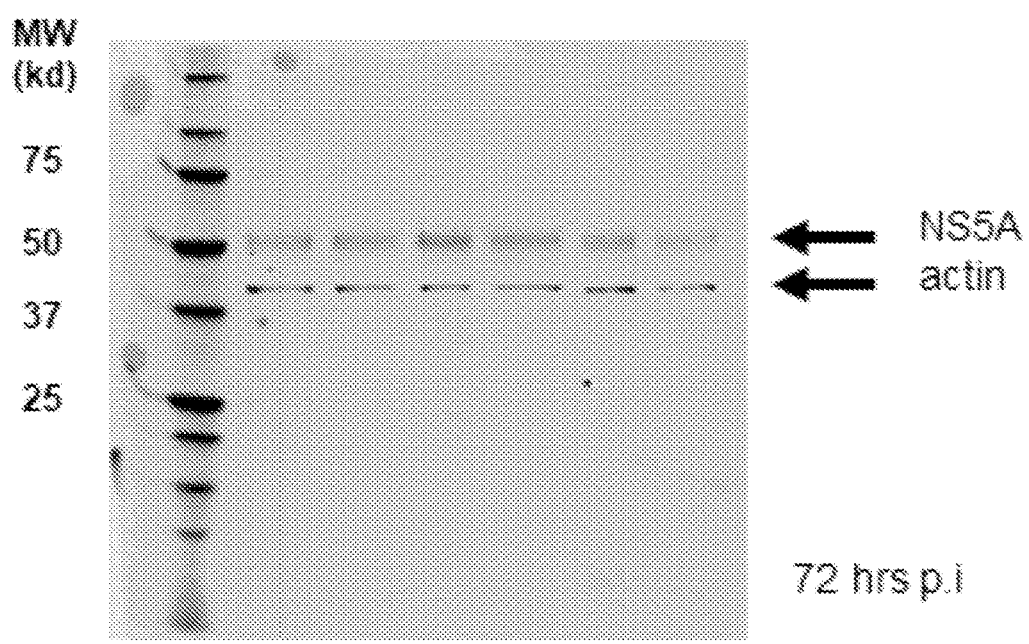

To further characterize the mode of action of the two lead compounds 12l and 12s, each of their respective enantiomers were independently synthesized and investigated their biological activities in both the HCV viral infection and cytotoxicity assays FIG. 9 (Table 5). As expected, only (+)-12l and (+)-12s displayed HCV inhibition, whereas the other enantiomers (−)-12l, and (−)-12s were found to be inactive and non-toxic. Interestingly, it was discovered that maximum cytotoxicity plateau of both active enantiomer (+)-12l and (+)-12s increased substantially compared to their racemic counterparts (±)-12l and (±)-12s. To verify this result, a secondary MTS cell viability assay was also performed on racemic compounds (±)-12k, (±)-12l, and (±)-12o, and showed nearly identical toxicity curves as were observed in the CellTiter-Glo assay. While these results warrant further investigation, they suggest a potential rationale for the observed SI enhancement in which the "inactive" enantiomers may reduce or otherwise mitigate the cytotoxic effects of the active species through an as-yet undefined mechanism.

Aglaroxin Analogues do not Affect HCV RNA Replication and Translation.

Figure 11B:
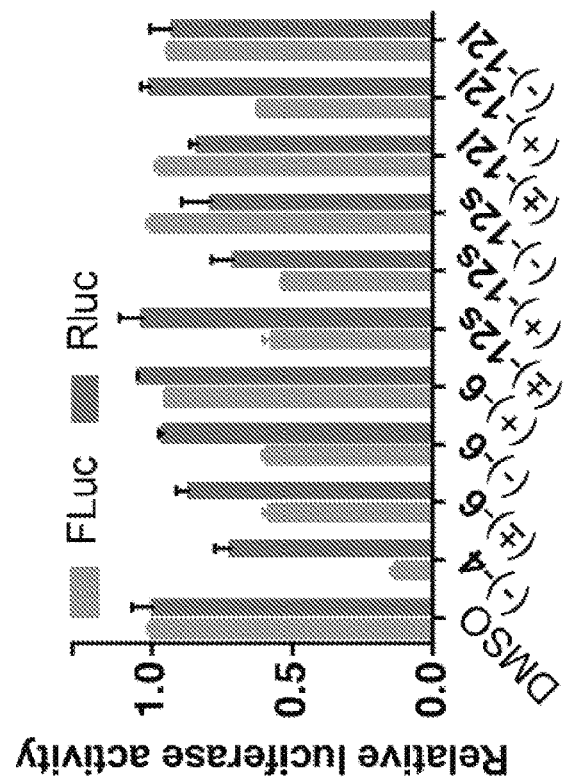
FIG. 11A-11B shows aglaroxin type analogs which displayed minimal translation inhibition in the comparison to (−)-4(CR 1-31-B).

Next, the ability of the aglaroxin C analogues to inhibit HCV RNA replication and mRNA translation was investigated using an HCV replicon system which harbors a full-length HCV Genotype 1b RNA genome. In replicon cells, HCV RNA replicates and is translated into viral proteins without forming infectious viruses. Hence, this system permits accurate assessment of any effects on viral RNA replication and translation. As shown in FIG. 10A-10D, compounds (+)-12l and (+)-12s when used at 2 µM for 3 h did not inhibit HCV RNA replication or protein synthesis. This data implies that the observed inhibitory effects of (+)-12l and (+)-12s were unlikely due to inhibition of viral RNA replication or mRNA translation. To corroborate these findings, an in vitro translation inhibition assay was assembled where a bicistronic reporter mRNA was programmed for translation in Krebs-2 extracts FIG. 11A-11B.

Figure 11A:
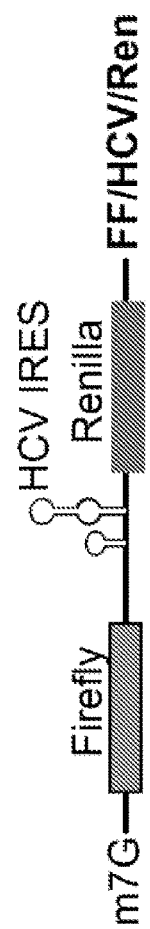

In this system, translation of the Firefly luciferase (FLuc) translation is cap-dependent whereas *Renilla* luciferase (RLuc) translation is dependent upon the HCV internal ribosome entry site (IRES) FIG. 11A. It was observed that translation inhibition of firefly luciferase by 6 and analogues 12l and 12s were minimal in comparison with CR-1-31-B FIG. 1-4, a highly potent rocaglate translation inhibitor showing strong inhibition of cap-dependent protein synthesis FIG. 11B. This data suggests that HCV mRNA translation is not inhibited by 6 and its analogues 12l and 12s.

Figure 12B:
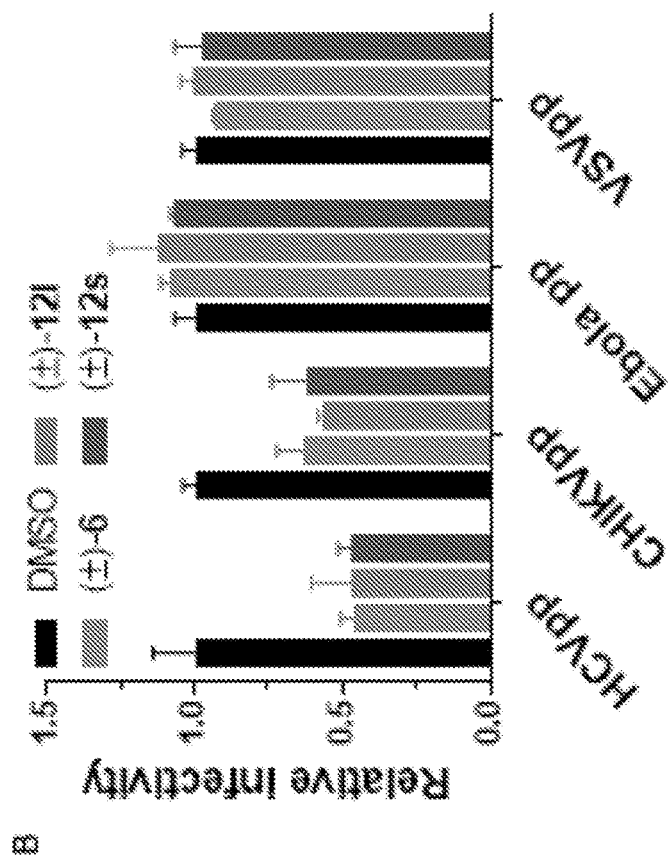
FIG. 12A-12D demonstrates that aglaroxin C (6) and its analogues (12l & 12s) inhibit viral entry.
Figure 12A:
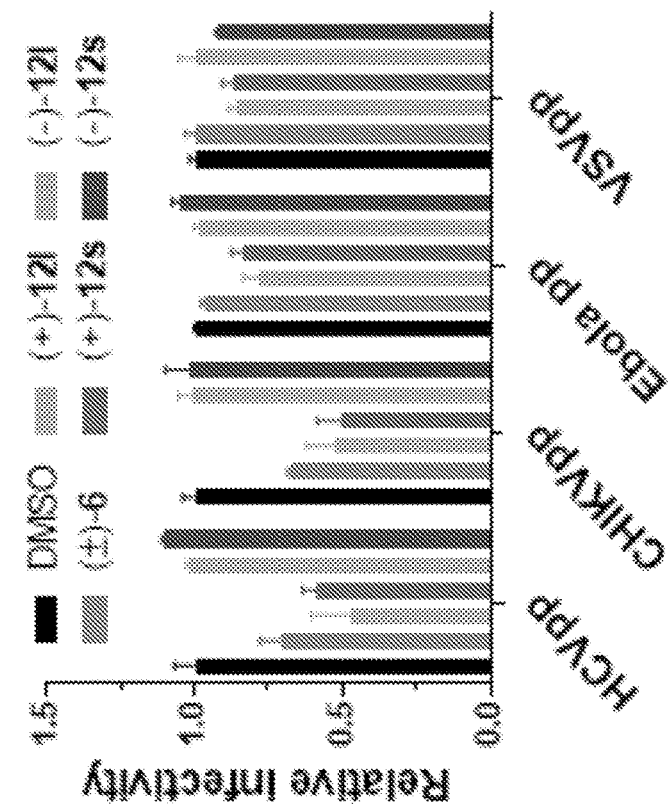
Figure 12D:
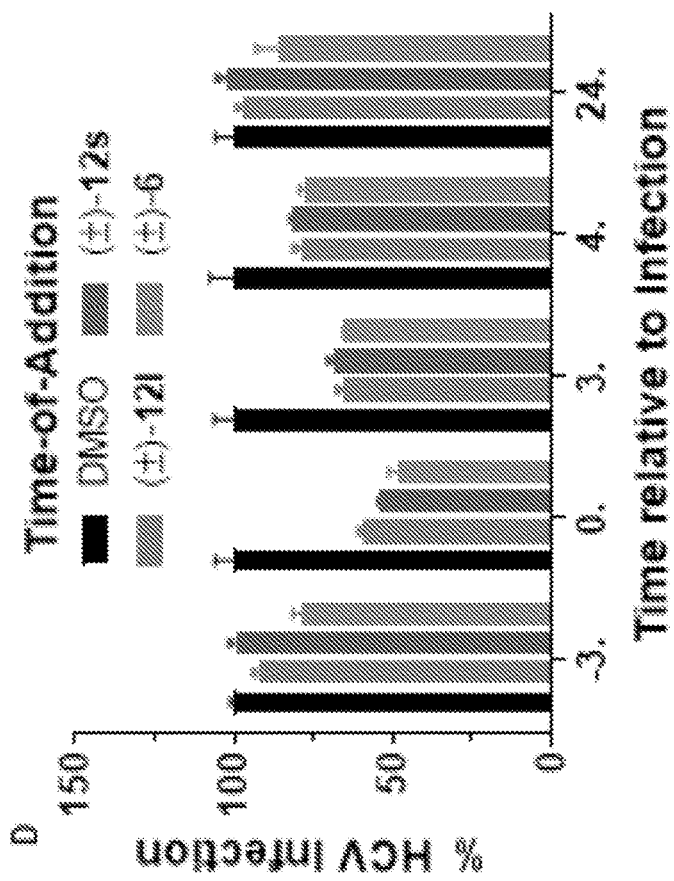
Figure 12C:
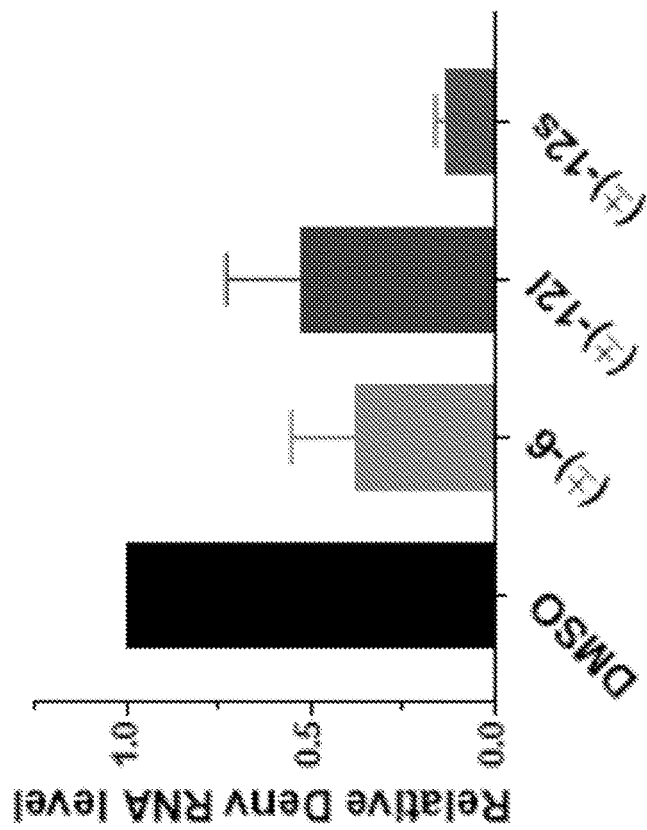

Aglaroxin Analogues Inhibit HCV Entry. As aglaroxin C was previously reported to inhibit HCV entry, two sets of experiments were carried out to test whether compounds 12l and 12s also inhibit viral entry. Firstly, infectious lentiviral pseudotypes bearing glycoproteins of HCV (HCVpp), Chikungunya virus (CHIKVpp), Ebola virus (Ebolapp), and vesicular stomatitis virus (VSVpp) were generated. Compositionally, these pseudotyped viruses differ only in viral envelopes because they are packaged using the same lentiviral reporter construct with a separate construct expressing specified viral envelope protein. Hence, the only difference among these pseudoviral particles is the mode of entry, which is dictated by the particular viral glycoprotein found on the viral envelopes. Compounds 12l and 12s, as both the racemates and single (+)-enantiomers, specifically inhibited HCVpp and CHIKVpp but not Ebolapp and VSVpp FIG. 12A-12B. Interestingly, like rocaglamide, compounds (+)-12l and (+)-12s as well as their racemic versions also inhibited Dengue virus infection FIG. 12C. It is worth mentioning that HCV, Dengue virus, and CHIKV all utilize PHBs to enter cells; further studies are warranted to determine whether compounds 12l and 12s directly target PHBs. Secondly, to confirm inhibition of HCV entry, time-of-addition experiments were performed using the lead compounds 12l and 12s wherein compounds were added at different times relative to when the virus was added to cells. Similar to 6, 12l and 12s displayed maximal anti-HCV activity when added together with the virus, but partially lost their activity when added 3 h after infection was initiated FIG. 12D. This finding confirmed that 12l and 12s are preferentially inhibiting viral entry.

Summary

Figure 13:
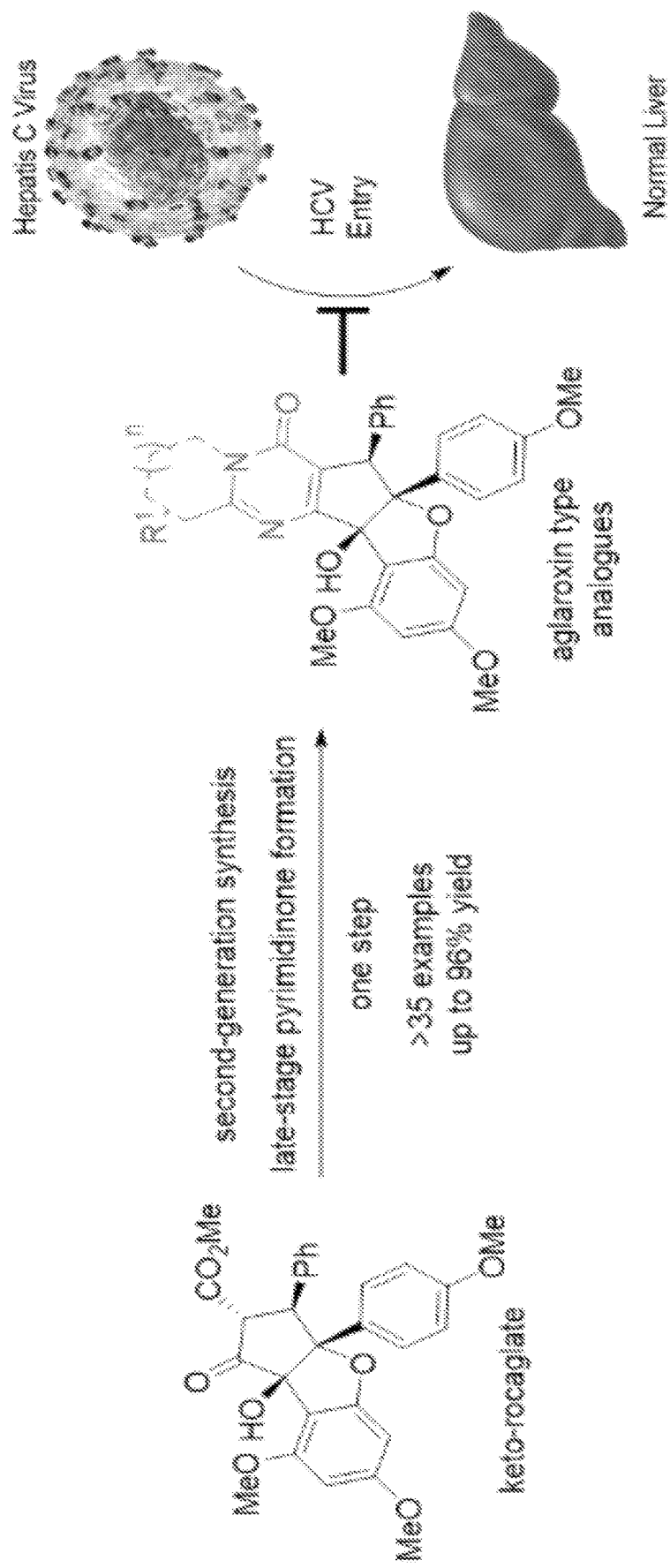
FIG. 13 shows a summary of FIGS. 1-12.

In summary, a second-generation synthesis of aglaroxin C using late-stage, direct pyrimidinone formation of a ketorocaglate scaffold was developed and described herein. Using this method, commercially available amidines were used as reaction partners to synthesize a library of over forty aglaroxin C analogues. Among newly synthesized analogues, it was successfully demonstrated SAR for inhibition of HCV infection and identified two aryl pyrimidinone lead compounds, 12l and 12s, which have low cytotoxicities to Huh 7.5.1 cells. Additional biological studies with 12l and 12s indicate that the mechanism of inhibition of HCV infection is through inhibition of HCV viral entry, rather than by blocking viral replication and translation. Finally, 12l and 12s are also effective against infection of other viruses including Dengue and Chikungunya, both of which have been found to use prohibitins (PHBs) as an entry factor. These studies illustrate the power of chemical synthesis to bias inhibition of HCV viral entry vs. translation inhibition and improve properties including therapeutic index FIG. 13.

References

Lu King, M.; Chiang, C.-C.; Ling, H.-C.; Fujita, E.; Ochiai, M.; McPhail, A. T. X-Ray Crystal Structure of Rocaglamide, a Novel Antileukemic 1H-Cyclopenta[b]benzofuran from *Aglaia elliptifolia J Chem. Soc., Chem. Commun.* 1982, 1150.

For isolation of aglaroxin C, see, e.g., (a) Kokpol, U.; Venaskulchai, B.; Simpson, J.; Weavers, R. T. Isolation and X-Ray Structure Determination of a Novel Pyrimidinone from *Aglaia odorata. J Chem. Soc., Chem. Commun.* 1994, 773; (b) Ohse, T.; Ohba, S.; Yamamoto, T.; Koyano, T.; Umezawa, K. Cyclopentabenzofuran Lignan Protein Synthesis Inhibitors from *Aglaia odorata. J. Nat. Prod.* 1996, 59, 650; (c) Nugroho, B. W.; Edrada, R. A.; Giissregen, B.; Wray, V.; Witte, L.; Proksch, P. Insecticidal Rocaglamide Derivatives from *Aglaia duppereana. Phytochemistry* 1997, 44, 1455.

For general reviews of rocaglate natural products, see, e.g., (a) Ebada, S. S.; Lajkiewicz, N.; Porco, J. A., Jr.; Li-Weber, M.; Proksch, P. Chemistry and Biology of Rocaglamides (=Flavaglines) and Related Derivatives from *Aglaia* Species (Meliaceae). In *Progress in the Chemistry of Organic Natural Products* Vol. 94; Kinghorn, A. D., Falk, H., Kobayashi, J., Eds.; Springer Vienna: Vienna, 2011, p 1; (b) Ribeiro, N.; Thuaud, F.; Nebigil, C.; Désaubry, L. Recent Advances in the Biology and Chemistry of the Flavaglines. *Bioorg. Med. Chem.* 2012, 20, 1857. (c) Pan, L.; Woodard, J. L.; Lucas, D. M.; Fuchs, J. R.; Kinghorn, A. D. Rocaglamide, Silvestrol and Structurally Related Bioactive Compounds from *Aglaia* Species *Nat. Prod. Rep.* 2014, 31, 924.

For reviews of the synthesis of rocaglates, see, e.g., (a) Peter, P.; RuAngelie, E.; Rainer, E.; Frank, I. B.; Bambang, W. N. Chemistry and Biological Activity of Rocaglamide Derivatives and Related Compounds in *Aglaia* Species (Meliaceae). *Curr. Org. Chem.* 2001, 5, 923; (b) Cai, X.-h.; Xie, B.; Guo, H. Progress in the Total Synthesis of Rocaglamide. *ISRN Org. Chem.* 2011, 2011, 7; (c) Zhao, Q.; Abou-Hamdan, H.; Desaubry, L. Recent Advances in the Synthesis of Flavaglines, a Family of Potent Bioactive Natural Compounds Originating from Traditional Chinese Medicine. *Eur. J. Org. Chem.* 2016, 2016, 5908.

Hwang, B. Y.; Su, B.-N.; Chai, H.; Mi, Q.; Kardono, L. B. S.; Afriastini, J. J.; Riswan, S.; Santarsiero, B. D.; Mesecar, A. D.; Wild, R.; Fairchild, C. R.; Vite, G. D.; Rose, W. C.; Farnsworth, N. R.; Cordell, G. A.; Pezzuto, J. M.; Swanson, S. M.; Kinghorn, A. D. Silvestrol and Episilvestrol, Potential Anticancer Rocaglate Derivatives from *Aglaia silvestris*. *J. Org. Chem.* 2004, 69, 3350.

(a) Cencic, R.; Carrier, M.; Trnkus, A.; Porco, J. A., Jr.; Minden, M.; Pelletier, J. Synergistic Effect of Inhibiting Translation Initiation in Combination with Cytotoxic Agents in Acute Myelogenous Leukemia Cells. *Leukemia Res.* 2010, 34, 535; (b) Lin, C.-J.; Nasr, Z.; Premsrirut, Prem K.; Porco, J. A., Jr.; Hippo, Y.; Lowe, Scott W.; Pelletier, J. Targeting Synthetic Lethal Interactions between Myc and the eIF4F Complex Impedes Tumorigenesis. *Cell Rep.* 2012, 1, 325; (c) Sadlish, H.; Galicia-Vazquez, G.; Paris, C. G.; Aust, T.; Bhullar, B.; Chang, L.; Helliwell, S. B.; Hoepfner, D.; Knapp, B.; Riedl, R.; Roggo, S.; Schuierer, S.; Studer, C.; Porco, J. A., Jr.; Pelletier, J.; Movva, N. R. Evidence for a Functionally Relevant Rocaglamide Binding Site on the eIF4A-RNA Complex. *ACS Chem. Bio.* 2013, 8, 1519; (d) Robert, F.; Roman, W.; Bramoullé, A.; Fellmann, C.; Roulston, A.; Shustik, C.; Porco, J. A., Jr.; Shore, G. C.; Sebag, M.; Pelletier, J. Translation Initiation Factor eIF4F Modifies the Dexamethasone Response in Multiple Myeloma. *PNAS* 2014, 111, 13421; (e) Pelletier, J.; Graff, J.; Ruggero, D.; Sonenberg, N. Targeting the eIF4F Translation Initiation Complex: A Critical *Nexus* for Cancer Development. *Cancer Res.* 2015, 75, 250.

(a) Cencic, R.; Carrier, M.; Galicia-Vázquez, G.; Bordeleau, M.-E.; Sukarieh, R.; Bourdeau, A.; Brem, B.; Teodoro, J. G.; Greger, H.; Tremblay, M. L.; Porco, J. A., Jr., Jr.; Pelletier, J. Antitumor Activity and Mechanism of Action of the Cyclopenta[b]benzofuran, Silvestrol. *PLOS ONE* 2009, 4, e5223; (b) Wolfe, A. L.; Singh, K.; Zhong, Y.; Drewe, P.; Rajasekhar, V. K.; Sanghvi, V. R.; Mavrakis, K. J.; Jiang, M.; Roderick, J. E.; Van der Meulen, J.; Schatz, J. H.; Rodrigo, C. M.; Zhao, C.; Rondou, P.; de Stanchina, E.; Teruya-Feldstein, J.; Kelliher, M. A.; Speleman, F.; Porco, J. A., Jr.; Pelletier, J.; Raitsch, G.; Wendel, H.-G. RNA G-quadruplexes Cause eIF4A-dependent Oncogene Translation in Cancer. *Nature* 2014, 513, 65; (c) Chu, J.; Cencic, R.; Wang, W.; Porco, J. A., Jr.; Pelletier, J. Translation Inhibition by Rocaglates Is Independent of eIF4E Phosphorylation Status. *Mol. Cancer Ther.* 2016, 15, 136; (d) Langlais, D.; Cencic, R.; Moradin, N.; Kennedy, J. M.; Ayi, K.; Brown, L. E.; Crandall, I.; Tarry, M. J.; Schmeing, M.; Kain, K. C.; Porco, J. A., Jr.; Pelletier, J.; Gros, P. Rocaglates as Dual-targeting Agents for Experimental Cerebral Malaria. *PNAS* 2018, 115, e2366.

(a) Iwasaki, S.; Floor, S. N.; Ingolia, N. T. Rocaglates Convert DEAD-box Protein eIF4A into a Sequence-selective Translational Repressor. *Nature* 2016, 534, 558; (b) Chu, J.; Galicia-Vazquez, G.; Cencic, R.; Mills, John R.; Katigbak, A.; Porco, J. A., Jr., Jr.; Pelletier, J. CRISPR-Mediated Drug-Target Validation Reveals Selective Pharmacological Inhibition of the RNA Helicase, eIF4A. *Cell Rep.* 2016, 15, 2340.

For chemical synthesis of rocaglate natural products, see, e.g., (a) Kraus, G. A.; Sy, J. O. A Synthetic Approach to Rocaglamide via Reductive Cyclization of δ-Keto Nitriles. *J. Org. Chem.* 1989, 54, 77; (b) Trost, B. M.; Greenspan, P. D.; Yang, B. V.; Saulnier, M. G. An Unusual Oxidative Cyclization. A Synthesis and Absolute Stereochemical Assignment of (−)-Rocaglamide. *J. Am. Chem. Soc.* 1990, 112, 9022; (c) Davey, A. E.; Schaeffer, M. J.; Taylor, R. J. K. Enantioselective Synthesis of Cyclopenta[b]benzofurans via An Organocatalytic Intramolecular Double Cyclization. *J. Chem. Soc., Chem. Commun.* 1991, 1137; (d) Davey, A. E.; Schaeffer, M. J.; Taylor, R. J. K. Synthesis of the Novel Anti-leukaemic Tetrahydrocyclopenta[b]benzofuran, Rocaglamide and Related Synthetic Studies *J. Chem. Soc., Perkin Trans.* 1 1992, 2657; (e) Dobler, M. R.; Bruce, I.; Cederbaum, F.; Cooke, N. G.; Diorazio, L. J.; Hall, R. G.; Irving, E. Total Synthesis of (±)-Rocaglamide and Some Aryl Analogues. *Tetrahedron Lett.* 2001, 42, 8281; (f) Thede, K.; Diedrichs, N.; Ragot, J. P. Stereoselective Synthesis of (±)-Rocaglaol Analogues. *Org. Lett.* 2004, 6, 4595; (g) Gerard, B.; Jones, G.; Porco, J. A., Jr. A Biomimetic Approach to the Rocaglamides Employing Photogeneration of Oxidopyryliums Derived from 3-Hydroxyflavones. *J Am. Chem. Soc.* 2004, 126, 13620; (h) Diedrichs, N.; Ragot, J. P.; Thede, K. A Highly Efficient Synthesis of Rocaglaols by a Novel α-Arylation of Ketones. *Eur. J Org. Chem.* 2005, 2005, 1731; (i) Gerard, B.; Sangji, S.; O'Leary, D. J.; Porco, J. A., Jr. Enantioselective Photocycloaddition Mediated by Chiral Brönsted Acids: Asymmetric Synthesis of the Rocaglamides. *J. Am. Chem. Soc.* 2006, 128, 7754; (j) Sous, M. E.; Khoo, M. L.; Holloway, G.; Owen, D.; Scammells, P. J.; Rizzacasa, M. A. Total Synthesis of (−)-Episilvestrol and (−)-Silvestrol. *Angew. Chem. Int. Ed.* 2007, 46, 7835; (k) Gerard, B.; Cencic, R.; Pelletier, J.; Porco, J. A., Jr. Enantioselective Synthesis of the Complex Rocaglate (−)-Silvestrol. *Angew. Chem. Int. Ed.* 2007, 46, 7831; (l) Malona, J. A.; Cariou, K.; Frontier, A. J. *J. Am. Chem. Soc.* 2009, 131, 7560; (m) Magnus, P.; Freund, W. A.; Moorhead, E. J.; Rainey, T. Nazarov Cyclization Initiated by Peracid Oxidation: The Total Synthesis of (±)-Rocaglamide. *J. Am. Chem. Soc.* 2012, 134, 6140; (n) Magnus, P.; Freund, W. A.; Moorhead, E. J.; Rainey, T. Formal Synthesis of (±)-Methyl Rocaglate Using an Unprecedented Acetyl Bromide Mediated Nazarov Reaction. *J. Am. Chem. Soc.* 2012, 134, 6140; (o) Lajkiewicz, N. J.; Roche, S. P.; Gerard, B.; Porco, J. A., Jr. Enantioselective Photocycloaddition of 3-Hydroxyflavones: Total Syntheses and Absolute Configuration Assignments of (+)-Ponapensin and (+)-Elliptifoline. *J. Am. Chem. Soc.* 2012, 134, 13108; (p) Stone, S. D.; Lajkiewicz, N. J.; Whitesell, L.; Hilmy, A.; Porco, J. A., Jr. Biomimetic Kinetic Resolution: Highly Enantio- and Diastereoselective Transfer Hydrogenation of Aglain Ketones to Access Flavagline Natural Products. *J. Am. Chem. Soc.* 2015, 137, 525; (q) Wang, W.; Clay, A.; Krishnan, R.; Lajkiewicz, N. J.; Brown, L. E.; Sivaguru, J.; Porco, J. A., Jr. Total Syntheses of the Isomeric Aglain Natural Products Foveoglin A and Perviridisin B: Selective Excited-State Intramolecular Proton-Transfer Photocycloaddition. *Angew. Chem. Int. Ed.* 2017, 56, 14479.

For representative studies of rocaglate analogues from academia, see, e.g., (a) Roche, S. P.; Cencic, R.; Pelletier, J.; Porco, J. A., Jr. Biomimetic Photocycloaddition of 3-Hydroxyflavones: Synthesis and Evaluation of Rocaglate Derivatives as Inhibitors of Eukaryotic Translation. *Angew. Chem. Int. Ed.* 2010, 49, 6533; (b) Thuaud, F.; Ribeiro, N.; Gaiddon, C.; Cresteil, T.; Desaubry, L. Novel Flavaglines Displaying Improved Cytotoxicity. *J. Med. Chem.* 2011, 54, 411; (c) Rodrigo, C. M.; Cencic, R.; Roche, S. P.; Pelletier, J.; Porco, J. A., Jr., Synthesis of Rocaglamide Hydroxamates and Related Compounds as Eukaryotic Translation Inhibitors: Synthetic and Biological Studies. *J. Med. Chem.* 2012, 55, 558; (d) Hawkins, B. C.; Lindqvist, L. M.; Nhu, D.; Sharp, P. P.; Segal, D.; Powell, A. K.; Campbell, M.; Ryan, E.; Chambers, J. M.; White, J. M.; Rizzacasa, M. A.; Lessene, G.; Huang, D. C. S.; Burns, C. J. Simplified Silvestrol Analogues with Potent Cytotoxic Activity. *ChemMedChem* 2014, 9, 1556; (e) Lajkiewicz, N. J.; Cognetta, A. B.; Niphakis, M. J.; Cravatt, B. F.; Porco, J. A., Jr. Remodeling Natural Products: Chemistry and Serine Hydrolase Activity of a Rocaglate-Derived β-Lactone. *J. Am. Chem. Soc.* 2014, 136, 2659; (f) Wang, W.; Cencic, R.; Whitesell, L.; Pelletier, J.; Porco, J. A., Jr. Synthesis of Aza-Rocaglates via ESIPT-Mediated (3+2) Photocycloaddition. *Chem. Eur. J* 2016, 22, 12006; (g) Zhao, Q.; Tijeras-Raballand, A.; de Gramont, A.; Raymond, E.; Désaubry, L. Bioisosteric Modification of Flavaglines. *Tetrahedron Lett.* 2016, 57, 2943.

For representative medicinal remodeling of rocaglates from industry, see, e.g., (a) Bruce, I.; Cooke, N. G.; Diorazio, L. J.; Hall, R. G.; Irving, E. Synthesis of the Carbocyclic Analogue of (±)-Rocaglamide. *Tetrahedron Lett.* 1999, 40, 4279; (b) Liu, T.; Nair, S. J.; Lescarbeau, A.; Belani, J.; Peluso, S.; Conley, J.; Tillotson, B.; O'Hearn, P.; Smith, S.; Slocum, K.; West, K.; Helble, J.; Douglas, M.; Bahadoor, A.; Ali, J.; McGovern, K.; Fritz, C.; Palombella, V. J.; Wylie, A.; Castro, A. C.; Tremblay, M. R. Synthetic Silvestrol Analogues as Potent and Selective Protein Synthesis Inhibitors. *J. Med. Chem.* 2012, 55, 8859.

(a) Liu, S.; Wang, W.; Brown, L. E.; Qiu, C.; Lajkiewicz, N.; Zhao, T.; Zhou, J.; Porco, J. A., Jr.; Wang, T. T. A Novel Class of Small Molecule Compounds that Inhibit Hepatitis C Virus Infection by Targeting the Prohibitin-CRaf Pathway. *EBioMedicine* 2015, 2, 1600; (b) Wang, T. T.; Liu, S.; Wang, W.; Lajkiewicz, N.; Porco, J. A., Jr Aglaroxin C and Derivatives as HCV Entry Inhibitors. US patent 2018 U.S. Pat. No. 10,085,988 B1.

For other inhibitors of HCV viral entry, see, e.g., (a) Calland, N.; Sahuc, M.-E.; Belouzard, S.; Pene, V.; Bonnafous, P.; Mesalam, A. A.; Deloison, G.; Descamps, V.; Sahpaz, S.; Wychowski, C.; Lambert, O.; Brodin, P.; Duverlie, G.; Meuleman, P.; Rosenberg, A. R.; Dubuisson, J.; Rouille, Y.; Seron, K. Polyphenols Inhibit Hepatitis C Virus Entry by a New Mechanism of Action. *J Virol.* 2015, 89, 1005; (b) Lin, L.-T.; Chung, C.-Y.; Hsu, W.-C.; Chang, S.-P.; Hung, T.-C.; Shields, J.; Russell, R. S.; Lin, C.-C.; Li, C.-F.; Yen, M.-H.; Tyrrell, D. L. J.; Lin, C.-C.; Richardson, C. D. Saikosaponin b2 is a Naturally Occurring Terpenoid That Efficiently Inhibits Hepatitis C Virus Entry. *J Hepatol.* 2015, 62, 541; (c) Qian, X.-J.; Zhang, X.-L.; Zhao, P.; Jin, Y.-S.; Chen, H.-S.; Xu, Q.-Q.; Ren, H.; Zhu, S.-Y.; Tang, H.-L.; Zhu, Y.-Z.; Qi, Z.-T. A Schisandra-Derived Compound Schizandronic Acid Inhibits Entry of Pan-HCV Genotypes into Human Hepatocytes. *Sci. Rep.* 2016, 6, 27268; (d) Bose, M.; Kamra, M.; Mullick, R.; Bhattacharya, S.; Das, S.; Karande, A. A. A Plant-derived Dehydrorotenoid: a New Inhibitor of Hepatitis C Virus Entry. *FEBS Lett.* 2017, 591, 1305.

Kuadkitkan, A.; Wikan, N.; Fongsaran, C.; Smith, D. R. Identification and Characterization of Prohibitin as a Receptor Protein Mediating DENV-2 Entry into Insect Cells. *Virology* 2010, 406, 149.

Wintachai, P.; Wikan, N.; Kuadkitkan, A.; Jaimipuk, T.; Ubol, S.; Pulmanausahakul, R.; Auewarakul, P.; Kasinrerk, W.; Weng, W.; Panyasrivanit, M.; Paemanee, A.; Kittisenachai, S.; Roytrakul, S.; Smith, D. R. Identification of Prohibitin as a Chikungunya Virus Receptor Protein. *J. Med. Virol.* 2012, 84, 1757.

Vos, T.; Allen, C.; Arora, M.; Barber, R. M.; Bhutta, Z. A.; Brown, A.; Carter, A.; Casey, D. C.; Charlson, F. J.; Chen, A. Z.; Coggeshall, M.; Cornaby, L.; Dandona, L.; Dicker, D. J.; Dilegge, T.; Erskine, H. E.; Ferrari, A. J.; Fitzmaurice, C.; Fleming, T.; Forouzanfar, M. H.; Fullman, N.; Gething, P. W.; Goldberg, E. M.; Graetz, N.; Haagsma, J. A.; Hay, S. I.; Johnson, C. O.; Kassebaum, N. J.; Kawashima, T.; Kemmer, L.; Khalil, I. A.; Kinfu, Y.; Kyu, H. H.; Leung, J.; Liang, X.; Lim, S. S.; Lopez, A. D.; Lozano, R.; Marczak, L.; Mensah, G. A.; Mokdad, A. H.; Naghavi, M.; Nguyen, G.; Nsoesie, E.; Olsen, H.; Pigott, D. M.; Pinho, C.; Rankin, Z.; Reinig, N.; Salomon, J. A.; Sandar, L.; Smith, A.; Stanaway, J.; Steiner, C.; Teeple, S.; Thomas, B. A.; Troeger, C.; Wagner, J. A.; Wang, H.; Wanga, V.; Whiteford, H. A.; Zoeckler, L.; Abajobir, A. A.; Abate, K. H.; Abbafati, C.; Abbas, K. M.; Abd-Allah, F.; Abraham, B.; Abubakar, I.; Abu-Raddad, L. J.; Abu-Rmeileh, N. M. E.; Ackerman, I. N.; Adebiyi, A. O.; Ademi, Z.; Adou, A. K.; Afanvi, K. A.; Agardh, E. E.; Agarwal, A.; Kiadaliri, A. A.; Ahmadieh, H.; Ajala, O. N.; Akinyemi, R. O.; Akseer, N.; Al-Aly, Z.; Alam, K.; Alam, N. K. M.; Aldhahri, S. F.; Alegretti, M. A.; Alemu, Z. A.; Alexander, L. T.; Alhabib, S.; Ali, R.; Alkerwi, A. a.; Alla, F.; Allebeck, P.; Al-Raddadi, R.; Alsharif, U.; Altirkawi, K. A.; Alvis-Guzman, N.; Amare, A. T. Global, Regional, and National Incidence, Prevalence, and Years Lived with Disability for 310 Diseases and Injuries, 1990-2015: a Systematic Analysis for the Global Burden of Disease Study 2015. *The Lancet* 2016, 388, 1545.

Denniston, M. M.; Jiles, R. B.; Drobeniuc, J.; Klevens, R. M.; Ward, J. W.; McQuillan, G. M.; Holmberg, S. D. Chronic Hepatitis C Virus Infection in the United States, National Health and Nutrition Examination Survey 2003 to 2010. *Ann. Intern. Med.* 2014, 160, 293.

(1) Wang, H.; Naghavi, M.; Allen, C.; Barber, R. M.; Bhutta, Z. A.; Carter, A.; Casey, D. C.; Charlson, F. J.; Chen, A. Z.; Coates, M. M.; Coggeshall, M.; Dandona, L.; Dicker, D. J.; Erskine, H. E.; Ferrari, A. J.; Fitzmaurice, C.; Foreman, K.; Forouzanfar, M. H.; Fraser, M. S.; Fullman, N.; Gething, P. W.; Goldberg, E. M.; Graetz, N.; Haagsma, J. A.; Hay, S. I.; Huynh, C.; Johnson, C. O.; Kassebaum, N. J.; Kinfu, Y.; Kulikoff, X. R.; Kutz, M.; Kyu, H. H.; Larson, H. J.; Leung, J.; Liang, X.; Lim, S. S.; Lind, M.; Lozano, R.; Marquez, N.; Mensah, G. A.; Mikesell, J.; Mokdad, A. H.; Mooney, M. D.; Nguyen, G.; Nsoesie, E.; Pigott, D. M.; Pinho, C.; Roth, G. A.; Salomon, J. A.; Sandar, L.; Silpakit, N.; Sligar, A.; Sorensen, R. J. D.; Stanaway, J.; Steiner, C.; Teeple, S.; Thomas, B. A.; Troeger, C.; VanderZanden, A.; Vollset, S. E.; Wanga, V.; Whiteford, H. A.; Wolock, T.; Zoeckler, L.; Abate, K. H.; Abbafati, C.; Abbas, K. M.; Abd-Allah, F.; Abera, S. F.; Abreu, D. M. X.; Abu-Raddad, L. J.; Abyu, G. Y.; Achoki, T.; Adelekan, A. L.; Ademi, Z.; Adou, A. K.; Adsuar, J. C.; Afanvi, K. A.; Afshin, A.; Agardh, E. E.; Agarwal, A.; Agrawal, A.; Kiadaliri, A. A.; Ajala, O. N.; Akanda, A. S.; Akinyemi, R. O.; Akinyemiju, T. F.; Akseer, N.; Lami, F. H. A.; Alabed, S.; Al-Aly, Z.; Alam, K.; Alam, N. K. M.; Alasfoor, D.; Aldhahri, S. F.; Aldridge, R. W.; Alegretti, M. A.; Aleman, A. V.; Alemu, Z.

A.; Alexander, L. T. Global, Regional, and National Life Expectancy, All-cause Mortality, and Cause-specific Mortality for 249 Causes of Death, 1980-2015: a Systematic Analysis for the Global Burden of Disease Study 2015. *The Lancet* 2016, 388, 1459.

For a comprehensive review of DAAs for HCV, see, e.g., Gotte, M.; Feld, J. J. Direct-acting Antiviral Agents for Hepatitis C: Structural and Mechanistic Insights. *Nat. Rev. Gastroenterol. Hepatol.* 2016, 13, 338.

Xiao, F.; Fofana, I.; Thumann, C.; Mailly, L.; Alles, R.; Robinet, E.; Meyer, N.; Schaeffer, M.; Habersetzer, F.; Doffoël, M.; Leyssen, P.; Neyts, J.; Zeisel, M. B.; Baumert, T. F. Synergy of Entry Inhibitors with Direct-acting Antivirals Uncovers Novel Combinations for Prevention and Treatment of Hepatitis C. *Gut* 2015, 64, 483.

Romano, K. P.; Ali, A.; Aydin, C.; Soumana, D.; Özen, A.; Deveau, L. M.; Silver, C.; Cao, H.; Newton, A.; Petropoulos, C. J.; Huang, W.; Schiffer, C. A. The Molecular Basis of Drug Resistance against Hepatitis C Virus NS3/4A Protease Inhibitors. *PLOS Pathog.* 2012, 8, e1002832.

(a) Tong, X.; Le Pogam, S.; Li, L.; Haines, K.; Piso, K.; Baronas, V.; Yan, J.-M.; So, S.-S.; Klumpp, K.; Nájera, I. In Vivo Emergence of aNovel Mutant L159F/L320F in the NS5B Polymerase Confers Low-Level Resistance to the HCV Polymerase Inhibitors Mericitabine and Sofosbuvir. *J. Infect. Dis.* 2014, 209, 668; (b) Walker, A.; Filke, S.; Liibke, N.; Obermeier, M.; Kaiser, R.; Häussinger, D.; Timm, J.; Bock, H. H. Detection of a Genetic Footprint of the Sofosbuvir Resistance-associated Substitution S282T after HCV Treatment Failure. *Virol. J* 2017, 14, 106.

For a recent review of current HCV entry inhibitor development, see, e.g., Qian, X.-J.; Zhu, Y.-Z.; Zhao, P.; Qi, Z.-T. Entry Inhibitors: New Advances in HCV Treatment. *Emerg. Microbes Infect.* 2016, 5, e3.

He, S.; Li, K.; Lin, B.; Hu, Z.; Xiao, J.; Hu, X.; Wang, A. Q.; Xu, X.; Ferrer, M.; Southall, N.; Zheng, W.; Aubé, J.; Schoenen, F. J.; Marugan, J. J.; Liang, T. J.; Frankowski, K. J. Development of an Aryloxazole Class of Hepatitis C Virus Inhibitors Targeting the Entry Stage of the Viral Replication Cycle. *J Med. Chem.* 2017, 60, 6364.

Yueh, H.; Gao, Q.; Porco, J. A.; Beeler, A. B. A Photochemical Flow Reactor for Large Scale Syntheses of Aglain and Rocaglate Natural Product Analogues. *Bioorg. Med. Chem.* 2017, 25, 6197.

For approved drugs containing the pyrimidinone substructure and their synthesis, see, e.g., a) risperidone: Kim, D.-m.; Kang, M.-S.; Kim, J. S.; Jeong, J.-H. An Efficient Synthesis of Risperidonevia Stille Reaction: Antipsychotic, 5-$HT_2$, and Dopamine-$D_2$-antagonist. *Arch. Pharm. Res.* 2005, 28, 1019; b) paliperidone: Solanki, P. V.; Uppelli, S. B.; Pandit, B. S.; Mathad, V. T. An Improved and Efficient Process for the Production of Highly Pure Paliperidone, a Psychotropic Agent, via DBU Catalyzed N-Alkylation. *ACS Sustainable Chem. Eng.* 2013, 1, 243; c) Fimasartan: Kim, T. W.; Yoo, B. W.; Lee, J. K.; Kim, J. H.; Lee, K.-T.; Chi, Y. H.; Lee, J. Y. Synthesis and Antihypertensive Activity of Pyrimidin-4(3H)-one Derivatives as Losartan Analogue for New Angiotensin II Receptor Type 1 ($AT_1$) Antagonists. *Bioorg. Med. Chem. Lett.* 2012, 22, 1649.

For selected synthesis of natural products containing pyrimidinones, see, e.g., (a) Doveston, R. G.; Steendam, R.; Jones, S.; Taylor, R. J. K. Total Synthesis of an Oxepine Natural Product, (±)-Janoxepin. *Org. Lett.* 2012, 14, 1122; (b) Santos, M. F. C.; Harper, P. M.; Williams, D. E.; Mesquita, J. T.; Pinto, E. G.; da Costa-Silva, T. A.; Hajdu, E.; Ferreira, A. G.; Santos, R. A.; Murphy, P. J.; Andersen, R. J.; Tempone, A. G.; Berlinck, R. G. S. Anti-parasitic Guanidine and Pyrimidine Alkaloids from the Marine Sponge Monanchora arbuscular. *J Nat. Prod.* 2015, 78, 1101.

For the Traube purine synthesis, see, e.g., (a) Traube, W. Ueber Guanidinderivate Zweibasischer Säuren. *Ber. Dtsch. Chem. Ges.* 1893, 26, 2551; (b) Traube, W.; Schottländer, F.; Goslich, C.; Peter, R.; Meyer, F. A.; Schliiter, H.; Steinbach, W.; Bredow, K. Über Ortho-diamino-pyrimidine und ihre Überfiihrung in Purine. *Ann. Chem.* 1923, 432, 266.

For selected pyrimidinone syntheses from 1,3-dicarbonyl substrates, see, e.g., (a) Lal, B.; D'Sa, A. S.; Kulkami, B. K.; de Souza, N. J. A Convenient One-pot Entry into Novel 2-Substituted-6,7-dihydro-4H-Pyrimido(2,1-a) Isoquinolin-4-ones. *Tetrahedron* 1990, 46, 1323; (b) Venkatesan, A. M.; Levin, J. I.; Baker, J. S.; Chan, P. S.; Bailey, T.; Coupet, J. Substituted 4H-Pyrido[1,2-a]pyrimidin-4-one Angiotensin II Receptor Antagonists. *Bioorg. Med. Chem. Lett.* 1994, 4, 183; (c) Taylor, E. C.; Zhou, P.; Tice, C. M. 6-Trifluoromethanesulfonyloxy-4(3H)-pyrimidinones as Versatile Intermediates for the Synthesis of 6-Functionalized 4(3H)-Pyrimidinones. *Tetrahedron Lett.* 1997, 38, 4343; (d) Puig-de-la-Bellacasa, R.; Giménez, L.; Pettersson, S.; Pascual, R.; Gonzalo, E.; Esté, J. A.; Clotet, B.; Borrell, J. I.; Teixidó, J. Diverse Combinatorial Design, Synthesis and In Vitro Evaluation of New HEPT Analogues as Potential Non-nucleoside HIV-1 Reverse Transcription Inhibitors. *Eur. J Med. Chem.* 2012, 54, 159; (e) Guirado, A.; Alarcón, E.; Vicente, Y.; Andreu, R.; Bautista, D.; Gálvez, J. A New Convenient Synthetic Approach to Diarylpyrimidines. *Tetrahedron* 2016, 72, 3922

(a) Katritzky, A. R.; Yousaf, T. I. A C-13 Nuclear Magnetic Resonance Study of the Pyrimidine Synthesis by the Reactions of 1,3-Dicarbonyl Compounds with Amidines and Ureas *Can. J. Chem.* 1986, 64, 2087. (b) Katritzky, A. R.; Ostercamp, D. L.; Yousaf, T. I. The Mechanisms of Heterocyclic Ring Closures. *Tetrahedron* 1987, 43, 5171.

For imidoyl ketene generation and subsequent cyclization, see, e.g., (a) Ham, S.; Bimey, D. M. Imidoylketene: An ab Initio Study of Its Conformations and Reactions. *J. Org. Chem.* 1996, 61, 3962; (b) Alajarín, M.; Ortin, M.-M.; Sánchez-Andrada, P.; Vidal, A.; Bautista, D. From Ketenimines to Ketenes to Quinolones: Two Consecutive Pseudopericyclic Events. *Org. Lett.* 2005, 7, 5281; (c) Abe, T.; Kida, K.; Yamada, K. A Copper-Catalyzed Ritter-type Cascade via Iminoketene for the Synthesis of Quinazolin-4(3H)-ones and Diazocines. *Chem. Commun.* 2017, 53, 4362.

Schönherr, H.; Cernak, T. Profound Methyl Effects in Drug Discovery and a Call for New C—H Methylation Reactions. *Angew. Chem. Int. Ed.* 2013, 52, 12256.

Dye, J. F.; Somers, S. S.; Guillou, P. J. Simplified Quantitation of Cytotoxicity by Integration of Specific Lysis against Effector Cell Concentration at a Constant Target Cell Concentration and Measuring the Area Under the Curve. *J Immunol. Methods* 1991, 138, 1.

(a) Sheeran, T. P.; Jackson, F. R.; Dawes, P. T.; Collins, M.; Shadforth, M. F. Measurement of Natural Killer Cell Cytotoxicity by Area Under a Cytotoxic Curve: A Method Suitable for Rheumatoid Arthritis. *J. Immunol. Methods* 1988, 115, 95; (b) Brown, C.; Havener, T.; Everitt, L.; McLeod, H.; Motsinger-Reif, A. A Comparison of Association Methods for Cytotoxicity Mapping in Pharmacogenomics. *Front. Genet.* 2011, 2; (c) Huang, S.; Pang, L. Comparing Statistical Methods for Quantifying Drug Sensitivity Based on In Vitro Dose-Response Assays. *Assay Drug Dev. Technol.* 2012, 10, 88.

Scholle, F.; Li, K.; Bodola, F.; Ikeda, M.; Luxon, B. A.; Lemon, S. M. Virus-Host Cell Interactions during Hepatitis C Virus RNA Replication: Impact of Polyprotein Expression on the Cellular Transcriptome and Cell Cycle Association with Viral RNA Synthesis. *J. Virol.* 2004, 78, 1513. Novac, O.; Guenier, A. S.; Pelletier, J. Inhibitors of Protein Synthesis Identified by a High Throughput Multiplexed Translation Screen. *Nucleic Acids Res.* 2004, 32, 902.

Example 2: Supporting Data

Unless otherwise stated, reactions were performed under argon using freshly purified solvents, which were purified using solvent purification columns purchased from Innovative Technology (SPS-400-6, 2005). Reactions were monitored by thin-layer chromatography with E. Merck silica gel 60 $F_{254}$ pre-coated plates (0.25 mm). All work-up and purification procedures were carried out with reagent-grade solvents in air. Flash chromatography was performed with the indicated solvents using silica gel (particle size 40-63 μm) purchased from Sorbent Technologies. Infrared spectra were recorded on a Nicolet Nexus 670 FT-IR spectrophotometer. $^1$H and $^{13}$C NMR spectra were recorded on Varian Inova-400 MHz, 500 MHz. Chemical shifts are reported relative to internal chloroform (CDCl$_3$: $^1$H, δ=7.26 ppm, $^{13}$C, δ=77.36 ppm), benzene (C$_6$D$_6$: $^1$H, δ=7.15 ppm, $^{13}$C, δ=128.62 ppm), toluene (C$_7$D$_8$: $^1$H, δ=2.09 ppm, $^{13}$C, δ=20.4 ppm), methanol (CD$_3$OD: $^1$H, δ=3.31 ppm, $^{13}$C, δ=49.15 ppm) dichloromethane (CD$_2$Cl$_2$: $^1$H, δ=5.36 ppm, $^{13}$C, δ=53.84 ppm). Coupling constants are in Hz and are reported as d (doublet), t (triplet), q (quartet), bs (broad singlet), and m (multiplet). High-resolution mass spectra were obtained in the Boston University Chemical Instrumentation Center (BU-CIC) using a Waters Q-TOF API-US mass spectrometer. Melting points were recorded on a Mel-Temp apparatus (Laboratory Devices). Analytical LCMS was performed on a Waters Acquity UPLC (Ultra Performance Liquid Chromatography (Waters MassLynx Version 4.1) with a Binary solvent manager, SQ mass spectrometer, Water 2996 PDA (PhotoDiode Array) detector, and ELSD (Evaporative Light Scattering Detector). An Acquity UPLC BEH C18 1.7 μm column was used for analytical UPLC-MS. Optical rotations were recorded on an AUTOPOL III digital polarimeter at 589 nm, and specific rotations are given [α]D 20 (concentration in grams/100 mL solvent). Chiral HPLC analysis of enantioenriched compounds was performed using a Waters 1525 Binary HPLC Pump with a Waters 2487 diode array detector. Preparative HPLC was performed on a Gilson PLC2020 using a Waters SunFire™ Prep C18 OBD™ 5 μm 19×50 mm column.

Materials. Chemicals were purchased from Sigma-Aldrich, Fisher or Alfa Aesar, TCI, Oakwood, Enamine BB, Combi-blocks, and Strem Chemicals and were used without further purification.

Cells and Antibodies. The human liver cell line Huh7.5.1 was provided by Scripps Research Institute. The full-length HCV Genotype 1b-replicon-containing cell line 2-3(+) was a gift from University of North Carolina, Chapel Hill, N.C. The *Aedes albopictus* cell line C6/36 was purchased from American Type Culture Collection (ATCC) (CRL-1660). All cell lines were maintained in DMEM supplemented with 5% penicillin and streptomycin, 1% NEAA, and 10% fetal bovine serum (FBS) (Gemini Bio-Products). The β-actin antibody (clone AC-74) was purchased from Sigma. The HCV NS5A monoclonal antibody 9E10 was a gift from Rockefeller University. Secondary antibodies were purchased from Jackson ImmunoResearch Laboratories, Inc, and Molecular Probes (Invitrogen). Primer sequences are: Dengue 16681: F: 5'-CCTGGGAAGAGTGATGGTTATG-3' (SEQ ID NO: 3); R: 5'-GCTGCTAGTAGGGCAAGA-TAAG-3' (SEQ ID NO: 4). GAPDH: F: 5'-TGCACCAC-CAACTGCTTA-3' (SEQ ID NO: 5); R: 5'-GGATGCAGGGATGATGTTC-3' (SEQ ID NO: 6).

Viruses.

Detailed descriptions about production and infection of HCVpp, CHIKVpp, VSV-Gpp, JFH1-HCVcc, and HCVcc-Luc have been published elsewhere. The Ebola virus envelope expressing construct was a gift from University of Iowa, IA. Dengue virus (Thailand 16681 serotype 2 strain) was propagated in C6/36 cells.

HCVcc Time-of-Addition Assay.

Detailed protocols have been previously published. In brief, HCVcc-Luc was added to Huh7.5.1 cells at 37° C. and incubated for 3 h. HCVcc-Luc (HCV virus carrying a luciferase reporter) was added to Huh7.5.1 cells at 37° C. and incubated for 3 h. At the indicated time points, 0.5 μM of each compound or DMSO was added into the media and incubated for 3 h prior to removal. Infected cells were incubated at 37° C. for an additional 48 h prior to conducting the luciferase assay (mean of n=3; error bars, s.d.). Data was calculated as percentages of infections relative to that of DMSO treated cells (arbitrarily set to 100).

In Vitro Transcriptions and Translations.

In vitro transcriptions and translations were performed as described previously. Plasmid encoding the bicistronic FF/HCV/Ren open reading frame was linearized with BamHI and m$^7$Gppp-capped mRNA was produced by in vitro transcription reactions using SP6 RNA polymerase. In vitro translation reactions were performed with S10 extracts prepared from Kreb-2 cells and programmed with 4 ng/uL of in vitro transcribed mRNA. Firefly (FF) and *Renilla* (Ren) luciferase activities were measured on a Berthold Lumat LB9507 Luminometer and values normalized against vehicle control, which was set at 1.

Figure 15:
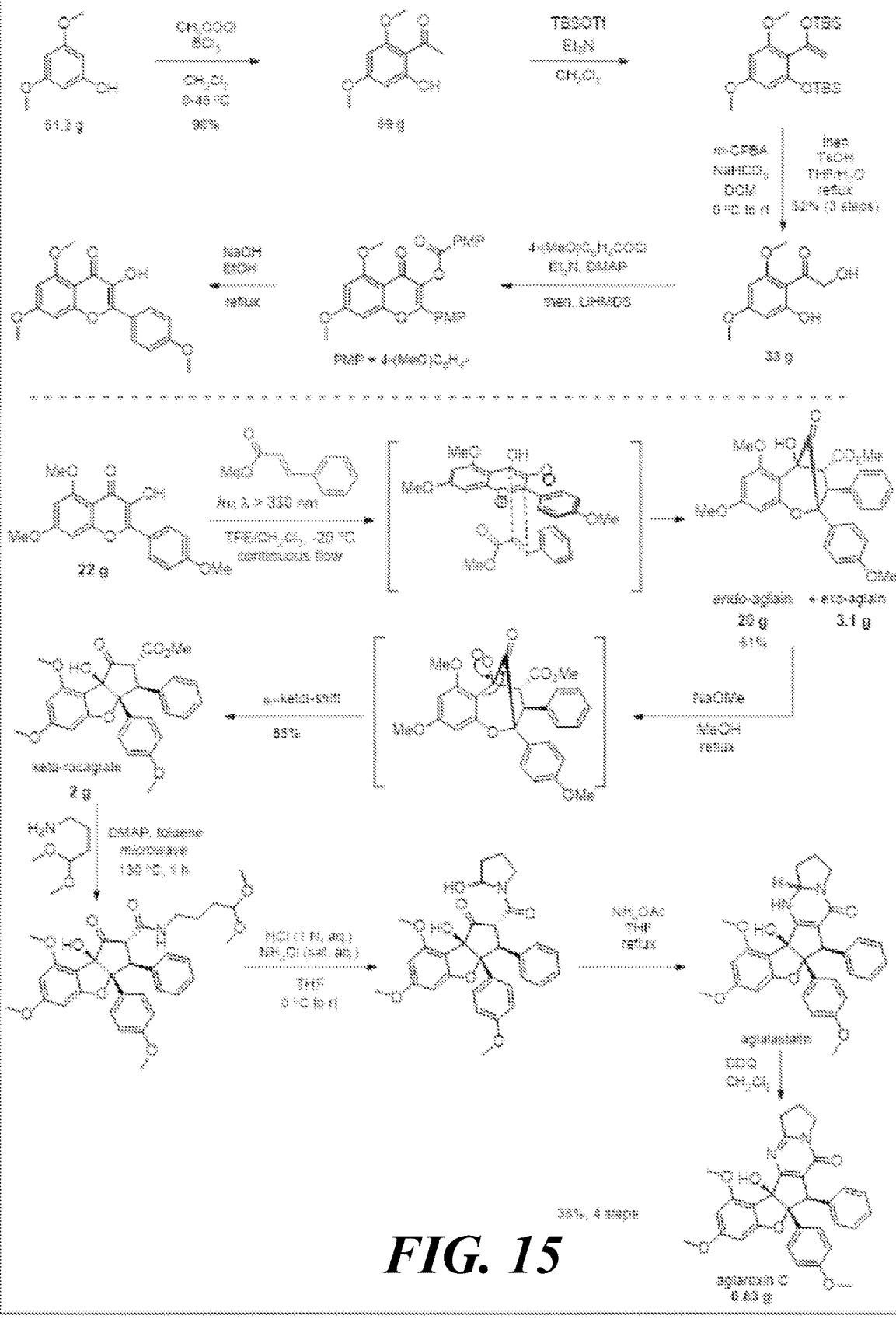
FIG. 15 shows the synthesis of keto-rocaglate and first-generation synthesis of aglaroxin C.

Synthesis of keto-rocaglate 9 was accomplished using previously reported conditions FIG. 15 (Scheme SI1).

A graphic comparison between aglaroxin analogues as viral entry inhibitors and current DAA treatment for HCV is shown in FIG. 14.

Example 3: Experimental Procedures and Characterization Data

The synthesis of keto-rocaglate and first-generation synthesis of aglaroxin C are shown in FIG. 15.

General method for direct pyrimidinone formation
Modified Protocol for Keto-Rocaglate Purification

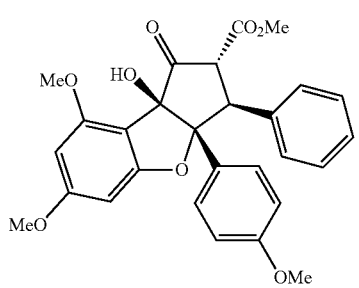

9

Keto-rocaglate 9 was synthesized according to our previous experimental procedure. An α-ketol-shift FIG. 15 (Scheme SI1) was used to generate keto-rocaglate 9 from the endo-aglain precursor; 3-hydroxyflavone was found in crude products which was found to be inseparable from ketorocaglate 9 using silica gel chromatography. To provide accurate yields for the subsequent analogue synthesis, an improved purification protocol was developed using trituration with toluene in which case keto-rocaglate 9 was obtained as a white powder.

General Method for Direct Pyrimidinone Formation:

Two general methods were established according to amidine source employed:

Method a, Scheme 1.

Direct pyrimidinone formation using a free-based amidine:

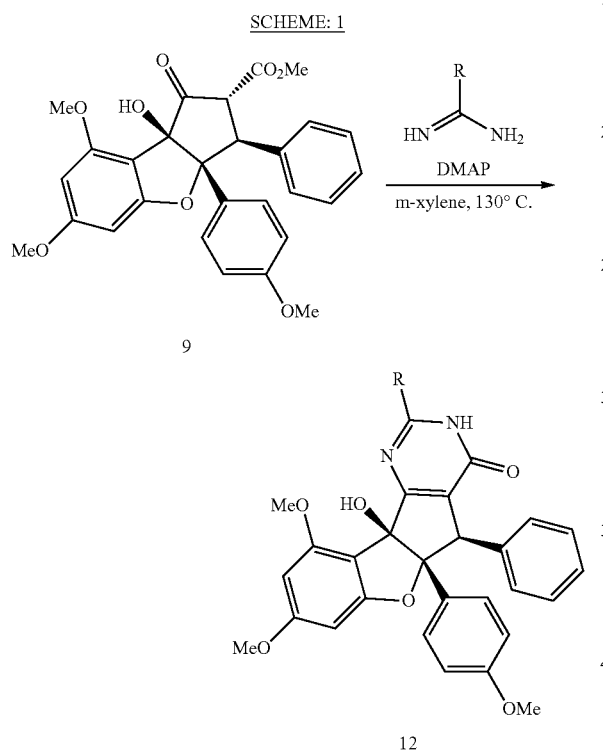

When free-based amidine was used for the pyrimidinone condensation, extra base was found to be unnecessary. Keto-rocaglate 9 (1.0 equiv), DMAP (0.3 equiv) and amidine (3.0 equiv) were combined in a vial or flask with a stir bar. The reaction vessel was charged with nitrogen followed by the addition of m-xylene to obtain a solution (0.025 M in substrate). After the mixture was stirred for 2-5 min to give a clear solution, the reaction mixture was placed on a pre-heated heating block at 130° C. (pre-heating the heating apparatus was found to be critical to minimize formation of oxazoline 15). The reaction was heated at 130° C. for an additional 45 min. Reaction progress was determined by crude $^1$H NMR or TLC analyses. Once the reaction was completed, saturated aqueous ammonium chloride solution was added to quench the reaction at room temperature. The crude product was extracted three times with ethyl acetate or dichloromethane according to the solubility of the crude product, dried through sodium sulfate, and concentrated using a nitrogen stream as m-xylene is difficult to remove using rotary evaporation. Flash chromatography was finally used to purify the desired pyrimidinone product.

Method B, Scheme 2.

Direct pyrimidinone formation using acidified amidine salt:

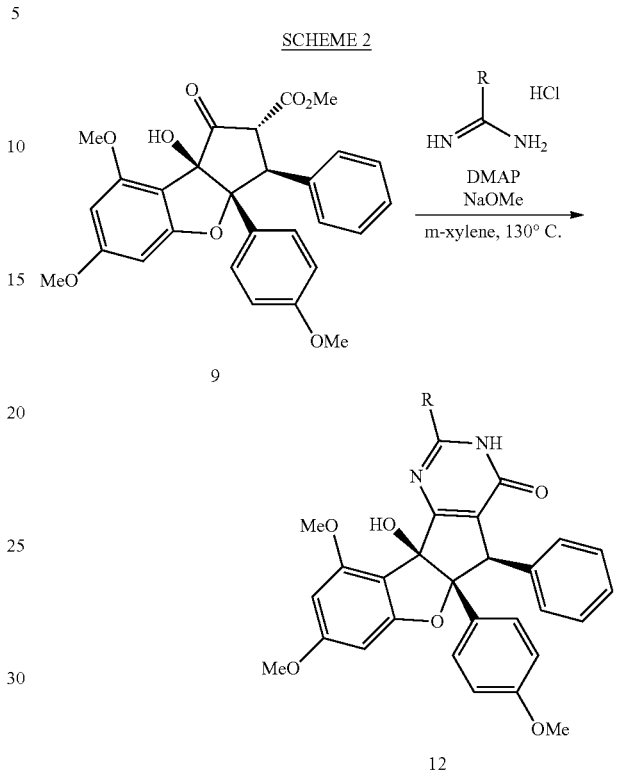

It was discovered that a stepwise free-base protocol was unpractical, as the free-based amidines were either water soluble or volatile. Therefore, when amidine hydrochloride was used for condensations, an in-situ free-basing protocol was employed. In a reaction vial with 4 Å molecular sieves, stir bar, and amidine hydrochloride (3.0 equiv) under nitrogen, m-xylene (0.025 M) was added followed by freshly prepared NaOMe (1.0 M, 2.95 equiv). The mixture was vigorously stirred at room temperature for 15-30 minutes according to the disappearance of the crystalline amidine hydrochloride salt. The reaction vial was centrifuged to remove formed sodium chloride, and the clear upper-layer solution of amidine was transferred to a separate reaction vial with keto-rocaglate 9 (1.0 equiv), DMAP (0.3 equiv), and a stir bar under nitrogen. The mixture was stirred for 2-5 min to afford a clear solution, and the reaction mixture was placed on a pre-heated heating block at 130° C. The reaction was heated at 130° C. for an additional 45 minutes. Reaction progress was determined by crude $^1$H NMR or TLC analyses. Once the reaction was completed, saturated ammonium chloride aqueous solution was added to quench the reaction at room temperature. The crude product was extracted three times with ethyl acetate or $CH_2Cl_2$ according to the solubility of the product, dried using sodium sulfate, and concentrated using a nitrogen stream. Silica gel chromatography was used to purify the desired pyrimidinone product.

When the reaction scale was larger than 100 mg, the methanol was removed from reaction system after the free-basing step. This operation helped the reaction mixture quickly reach 130° C. and minimize formation of the undesired product 15.

Compounds Characterization

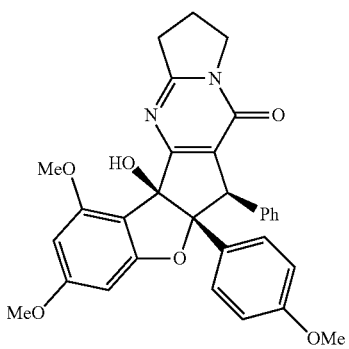

Aglaroxin C(6)

$^{1}$H NMR (500 MHz, Chloroform-d) δ 7.12-7.03 (m, 5H), 6.92-6.86 (m, 2H), 6.55 (d, J=9.0 Hz, 2H), 6.20 (d, J=1.9 Hz, 1H), 6.05 (d, J=1.9 Hz, 1H), 4.69 (s, 1H), 4.10 (dddd, J=32.8, 12.7, 8.3, 6.4 Hz, 2H), 3.84 (s, 3H), 3.79 (s, 3H), 3.66 (s, 3H), 3.33 (s, 1H), 3.26 (dt, J=16.9, 8.1 Hz, 1H), 3.21-3.12 (m, 1H), 2.26 (dddd, J=15.3, 13.3, 6.7, 2.1 Hz, 2H). $^{13}$C NMR (126 MHz, Chloroform-d) δ 166.7, 166.0, 163.4, 160.8, 159.1, 158.6, 158.0, 136.9, 129.3, 128.9, 127.7, 127.0, 126.7, 121.6, 112.2, 107.2, 103.6, 92.6, 90.3, 89.0, 56.9, 55.6, 55.6, 55.0, 46.7, 32.8, 19.5. m.p. 155-159° C.; IR vmax (film): 1676, 1612, 1549, 1514, 1251, 1220, 1149. HR/MS: m/z Calcd for [C$_{31}$H$_{29}$N$_{2}$O$_{6}$]+ 525.2026, found 525.2025 (0.1904 ppm). rf=0.2 (EA:Hex=5:1).

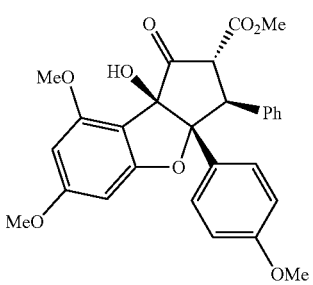

(±)-Keto-rocaglate or methyl (2S,3R,3aR,8bR)-8b-hydroxy-6,8-dimethoxy-3a-(4-methoxyphenyl)-1-oxo-3-phenyl-2,3,3a,8b-tetrahydro-1H-cyclopenta[b]benzofuran-2-carboxylate (9)

Keto-rocaglate was synthesized according to our previous protocol; this compound shows tautomerism between enol (E) and ketone (K) forms. $^{1}$H NMR (500 MHz, CDCl$_{3}$) δ 7.13-7.07 (m, 3H, K & m, 3H, E), f7.01 (d, J=9.0 Hz, 2H, E), 6.94 (d, J=8.9 Hz, 2H, K), 6.93-6.89 (m, 2H, K & m, 2H, E), 6.68 (d, J=8.9 Hz, 2H, K), 6.53 (d, J=9.1 Hz, 1H, E), 6.35 (d, J=2.0 Hz, 1H, K), 6.19 (d, J=1.9 Hz, 1H, E), 6.11 (d, J=2.0 Hz, 1H, K), 6.05 (d, J=1.9 Hz, 1H, E), 4.48 (s, 1H, E), 4.24 (d, J=13.3 Hz, 1H, K), 4.06 (d, J=13.2 Hz, 1H, K), 3.86 (s, 3H, K), 3.83 (s, 3H, E), 3.82 (s, 3H, K), 3.79 (s, 3H, E), 3.71 (s, 3H, K), 3.66 (s, 3H, K), 3.66 (s, 3H, E), 3.59 (s, 3H, E), 3.34 (s, 1H, E), 3.04 (s, 1H, K). 13C NMR (126 MHz, CDCl$_{3}$) δ 203.5, 172.2, 170.2, 167.4, 165.1, 163.7, 161.2, 160.9, 159.1, 158.7, 158.7, 158.2, 139.0, 135.5, 129.2, 129.27, 128.1, 128.0, 127.8, 127.3, 127.1, 126.8, 125.5, 113.4, 112.2, 106.2, 105.9, 102.5, 100.8, 99.5, 93.1, 92.6, 90.0, 89.2, 89.1, 88.7, 57.0, 56.6, 55.9, 55.9, 55.8, 55.8, 55.3, 55.1, 53.1, 52.1, 51.7. ESI MS m/z: 491.3, [M+H]+. rf=NA (stripe on TLC, EA:Hex=1:1).

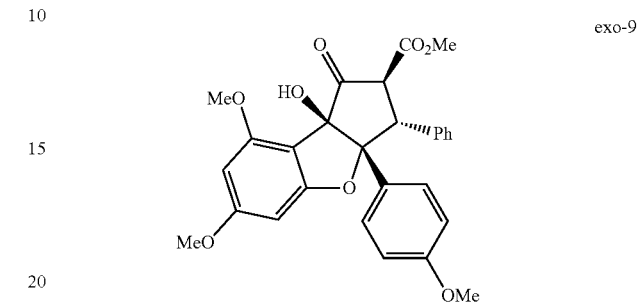

(±)-Exo-keto-rocaglate or methyl (2S,3R,3aR,8bR)-8b-hydroxy-6,8-dimethoxy-3a-(4-methoxyphenyl)-1-oxo-3-phenyl-2,3,3a,8b-tetrahydro-1H-cyclopenta[b]benzofuran-2-carboxylate (exo-9)

Exo-keto-rocaglate was synthesized according to our previous protocol; this compound shows tautomerism between enol (E) and ketone (K) forms. $^{1}$H NMR (500 MHz, CDCl$_{3}$) δ 7.44 (d, J=8.8 Hz, 2H, E), 7.35 (d, J=8.9 Hz, 2H, K), 7.24-7.18 (m, 3H, K), 7.16-7.08 (m, 3H, E), 7.07-7.02 (m, 2H, K), 6.93 (d, J=8.9 Hz, 2H, E), 6.89 (d, J=8.9 Hz, 2H, K), 6.82 (d, J=7.1 Hz, 2H, E), 6.15 (d, J=1.9 Hz, 1H, K), 6.02 (d, J=1.9 Hz, 1H, K), 6.00 (d, J=2.0 Hz, 1H, E), 5.63 (d, J=2.0 Hz, 1H, E), 4.69 (s, 1H, E), 4.43 (d, J=14.4 Hz, 1H, K), 4.38 (d, J=14.3 Hz, 1H, K), 3.84 (s, 3H, E), 3.82 (s, 3H, E), 3.80 (s, 3H, K), 3.79 (s, 3H, K), 3.77 (s, 3H, K), 3.72 (s, 3H, K), 3.65 (s, 3H, E), 3.63 (s, 3H, E), 3.49 (s, 1H, K). $^{13}$C NMR (126 MHz, CDCl$_{3}$) δ 203.2, 172.1, 169.5, 168.3, 164.7, 163.8, 161.9, 161.7, 159.4, 159.3, 158.1, 157.5, 137.7, 134.0, 130.4, 128.7, 128.2, 128.2, 128.1, 127.6, 127.4, 127.3, 126.6, 113.8, 113.5, 113.4, 106.6, 104.0, 103.0, 98.0, 97.2, 92.5, 92.3, 88.4, 88.1, 86.8, 58.0, 55.71, 55.69, 55.57, 55.55, 55.23, 55.19, 54.8, 54.2, 52.7, 51.7. ESI MS m/z: 491.3, [M+H]+. rf=NA (stripe on TLC, EA:Hex=1:1).

SCHEME 3

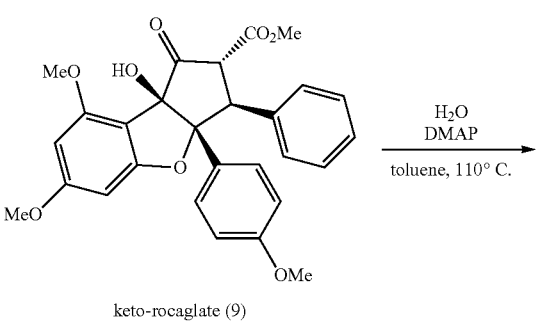

keto-rocaglate (9)

(3S,3aR,8bR)-8b-Hydroxy-6,8-dimethoxy-3a-(4-methoxyphenyl)-3-phenyl-2,3,3a,8b-tetrahydro-1H-cyclopenta[b]benzofuran-1-one (14)

Ketone product 14 was obtained via thermal decarboxylation. The starting material keto-rocaglate (9) was combined with DMAP (0.3 equiv) and stir bar in a 4 mL vial, Scheme FI. 83. A drop of water was added to the reaction mixture after the addition of m-xylene as reaction solvent. The reaction was heated at 110° C. for 3 h. After concentration, the crude product was purified using flash chromatography to afford the decarboxylated product 14 in quantitative yield. $^1$HNMR (500 MHz, CDCl$_3$) δ 7.14-7.07 (m, 3H), 6.98-6.92 (m, 4H), 6.68 (d, J=8.9 Hz, 2H), 6.34 (d, J=2.0 Hz, 1H), 6.10 (d, J=2.0 Hz, 1H), 3.89 (dd, J=12.4, 9.9 Hz, 1H), 3.85 (s, 3H), 3.83 (s, 3H), 3.71 (s, 3H), 3.10 (s, 1H), 3.05 (dd, J=19.8, 10.0 Hz, 1H), 2.98 (dd, J=19.8, 12.4 Hz, 1H). $^{13}$C NMR (126 MHz, CDCl$_3$) δ 210.7, 164.7, 161.2, 158.8, 158.4, 137.2, 128.0, 127.9, 127.8, 126.8, 125.8, 113.1, 106.5, 101.2, 92.6, 89.7, 88.8, 55.7, 55.6, 55.1, 48.6, 39.9.

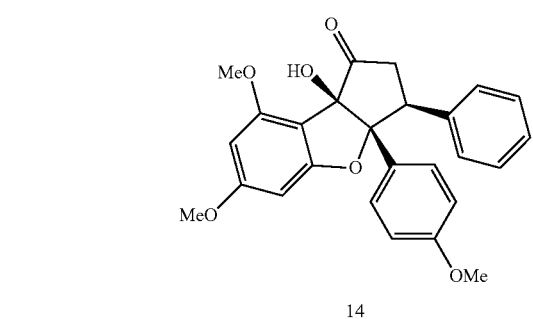

14

SCHEME 4

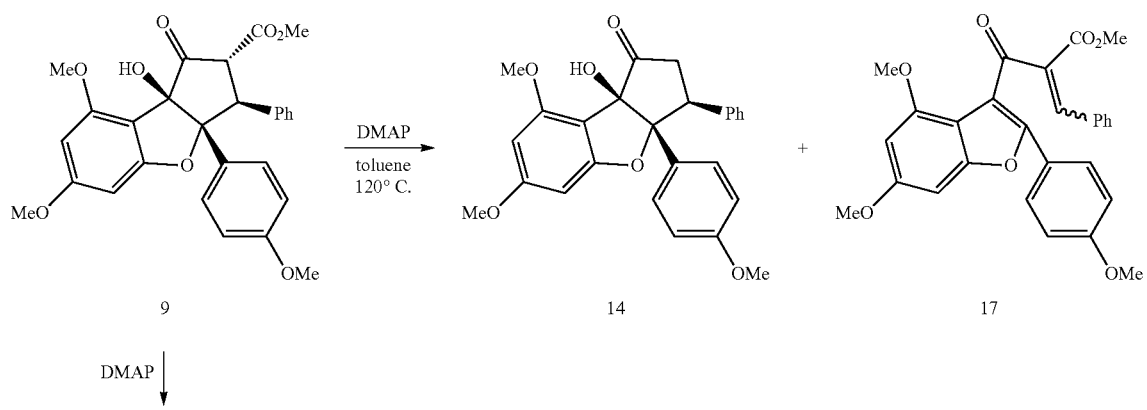

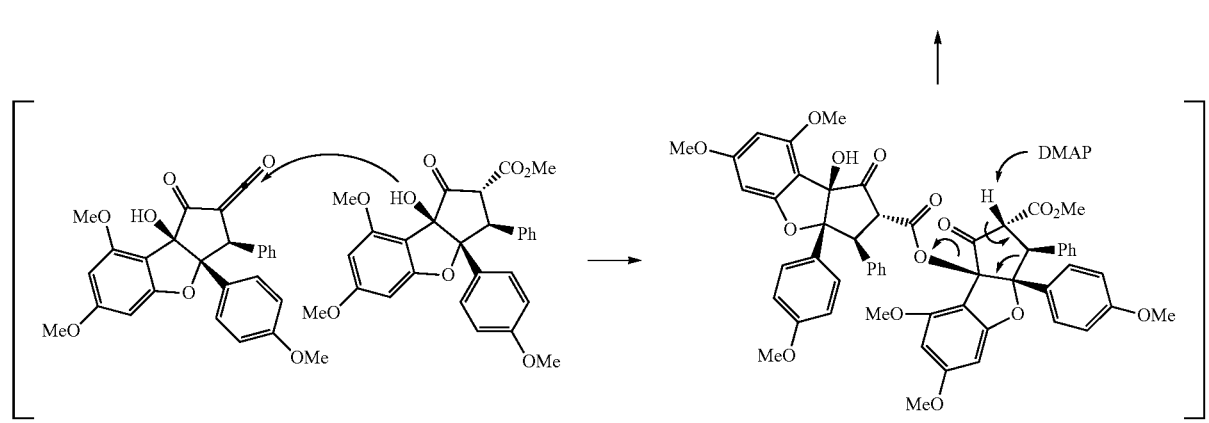

Methyl 2-(4,6-dimethoxy-2-(4-methoxyphenyl)benzofuran-3-carbonyl)-3-phenylacrylate (17)

As a mechanistic control experiment (mechanism above was displayed as alternative mechanism for retro-Nazarov reaction), azeotropically-dried keto-rocaglate 9 (25 mg) and DMAP (3.0 mg) was dissolved in 0.25 mL of pre-dried toluene-$d_8$ (0.025 M, dried with 4 Å molecular sieves, contains 43 ppm water as measured by Carl-Fischer titration) under nitrogen in a 4 mL reaction vial, Scheme 4. The mixture was heated at 120° C. for 12 h and was then, concentrated. Decarboxylated product 14 (~54% NMR yield), retro-Nazarov product 17 (~24% NMR yield), and keto-rocaglate 9 (~20% NMR yield) were found after reaction completion. A plausible mechanism is shown in the Scheme above, wherein one molecule of retro-Nazarov product 17 may be generated along with one molecule of decarboxylated product 14. This control experiment matches our observation that reducing the amount of nucleophile or use of amidines with low nucleophilicity generally afford greater amounts of the retro-Nazarov product 17 and decarboxylated product 14. Preparative TLC was employed to isolate the two retro-Nazarov isomers using 10% hexanes in $CH_2Cl_2$ as the eluent. However, the two isomers were found to interconvert within 24 h in chloroform. For the major retro-Nazarov isomer: $^1$H NMR (400 MHz, $CDCl_3$) δ 7.89 (d, J=8.9 Hz, 1H), 7.78 (s, 1H), 7.12 (t, J=7.0 Hz, 1H), 7.04-6.91 (m, 5H), 6.50 (d, J=2.0 Hz, 1H), 6.30 (d, J=2.0 Hz, 1H), 3.89 (s, 3H), 3.85 (s, 3H), 3.80 (s, 3H), 3.77 (s, 3H). $^{13}$C NMR (101 MHz, $CDCl_3$) δ 189.5, 165.8, 161.1, 159.3, 159.0, 155.2, 153.7, 142.1, 134.5, 133.4, 131.1, 129.3, 129.3, 127.8, 122.3, 117.1, 113.4, 109.9, 95.2, 87.6, 55.7, 55.4, 55.3, 52.3. ESI MS m/z: 473.2, [M+H]+. For the minor isomer: $^1$H NMR (400 MHz, $CDCl_3$) δ 7.73 (d, J=8.9 Hz, 2H), 7.38-7.27 (m, 6H), 6.93 (d, J=8.9 Hz, 2H), 6.70 (d, J=1.9 Hz, 1H), 6.31 (d, J=1.9 Hz, 1H), 3.89 (s, 3H), 3.87 (s, 3H), 3.82 (s, 3H), 3.80 (s, 3H). ESI MS m/z: 473.2, [M+H]+.

Methyl (3R,3aR,8bS)-1-benzimidamido-8b-hydroxy-6,8-dimethoxy-3a-(4-methoxyphenyl)-3-phenyl-3a,8b-dihydro-3H-cyclopenta[b]benzofuran-2-carboxylate, enamine (23)

Enamine 23 (28% yield) was observed and isolated from a 250 mg scale reaction for 12a as precipitates after 10 minutes under the standard conditions. However, enamine 23 can also be synthesized using an alternative method below:

The reaction solvent (toluene-d8, $C_7D_8$) was pre-treated with 4 Å molecular sieves to remove trace amounts of water. Benzylamidine (7.4 mg, 0.06 mmol) and keto-rocaglate 9 (10 mg, 0.02 mmol) was dried azeotropically in benzene at rt under high vacuum. Toluene-d8 (0.6 mL) was added to dissolve the mixed solids, and the resulting clear solution was transferred into an NMR tube under nitrogen. After 30 min at rt, the solution became cloudy. After heating for 12 h, a pale-yellow precipitate formed, which was triturated with $CH_2Cl_2$ to afford the pure enamine 23 (6.9 mg, 0.012 mmol) in 60% yield, Scheme 5. Enamine product 23 could only be dissolved in DMSO and was stored in DMSO for at least 6 months. $^1$H NMR (500 MHz, $(CD_3)_2SO$) δ 7.88 (d, J=7.1 Hz, 2H), 7.73-7.69 (m, 1H), 7.60 (dd, J=8.2, 7.3 Hz, 2H), 6.98 (d, J=8.9 Hz, 2H), 6.90 (dd, J=7.8, 6.4 Hz, 2H), 6.87-6.80 (m, 3H), 6.48 (d, J=9.0 Hz, 2H), 6.27 (d, J=2.0 Hz, 1H), 6.07 (d, J=2.0 Hz, 1H), 4.04 (s, 1H), 3.75 (s, 3H), 3.70 (s, 3H), 3.56 (s, 3H), 3.22 (s, 3H). $^{13}$C NMR (126 MHz, $(CD_3)_2SO$) δ 182.0, 166.5, 166.3, 162.4, 160.5, 158.2, 157.6, 143.3, 133.7, 130.0, 129.6, 129.3, 129.0, 128.7, 128.4, 126.8, 125.2, 111.9, 110.8, 100.2, 92.3, 89.5, 89.2, 88.3, 57.9, 55.9, 55.6, 55.2, 49.0. HR/MS: m/z Calcd for $[C_{35}H_{32}N_2O_7+H_3O]$+ 611.2393, found 611.2204.

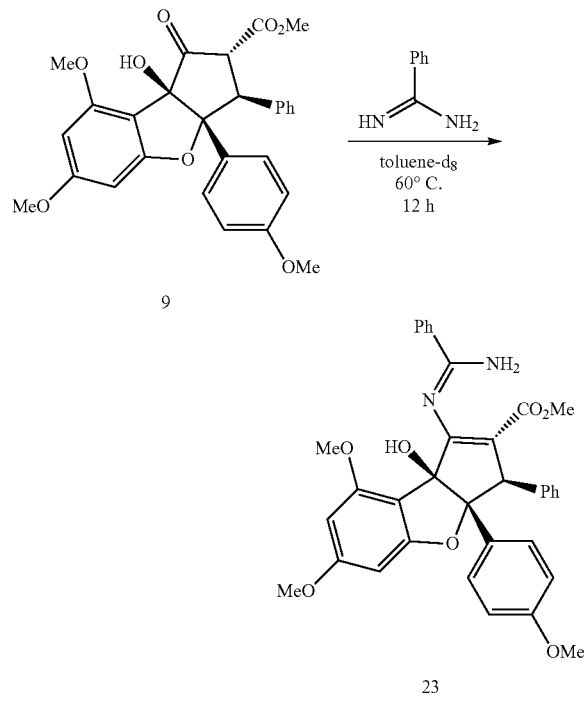

SCHEME 5

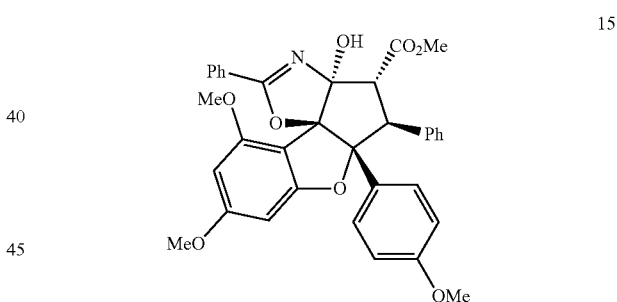

Methyl (3aR,4R,5S,5aR,10bR)-3a-hydroxy-8,10-dimethoxy-5a-(4-methoxyphenyl)-2,5-diphenyl-3a,4,5,5a-tetrahydrobenzofuro[3',2':2,3]cyclopenta[1,2-d]oxazole-4-carboxylate (15)

$^1$H NMR (400 MHz, $CDCl_3$) δ 7.82-7.73 (m, 2H), 7.47 (t, J=7.4 Hz, 1H), 7.33 (t, J=7.7 Hz, 2H), 7.14-6.94 (m, 7H), 6.53 (d, J=8.9 Hz, 2H), 6.39 (d, J=1.9 Hz, 1H), 6.14 (d, J=1.9 Hz, 1H), 4.78 (s, 1H), 4.33 (d, J=14.4 Hz, 1H), 4.04 (d, J=14.3 Hz, 1H), 3.87 (s, 3H), 3.79 (s, 3H), 3.75 (s, 3H), 3.62 (s, 3H). $^{13}$C NMR (101 MHz, $CDCl_3$) δ 169.5, 165.1, 164.6, 161.3, 158.7, 157.1, 135.8, 132.1, 129.0, 128.2, 127.9, 127.8, 127.6, 126.8, 126.7, 126.7, 113.0, 105.6, 102.2, 102.2, 101.8, 93.2, 89.8, 57.9, 55.9, 55.8, 55.1, 54, 52.5. m.p. 254-257° C. ($CDCl_3$); IR vmax (film): 2950, 1746, 1629, 1603, 1515, 1381, 1151. HR/MS: m/z Calcd for $[C_{35}H_{32}NO_8]$+ 594.2128, found 594.2132 (0.8414 ppm). rf=0.4 (EA:Hex=1:2).

SCHEME 6

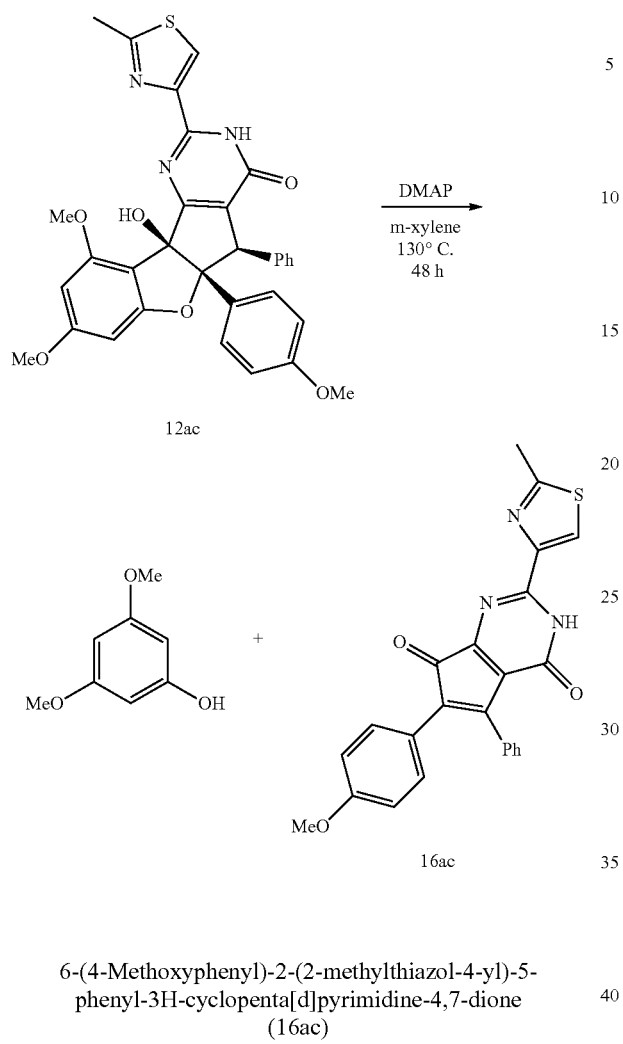

12ac 6-(4-Methoxyphenyl)-2-(2-methylthiazol-4-yl)-5-phenyl-3H-cyclopenta[d]pyrimidine-4,7-dione (16ac)

Very poor solubility of the dark blue solid 16a (see article text Table 1, FIG. 4) was observed in CDCl$_3$, whereas excellent solubility of 16ac in CDCl$_3$ was observed to afford a dark purple solution. Therefore, 16ac was used as a representative fragmentation product and employed a control reaction to understand the fragmentation of pyrimidinone 12a. To 5 mg of compound 12ac and 0.5 mg DMAP (0.5 equiv), 0.2 mL of m-xylene was added. The reaction mixture was stirred at 130° C. for 48 h. The crude product was concentrated which was followed by purification using flash chromatography (3% acetone in CH$_2$Cl$_2$) which afforded 3.1 mg of 16ac as a dark blue solid (84% yield), Scheme 6. $^1$H NMR (400 MHz, CDCl$_3$) δ 8.41 (s, 1H), 7.50-7.42 (m, 2H), 7.42-7.32 (m, 3H), 7.14 (d, J=8.9 Hz, 2H), 6.79 (d, J=9.0 Hz, 2H), 3.79 (s, 3H), 2.78 (s, 3H). $^{13}$C NMR (101 MHz, CDCl$_3$) δ 196.5, 167.7, 159.3, 155.9, 154.5, 153.6, 153.3, 146.4, 132.0, 131.3, 129.7, 129.5, 127.8, 127.7, 126.1, 124.4, 122.3, 113.8, 55.2, 19.2. m.p.>260° C. (CH$_2$Cl$_2$); IR vmax (film): 2928, 1693, 1510, 1251, 1173, 844. HR/MS: m/z Calcd for [C$_{24}$H$_{18}$N$_3$O$_3$S]+ 428.1069, found 428.1086 (3.9710 ppm). rf=0.4 (EA:Hex=1:2).

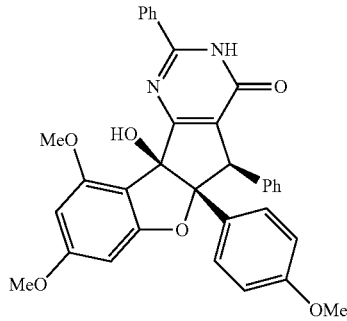

12a (5R,5aR,10bS)-10b-Hydroxy-8,10-dimethoxy-5a-(4-methoxyphenyl)-2,5-diphenyl-3,5,5a,10b-tetrahydro-4H-benzofuro[2',3':4,5]cyclopenta[1,2-d]pyrimidin-4-one (12a)

All the following pyrimidinone condensations were performed using 25 mg of keto-rocaglate 9. Yields were calculated after product purification using a pipet column or via preparative TLC. All aglaroxin C analogues were generally obtained as white solids; in a few cases, minor yellow impurities were removed by trituration using 10% ethyl acetate in hexanes. $^1$H NMR (500 MHz, CDCl$_3$) δ 8.09 (d, J=7.2 Hz, 1H), 7.39 (tt, J=7.5, 1.2 Hz, 1H), 7.15-7.08 (m, 7H), 7.04-7.00 (m, 2H), 6.57 (d, J=9.0 Hz, 1H), 6.23 (d, J=1.9 Hz, 1H), 6.05 (d, J=1.9 Hz, 1H), 4.77 (s, 1H), 3.85 (s, 3H), 3.79 (s, 3H), 3.67 (s, 3H), 3.58 (s, 1H). $^{13}$C NMR (126 MHz, CDCl$_3$) δ 168.4, 163.6, 162.5, 160.7, 158.6, 158.4, 136.9, 131.7, 131.7, 129.4, 128.7, 127.7, 127.6, 126.9, 126.7, 121.7, 112.3, 107.4, 104.1, 92.7, 89.9, 89.0, 57.6, 55.6, 55.0. m.p. 196-198° C. (CDCl$_3$); IR vmax (film): 2961, 2838, 1680, 1623, 1540, 1513, 1501, 1454, 1250, 1148, 1020, 813, 731, 699, 573. HR/MS: m/z Calcd for [C$_{34}$H$_{29}$N$_2$O$_6$]+ 561.2026, found 561.2029 (0.5346 ppm). rf=0.6 (3% acetone in CH$_2$Cl$_2$)

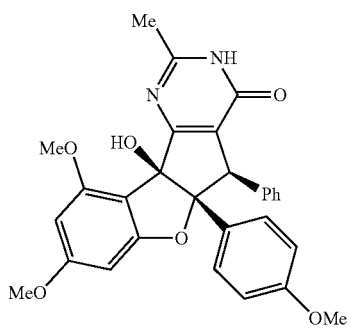

12b (5R,5aR,10bS)-10b-Hydroxy-8,10-dimethoxy-5a-(4-methoxyphenyl)-2-methyl-5-phenyl-3,5,5a,10b-tetrahydro-4H-benzofuro[2',3':4,5]cyclopenta[1,2-d]pyrimidin-4-one (12b)

$^1$H NMR (500 MHz, CDCl$_3$) δ 7.09-6.98 (m, 5H), 6.93-6.84 (m, 2H), 6.56 (d, J=9.0 Hz, 2H), 6.20 (d, J=2.0 Hz, 1H), 6.04 (d, J=1.9 Hz, 1H), 4.67 (s, 1H), 3.81 (s, 3H), 3.79 (s, 3H), 3.66 (s, 3H), 3.30 (s, 1H), 2.32 (s, 3H). $^{13}$C NMR (126

MHz, CDCl₃) δ 168.1, 163.6, 162.3, 160.8, 160.6, 158.6, 158.1, 136.7, 129.2, 128.8, 127.6, 126.8, 126.7, 121.4, 112.2, 107.1, 103.6, 92.7, 90.2, 89.0, 57.0, 55.6, 55.0, 21.8. ESI MS m/z: 499.1, [M+H]+. rf=0.5 (5% acetone in CH₂Cl₂).

57.4, 55.6, 55.4, 55.0, 34.3, 20.8, 20.0. ESI MS m/z: 527.3, [M+H]+. rf=0.6 (5% acetone in CH₂Cl₂).

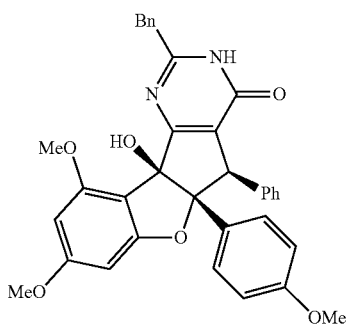

(5R,5aR,10bS)-2-Benzyl-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12c)

¹H NMR (500 MHz, CDCl₃) δ 7.19-7.15 (m, 5H), 7.10-7.04 (m, 5H), 6.94-6.88 (m, 2H), 6.58 (d, J=9.0 Hz, 2H), 6.23 (d, J=1.9 Hz, 1H), 6.06 (d, J=1.9 Hz, 1H), 4.63 (s, 1H), 3.98 (d, J=14.4 Hz, 1H), 3.82 (d, J=14.4 Hz, 1H), 3.81 (s, 6H), 3.67 (s, 3H), 3.24 (s, 1H). ¹³C NMR (126 MHz, CDCl₃) δ 168.1, 163.7, 162.0, 161.8, 160.8, 158.6, 158.1, 136.5, 134.8, 129.4, 129.3, 128.7, 128.6, 127.5, 127.3, 126.8, 126.7, 121.5, 112.3, 107.2, 104.2, 92.7, 89.8, 88.9, 57.3, 55.6, 55.5, 55.0, 41.7. ESI MS m/z: 575.3, [M+H]+. rf=0.5 (3% acetone in CH₂Cl₂).

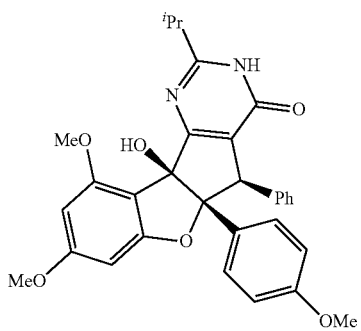

(5R,5aR,10bS)-10b-Hydroxy-2-isopropyl-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12d)

¹H NMR (400 MHz, CDCl₃) δ 7.12-7.00 (m, 5H), 6.95-6.85 (m, 2H), 6.56 (d, J=8.9 Hz, 2H), 6.21 (d, J=1.9 Hz, 1H), 6.03 (d, J=1.9 Hz, 1H), 4.65 (s, 1H), 3.80 (s, 6H), 3.66 (s, 3H), 3.41 (s, 1H), 2.83 (p, J=6.9 Hz, 1H), 1.22 (t, J=7.4 Hz, 6H). ¹³C NMR (101 MHz, CDCl₃) δ 168.1, 168.0, 163.5, 161.9, 160.6, 158.5, 158.0, 136.7, 129.3, 128.7, 127.5, 127.0, 126.5, 121.1, 112.2, 107.5, 103.9, 92.6, 89.8, 88.9,

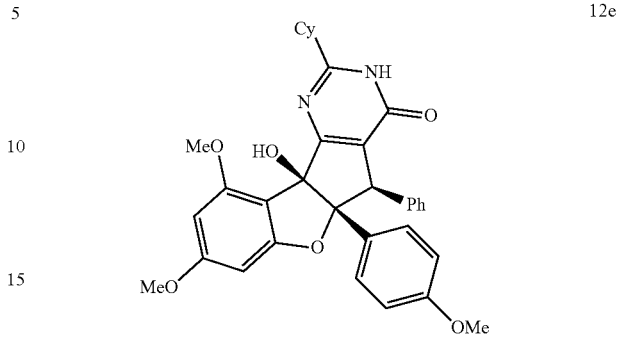

(5R,5aR,10bS)-2-Cyclohexyl-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12e)

¹H NMR (400 MHz, CDCl₃) δ 7.03-6.92 (m, 5H), 6.87-6.79 (m, 2H), 6.50 (d, J=8.9 Hz, 2H), 6.19 (d, J=2.0 Hz, 1H), 6.00 (d, J=2.0 Hz, 1H), 4.52 (s, 1H), 3.76 (s, 3H), 3.75 (s, 3H), 3.61 (s, 3H), 2.95 (s, 1H), 2.55 (tt, J=12.0, 3.5 Hz, 1H), 1.95-1.81 (m, 2H), 1.80-1.68 (m, 2H), 1.56 (m, 3H), 1.32-1.16 (m, 2H), 1.16-1.04 (m, 1H). ¹³CNMR (101 MHz, CDCl₃+CD₃OD) δ 168.1, 167.1, 163.5, 161.5, 160.6, 158.4, 158.0, 136.4, 129.1, 128.5, 127.3, 127.0, 126.4, 120.9, 112.1, 107.6, 104.3, 92.5, 89.3, 88.9, 57.3, 55.6, 55.3, 55.0, 44.0, 30.8, 30.1, 25.8, 25.6, 25.4. ESI MS m/z: 567.2, [M+H]+. rf=0.2 (5% acetone in CH₂Cl₂).

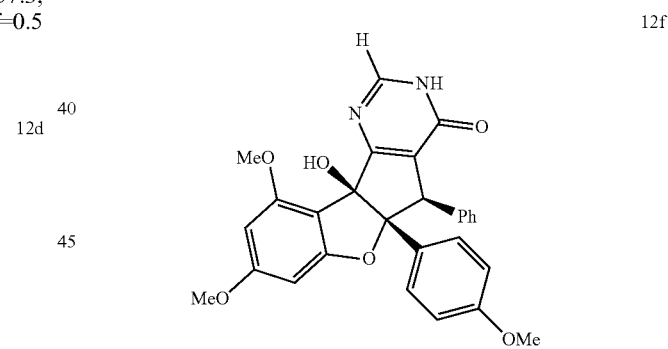

(5R,5aR,10bS)-10b-Hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12f)

The amidine reaction partner carbomethoxyformamidine was used at a concentration of 0.2 M. Spontaneous decarboxylation occurred to afford pyrimidinone 12f. ¹HNMR (500 MHz, (CD₃)₂SO) δ 8.25 (s, 1H), 7.07-7.00 (m, 3H), 6.97 (d, J=8.9 Hz, 2H), 6.82-6.77 (m, 2H), 6.51 (d, J=8.9 Hz, 2H), 6.22 (d, J=1.9 Hz, 1H), 6.09 (d, J=2.0 Hz, 1H), 5.93 (s, 1H), 4.40 (s, 1H), 3.72 (s, 3H), 3.71 (s, 3H), 3.58 (s, 3H). ¹³C NMR (126 MHz, (CD₃)₂SO) δ 167.3, 163.0, 160.6, 159.7, 158.6, 158.3, 151.4, 137.8, 129.6, 129.3, 128.2, 127.8, 126.8, 124.3, 112.2, 108.2, 102.5, 92.9, 90.6, 89.4, 57.0, 55.9, 55.9, 55.4, 55.2. ESI MS m/z: 485.2, [M+H]+. rf=0.3 (3% acetone in CH₂Cl₂).

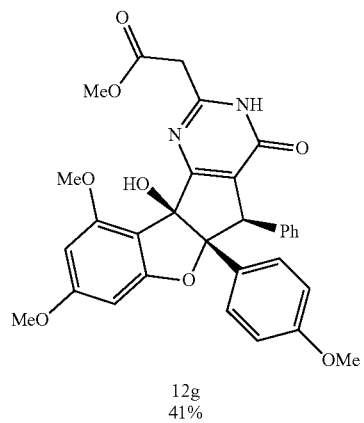
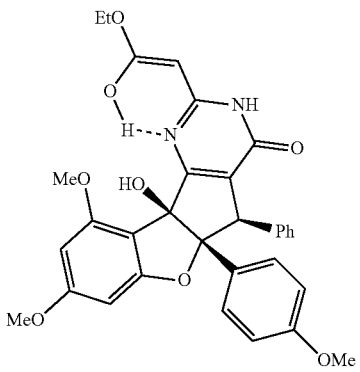

12g
41%

Methyl 2-((5R,5aR,10bS)-10b-hydroxy-8,10-dimethoxy-5a-(4-methoxyphenyl)-4-oxo-5-phenyl-4,5,5a,10b-tetrahydro-3H-benzofuro[2',3':4,5]cyclopenta[1,2-d]pyrimidin-2-yl)acetate (12g)

Ethyl 2-amidinoacetate hydrochloride was used as a condensation partner. However, it was discovered that ester exchange occurred during the reaction due to the presence of methanol in the reaction system. Accordingly, a 41% yield of 12g was isolated along with the corresponding ethyl ester (see $^1$H NMR spectrum on page S92). Additionally, slow tautomerization of the products was noticed, wherein both tautomers were separated using PTLC (two bands). Two tautomers were found to transform into each other during product elution. The ratio of the major and minor tautomers was 10:1. NMR data for the major tautomer: $^1$H NMR (500 MHz, CDCl$_3$) δ 7.11-7.02 (m, 5H), 6.88 (dd, J=6.6, 2.8 Hz, 2H), 6.55 (d, J=9.0 Hz, 2H), 6.20 (d, J=1.9 Hz, 1H), 6.04 (d, J=2.0 Hz, 1H), 4.68 (s, 1H), 3.80 (s, 3H), 3.79 (s, 3H), 3.76 (d, J=1.4 Hz, 1H), 3.69 (s, 3H), 3.66 (s, 3H). $^{13}$C NMR (126 MHz, CDCl$_3$) δ 168.7, 167.1, 163.6, 160.8, 160.6, 158.6, 158.1, 155.8, 136.4, 129.2, 128.8, 127.7, 126.8, 126.7, 123.1, 112.3, 107.0, 103.4, 92.7, 90.2, 89.0, 57.1, 55.60, 55.57, 55.0, 52.7, 39.9. ESI MS m/z: 557.4, [M+H]+. rf=0.7 (5% acetone in CH$_2$Cl$_2$).

(5R,5aR,10bS)-2-Cyclopropyl-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12h)

$^1$H NMR (500 MHz, CDCl$_3$) δ 7.03 (t, J=5.9 Hz, 5H), 6.95-6.84 (m, 2H), 6.55 (d, J=8.5 Hz, 2H), 6.21 (s, 1H), 6.02 (s, 1H), 4.63 (s, 1H), 3.79 (s, 3H), 3.78 (s, 3H), 3.66 (s, 3H), 3.44 (bs, 1H), 1.67 (bs, 1H), 1.33 (bs, 1H), 1.10 (bs, 1H), 0.95 (d, J=8.3 Hz, 2H). $^{13}$C NMR (126 MHz, CDCl$_3$) δ 168.7, 166.0, 163.5, 162.3, 160.6, 158.5, 157.9, 136.8, 129.3, 128.6, 127.4, 127.0, 126.4, 119.6, 112.2, 107.5, 103.8, 92.5, 89.6, 88.9, 57.4, 55.6, 55.3, 55.0, 14.2, 11.1, 10.5. ESI MS m/z: 525.5, [M+H]+. rf=0.15 (EA:Hex=2:1).

(5R,5aR,10bS)-10b-Hydroxy-8,10-dimethoxy-2-(methoxymethyl)-5a-(4-methoxyphenyl)-5-phenyl-3,5,5a,10b-tetrahydro-4H-benzofuro[2',3':4,5]cyclopenta[1,2-d]pyrimidin-4-one (12i)

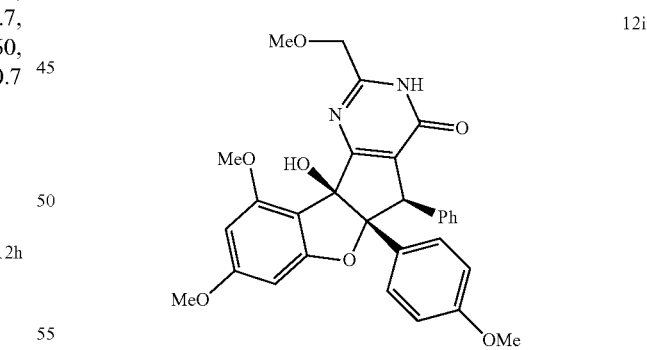

12h

12i

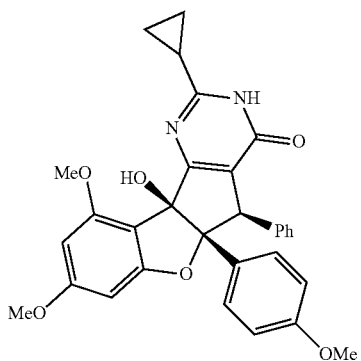

$^1$H NMR (400 MHz, CDCl$_3$) δ 7.10-7.02 (m, 5H), 6.92-6.86 (m, 2H), 6.56 (d, J=8.5 Hz, 2H), 6.21 (d, J=2.0 Hz, 1H), 6.04 (d, J=2.0, 1H), 4.71 (s, 1H), 4.55 (d, J=15.4 Hz, 1H), 4.46 (d, J=15.4 Hz, 1H), 3.81 (s, 3H), 3.79 (s, 3H), 3.66 (s, 3H), 3.47 (d, 3H), 3.20 (s, 1H). $^{13}$C NMR (101 MHz, CDCl$_3$) δ 166.7, 163.6, 160.9, 159.9, 159.6, 158.6, 158.4, 136.6, 129.2, 128.8, 127.7, 126.8, 126.8, 123.2, 112.3, 107.0, 103.4, 92.7, 90.3, 89.1, 70.8, 59.5, 57.1, 55.61, 55.58, 55.0. ESI MS m/z: 529.2, [M+H]+. rf=0.1 (2% acetone in CH$_2$Cl$_2$).

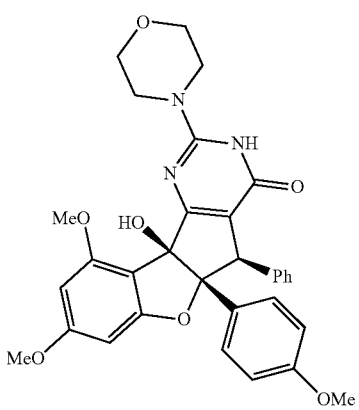

(5R,5aR,10bS)-10b-Hydroxy-8,10-dimethoxy-5a-(4-methoxyphenyl)-2-morpholino-5-phenyl-3,5,5a,10b-tetrahydro-4H-benzofuro[2',3':4,5]cyclopenta[1,2-d]pyrimidin-4-one (12j)

$^1$H NMR (500 MHz, CDCl$_3$) δ 7.07-7.00 (m, 5H), 6.89 (dd, J=7.5, 2.1 Hz, 2H), 6.54 (d, J=9.0 Hz, 2H), 6.22 (d, J=2.0 Hz, 1H), 6.02 (d, J=2.0 Hz, 1H), 4.49 (s, 1H), 3.79 (s, 3H), 3.74 (s, 3H), 3.65 (s, 3H), 3.54-3.43 (m, 4H), 3.39-3.25 (m, 5H). $^{13}$C NMR (126 MHz, CDCl$_3$) δ 169.9, 163.4, 163.1, 160.7, 158.4, 158.0, 155.6, 137.7, 129.2, 128.5, 127.2, 127.1, 126.3, 112.2, 110.3, 107.7, 104.0, 92.5, 89.7, 88.9, 66.1, 57.2, 55.6, 55.3, 55.0, 44.8. ESI MS m/z: 570.4, [M+H]+. rf=0.2 (10% acetone in CH$_2$Cl$_2$).

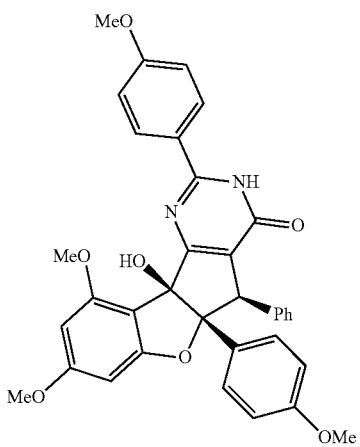

(5R,5aR,10bS)-10b-Hydroxy-8,10-dimethoxy-2,5a-bis(4-methoxyphenyl)-5-phenyl-3,5,5a,10b-tetrahydro-4H-benzofuro[2',3':4,5]cyclopenta[1,2-d]pyrimidin-4-one (12k)

$^1$H NMR (400 MHz, CDCl$_3$) δ 8.07 (d, J=8.6 Hz, 2H), 7.15-7.08 (m, 5H), 7.07-7.01 (m, 2H), 6.60-6.51 (m, 4H), 6.24 (d, J=2.0 Hz, 1H), 6.05 (d, J=2.0 Hz, 1H), 4.76 (s, 1H), 3.84 (s, 3H), 3.80 (s, 6H), 3.67 (s, 3H), 3.52 (s, 1H). $^{13}$C NMR (101 MHz, CDCl$_3$) δ 168.6, 163.6, 162.6, 162.3, 160.7, 158.5, 158.2, 158.0, 137.0, 129.5, 129.4, 128.6, 127.5, 126.9, 126.6, 124.1, 120.5, 114.1, 112.2, 107.5, 104.1, 92.6, 89.8, 89.0, 57.6, 55.62, 55.60, 55.5, 55.0. ESI MS m/z: 591.3, [M+H]+. rf=0.3 (1% acetone in CH$_2$Cl$_2$).

(5R,5aR,10bS)-10b-Hydroxy-8,10-dimethoxy-5a-(4-methoxyphenyl)-5-phenyl-2-(p-tolyl)-3,5,5a,10b-tetrahydro-4H-benzofuro[2',3':4,5]cyclopenta[1,2-d]pyrimidin-4-one (12l)

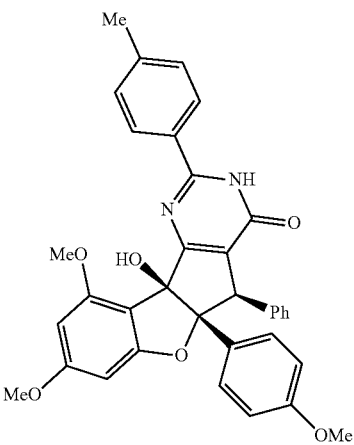

1. $^1$H NMR (500 MHz, CD$_2$Cl$_2$+CD$_3$OD) δ 8.00 (d, J=8.3 Hz, 2H), 7.34 (d, J=7.6 Hz, 1H), 7.09-7.03 (m, 5H), 6.95-6.89 (m, 2H), 6.53 (d, J=9.0 Hz, 2H), 6.25 (d, J=1.9 Hz, 1H), 6.09 (d, J=2.0 Hz, 1H), 4.59 (s, 1H), 3.84 (s, 3H), 3.78 (s, 3H), 3.63 (s, 3H), 2.43 (s, 3H). $^{13}$C NMR (101 MHz, CDCl$_3$) δ 168.5, 163.6, 162.6, 160.7, 158.8, 158.6, 158.1, 142.2, 137.1, 129.4, 129.0, 128.7, 127.7, 127.6, 127.0, 126.6, 121.1, 112.2, 107.5, 104.1, 92.6, 89.9, 89.0, 57.6, 55.6, 55.6, 55.0, 21.5. m.p.>260° C. (CDCl$_3$); IR vmax (film): 1663, 1623, 1544, 1515, 1455, 1253, 1203, 1149, 1023, 829. HR/MS: m/z Calcd for [C$_{35}$H$_{31}$N$_2$O$_6$]+ 575.2182, found 575.2186 (0.6954 ppm). rf=0.4 (1% acetone in CH$_2$Cl$_2$).

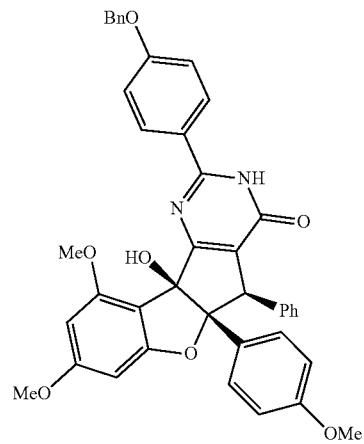

(5R,5aR,10bS)-2-(4-(Benzyloxy)phenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12m)

$^1$H NMR (500 MHz, (CD$_3$)$_2$SO) δ 8.21 (d, J=8.6 Hz, 2H), 7.49-7.46 (m, 2H), 7.40 (t, J=7.4 Hz, 2H), 7.36-7.32 (m,

1H), 7.19 (d, J=9.0 Hz, 2H), 7.06-7.01 (m, 3H), 6.99 (d, J=8.9 Hz, 2H), 6.85 (dd, J=6.9, 2.7 Hz, 2H), 6.52 (d, J=9.0 Hz, 2H), 6.26 (d, J=2.0 Hz, 1H), 6.12 (d, J=2.0 Hz, 1H), 5.93 (s, 1H), 5.21 (s, 2H), 4.41 (s, 1H), 3.79 (s, 3H), 3.73 (s, 3H), 3.58 (s, 3H). $^{13}$C NMR (126 MHz, (CD$_3$)$_2$SO) δ 167.7, 163.1, 161.6, 161.0, 160.6, 158.7, 158.3, 158.0, 138.0, 137.0, 130.1, 129.6, 129.2, 128.9, 128.5, 128.3, 128.3, 127.7, 126.7, 125.1, 120.8, 115.3, 112.2, 108.6, 103.2, 93.0, 90.3, 89.4, 69.9, 57.3, 55.98, 55.94, 55.2. ESI MS m/z: 667.3, [M+H]+. rf=0.4 (1% acetone in CH$_2$Cl$_2$).

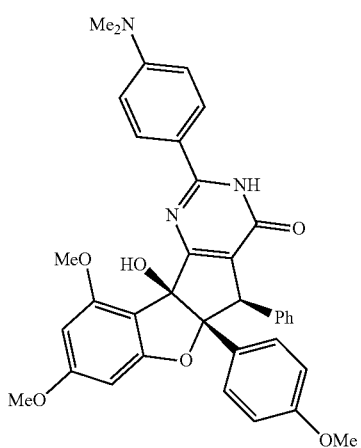

(5R,5aR,10bS)-2-(4-(Dimethylamino)phenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12n)

The product was isolated as pale-yellow solids. The para-N,N-dimethylaniline motif gives this compound strong fluorescence under sunlight, which may be useful for future mechanistic and target ID studies. The excitation/emission profiles of 12n are provided on page S74. $^1$H NMR (500 MHz, CDCl$_3$+CD$_3$OD) δ 7.93 (d, J=8.8 Hz, 2H), 6.99 (d, J=8.7 Hz, 2H), 6.97-6.93 (m, 3H), 6.86-6.81 (m, 2H), 6.67 (d, J=8.9 Hz, 2H), 6.46 (d, J=8.8 Hz, 2H), 6.15 (d, J=2.0 Hz, 1H), 5.98 (d, J=2.0 Hz, 1H), 3.78 (s, 3H), 3.72 (s, 3H), 3.57 (s, 3H), 3.00 (s, 6H). $^{13}$C NMR (126 MHz, CDCl$_3$+CD$_3$OD) δ 168.8, 163.7, 162.0, 160.8, 159.0, 158.5, 158.3, 153.0, 137.0, 129.4, 129.3, 129.1, 128.8, 127.6, 127.4, 126.6, 119.5, 118.6, 112.2, 111.6, 108.0, 104.2, 92.8, 89.7, 89.1, 57.6, 55.7, 55.6, 55.1, 40.1.

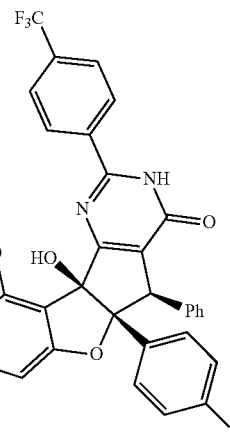

(5R,5aR,10bS)-10b-Hydroxy-8,10-dimethoxy-5a-(4-methoxyphenyl)-5-phenyl-2-(4-(trifluoromethyl)phenyl)-3,5,5a,10b-tetrahydro-4H-benzofuro[2',3':4,5]cyclopenta[1,2-d]pyrimidin-4-one (12o)

$^1$H NMR (400 MHz, CD$_2$Cl$_2$) δ 8.29-8.24 (m, 2H), 7.71 (d, J=8.2 Hz, 2H), 7.10-7.05 (m, 5H), 6.97-6.92 (m, 2H), 6.55 (d, J=9.2 Hz, 2H), 6.26 (d, J=2.0 Hz, 1H), 6.09 (d, J=2.0 Hz, 1H), 4.64 (s, 1H), 3.83 (s, 3H), 3.79 (s, 3H), 3.78 (s, 3H), 3.64 (s, 3H). $^{13}$C NMR (101 MHz, CDCl$_3$+CD$_3$OD) δ 168.2, 163.6, 161.7, 160.7, 158.4, 158.1, 157.2, 136.4, 135.3, 133.1 (q, J=32.6 Hz), 129.1, 128.6, 128.2, 127.4, 126.9, 126.6, 125.6 (q, J=3.7 Hz), 123.6 (q, J=270.9 Hz), 122.6, 112.1, 107.3, 104.1, 92.6, 89.5, 89.0, 57.5, 55.44, 55.36, 54.9. ESI MS m/z: 629.2, [M+1-1]+. rf=0.1 (EA:Hex=2:1).

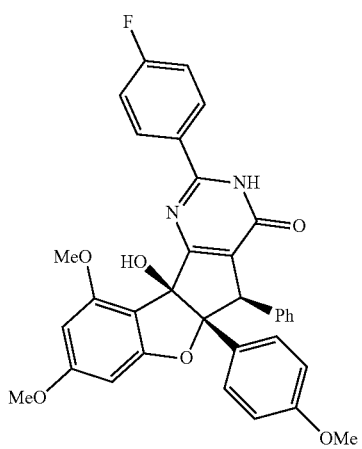

(5R,5aR,10bS)-2-(4-Fluorophenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12p)

$^1$H NMR (400 MHz, CDCl$_3$) δ 8.16-8.04 (m, 2H), 7.17-7.07 (m, 5H), 7.05-6.90 (m, 2H), 6.74 (t, J=8.5 Hz, 2H), 6.62-6.47 (m, 2H), 6.24 (d, J=2.1 Hz, 1H), 6.05 (d, J=2.2 Hz,

1H), 4.75 (s, 1H), 3.84 (s, 3H), 3.80 (s, 3H), 3.67 (s, 3H), 3.49 (s, 1H). $^{13}$C NMR (101 MHz, CDCl$_3$) δ 168.66, 164.94 (d, J=252 Hz), 163.7, 162.7, 160.7, 158.6, 158.0, 157.6, 136.8, 130.2 (d, J=9.2 Hz), 129.4, 128.6, 127.9, 127.8, 127.6, 126.8 (d, J=3.3 Hz), 121.4, 115.8 (d, J=22.0 Hz), 112.3, 107.3, 104.2, 92.7, 89.8, 89.0, 57.6, 55.63, 55.60, 55.0. ESI MS m/z: 579.3, [M+1-1]+. rf=0.1 (EA:Hex=2:1).

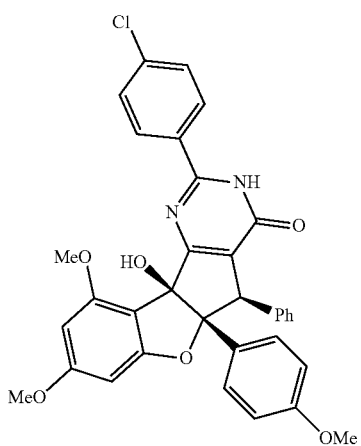

(5R,5aR,10bS)-2-(4-Chlorophenyl)-10b-hydroxy-8,
10-dimethoxy-5a-(4-methoxyphenyl)-5-phenyl-3,5,
5a,10b-tetrahydro-4H-benzofuro[2',3':4,5]cyclopenta
[1,2-d]pyrimidin-4-one (12q)

$^1$H NMR (500 MHz, CD$_2$Cl$_2$+CD$_3$OD) δ 8.07 (d, J=8.6 Hz, 2H), 7.44 (d, J=8.6 Hz, 2H), 7.10-7.02 (m, 5H), 6.96-6.89 (m, 2H), 6.53 (d, J=9.0 Hz, 2H), 6.25 (d, J=2.0 Hz, 1H), 6.08 (d, J=2.0 Hz, 1H), 4.60 (s, 1H), 3.82 (s, 3H), 3.78 (s, 3H), 3.63 (s, 3H). $^{13}$C NMR (126 MHz, CD$_2$Cl$_2$+CD$_3$OD) δ 168.4, 164.3, 162.2, 161.2, 159.1, 158.7, 158.3, 138.7, 137.2, 131.3, 129.8, 129.7, 129.6, 129.1, 127.9, 127.7, 127.1, 122.5, 112.5, 108.0, 104.8, 93.0, 90.0, 89.5, 58.0, 56.0, 55.9, 55.4. ESI MS m/z: 595.3, [M+H]+. rf=0.2 (EA:Hex=1:1).

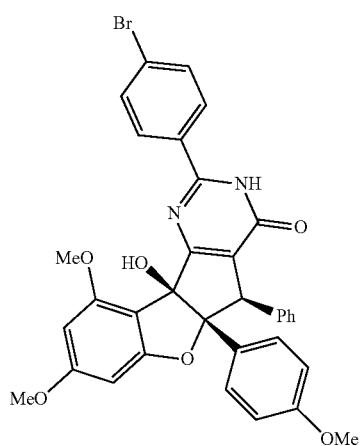

(5R,5aR,10bS)-2-(4-Bromophenyl)-10b-hydroxy-8,
10-dimethoxy-5a-(4-methoxyphenyl)-5-phenyl-3,5,
5a,10b-tetrahydro-4H-benzofuro[2',3':4,5]cyclopenta
[1,2-d]pyrimidin-4-one (12r)

$^1$H NMR (400 MHz, CD$_2$Cl$_2$+CD$_3$OD) δ 8.02 (d, J=8.6 Hz, 2H), 7.62 (d, J=8.6 Hz, 2H), 7.12-7.04 (m, 5H), 6.95 (dd, J=6.6, 2.9 Hz, 2H), 6.56 (d, J=9.0 Hz, 2H), 6.27 (d, J=1.9 Hz, 1H), 6.10 (d, J=2.0 Hz, 1H), 4.62 (s, 1H), 3.84 (s, 3H), 3.80 (s, 3H), 3.65 (s, 3H). $^{13}$C NMR (126 MHz, CD$_2$Cl$_2$+CD$_3$OD) δ 168.2, 164.3, 161.1, 159.1, 158.6, 158.6, 158.3, 137.2, 132.6, 131.6, 129.8, 129.7, 129.2, 127.9, 127.6, 127.2, 127.1, 122.6, 112.6, 108.0, 104.7, 93.0, 90.1, 89.6, 58.0, 56.1, 56.0, 55.4. ESI MS m/z: 640.4. 642.4, [M+1-1]+.

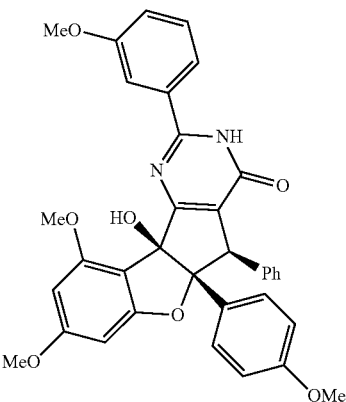

(5R,5aR,10bS)-10b-Hydroxy-8,10-dimethoxy-2-(3-methoxyphenyl)-5a-(4-methoxyphenyl)-5-phenyl-3,
5,5a,10b-tetrahydro-4H-benzofuro[2',3':4,5]cyclo-penta[1,2-d]pyrimidin-4-one (12s)

$^1$H NMR (500 MHz, CDCl$_3$) δ 7.72 (t, J=2.1 Hz, 1H), 7.63 (dt, J=7.6, 1.3 Hz, 1H), 7.10-7.05 (m, 5H), 7.03 (t, J=7.9 Hz, 1H), 7.00-6.94 (m, 3H), 6.56 (d, J=9.0 Hz, 2H), 6.21 (d, J=1.9 Hz, 1H), 6.05 (d, J=1.9 Hz, 1H), 4.76 (s, 1H), 3.85 (s, 3H), 3.79 (s, 3H), 3.71 (s, 3H), 3.66 (s, 3H), 3.65 (bs, 1H). $^{13}$C NMR (126 MHz, CDCl$_3$) δ 168.3, 163.5, 162.2, 160.7, 159.8, 158.6, 158.5, 158.0, 136.8, 133.0, 129.8, 129.3, 128.8, 127.6, 127.0, 126.8, 121.9, 119.9, 118.8, 112.2, 112.0, 107.4, 103.6, 92.6, 90.1, 89.1, 57.5, 55.60, 55.57, 55.3, 55.0. m.p. 159-162° C.; IR vmax (film): 2932, 2838, 1660, 1611, 1547, 1514, 1500, 1465, 1250, 1220, 1148, 1112, 1041, 980, 817, 699. HR/MS: m/z Calcd for [C$_{35}$H$_{31}$N$_2$O$_7$]+ 591.2131, found 591.2115 (2.7063 ppm). rf=0.4 (3% acetone in CH$_2$Cl$_2$).

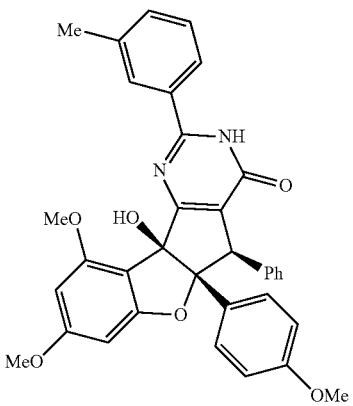

(5R,5aR,10bS)-10b-Hydroxy-8,10-dimethoxy-5a-(4-methoxyphenyl)-5-phenyl-2-(m-tolyl)-3,5,5a,10b-tetrahydro-4H-benzofuro[2',3':4,5]cyclopenta[1,2-d]pyrimidin-4-one (12t)

$^1$H NMR (500 MHz, CDCl$_3$) δ 8.04 (s, 1H), 7.86 (d, J=7.4 Hz, 1H), 7.22 (d, J=7.6 Hz, 1H), 7.12-7.06 (m, 5H), 7.01-6.96 (m, 3H), 6.56 (d, J=9.0 Hz, 2H), 6.22 (d, J=1.8 Hz, 1H), 6.05 (d, J=1.9 Hz, 1H), 4.78 (s, 1H), 3.86 (s, 3H), 3.79 (s, 3H), 3.67 (s, 3H), 3.58 (bs, 1H), 2.21 (s, 3H). $^{13}$C NMR (126 MHz, CDCl$_3$) δ 168.3, 163.5, 162.4, 160.7, 158.7, 158.6, 158.1, 138.5, 136.9, 132.6, 131.6, 129.3, 128.8, 128.6, 128.4, 127.6, 127.0, 126.7, 124.7, 121.6, 112.21 107.5, 103.7, 92.6, 90.0, 89.0, 57.6, 55.60, 55.56, 55.0, 21.3. ESI MS m/z: 575.3, [M+H]+. rf=0.35 (3% acetone in CH$_2$Cl$_2$).

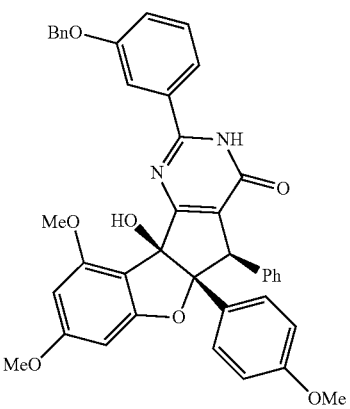

(5R,5aR,10bS)-2-(3-(Benzyloxy)phenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12u)

$^1$H NMR (500 MHz, CDCl$_3$) δ 7.87 (t, J=2.1 Hz, 1H), 7.61 (d, J=7.8 Hz, 1H), 7.43-7.36 (m, 4H), 7.36-7.31 (m, 1H), 7.08 (d, J=9.0 Hz, 2H), 7.06-7.02 (m, 4H), 6.99 (t, J=7.9 Hz, 1H), 6.95-6.90 (m, 2H), 6.56 (d, J=9.0 Hz, 2H), 6.21 (d, J=1.9 Hz, 1H), 6.05 (d, J=1.9 Hz, 1H), 5.09 (d, J=11.8 Hz, 1H), 5.06 (d, J=11.7 Hz, 1H), 4.76 (s, 1H), 3.84 (s, 3H), 3.79 (s, 3H), 3.66 (s, 3H). $^{13}$C NMR (126 MHz, CDCl$_3$) δ 168.2, 163.5, 162.3, 160.7, 158.9, 158.6, 158.4, 158.0, 136.8, 136.7, 133.0, 130.0, 129.3, 128.8, 128.6, 128.0, 127.6, 127.5, 126.9, 126.8, 122.0, 120.1, 119.3, 113.4, 112.2, 107.4, 103.6, 92.6, 90.1, 89.1, 69.9, 57.5, 55.62, 55.59, 55.0. ESI MS m/z: 667.5, [M+H]+. rf=0.3 (3% acetone in CH$_2$Cl$_2$).

(5R,5aR,10bS)-2-(2-Ethoxyphenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12v)

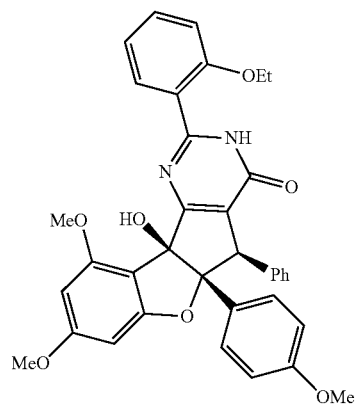

$^1$H NMR (400 MHz, CDCl$_3$) δ 8.71 (dd, J=8.0, 1.8 Hz, 1H), 7.51 (ddd, J=8.8, 7.3, 1.8 Hz, 1H), 7.17-7.02 (m, 7H), 6.96 (dd, J=7.5, 2.0 Hz, 2H), 6.57 (d, J=9.0 Hz, 2H), 6.23 (d, J=1.9 Hz, 1H), 6.06 (d, J=1.9 Hz, 1H), 4.79 (s, 1H), 4.31 (q, J=7.0 Hz, 2H), 3.88 (s, 3H), 3.79 (s, 3H), 3.67 (s, 3H), 3.61 (s, 1H), 1.58 (t, J=7.0 Hz, 3H). $^{13}$C NMR (101 MHz, CDCl$_3$) δ 167.0, 163.4, 160.7, 159.7, 158.5, 158.0, 157.3, 157.2, 136.8, 133.7, 131.7, 129.3, 128.9, 127.7, 127.1, 126.7, 121.9, 121.6, 119.0, 112.7, 112.2, 107.5, 103.3, 92.6, 90.4, 89.0, 65.3, 57.6, 55.61, 55.60, 55.0, 14.6. ESI MS m/z: 605.2, [M+H]+. rf=0.3 (2% acetone in CH$_2$Cl$_2$).

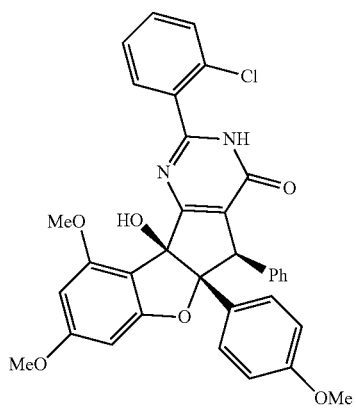

(5R,5aR,10bS)-2-(2-Chlorophenyl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12w)

$^1$H NMR (500 MHz, CDCl$_3$+CD$_3$OD) δ 7.81 (d, J=7.4 Hz, 1H), 7.44-7.37 (m, 2H), 7.24 (ddd, J=7.8, 6.5, 2.1 Hz, 1H), 7.12-7.08 (m, 5H), 6.96-6.92 (m, 2H), 6.57 (d, J=9.0 Hz, 2H), 6.22 (d, J=1.9 Hz, 1H), 6.06 (d, J=1.9 Hz, 1H), 4.74 (s, 1H), 3.83 (s, 3H), 3.80 (s, 3H), 3.67 (s, 3H), 3.51 (s, 1H). $^{13}$C NMR (126 MHz, CDCl$_3$+CD$_3$OD) δ 167.4, 163.6, 160.8, 160.4, 158.6, 158.1, 157.3, 136.5, 132.2, 131.99, 131.94, 131.4, 130.8, 129.3, 128.9, 127.7, 127.2, 126.82, 126.81, 123.0, 112.2, 107.1, 103.5, 92.7, 90.3, 89.0, 57.4, 55.62, 55.58, 55.0. ESI MS m/z: 596.3, [M+H]+. rf=0.3 (2% acetone in CH$_2$Cl$_2$).

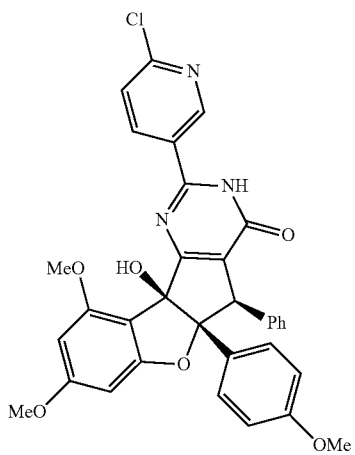

12x (5R,5aR,10bS)-2-(6-Chloropyridin-3-yl)-10b-hydroxy-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12x)

$^1$H NMR (500 MHz, CD$_2$Cl$_2$+CD$_3$OD) δ 9.13 (s, 1H), 8.39 (d, J=8.4 Hz, 1H), 7.39 (d, J=8.4 Hz, 1H), 7.09-7.01 (m, 5H), 6.94-6.88 (m, 2H), 6.56-6.51 (m, 2H), 6.25 (d, J=1.9 Hz, 1H), 6.08 (d, J=1.8 Hz, 1H), 4.62 (s, 1H), 3.82 (s, 3H), 3.78 (s, 3H), 3.63 (s, 3H). $^{13}$C NMR (126 MHz, CD$_2$Cl$_2$+CD$_3$OD) δ 168.6, 164.3, 162.1, 161.2, 159.1, 158.7, 156.3, 154.6, 149.8, 138.5, 137.1, 129.8, 129.2, 128.3, 127.9, 127.7, 127.1, 125.0, 123.2, 112.5, 107.9, 104.6, 93.0, 90.2, 89.5, 58.0, 56.0, 55.9, 55.3. ESI MS m/z: 596.3, [M+H]+. rf=0.6 (10% acetone in CH$_2$Cl$_2$).

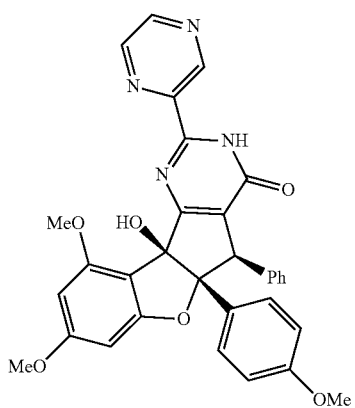

12y (5R,5aR,10bS)-10b-Hydroxy-8,10-dimethoxy-5a-(4-methoxyphenyl)-5-phenyl-2-(pyrazin-2-yl)-3,5,5a,10b-tetrahydro-4H-benzofuro[2',3':4,5]cyclopenta[1,2-d]pyrimidin-4-one (12y)

$^1$H NMR (400 MHz, CDCl$_3$) δ 9.78 (s, 1H), 8.78 (d, J=2.5 Hz, 1H), 8.61 (s, 1H), 7.16-7.06 (m, 5H), 7.00-6.91 (m, 2H), 6.57 (d, J=9.0 Hz, 2H), 6.21 (d, J=1.9 Hz, 1H), 6.07 (d, J=1.9 Hz, 1H), 4.85 (s, 1H), 3.91 (s, 3H), 3.78 (s, 3H), 3.67 (s, 3H). $^{13}$C NMR (101 MHz, CDCl$_3$) δ 166.7, 163.6, 160.8, 159.1, 158.7, 158.1, 154.1, 147.2, 144.4, 143.3, 143.1, 136.5, 129.3, 129.1, 127.9, 127.1, 126.8, 126.4, 112.2, 106.8, 102.8, 92.6, 90.6, 89.1, 57.5, 55.69, 55.62, 55.0. ESI MS m/z: 563.2, [M+H]+. rf=0.6 (10% acetone in CH$_2$Cl$_2$).

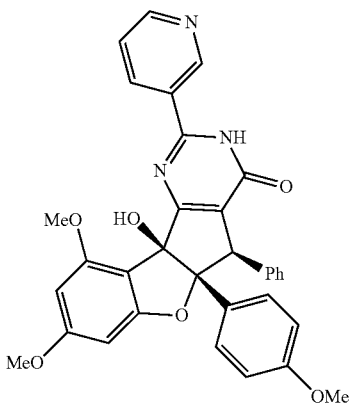

12z (5R,5aR,10bS)-10b-Hydroxy-8,10-dimethoxy-5a-(4-methoxyphenyl)-5-phenyl-2-(pyridin-3-yl)-3,5,5a,10b-tetrahydro-4H-benzofuro[2',3':4,5]cyclopenta[1,2-d]pyrimidin-4-one (12z)

$^1$H NMR (500 MHz, CD$_2$Cl$_2$) δ 9.30 (d, J=2.3 Hz, 1H), 8.69 (dd, J=5.0, 0.8 Hz, 1H), 8.44 (dt, J=8.1, 1.9 Hz, 1H), 7.44 (ddd, J=8.1, 4.9, 0.9 Hz, 1H), 7.12-7.03 (m, 5H), 6.97-6.91 (m, 2H), 6.54 (d, J=9.0 Hz, 2H), 6.25 (d, J=2.0 Hz, 1H), 6.09 (d, J=2.0 Hz, 1H), 4.64 (s, 1H), 3.84 (s, 3H), 3.79 (s, 3H), 3.64 (s, 3H). $^{13}$C NMR (126 MHz, CD$_2$Cl$_2$) δ 168.4, 164.3, 162.0, 161.2, 159.1, 158.7, 157.1, 152.1, 149.1, 137.2, 136.2, 129.8, 129.4, 129.2, 127.9, 127.7, 127.1, 124.4, 123.2, 112.5, 107.9, 104.5, 93.0, 90.2, 89.5, 58.0, 56.0, 55.9, 55.4. ESI MS m/z: 562.3, [M+H]+. rf=0.3 (10% acetone in CH$_2$Cl$_2$).

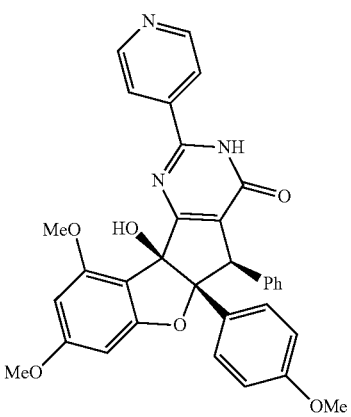

(5R,5aR,10bS)-10b-Hydroxy-8,10-dimethoxy-5a-(4-methoxyphenyl)-5-phenyl-2-(pyridin-4-yl)-3,5,5a,10b-tetrahydro-4H-benzofuro[2',3':4,5]cyclopenta[1,2-d]pyrimidin-4-one (12aa)

2. $^1$H NMR (500 MHz, CD$_2$Cl$_2$) δ 8.67 (d, J=6.1 Hz, 2H), 8.09 (d, J=6.2 Hz, 2H), 7.09-7.03 (m, 5H), 6.95-6.90 (m, 2H), 6.54 (d, J=9.0 Hz, 2H), 6.25 (d, J=1.9 Hz, 1H), 6.09 (d, J=2.0 Hz, 1H), 4.62 (s, 1H), 3.84 (s, 3H), 3.78 (s, 3H), 3.64 (s, 3H). $^{13}$C NMR (101 MHz, CDCl$_3$+CD$_3$OD) δ 169.8, 168.0, 163.3, 161.6, 160.5, 158.2, 158.0, 149.2, 146.3, 137.8, 129.3, 128.6, 127.6, 127.2, 126.2, 122.4, 120.5, 112.0, 108.5, 103.9, 92.4, 89.7, 89.0, 57.9, 55.44, 55.35, 54.9. ESI MS m/z: 562.3, [M+H]+. rf=0.6 (10% acetone in CH$_2$Cl$_2$).

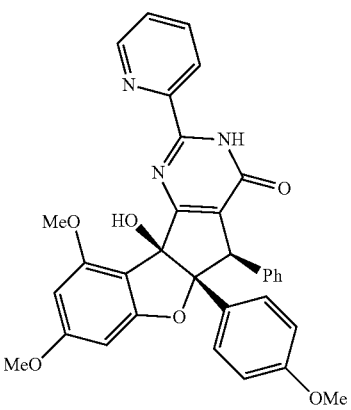

(5R,5aR,10bS)-10b-Hydroxy-8,10-dimethoxy-5a-(4-methoxyphenyl)-5-phenyl-2-(pyridin-2-yl)-3,5,5a,10b-tetrahydro-4H-benzofuro[2',3':4,5]cyclopenta[1,2-d]pyrimidin-4-one (12ab)

$^1$H NMR (400 MHz, CDCl$_3$) δ 8.65 (d, J=3.9 Hz, 1H), 8.59 (d, J=7.9 Hz, 1H), 7.92 (t, J=7.8 Hz, 1H), 7.49 (dd, J=7.4, 4.0 Hz, 1H), 7.19-7.04 (m, 5H), 6.98-6.92 (m, 2H), 6.57 (d, J=8.9 Hz, 2H), 6.22 (d, J=1.8 Hz, 1H), 6.06 (d, J=1.9 Hz, 1H), 4.82 (s, 1H), 3.89 (s, 3H), 3.79 (s, 3H), 3.67 (s, 3H), 3.56 (s, 1H). $^{13}$C NMR (101 MHz, CDCl$_3$) δ 167.0, 163.5, 160.8, 159.3, 158.6, 158.0, 155.6, 148.9, 148.0, 137.5, 136.6, 129.3, 128.9, 127.8, 126.9, 126.5, 125.2, 122.2, 112.2, 107.2, 103.2, 92.7, 90.4, 89.1, 57.5, 55.62, 55.61, 55.0. ESI MS m/z: 562.4, [M+H]+. rf=0.2 (10% acetone in CH$_2$Cl$_2$).

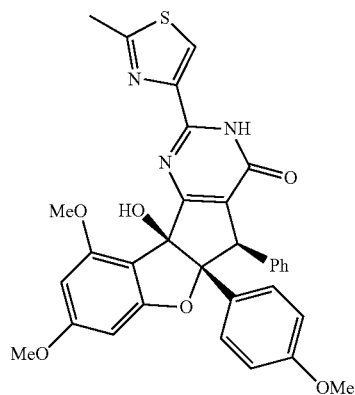

(5R,5aR,10bS)-10b-Hydroxy-8,10-dimethoxy-5a-(4-methoxyphenyl)-2-(2-methylthiazol-4-yl)-5-phenyl-3,5,5a,10b-tetrahydro-4H-benzofuro[2',3':4,5]cyclopenta[1,2-d]pyrimidin-4-one (12ac)

$^1$H NMR (500 MHz, CDCl$_3$) δ 8.26 (s, 1H), 7.13-7.05 (m, 5H), 6.98-6.89 (m, 2H), 6.57 (d, J=9.0 Hz, 2H), 6.22 (d, J=1.9 Hz, 1H), 6.05 (d, J=2.0 Hz, 1H), 4.78 (s, 1H), 3.86 (s, 3H), 3.79 (s, 3H), 3.67 (s, 3H), 3.49 (s, 1H), 2.75 (s, 3H). $^{13}$C NMR (126 MHz, CDCl$_3$) δ 167.3, 167.2, 163.5, 160.8, 159.2, 158.6, 158.0, 152.6, 147.1, 136.7, 129.2, 128.9, 127.8, 126.92, 126.86, 123.5, 122.6, 112.2, 107.2, 103.2, 92.7, 90.4, 89.1, 57.4, 55.64, 55.60, 55.0, 19.2. ESI MS m/z: 582.3, [M+H]+. rf=0.5 (2% acetone in CH$_2$Cl$_2$).

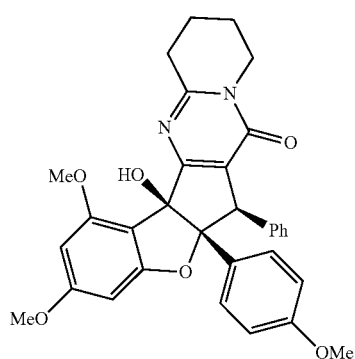

(5aR,6R,13bS)-13b-Hydroxy-1,3-dimethoxy-5a-(4-methoxyphenyl)-6-phenyl-6,9,10,11,12,13b-hexahydrobenzofuro[2',3':4,5]cyclopenta[1,2-d]pyrido[1,2-a]pyrimidin-7(5aH)-one (12ad)

$^1$H NMR (400 MHz, CDCl$_3$) δ 7.11-7.02 (m, 5H), 6.91-6.86 (m, 2H), 6.56 (d, J=9.0 Hz, 2H), 6.20 (d, J=1.9 Hz, 1H), 6.05 (d, J=1.8 Hz, 1H), 4.70 (s, 1H), 4.02 (dt, J=12.8, 5.6 Hz, 1H), 3.86 (dt, J=12.8, 5.6 Hz, 1H), 3.84 (s, 3H), 3.79 (s, 3H), 3.66 (s, 3H), 3.27 (s, 1H), 3.07 (dd, J=12.0, 6.3 Hz, 2H), 2.03-1.86 (m, 4H). $^{13}$C NMR (101 MHz, CDCl$_3$) δ 164.5, 163.4, 161.6, 160.8, 160.1, 158.6, 158.1, 137.0, 129.2, 128.9, 127.7, 127.1, 126.7, 120.7, 112.2, 107.4, 103.4, 92.7, 90.5, 89.0, 57.5, 55.64, 55.58, 55.0, 42.4, 32.1, 21.9, 19.1. ESI MS m/z: 539.2, [M+H]+. rf=0.2 (EA:Hex=5:1).

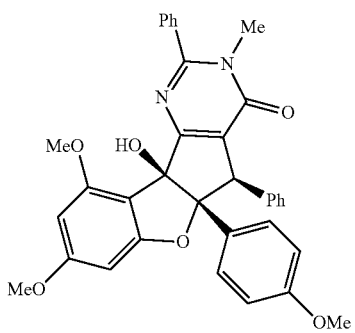

12ae (5R,5aR,10bS)-10b-Hydroxy-8,10-dimethoxy-5a-(4-methoxyphenyl)-3-methyl-2,5-diphenyl-3,5,5a,10b-tetrahydro-4H-benzofuro[2',3':4,5]cyclopenta[1,2-d]pyrimidin-4-one (12ae)

Unlike the cycloamidines, N-substituted amidines was less reactive which led to the formation of decarboxylated product 14 and retro-Nazarov products 17. Meanwhile, small amount of oxazoline 15 was found as the only undesired product. The assignment of regioselectivity was supports by 2D NMR data showing on page S119. ¹H NMR (500 MHz, CDCl₃) δ 7.64-7.59 (m, 2H), 7.57-7.49 (m, 3H), 7.13 (d, J=9.0 Hz, 2H), 7.11-7.04 (m, 3H), 6.98-6.94 (m, 2H), 6.57 (d, J=9.0 Hz, 2H), 6.23 (d, J=2.0 Hz, 1H), 6.07 (d, J=2.0 Hz, 1H), 4.76 (s, 1H), 3.83 (s, 3H), 3.81 (s, 3H), 3.67 (s, 3H), 3.46 (s, 3H), 3.41 (s, 1H). ¹³C NMR (126 MHz, CDCl₃) δ 164.7, 163.5, 162.1, 160.8, 160.6, 158.6, 158.0, 136.8, 135.1, 130.4, 129.3, 128.8, 128.64, 128.60, 127.7, 127.0, 126.7, 121.5, 112.2, 107.5, 103.8, 92.7, 90.1, 89.0, 57.8, 55.63, 55.55, 55.0, 34.6. ESI MS m/z: 575.3, [M+H]+. rf=0.3 (EA:Hex=2:1).

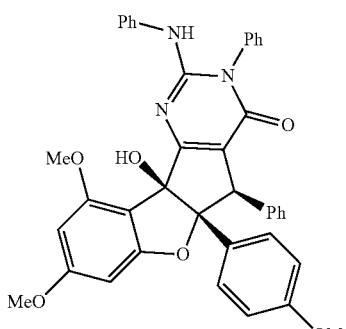

12af (5R,5aR,10bS)-10b-Hydroxy-8,10-dimethoxy-5a-(4-methoxyphenyl)-3,5-diphenyl-2-(phenylamino)-3,5,5a,10b-tetrahydro-4H-benzofuro[2',3':4,5]cyclopenta[1,2-d]pyrimidin-4-one (12af)

¹H NMR (500 MHz, CDCl₃) δ 7.64-7.51 (m, 5H), 7.39 (dd, J=8.2, 2.0 Hz, 1H), 7.33 (dt, J=7.7, 1.8 Hz, 1H), 7.31-7.27 (m, 2H), 7.15 (d, J=8.9 Hz, 2H), 7.10-7.02 (m, 4H), 7.00-6.96 (m, 2H), 6.57 (d, J=8.9 Hz, 2H), 6.22 (d, J=1.8 Hz, 1H), 6.18 (s, 1H), 6.06 (d, J=1.9 Hz, 1H), 4.79 (s, 1H), 3.86 (s, 3H), 3.81 (s, 1H), 3.80 (s, 3H), 3.67 (s, 3H). ¹³C NMR (126 MHz, CDCl₃) δ 165.5, 163.3, 160.8, 160.1, 158.5, 157.9, 152.3, 137.8, 134.2, 130.8, 130.2, 129.3, 129.2, 128.9, 128.8, 128.7, 127.7, 127.5, 126.6, 123.8, 120.3, 115.3, 112.0, 107.2, 102.8, 92.2, 91.1, 89.0, 57.5, 55.6, 55.5, 55.0. ESI MS m/z: 652.4, [M+H]+. rf=0.4 (EA:Hex=1:1).

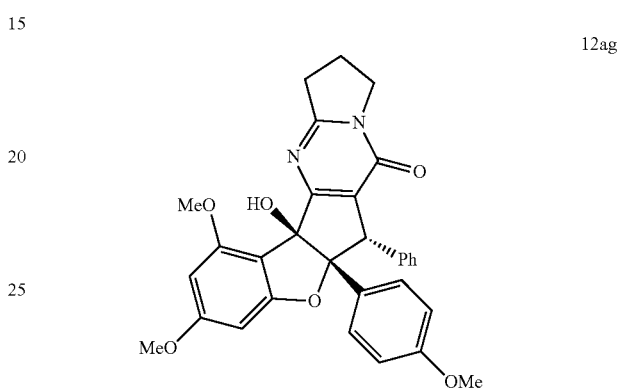

12ag (6S,6aR,11bS)-11b-hydroxy-9,11-dimethoxy-6a-(4-methoxyphenyl)-6-phenyl-1,2,3,6,6a,11b-hexahydro-5H-benzofuro[2',3':4,5]cyclopenta[1,2-d]pyrrolo[1,2-a]pyrimidin-5-one (12ag)

¹H NMR (500 MHz, CDCl₃) δ 7.39 (d, J=8.8 Hz, 2H), 7.15-7.06 (m, 3H), 6.90 (d, J=8.9 Hz, 2H), 6.79 (d, J=7.0 Hz, 3H), 5.99 (d, J=2.0 Hz, 1H), 5.68 (d, J=2.0 Hz, 1H), 4.98 (s, 1H), 4.13 (hept, J=6.8, 6.2 Hz, 2H), 3.83 (s, 3H), 3.81 (s, 3H), 3.64 (s, 3H), 3.31-3.18 (m, 2H), 2.78 (s, 1H), 2.30 (dt, J=13.8, 7.0 Hz, 2H). ¹³C NMR (126 MHz, CDCl₃) δ 166.8, 166.4, 163.6, 161.9, 159.3, 158.9, 157.6, 135.8, 130.3, 128.8, 127.5, 127.4, 126.8, 122.5, 113.5, 107.6, 100.0, 92.4, 90.1, 88.1, 57.5, 55.6, 55.5, 55.2, 46.8, 32.8, 19.5. ESI MS m/z: 525.2, [M+H]+. rf=0.4 (EA:Hex=4:1).

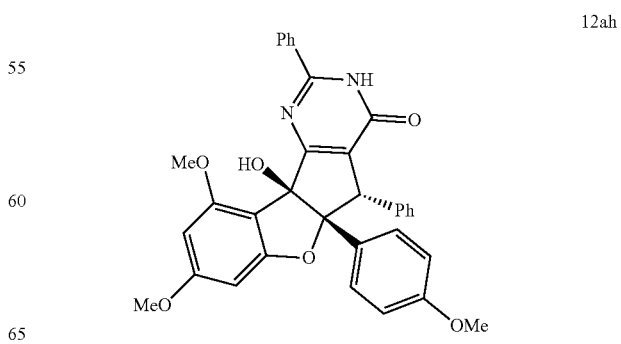

12ah

(5S,5aR,10bS)-10b-Hydroxy-8,10-dimethoxy-5a-(4-methoxyphenyl)-2,5-diphenyl-3,5,5a,10b-tetrahydro-4H-benzofuro[2',3':4,5]cyclopenta[1,2-d]pyrimidin-4-one (12ah)

3. The product was isolated as pale-yellow solids. $^1$H NMR (500 MHz, Chloroform-d) δ 8.04 (d, J=7.1 Hz, 1H), 7.51-7.47 (m, 1H), 7.45-7.40 (m, 2H), 7.34 (d, J=8.9 Hz, 2H), 7.10-7.00 (m, 3H), 6.83 (d, J=8.9 Hz, 2H), 6.77-6.71 (m, 2H), 5.93 (d, J=2.0 Hz, 1H), 5.62 (d, J=2.0 Hz, 1H), 4.95 (s, 1H), 3.79 (s, 3H), 3.73 (s, 3H), 3.57 (s, 3H). $^{13}$C NMR (101 MHz, cd$_3$od) δ 168.1, 163.6, 161.6, 161.4, 159.4, 159.1, 157.7, 135.9, 132.3, 131.9, 131.2, 128.7, 128.6, 127.7, 127.3, 127.2, 126.6, 123.2, 113.3, 108.0, 99.6, 92.2, 88.9, 88.0, 58.0, 55.21, 55.18, 54.9. ESI MS m/z: 561.4, [M+H]+. rf=0.3 (EA:Hex=1:1).

Late-Stage Functionalization of Aglaroxin C Analogues:

SCHEME 7

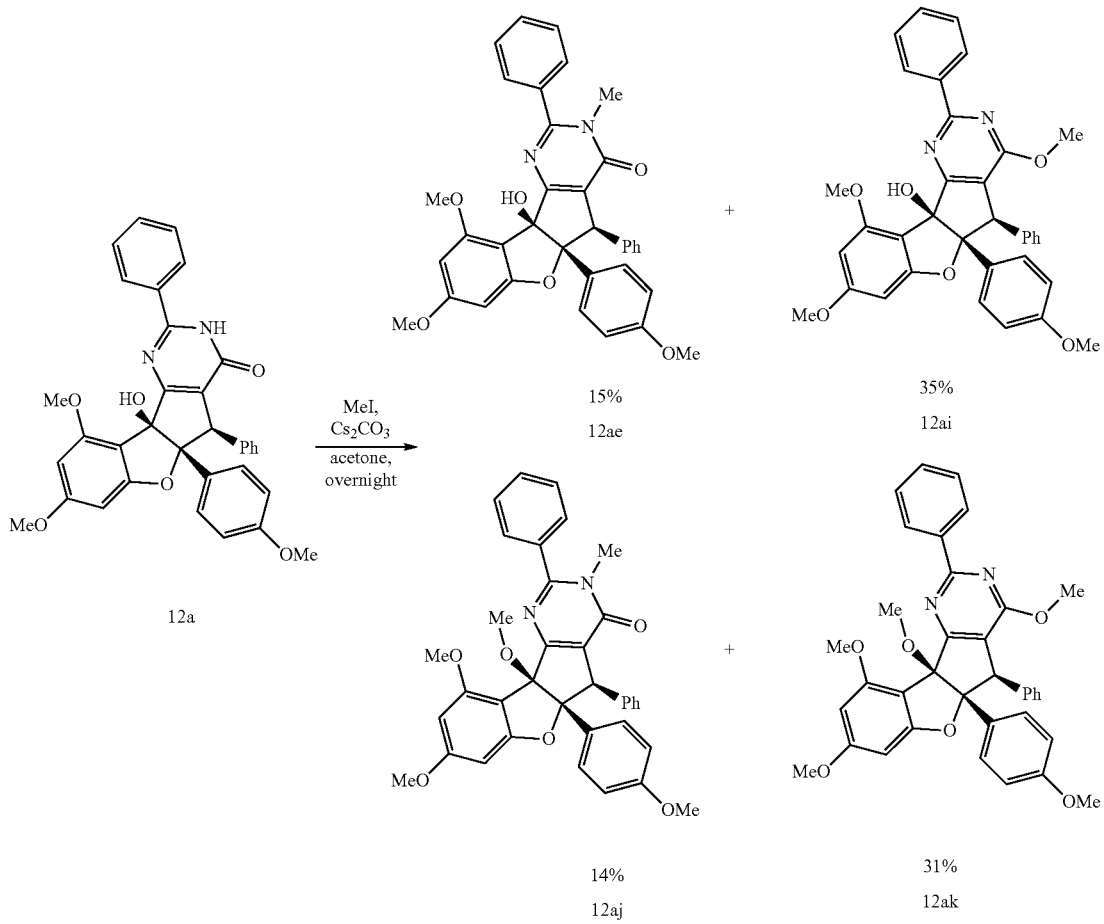

Methylation of Pyrimidinone 12a

To mixture of 18.2 mg 12a and 21.1 mg of Cs$_2$CO$_3$ (2 equiv), 0.6 mL of an acetone solution of MeI (3.0 µL, 1.5 equiv) was added dropwise at rt. The reaction was stirred overnight. After quenching the reaction with sat. aq. ammonium chloride, the mixture of crude products was obtained by extraction with ethyl acetate, drying with Na$_2$SO$_4$, filtration, and concentration. The mixture was isolated using preparative TLC using 2% acetone in CH$_2$Cl$_2$ as eluent. Four products 12ae, 12ai, 12aj, and 12ak were isolated in 15%, 35%, 14%, and 31% yields, respectively, Scheme 7. Of note, 12ae was synthesized using direct pyrimidinone formation (see characterization data on pages S22) The $^1$HNMR signal for the tertiary methoxys in 12aj and 12ak was shielded by the phloroglucinol ring and was found at □ 2.63 ppm and 2.72 ppm, respectively.

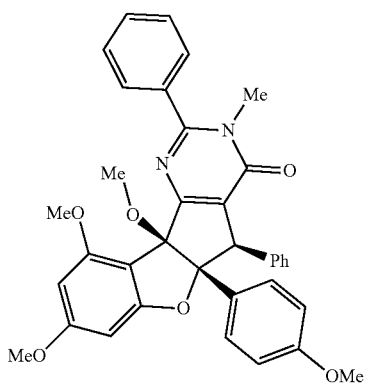

(5R,5aR,10bS)-8,10,10b-Trimethoxy-5a-(4-methoxyphenyl)-3-methyl-2,5-diphenyl-3,5,5a,10b-tetrahydro-4H-benzofuro[2',3':4,5]cyclopenta[1,2-d]pyrimidin-4-one (12ai)

$^1$H NMR (500 MHz, CDCl$_3$) δ 7.66-7.59 (m, 2H), 7.54-7.50 (m, 3H), 7.17 (d, J=9.0 Hz, 2H), 7.08-6.97 (m, 3H), 6.90-6.81 (m, 2H), 6.56 (d, J=9.0 Hz, 2H), 6.33 (d, J=2.0 Hz, 1H), 6.13 (d, J=2.0 Hz, 1H), 4.47 (s, 1H), 3.87 (s, 6H), 3.68 (s, 3H), 3.41 (s, 3H), 2.62 (s, 3H). $^{13}$C NMR (126 MHz, CDCl$_3$) δ 164.9, 164.1, 161.6, 161.5, 160.1, 158.7, 158.4, 136.0, 135.4, 130.2, 129.0, 128.64, 128.55, 127.7, 127.4, 127.2, 126.3, 120.9, 112.2, 104.1, 103.5, 93.8, 92.6, 88.8, 58.9, 55.7, 55.4, 55.0, 51.8, 34.3. m.p. 134-138° C. (CDCl$_3$); IR vmax (film): 1679, 1616, 1594, 1515, 1497, 1425, 1249, 1148, 1075, 818, 700. HR/MS: m/z Calcd for [C$_{36}$H$_{33}$N$_2$O$_6$]+ 589.2339, found 589.2323 (2.7154 ppm). rf=0.2 (2% acetone in CH$_2$Cl$_2$).

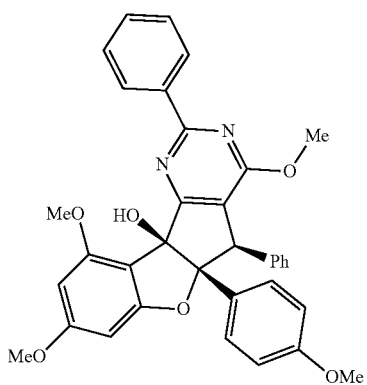

(5R,5aR,10bS)-4,8,10-Trimethoxy-5a-(4-methoxyphenyl)-2,5-diphenyl-5,5a-dihydro-10bH-benzofuro[2',3':4,5]cyclopenta[1,2-d]pyrimidin-10b-ol (12aj)

$^1$H NMR (500 MHz, CDCl$_3$) δ 8.62-8.57 (m, 2H), 7.54-7.47 (m, 3H), 7.09-7.01 (m, 3H), 7.03 (d, J=9.0 Hz, 2H), 6.88-6.82 (m, 2H), 6.55 (d, J=9.0 Hz, 2H), 6.24 (d, J=1.9 Hz, 1H), 6.06 (d, J=2.0 Hz, 1H), 4.75 (s, 1H), 3.95 (s, 3H), 3.87 (s, 3H), 3.80 (s, 3H), 3.70 (s, 1H), 3.66 (s, 3H). $^{13}$C NMR (126 MHz, CDCl$_3$) δ 171.7, 166.3, 164.8, 163.6, 160.5, 158.6, 158.1, 137.7, 136.9, 130.6, 129.2, 128.5, 128.4, 128.4, 127.5, 126.9, 126.6, 116.4, 112.3, 108.0, 104.7, 92.7, 89.4, 89.1, 57.4, 55.67, 55.61, 55.0, 53.6. ESI MS m/z: 575.3, [M+H]+. rf=0.2 (2% acetone in CH$_2$Cl$_2$).

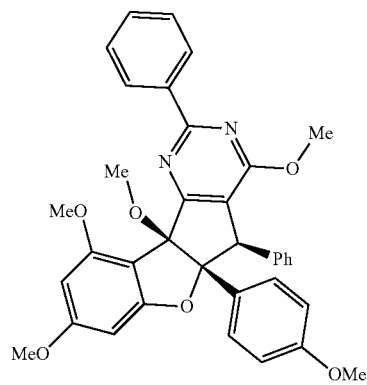

(5R,5aR,10bS)-4,8,10,10b-Tetramethoxy-5a-(4-methoxyphenyl)-2,5-diphenyl-5a,10b-dihydro-5H-benzofuro[2',3':4,5]cyclopenta[1,2-d]pyrimidine (12ak)

$^1$H NMR (400 MHz, CDCl$_3$) δ 8.64-8.61 (m, 2H), 7.52-7.47 (m, 3H), 7.05 (d, J=8.9 Hz, 2H), 7.03-6.98 (m, 3H), 6.83-6.76 (m, 2H), 6.51 (d, J=8.9 Hz, 2H), 6.34 (d, J=2.0 Hz, 1H), 6.10 (d, J=2.0 Hz, 1H), 4.50 (s, 1H), 3.87 (s, 3H), 3.86 (s, 3H), 3.81 (s, 3H), 3.66 (s, 3H), 2.75 (s, 3H). $^{13}$C NMR (126 MHz, CDCl$_3$) δ 171.2, 165.8, 164.6, 164.1, 161.4, 159.0, 158.4, 138.1, 136.3, 130.4, 129.1, 128.7, 128.2, 127.6, 127.3, 127.1, 126.2, 115.9, 112.2, 104.8, 103.7, 93.7, 92.7, 88.9, 58.1, 55.7, 55.6, 55.0, 53.3, 51.9. ESI MS m/z: 589.3, [M+H]+. rf=0.2 (2% acetone in CH$_2$Cl$_2$).

SCHEME 8

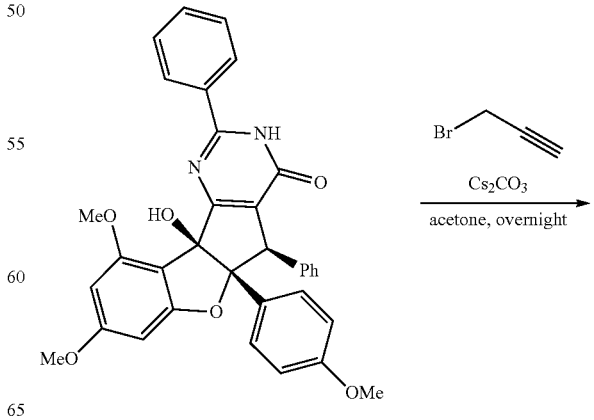

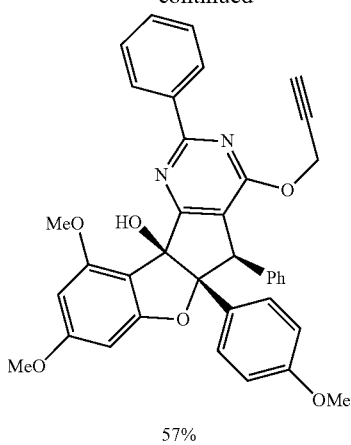

57%

12a1

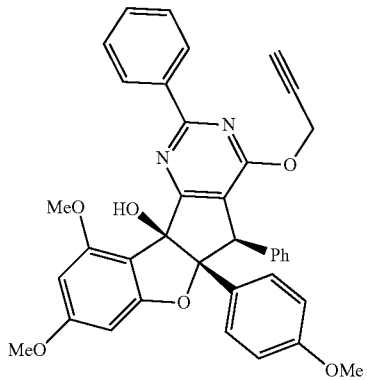

12a1

(5R,5aR,10bS)-8,10-Dimethoxy-5a-(4-methoxyphenyl)-2,5-diphenyl-4-(prop-2-yn-1-yloxy)-5,5a-dihydro-10bH-benzofuro[2',3':4,5]cyclopenta[1,2-d]pyrimidin-10b-ol (12a1)

$^1$H NMR (400 MHz, CDCl$_3$) δ 8.64-8.58 (m, 2H), 7.54-7.46 (m, 3H), 7.09-6.99 (m, 5H), 6.89-6.82 (m, 2H), 6.54 (d, J=9.0 Hz, 2H), 6.25 (d, J=1.9 Hz, 1H), 6.06 (d, J=1.9 Hz, 1H), 5.01 (d, J=2.3 Hz, 2H), 4.77 (s, 1H), 3.86 (s, 3H), 3.80 (s, 3H), 3.65 (s, 3H), 2.36 (d, J=2.3 Hz, 1H). $^{13}$C NMR (101 MHz, CDCl$_3$) δ 172.5, 164.6, 164.6, 163.7, 160.5, 158.6, 158.1, 137.5, 136.5, 130.7, 129.3, 128.46, 128.44, 128.38, 127.4, 126.8, 126.6, 116.5, 112.3, 107.9, 104.9, 92.8, 89.3, 89.1, 78.3, 74.3, 57.4, 55.66, 55.61, 55.0, 53.3. ESI MS m/z: 599.4, [M+H]+. rf=0.65 (3% acetone in CH$_2$Cl$_2$).

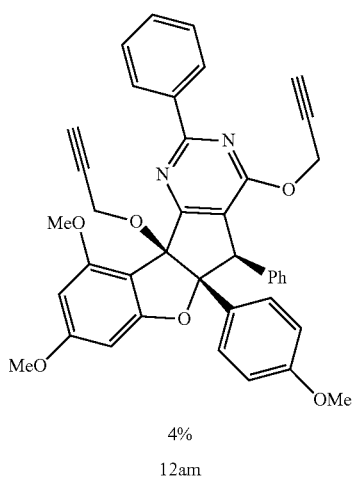

4%

12am

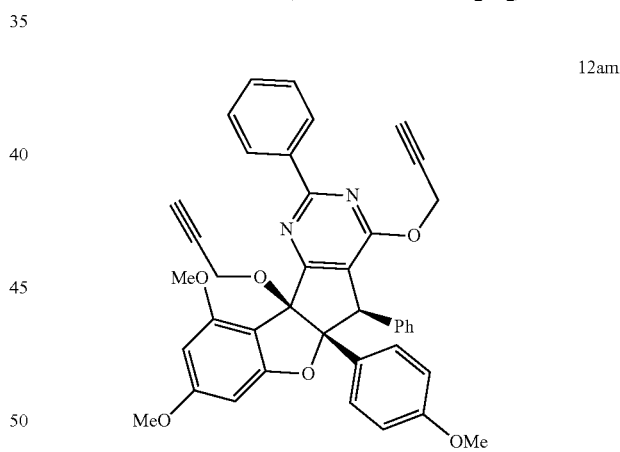

12am

Propargylation of 12a

To mixture of 15.5 mg of 12a and 27 mg of Cs$_2$CO$_3$ (3 equiv), 0.3 mL of an acetone solution of propargyl bromide (3.28 μL, 80 wt %, 1.1 equiv.) was added dropwise at room temperature. The reaction was stirred for 12 h. After quenching the reaction with ammonium chloride (sat. aq.), the mixture of crude products was obtained through ethyl acetate extraction, drying through Na$_2$SO$_4$, filtration, and concentration. The mixture was isolated using preparative TLC using 2% acetone in CH$_2$Cl$_2$ as eluent. Two major products, 12a1, 12am, were isolated in 57% and 4% yields, respectively, Scheme 8.

(5R,5aR,10bS)-8,10-Dimethoxy-5a-(4-methoxyphenyl)-2,5-diphenyl-4,10b-bis(prop-2-yn-1-yloxy)-5a,10b-dihydro-5H-benzofuro[2',3':4,5]cyclopenta[1,2-d]pyrimidine (12am)

$^1$H NMR (400 MHz, CDCl$_3$) δ 8.69-8.62 (m, 2H), 7.55-7.49 (m, 3H), 7.08-6.98 (m, 5H), 6.85-6.77 (m, 2H), 6.52 (d, J=8.8 Hz, 2H), 6.33 (d, J=2.0 Hz, 1H), 6.07 (d, J=2.0 Hz, 1H), 5.00 (dd, J=15.5, 2.3 Hz, 1H), 4.92 (dd, J=15.4, 2.4 Hz, 1H), 4.53 (s, 1H), 3.89 (dd, J=15.3, 2.4 Hz, 1H), 3.85 (s, 3H), 3.81 (s, 3H), 3.65 (s, 3H), 3.58 (dd, J=15.3, 2.5 Hz, 1H), 2.33 (t, J=2.3 Hz, 1H), 2.09 (t, J=2.5 Hz, 1H). $^{13}$C NMR (101 MHz, CDCl$_3$) δ 171.3, 164.5, 164.4, 164.2, 161.4, 159.3, 158.6, 137.7, 135.8, 130.6, 129.2, 128.7, 128.3, 127.8, 127.1, 126.8, 126.4, 116.1, 112.4, 105.2, 103.6, 93.5, 92.9, 89.0, 80.0, 78.3, 74.2, 72.9, 57.9, 55.65, 55.63, 55.0, 53.1, 52.8. ESI MS m/z: 637.5, [M+H]+. rf=0.7 (3% acetone in CH$_2$Cl$_2$).

SCHEME 9

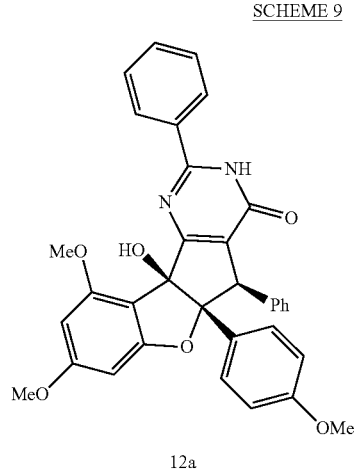
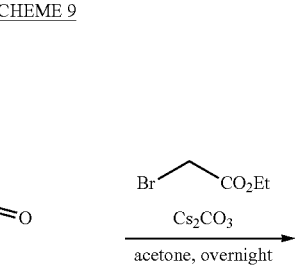

Alkylation of 12a

To mixture of 20 mg of 12a and 35 mg of Cs$_2$CO$_3$ (3 equiv), 0.4 mL of an acetone solution of ethyl 2-bromoacetate (6.5 mg, 1.1 equiv) was added dropwise at rt. The reaction was stirred for 12 h. After quenching reaction with sat. aq. ammonium chloride, the mixture of crude products was obtained through ethyl acetate extraction, drying with Na$_2$SO$_4$, filtration, and concentration. The crude product mixture was purified using preparative TLC using 2% acetone in CH$_2$Cl$_2$ as eluent to afford 10.3 mg (44% yield) of product 12an, Scheme 9.

Ethyl 2-(((5R,5aR,10bS)-10b-hydroxy-8,10-dimethoxy-5a-(4-methoxyphenyl)-2,5-diphenyl-5a,10b-dihydro-5H-benzofuro[2',3':4,5]cyclopenta[1,2-d]pyrimidin-4-yl)oxy)acetate (12an)

$^1$H NMR (500 MHz, CDCl$_3$) δ 8.55-8.49 (m, 2H), 7.53-7.45 (m, 3H), 7.09-7.04 (m, 3H), 7.02 (d, J=9.0 Hz, 2H), 6.97-6.92 (m, 2H), 6.55 (d, J=9.0 Hz, 2H), 6.28 (d, J=1.9 Hz, 1H), 6.07 (d, J=1.8 Hz, 1H), 4.91 (d, J=15.3 Hz, 1H), 4.80 (s, 1H), 4.75 (d, J=15.4 Hz, 1H), 4.19 (qd, J=7.2, 2.3 Hz, 2H), 3.85 (s, 3H), 3.81 (s, 3H), 3.66 (s, 3H), 3.60 (s, 1H), 1.24 (t, J=7.1 Hz, 3H). $^{13}$C NMR (126 MHz, CDCl$_3$) δ 172.7, 168.3, 164.6, 164.3, 163.8, 160.5, 158.6, 158.1, 137.3, 136.3, 130.8, 129.4, 128.37, 128.35, 128.32, 127.4 126.8, 126.6, 116.1, 112.3, 107.8, 105.3, 92.8, 89.1, 89.1, 62.9, 61.1, 57.5, 55.65, 55.64, 55.0, 14.2. ESI MS m/z: 647.5, [M+H]+. rf=0.4 (2% acetone in CH$_2$Cl$_2$).

SCHEME 10

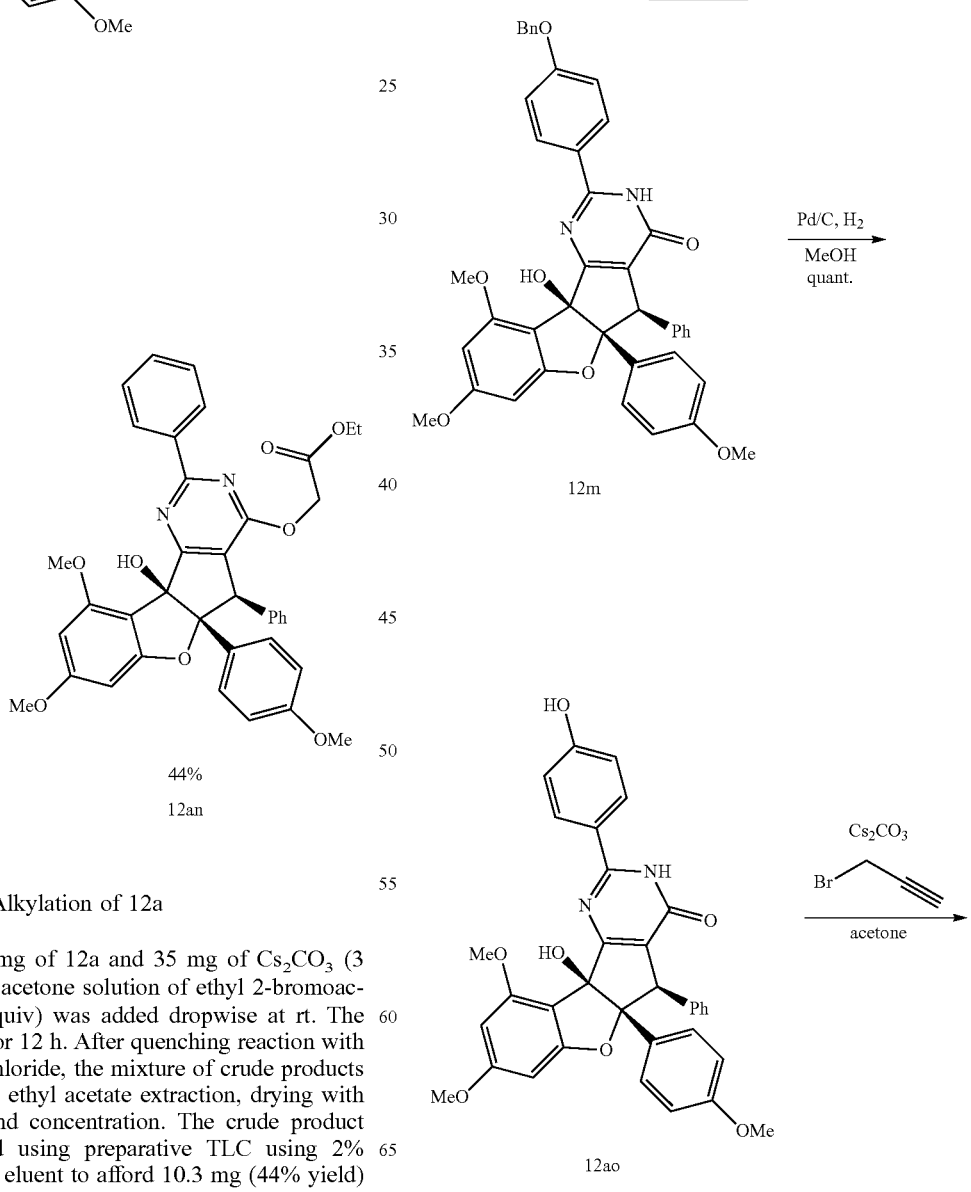

-continued

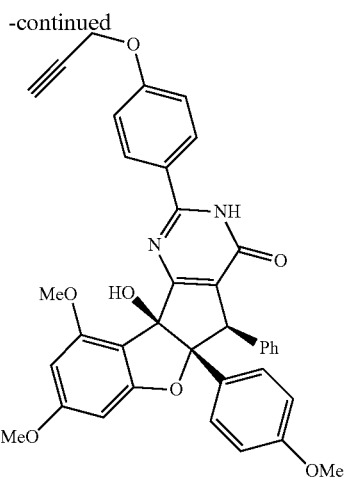

12ap

Hydrogenation of the Benzyl Protecting Group and Subsequent Propargylation

To demonstrate late-stage functionalization of the pyrimidinone scaffold, the benzyl group of 12m was hydrogenolyzed. Subsequent propargylation of the emerged phenol afford compound 12ap as a pull-down probe surrogate. To Pd/C catalyst (1 mg) under nitrogen, 0.2 mL of a methanol solution of 12m (5.2 mg, 0.4 M) was added which was followed by bubbling with hydrogen gas for 30 min. The reaction was stirred for additional 3 h under hydrogen. The reaction mixture was filtered through Celite® to afford the crude phenol product 12ao (4.3 mg) in quantitative yield, Scheme 10.

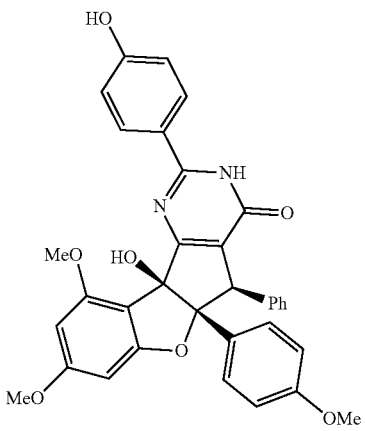

12ao (5R,5aR,10bS)-10b-Hydroxy-2-(4-hydroxyphenyl)-8,10-dimethoxy-5a-(4-methoxyphenyl)-5-phenyl-3,5,5a,10b-tetrahydro-4H-benzofuro[2',3':4,5]cyclopenta[1,2-d]pyrimidin-4-one (12ao)

$^1$H NMR (400 MHz, CD$_3$OD) δ 8.09 (d, J=8.8 Hz, 2H), 7.07 (d, J=9.0 Hz, 2H), 7.04-6.98 (m, 3H), 6.94 (d, J=8.8 Hz, 2H), 6.92-6.85 (m, 2H), 6.53 (d, J=9.0 Hz, 2H), 6.30 (d, J=2.0 Hz, 1H), 6.15 (d, J=2.0 Hz, 1H), 4.51 (s, 1H), 3.85 (s, 3H), 3.80 (s, 3H), 3.62 (s, 3H). $^{13}$C NMR (101 MHz, CD$_3$OD) δ 168.9, 163.9, 161.6, 161.2, 160.7, 158.8, 158.5, 158.4, 137.0, 129.7, 129.1, 128.5, 127.5, 126.9, 126.0, 123.3, 119.9, 115.2, 111.6, 107.8, 104.1, 92.2, 89.5, 88.6, 57.4, 54.7, 54.6, 54.0. 12ao crashed out in Methanol-d4 during the overnight experiment. ESI MS m/z: 577.4, [M+1-1]+.

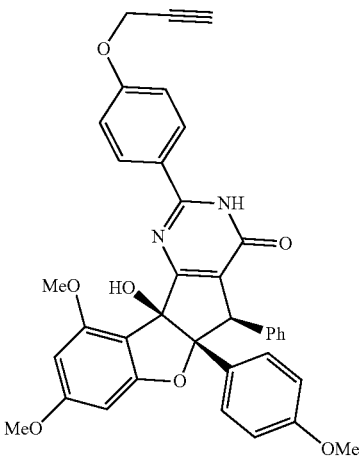

12ap (5R,5aR,10bS)-10b-Hydroxy-8,10-dimethoxy-5a-(4-methoxyphenyl)-5-phenyl-2-(4-(prop-2-yn-1-yloxy)phenyl)-3,5,5a,10b-tetrahydro-4H-benzofuro[2',3':4,5]cyclopenta[1,2-d]pyrimidin-4-one (12ap)

12ao was used in the following propargylation without further purification. To solid Cs$_2$CO$_3$ (7.6 mg, 3.0 equiv.) and a stir bar, 0.1 mL of an acetone solution of 4.5 mg 12ao (1.0 equiv) was added followed by 0.1 mL of an acetone solution of propargyl bromide (1.6 mg, 80 wt %, 1.4 equiv). The reaction mixture was stirred overnight. The reaction mixture was concentrated which was followed by extraction using ethyl acetate and ammonium chloride (sat. aq.). The crude product was purified using preparative TLC (eluent: EA:Hex=1:1) to afford 1.0 mg 12ap in 21% yield. $^1$H NMR (500 MHz, CDCl$_3$) δ 8.07 (d, J=8.7 Hz, 2H), 7.14-7.11 (m, 3H), 7.09 (d, J=8.9 Hz, 2H), 7.03-6.99 (m, 2H), 6.73 (d, J=8.6 Hz, 2H), 6.57 (d, J=8.9 Hz, 2H), 6.23 (d, J=1.8 Hz, 1H), 6.05 (d, J=1.8 Hz, 1H), 4.75 (s, 1H), 4.70 (d, J=2.3 Hz, 2H), 3.85 (s, 3H), 3.79 (s, 3H), 3.67 (s, 3H), 3.53 (s, 1H), 2.57 (t, J=2.3 Hz, 1H). $^{13}$C NMR (126 MHz, CDCl$_3$) δ 168.5, 163.6, 162.2, 160.7, 160.4, 158.6, 158.0, 158.0, 136.9, 129.4, 129.4, 128.7, 127.6, 126.9, 126.7, 125.0, 120.8, 115.0, 112.2, 107.4, 104.0, 92.7, 89.9, 89.0, 77.9, 76.0, 57.6, 55.8, 55.6, 55.0. ESI MS m/z: 614.5, [M+H]+. rf=0.6 (EA:Hex=2:1).

Example 4: Enantioselective Syntheses of CMLD012043 (12l) and CMLD012044 (12s)

3.1 Enantioselective Synthesis of (+)- and (−)-Tosyl Enol Rocaglates:

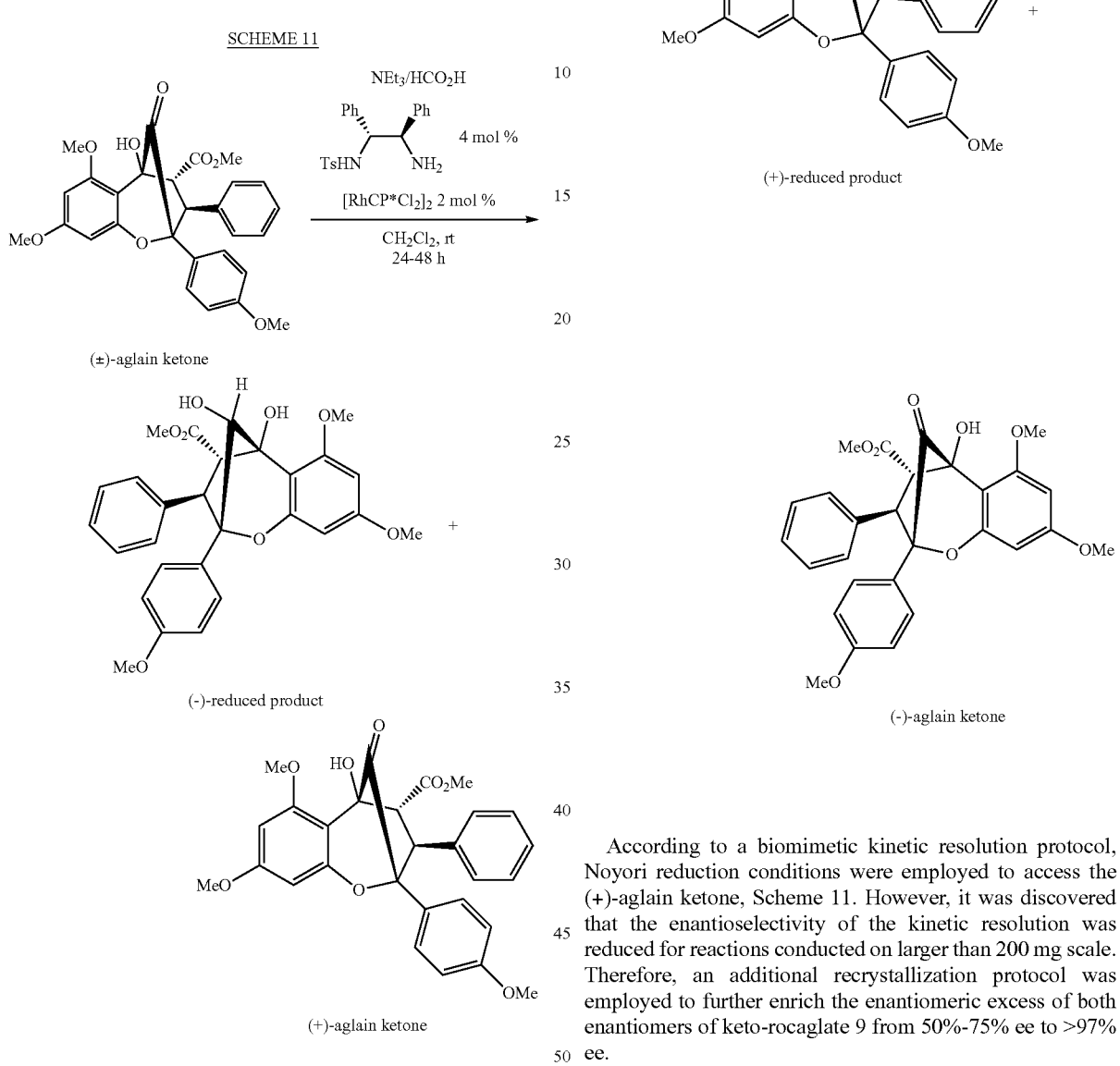

According to a biomimetic kinetic resolution protocol, Noyori reduction conditions were employed to access the (+)-aglain ketone, Scheme 11. However, it was discovered that the enantioselectivity of the kinetic resolution was reduced for reactions conducted on larger than 200 mg scale. Therefore, an additional recrystallization protocol was employed to further enrich the enantiomeric excess of both enantiomers of keto-rocaglate 9 from 50%-75% ee to >97% ee.

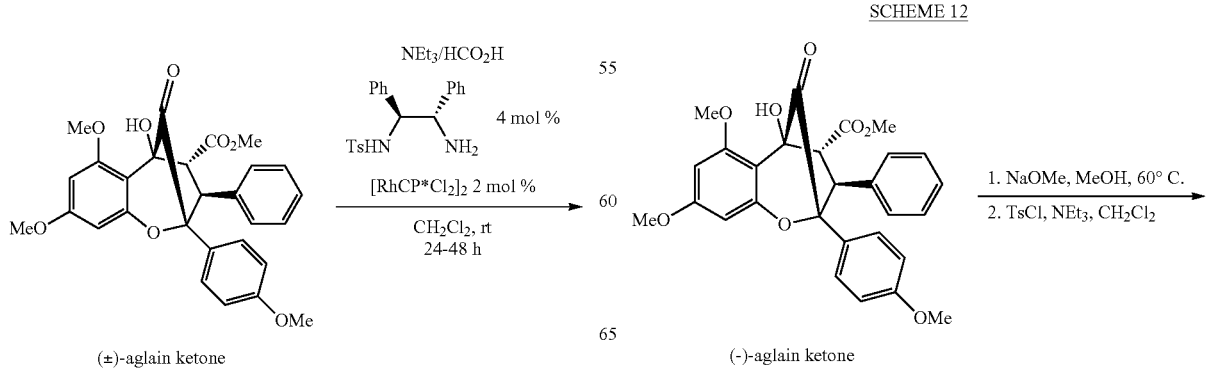

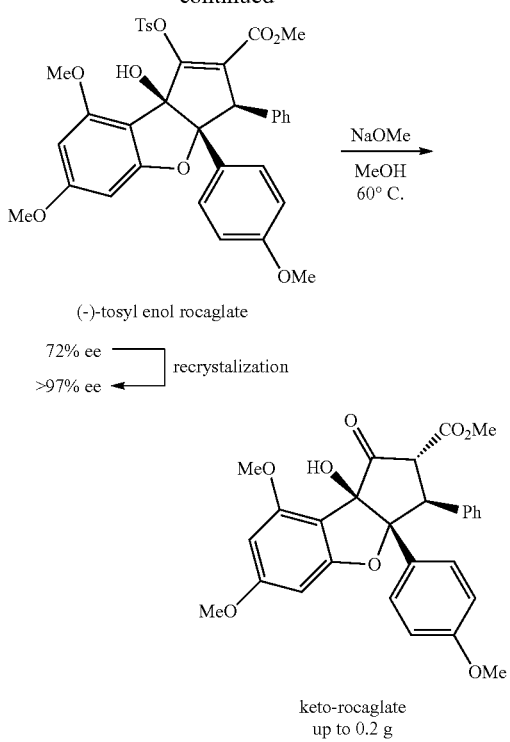

(−)-tosyl enol rocaglate

72% ee → recrystalization → >97% ee

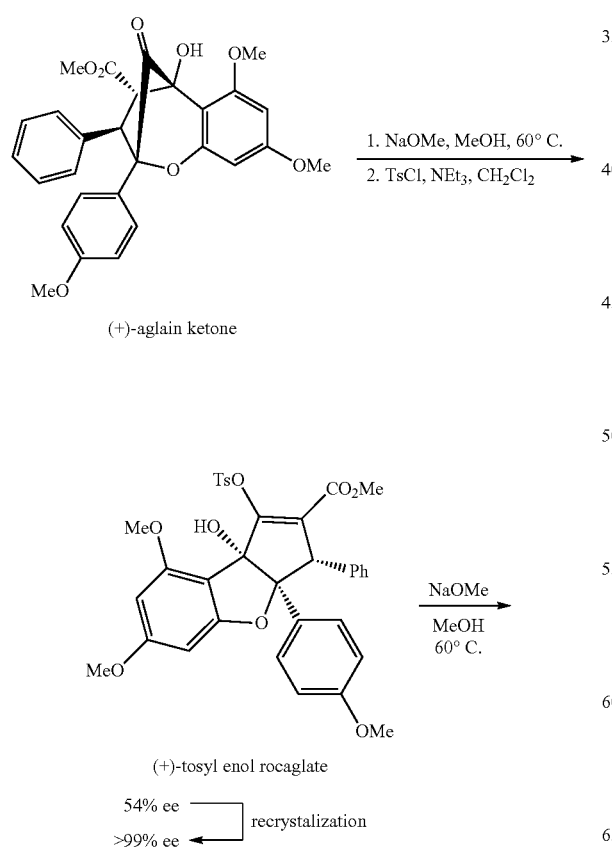

(+)-aglain ketone

1. NaOMe, MeOH, 60° C.
2. TsCl, NEt₃, CH₂Cl₂ keto-rocaglate
up to 0.2 g

NaOMe
MeOH
60° C.

(+)-tosyl enol rocaglate

54% ee → recrystalization → >99% ee

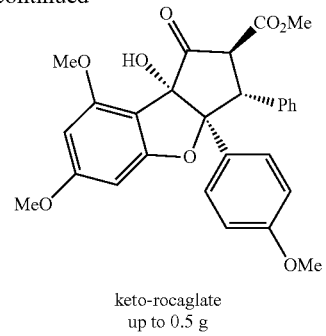

keto-rocaglate
up to 0.5 g

With both enantioenriched (+)- and (−)-aglain ketones in hand, α-ketol-shift afforded keto-rocaglate 7 which was followed by tosylation to afford the tosyl enol rocaglate, which was recrystallized from isopropanol. After several recrystallizations, enantioenriched (−)- and (+)-tosyl enol rocaglates were obtained. Subsequent removal of the tosylate protecting group afforded both enantiomers of keto-rocaglate 9, Scheme 12.

SCHEME 13

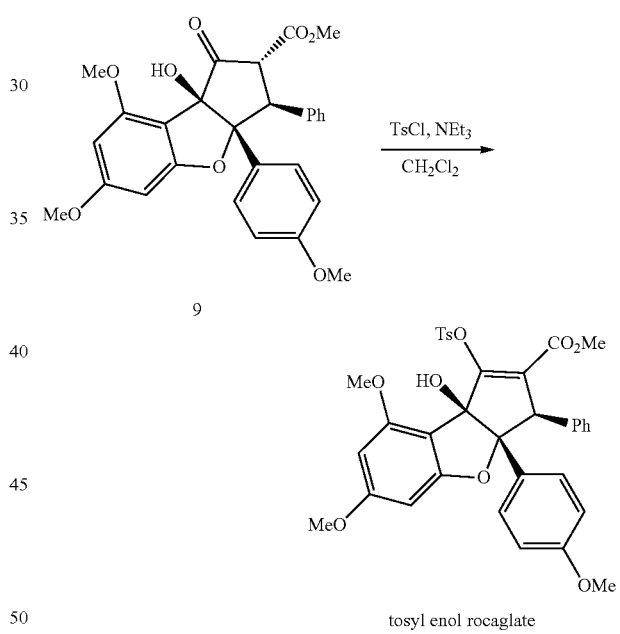

tosyl enol rocaglate

Methyl (3R,3aR,8bR)-8b-hydroxy-6,8-dimethoxy-3a-(4-methoxyphenyl)-3-phenyl-1-(tosyloxy)-3a,8b-dihydro-3H-cyclopenta[b]benzofuran-2-carboxylate
(tosyl enol rocaglate)

To keto-rocaglate 9 (561 mg, 1.14 mmol) and a stir bar, 7 mL of a dichloromethane solution of triethylamine (0.5 M, 3 equiv) was added followed by 5 mL of a dichloromethane solution of tosyl chloride (0.5 M, 2 equiv) at rt. The reaction was stirred for 2 h and was checked for completion using TLC analysis. The reaction was quenched with sat. aq. ammonium chloride. The crude product was obtained by extraction with ethyl acetate, drying with Na₂SO₄, filtration, and concentration. After flash chromatography (eluent: ethyl acetate:hexane=1:3, rf=0.4), 627 mg (0.972 mmol) of the pure tosyl enol rocaglate was obtained in 85% yield as a white powder, Scheme 13. $^1$H NMR (400 MHz, CDCl$_3$) δ 8.04 (d, J=8.3 Hz, 2H), 7.38 (d, J=8.1 Hz, 2H), 7.19-7.08 (m, 5H), 7.05 (d, J=9.0 Hz, 2H), 6.54 (d, J=9.0 Hz, 2H), 6.13 (d, J=1.9 Hz, 1H), 5.87 (d, J=1.9 Hz, 1H), 4.63 (s, 1H), 3.76 (s, 3H), 3.66 (s, 3H), 3.61 (s, 3H), 3.55 (s, 1H), 3.47 (s, 3H), 2.47 (s, 3H). $^{13}$C NMR (101 MHz, CDCl$_3$) δ 163.6, 163.0, 160.9, 158.6, 157.7, 153.4, 145.2, 137.5, 134.1, 129.5, 129.3, 129.2, 128.9, 128.0, 127.1, 126.7, 124.3, 112.0, 105.4, 99.4, 92.2, 89.7, 88.9, 58.9, 55.6, 55.0, 54.9, 51.8, 21.7. ESI MS m/z: 645.3, [M+H]+. The ee of yielding product was improved to >97% ee through crystallization in isopropanol upon heating.

3.2 Chiral HPLC Traces for (Q)-, (−)-, and (+)-Tosyl Enol Rocaglates

A WelkO column was used with an isocratic mobile phase of 40% isopropanol in hexanes at a flow rate of 1.0 mL/min for 30 min.

(±)-Tosyl enol rocaglate is shown in FIG. 16A. (−)-Tosyl enol rocaglate [α]D26=−223.220° (c=0.05, CH$_2$Cl$_2$) is shown in FIG. 16B. (+)-Tosyl enol rocaglate [α]D26=206.091° (c=0.05, CH2Cl2) is shown in FIG. 16C.

3.3 Removal of Tosyl Protecting Group

SCHEME 14 tosyl enol rocaglate

NaOMe
MeOH/CH$_2$Cl$_2$
6 h keto-rocaglate (9)

Tosyl enol rocaglate (400 mg, 0.62 mmol) was dissolved in 2.0 mL of dichloromethane which was followed by addition of 1 M NaOMe in MeOH (3.0 equiv) at room temperature. The reaction was stirred for 6 h and was checked completion by TLC analysis. After completion, the reaction was quenched by ammonium chloride (sat. aq.). Methanol was removed rotary evaporation and the product was obtained in quantitative yield through extraction with ethyl acetate (3 times), drying through sodium sulfate, and concentration. The crude product was used without further purification, Scheme 14.

3.4 Chiral HPLC Traces of (±)-, (−)-, and (+)-CMLD012043 (12l):

A ChiralCel OD column was used with an isocratic mobile phase of 20% isopropanol in hexanes at a flow rate of 1.0 mL/min for 30 min.

(±)-CMLD012043 (12l) is shown in FIG. 17A.

(−)-CMLD012043 (12l) [α]D26=−59.548° (c=0.02, CH2Cl2) is shown in FIG. 17B. Minor solvent residue at 5.9 min.

(+)-CMLD012043 (12l) [α]$_D^{26}$=75.200° (c=0.02, CH$_2$Cl$_2$). is shown in FIG. 17C. Minor solvent residue at 5.9 min 3.5 Chiral HPLC Trace of (±)-, (−)-, and (+)-CMLD012044 (12s):

A ChiralCel OD column was used with an isocratic mobile phase of 20% isopropanol in hexanes at a flow rate of 1.0 mL/min for 30 min.

(±)-CMLD012044 (12s) is shown in FIG. 18A.

(−)-CMLD012044 (12s) [α]D26=−61.796° (c=0.02, CH$_2$Cl$_2$) is shown in FIG. 18B.

(+)-CMLD012044 (12s) [α]D26=74.913° (c=0.02, CH$_2$Cl$_2$) is shown in FIG. 18C.

Example 5: X-Ray Crystal Structure of Oxazoline 15

Crystals of oxazoline 15 suitable for X-ray analysis were obtained by vapor diffusion from CHCl3/hexanes (FIG. 19). Crystallographic data have been deposited with the Cambridge Crystallographic Data Center (CCDC 1867925).

Refinement:

Crystal data, data collection and structure refinement details are summarized in the Tables below.

Results and Discussion

Computing Details

Data collection: APEX3 (Bruker, 2016); cell refinement: SAINT V8.38A (Bruker, 2006); data reduction: SAINT V8.38A (Bruker, 2016); program(s) used to solve structure: ShelXT (Sheldrick, 2015); program(s) used to refine structure: SHELXL (Sheldrick, 2015); molecular graphics: Olex2 (Dolomanov et al., 2009); software used to prepare material for publication: Olex2 (Dolomanov et al., 2009).

References

Sheldrick, G. M. (2008). *A Brief History of SHELX*. Acta Cryst. A 64, 112-122.

Sheldrick, G. M. (2015). *Crystal Structure Refinement with SHELXL*. Acta Cryst. C71, 3-8.

Bruker (2006). *SAINT*. Bruker Analytical X-ray Instruments Inc., Madison, Wis., USA.

Bruker (2016). *APEX3*. Bruker Analytical X-ray Instruments Inc., Madison, Wis., USA.

Krause, L., et al. (2015). *Comparison of Silver and Molybdenum Microfocus X-ray Sources for Single-Crystal Structure Determination*. J. Appl. Cryst. 48, 3-10 (2015).

Dolmanov, O. V., et al. (2009). *OLEX2: A complete structure solution, refinement and analysis program*. J. Appl. Cryst. 42, 339-341.

(zhang3a_0m)

Crystal Data

| | |
|---|---|
| $C_{35}H_{31}NO_8$ | F(000) = 2496 |
| $M_r$ = 593.61 | $D_x$ = 1.338 Mg m$^{-3}$ |
| Monoclinic, C2/c | Cu Kα radiation, λ = 1.54178 Å |
| a = 26.6128 (17) Å | Cell parameters from 9980 reflections |
| b = 10.4020 (7) Å | θ = 3.3-66.7° |
| c = 21.3640 (14) Å | μ = 0.78 mm$^{-1}$ |

-continued

| | |
|---|---|
| β = 94.776 (4)° | T = 100 K |
| V = 5893.6 (7) Å$^3$ | Prism |
| Z = 8 | 0.18 × 0.14 × 0.06 mm |

Data Collection

| | |
|---|---|
| Bruker APEX-II CCD diffractometer | 4678 reflections with I > 2σ(I) |
| φ and ω scans | $R_{int}$ = 0.068 |
| Absorption correction: multi-scan SADABS201612 (Bruker,2016/2) was used for absorption correction. wR2(int) was 0.0960 before and 0.0758 after correction. The Ratio of minimum to maximum transmission is 0.8247. The λ/2 correction factor is Not present. | $θ_{max}$ = 66.6°, $θ_{min}$ = 3.3° |
| $T_{min}$ = 0.621, $T_{max}$ = 0.753 | h = −31→31 |
| 33704 measured reflections | k = −12→12 |
| 5217 independent reflections | l = −21→25 |

Refinement

| | |
|---|---|
| Refinement on F$^2$ | Primary atom site location: dual |
| Least-squares matrix: full | Hydrogen site location: inferred from neighbouring sites |
| R[F$^2$ > 2σ(F$^2$)] = 0.069 | H-atom parameters constrained |
| wR(F$^2$) = 0.161 | w = 1/[σ$^2$(F$_o^2$) + (0.040P)$^2$ + 18.183P] where P = (F$_o^2$ + 2F$_c^2$)/3 |
| S = 1.10 | (Δ/σ)$_{max}$ < 0.001 |
| 5217 reflections | Δ⟩$_{max}$ = 0.36 e Å$^{-3}$ |
| 418 parameters | Δ⟩$_{min}$ = −0.41 e Å$^{-3}$ |
| 1 restraint | |

Special Details
Geometry.

All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.

Fractional Atomic Coordinates and Isotropic or Equivalent Isotropic Displacement Parameters (Å$^2$) for (zhang3a_0m)

| | x | y | z | $U_{iso}$*/$U_{eq}$ | Occ. (<1) |
|---|---|---|---|---|---|
| O5 | 0.59210 (6) | 0.37894 (18) | 0.23913 (8) | 0.0311 (4) | |
| O4 | 0.53474 (6) | 0.30325 (17) | 0.34125 (8) | 0.0309 (4) | |
| H4 | 0.540313 | 0.320767 | 0.305046 | 0.046* | |
| O2 | 0.68580 (7) | 0.2831 (2) | 0.42509 (8) | 0.0416 (5) | |
| O3 | 0.62109 (7) | 0.54304 (18) | 0.36020 (9) | 0.0364 (5) | |
| O7 | 0.46653 (7) | 0.3352 (2) | 0.46497 (10) | 0.0472 (5) | |
| O6 | 0.72816 (8) | 0.0834 (2) | 0.23268 (9) | 0.0486 (6) | |
| Ni | 0.53738 (8) | 0.5214 (2) | 0.36978 (10) | 0.0319 (5) | |
| O8 | 0.50853 (9) | 0.1533 (2) | 0.45203 (13) | 0.0607 (7) | |
| O1A | 0.71920 (13) | 0.7846 (4) | 0.59182 (15) | 0.0438 (10) | 0.779 (6) |
| C18 | 0.55849 (9) | 0.3939 (2) | 0.38232 (11) | 0.0252 (5) | |
| C11 | 0.63156 (9) | 0.3091 (3) | 0.26652 (12) | 0.0286 (6) | |
| C10 | 0.64096 (9) | 0.3242 (3) | 0.33144 (12) | 0.0281 (5) | |
| C9 | 0.61630 (9) | 0.4083 (3) | 0.37607 (11) | 0.0272 (5) | |
| C20 | 0.55413 (9) | 0.3495 (3) | 0.45100 (12) | 0.0283 (5) | |
| H20 | 0.554517 | 0.426481 | 0.477481 | 0.034* | |
| C12 | 0.66196 (9) | 0.2274 (3) | 0.23493 (12) | 0.0336 (6) | |
| H12 | 0.656136 | 0.215996 | 0.191759 | 0.040* | |
| C5A | 0.66444 (10) | 0.4777 (3) | 0.48300 (17) | 0.0311 (9) | 0.779 (6) |
| C6A | 0.71449 (10) | 0.4747 (3) | 0.50745 (14) | 0.0363 (10) | 0.779 (6) |
| H6A | 0.734875 | 0.405323 | 0.498962 | 0.044* | 0.779 (6) |
| C7A | 0.73407 (8) | 0.5756 (4) | 0.54459 (12) | 0.0376 (11) | 0.779 (6) |
| H7A | 0.767559 | 0.573592 | 0.560953 | 0.045* | 0.779 (6) |
| C2A | 0.70360 (11) | 0.6793 (3) | 0.55728 (11) | 0.0320 (9) | 0.779 (6) |
| C3A | 0.65355 (11) | 0.6822 (3) | 0.53283 (13) | 0.0326 (8) | 0.779 (6) |
| H3A | 0.633169 | 0.751632 | 0.541324 | 0.039* | 0.779 (6) |
| C4A | 0.63397 (9) | 0.5814 (3) | 0.49569 (17) | 0.0324 (8) | 0.779 (6) |
| H4A | 0.600484 | 0.583363 | 0.479334 | 0.039* | 0.779 (6) |
| C15 | 0.68022 (9) | 0.2584 (3) | 0.36230 (12) | 0.0354 (6) | |
| C23 | 0.60339 (9) | 0.2767 (3) | 0.46743 (12) | 0.0311 (6) | |
| H23 | 0.601640 | 0.199165 | 0.441266 | 0.037* | 0.801 (6) |
| H23A | 0.602512 | 0.192707 | 0.446569 | 0.037* | 0.199 (6) |
| C19 | 0.57344 (11) | 0.5944 (3) | 0.35823 (12) | 0.0351 (6) | |
| C13 | 0.70159 (10) | 0.1623 (3) | 0.26878 (13) | 0.0381 (7) | |
| C8 | 0.64409 (9) | 0.3652 (3) | 0.44068 (12) | 0.0319 (6) | |
| C21 | 0.50518 (10) | 0.2804 (3) | 0.45751 (13) | 0.0376 (7) | |
| C16 | 0.58518 (10) | 0.3789 (3) | 0.17193 (12) | 0.0412 (7) | |
| H16A | 0.615250 | 0.409935 | 0.155123 | 0.062* | |
| H16B | 0.557359 | 0.433721 | 0.158394 | 0.062* | |
| H16C | 0.578295 | 0.292946 | 0.157240 | 0.062* | |
| C14 | 0.71196 (10) | 0.1769 (3) | 0.33293 (14) | 0.0427(7) | |
| H14 | 0.738649 | 0.134557 | 0.354969 | 0.051* | |
| C30A | 0.61447 (17) | 0.2312 (4) | 0.53416 (19) | 0.0345 (10) | 0.801 (6) |
| C31A | 0.64510 (15) | 0.1243 (3) | 0.54698 (18) | 0.0383 (9) | 0.801 (6) |
| H31A | 0.656605 | 0.077722 | 0.513873 | 0.046* | 0.801 (6) |
| C24A | 0.56193 (14) | 0.7318 (3) | 0.3417 (3) | 0.0315 (12) | 0.588 (4) |
| C25A | 0.60273 (12) | 0.8145 (4) | 0.3391 (3) | 0.0725 (19) | 0.588 (4) |
| H25A | 0.635438 | 0.782961 | 0.345845 | 0.087* | 0.588 (4) |
| C26A | 0.59464 (17) | 0.9442 (4) | 0.3265 (3) | 0.080 (2) | 0.588 (4) |
| H26A | 0.621942 | 0.999574 | 0.324738 | 0.096* | 0.588 (4) |
| C27A | 0.5458 (2) | 0.9913 (3) | 0.3164 (3) | 0.077 (2) | 0.588 (4) |
| H27A | 0.540347 | 1.078151 | 0.307935 | 0.092* | 0.588 (4) |
| C28A | 0.50496 (15) | 0.9086 (4) | 0.3190 (3) | 0.091 (2) | 0.588 (4) |
| H28A | 0.472248 | 0.940115 | 0.312239 | 0.110* | 0.588 (4) |
| C29A | 0.51304 (13) | 0.7788 (4) | 0.3316 (3) | 0.0717 (19) | 0.588 (4) |
| H29A | 0.485743 | 0.723500 | 0.333347 | 0.086* | 0.588 (4) |
| C35A | 0.5972 (2) | 0.2969 (5) | 0.5845 (2) | 0.0524 (13) | 0.801 (6) |
| H35A | 0.576438 | 0.368286 | 0.577228 | 0.063* | 0.801 (6) |
| C17 | 0.77016 (14) | 0.0171 (4) | 0.26302 (17) | 0.0696 (12) | |
| H17A | 0.784778 | −0.037823 | 0.233317 | 0.104* | |
| H17B | 0.759186 | −0.033870 | 0.296780 | 0.104* | |

|  | x | y | z | $U_{iso}$*/$U_{eq}$ | Occ. (<1) |
|---|---|---|---|---|---|
| H17C | 0.794862 | 0.078266 | 0.279452 | 0.104* | |
| C32A | 0.65876 (16) | 0.0861 (5) | 0.60828 (19) | 0.0503 (11) | 0.801 (6) |
| H32A | 0.679941 | 0.015641 | 0.615786 | 0.060* | 0.801 (6) |
| C1A | 0.77125 (15) | 0.7919 (6) | 0.61427 (19) | 0.0516 (14) | 0.779 (6) |
| H1AA | 0.791778 | 0.780255 | 0.579820 | 0.077* | 0.779 (6) |
| H1AB | 0.778822 | 0.725790 | 0.644978 | 0.077* | 0.779 (6) |
| H1AC | 0.778113 | 0.874520 | 0.633085 | 0.077* | 0.779 (6) |
| C22 | 0.46080 (16) | 0.0856 (4) | 0.4532 (3) | 0.0858 (15) | |
| H22A | 0.437121 | 0.119081 | 0.420958 | 0.129* | |
| H22B | 0.447841 | 0.097320 | 0.493450 | 0.129* | |
| H22C | 0.465939 | −0.004412 | 0.446070 | 0.129* | |
| C34A | 0.6106 (2) | 0.2570 (6) | 0.6461 (2) | 0.0702 (18) | 0.801 (6) |
| H34A | 0.598736 | 0.301831 | 0.679600 | 0.084* | 0.801 (6) |
| C33A | 0.6414 (2) | 0.1507 (5) | 0.6575 (2) | 0.0650 (14) | 0.801 (6) |
| H33A | 0.650240 | 0.123797 | 0.698421 | 0.078* | 0.801 (6) |
| C24B | 0.5820 (2) | 0.7307 (4) | 0.3475 (4) | 0.0315 (12) | 0.412 (4) |
| C25B | 0.6239 (2) | 0.7875 (5) | 0.3243 (4) | 0.0725 (19) | 0.412 (4) |
| H25B | 0.651301 | 0.737125 | 0.315379 | 0.087* | 0.412 (4) |
| C26B | 0.6249 (3) | 0.9195 (6) | 0.3145 (4) | 0.080 (2) | 0.412 (4) |
| H26B | 0.653007 | 0.957500 | 0.298972 | 0.096* | 0.412 (4) |
| C27B | 0.5840 (3) | 0.9948 (4) | 0.3278 (4) | 0.077 (2) | 0.412 (4) |
| H27B | 0.584706 | 1.083123 | 0.321257 | 0.092* | 0.412 (4) |
| C28B | 0.5421 (3) | 0.9380 (6) | 0.3510 (4) | 0.091 (2) | 0.412 (4) |
| H28B | 0.514697 | 0.988373 | 0.359948 | 0.110* | 0.412 (4) |
| C29B | 0.5411 (2) | 0.8060 (6) | 0.3608 (4) | 0.0717 (19) | 0.412 (4) |
| H29B | 0.512990 | 0.767998 | 0.376355 | 0.086* | 0.412 (4) |
| O1B | 0.7494 (5) | 0.7159 (12) | 0.6008 (5) | 0.050 (3) | 0.221 (6) |
| C1B | 0.7357 (8) | 0.841 (2) | 0.5951 (8) | 0.047 (5) | 0.221 (6) |
| H1BA | 0.728208 | 0.861059 | 0.551532 | 0.070* | 0.221 (6) |
| H1BB | 0.762718 | 0.894071 | 0.612477 | 0.070* | 0.221 (6) |
| H1BC | 0.706265 | 0.855171 | 0.617332 | 0.070* | 0.221 (6) |
| C5B | 0.6707 (5) | 0.4479 (12) | 0.4871 (7) | 0.0311 (9) | 0.221 (6) |
| C6B | 0.7188 (4) | 0.4223 (11) | 0.5149 (6) | 0.0363 (10) | 0.221 (6) |
| H6B | 0.734276 | 0.344266 | 0.507575 | 0.044* | 0.221 (6) |
| C7B | 0.7437 (3) | 0.5135 (14) | 0.5537 (5) | 0.0376 (11) | 0.221 (6) |
| H7B | 0.775817 | 0.496393 | 0.572273 | 0.045* | 0.221 (6) |
| C2B | 0.7205 (4) | 0.6302 (12) | 0.5646 (5) | 0.0320 (9) | 0.221 (6) |
| C3B | 0.6725 (5) | 0.6557 (11) | 0.5368 (6) | 0.0326 (8) | 0.221 (6) |
| H3B | 0.656955 | 0.733768 | 0.544188 | 0.039* | 0.221 (6) |
| C4B | 0.6476 (4) | 0.5646 (14) | 0.4981 (7) | 0.0324 (8) | 0.221 (6) |
| H4B | 0.615412 | 0.581643 | 0.479489 | 0.039* | 0.221 (6) |
| C30B | 0.6213 (7) | 0.2623 (17) | 0.5375 (6) | 0.0345 (10) | 0.199 (6) |
| C35B | 0.6019 (7) | 0.3298 (18) | 0.5862 (8) | 0.0524 (13) | 0.199 (6) |
| H35B | 0.576073 | 0.389130 | 0.577512 | 0.063* | 0.199 (6) |
| C34B | 0.6210 (7) | 0.3087 (17) | 0.6479 (7) | 0.0702 (18) | 0.199 (6) |
| H34B | 0.607987 | 0.353903 | 0.680466 | 0.084* | 0.199 (6) |
| C33B | 0.6595 (6) | 0.2201 (17) | 0.6609 (4) | 0.0650 (14) | 0.199 (6) |
| H33B | 0.672338 | 0.206003 | 0.702158 | 0.078* | 0.199 (6) |
| C32B | 0.6790 (5) | 0.1526 (15) | 0.6122 (5) | 0.0503 (11) | 0.199 (6) |
| H32B | 0.704776 | 0.093329 | 0.620897 | 0.060* | 0.199 (6) |
| C31B | 0.6599 (5) | 0.1737 (14) | 0.5505 (5) | 0.0383 (9) | 0.199 (6) |
| H31B | 0.672862 | 0.128554 | 0.517943 | 0.046* | 0.199 (6) |

Atomic Displacement Parameters (Å$^2$) for (zhang3a_0m)

|  | U$^{11}$ | U$^{22}$ | U$^{33}$ | U$^{12}$ | U$^{13}$ | U$^{23}$ |
|---|---|---|---|---|---|---|
| O5 | 0.0262 (9) | 0.0422 (11) | 0.0247 (9) | 0.0046 (8) | 0.0015 (7) | 0.0035 (8) |
| O4 | 0.0285 (9) | 0.0327 (10) | 0.0320 (9) | −0.0067 (7) | 0.0061 (7) | −0.0042 (8) |
| O2 | 0.0269 (9) | 0.0718 (15) | 0.0258 (9) | 0.0160 (9) | 0.0008 (7) | −0.0017 (9) |
| O3 | 0.0403 (10) | 0.0350 (11) | 0.0341 (10) | −0.0138 (8) | 0.0050 (8) | 0.0009 (8) |
| O7 | 0.0312 (11) | 0.0692 (15) | 0.0423 (11) | −0.0054 (10) | 0.0099 (8) | −0.0023 (10) |
| O6 | 0.0401 (11) | 0.0700 (15) | 0.0370 (11) | 0.0235 (11) | 0.0109 (9) | −0.0014 (10) |
| N1 | 0.0375 (12) | 0.0273 (11) | 0.0319 (11) | 0.0061 (10) | 0.0087 (9) | 0.0035 (9) |
| O8 | 0.0534 (14) | 0.0405 (13) | 0.0890 (19) | −0.0133 (11) | 0.0104 (12) | 0.0234 (12) |
| O1A | 0.0227 (19) | 0.073 (3) | 0.0359 (15) | −0.0144 (18) | 0.0029 (13) | −0.0118 (17) |
| C18 | 0.0214 (11) | 0.0240 (12) | 0.0305 (12) | 0.0008 (9) | 0.0044 (9) | 0.0012 (10) |
| C11 | 0.0204 (11) | 0.0387 (15) | 0.0269 (12) | −0.0018 (10) | 0.0036 (9) | 0.0027 (11) |
| C10 | 0.0185 (11) | 0.0388 (14) | 0.0275 (12) | −0.0011 (10) | 0.0045 (9) | 0.0007 (11) |
| C9 | 0.0226 (12) | 0.0320 (14) | 0.0274 (12) | −0.0022 (10) | 0.0039 (9) | 0.0018 (11) |
| C20 | 0.0260 (12) | 0.0302 (14) | 0.0292 (13) | 0.0005 (10) | 0.0051 (10) | 0.0024 (11) |
| C12 | 0.0269 (13) | 0.0475 (17) | 0.0272 (13) | 0.0007 (12) | 0.0061 (10) | −0.0019 (12) |
| C5A | 0.0208 (15) | 0.050 (3) | 0.0231 (14) | 0.0005 (17) | 0.0038 (11) | −0.0004 (17) |
| C6A | 0.0239 (15) | 0.053 (3) | 0.0317 (17) | 0.0030 (19) | 0.0027 (12) | 0.0039 (19) |
| C7A | 0.0184 (16) | 0.066 (3) | 0.0277 (18) | 0.001 (2) | −0.0019 (13) | 0.005 (2) |
| C2A | 0.022 (2) | 0.052 (3) | 0.0218 (15) | −0.0050 (17) | 0.0020 (14) | 0.0004 (16) |
| C3A | 0.019 (2) | 0.050 (2) | 0.0291 (15) | 0.0013 (17) | 0.0074 (16) | −0.0040 (15) |

-continued

|  | $U^{11}$ | $U^{22}$ | $U^{33}$ | $U^{12}$ | $U^{13}$ | $U^{23}$ |
|---|---|---|---|---|---|---|
| C4A | 0.0176 (18) | 0.053 (2) | 0.0270 (13) | −0.0023 (16) | 0.0043 (15) | −0.0040 (14) |
| C15 | 0.0234 (12) | 0.0569 (18) | 0.0263 (13) | 0.0042 (12) | 0.0035 (10) | 0.0002 (12) |
| C23 | 0.0309 (13) | 0.0345 (14) | 0.0281 (13) | 0.0061 (11) | 0.0038 (10) | 0.0039 (11) |
| C19 | 0.0501 (17) | 0.0266 (14) | 0.0296 (13) | −0.0002 (12) | 0.0097 (12) | −0.0019 (11) |
| C13 | 0.0287 (13) | 0.0540 (18) | 0.0332 (14) | 0.0077 (12) | 0.0120 (11) | −0.0006 (13) |
| C8 | 0.0239 (12) | 0.0467 (16) | 0.0256 (12) | 0.0059 (11) | 0.0055 (10) | −0.0008 (11) |
| C21 | 0.0338 (15) | 0.0460 (17) | 0.0341 (14) | −0.0031 (13) | 0.0083 (11) | 0.0112 (13) |
| C16 | 0.0320 (14) | 0.065 (2) | 0.0263 (13) | 0.0070 (14) | 0.0019 (11) | 0.0062 (13) |
| C14 | 0.0265 (13) | 0.067 (2) | 0.0351 (15) | 0.0154 (13) | 0.0053 (11) | 0.0037 (14) |
| C30A | 0.0363 (19) | 0.036 (2) | 0.0310 (15) | 0.0009 (18) | 0.0025 (12) | 0.0051 (15) |
| C31A | 0.035 (2) | 0.039 (3) | 0.0419 (18) | −0.0013 (17) | 0.0037 (15) | 0.0100 (17) |
| C24A | 0.030 (4) | 0.0267 (16) | 0.039 (2) | 0.000 (2) | 0.007 (3) | −0.0005 (14) |
| C25A | 0.058 (5) | 0.040 (3) | 0.124 (6) | −0.008 (3) | 0.032 (4) | 0.013 (3) |
| C26A | 0.085 (5) | 0.036 (3) | 0.125 (6) | −0.013 (3) | 0.036 (4) | 0.011 (3) |
| C27A | 0.108 (5) | 0.024 (2) | 0.102 (5) | 0.010 (4) | 0.023 (5) | 0.003 (3) |
| C28A | 0.090 (5) | 0.039 (3) | 0.148 (8) | 0.024 (4) | 0.023 (5) | 0.021 (4) |
| C29A | 0.055 (4) | 0.038 (3) | 0.124 (6) | 0.009 (3) | 0.016 (3) | 0.019 (3) |
| C35A | 0.075 (3) | 0.050 (3) | 0.0331 (16) | 0.018 (2) | 0.0102 (16) | 0.0070 (19) |
| C17 | 0.059 (2) | 0.103 (3) | 0.050 (2) | 0.051 (2) | 0.0215 (16) | 0.013 (2) |
| C32A | 0.049 (2) | 0.053 (3) | 0.048 (2) | 0.004 (2) | −0.0022 (18) | 0.020 (2) |
| C1A | 0.026 (2) | 0.097 (4) | 0.032 (2) | −0.022 (3) | 0.0045 (16) | −0.008 (2) |
| C22 | 0.068 (3) | 0.065 (3) | 0.124 (4) | −0.032 (3) | 0.003 (3) | 0.038 (3) |
| C34A | 0.108 (4) | 0.073 (4) | 0.0307 (18) | 0.020 (3) | 0.009 (2) | 0.003 (2) |
| C33A | 0.092 (4) | 0.067 (4) | 0.034 (2) | 0.003 (3) | −0.005 (2) | 0.019 (2) |
| C24B | 0.030 (4) | 0.0267 (16) | 0.039 (2) | 0.000 (2) | 0.007 (3) | −0.0005 (14) |
| C25B | 0.058 (5) | 0.040 (3) | 0.124 (6) | −0.008 (3) | 0.032 (4) | 0.013 (3) |
| C26B | 0.085 (5) | 0.036 (3) | 0.125 (6) | −0.013 (3) | 0.036 (4) | 0.011 (3) |
| C27B | 0.108 (5) | 0.024 (2) | 0.102 (5) | 0.010 (4) | 0.023 (5) | 0.003 (3) |
| C28B | 0.090 (5) | 0.039 (3) | 0.148 (8) | 0.024 (4) | 0.023 (5) | 0.021 (4) |
| C29B | 0.055 (4) | 0.038 (3) | 0.124 (6) | 0.009 (3) | 0.016 (3) | 0.019 (3) |
| O1B | 0.040 (7) | 0.059 (8) | 0.048 (6) | −0.009 (6) | −0.012 (5) | 0.001 (5) |
| C1B | 0.031 (11) | 0.070 (14) | 0.038 (8) | −0.006 (8) | −0.005 (7) | −0.08 (9) |
| C5B | 0.0208 (15) | 0.050 (3) | 0.0231 (14) | 0.0005 (17) | 0.0038 (11) | −0.0004 (17) |
| C6B | 0.0239 (15) | 0.053 (3) | 0.0317 (17) | 0.0030 (19) | 0.0027 (12) | 0.0039 (19) |
| C7B | 0.0184 (16) | 0.066 (3) | 0.0277 (18) | 0.001 (2) | −0.0019 (13) | 0.005 (2) |
| C2B | 0.022 (2) | 0.052 (2) | 0.0218 (15) | −0.0050 (17) | 0.0020 (14) | 0.0004 (16) |
| C3B | 0.019 (2) | 0.050 (2) | 0.0291 (15) | 0.0013 (17) | 0.0074 (16) | −0.0040 (15) |
| C4B | 0.0176 (18) | 0.053 (2) | 0.0270 (13) | −0.0023 (16) | 0.0043 (15) | −0.0040 (14) |
| C30B | 0.0363 (19) | 0.036 (2) | 0.0310 (15) | 0.0009 (18) | 0.0025 (12) | 0.0051 (15) |
| C35B | 0.075 (3) | 0.050 (3) | 0.0331 (16) | 0.018 (2) | 0.0102 (16) | 0.0070 (19) |
| C34B | 0.108 (4) | 0.073 (4) | 0.0307 (18) | 0.020 (3) | 0.009 (2) | 0.003 (2) |
| C33B | 0.092 (4) | 0.067 (4) | 0.034 (2) | 0.003 (3) | −0.005 (2) | 0.019 (2) |
| C32B | 0.049 (2) | 0.053 (3) | 0.048 (2) | 0.004 (2) | −0.0022 (18) | 0.020 (2) |
| C31B | 0.035 (2) | 0.039 (3) | 0.0419 (18) | −0.0013 (17) | 0.0037 (15) | 0.0100 (17) |

Geometric Parameters (Å,°) for (zhang3a_0m)

| | | | | | |
|---|---|---|---|---|---|
| O5-C11 | 1.368 (3) | C25A-C26A | 1.3900 | C12-H12 | 0.9300 |
| O5-C16 | 1.432 (3) | C26A-H26A | 0.9300 | C12-C13 | 1.403 (4) |
| O4-H4 | 0.8200 | C26A-C27A | 1.3900 | C5A-C6A | 1.3900 |
| O4-C18 | 1.402 (3) | C27A-H27A | 0.9300 | C5A-C4A | 1.3900 |
| O2-C15 | 1.362 (3) | C27A-C28A | 1.3900 | C5A-C8 | 1.548 (3) |
| O2-C8 | 1.461 (3) | C28A-H28A | 0.9300 | C6A-H6A | 0.9300 |
| O3-C9 | 1.450 (3) | C28A-C29A | 1.3900 | C6A-C7A | 1.3900 |
| O3-C19 | 1.373 (3) | C29A-H29A | 0.9300 | C7A-H7A | 0.9300 |
| O7-C21 | 1.199 (3) | C35A-H35A | 0.9300 | C7A-C2A | 1.3900 |
| O6-C13 | 1.364 (3) | C35A-C34A | 1.398 (6) | C2A-C3A | 1.3900 |
| O6-C17 | 1.423 (4) | C17-H17A | 0.9600 | C3A-H3A | 0.9300 |
| N1-C18 | 1.457 (3) | C17-H17B | 0.9600 | C3A-C4A | 1.3900 |
| N1-C19 | 1.264 (3) | C17-H17C | 0.9600 | C4A-H4A | 0.9300 |
| O8-C21 | 1.330 (4) | C32A-H32A | 0.9300 | C15-C14 | 1.383 (4) |
| O8-C22 | 1.455 (4) | C32A-C33A | 1.360 (7) | C23-H23 | 0.9800 |
| O1A-C2A | 1.366 (5) | C1A-H1AA | 0.9600 | C23-H23A | 0.9800 |
| O1A-C1A | 1.430 (5) | C1A-H1AB | 0.9600 | C23-C8 | 1.566 (4) |
| C18-C9 | 1.562 (3) | C1A-H1AC | 0.9600 | C23-C30A | 1.508 (5) |
| C18-C20 | 1.552 (3) | C22-H22A | 0.9600 | C23-C30B | 1.540 (10) |
| C11-C10 | 1.398 (3) | C22-H22B | 0.9600 | C19-C24A | 1.498 (4) |
| C11-C12 | 1.386 (4) | C22-H22C | 0.9600 | C19-C24B | 1.458 (5) |
| C10-C9 | 1.486 (4) | C34A-H34A | 0.9300 | C13-C14 | 1.384 (4) |
| C10-C15 | 1.371 (4) | C34A-C33A | 1.387 (7) | C8-C5B | 1.452 (9) |
| C9-C8 | 1.576 (3) | C33A-H33A | 0.9300 | C16-H16A | 0.9600 |
| C20-H20 | 0.9800 | C24B-C25B | 1.3900 | C16-H16B | 0.9600 |
| C20-C23 | 1.529 (3) | C24B-C29B | 1.3900 | C16-H16C | 0.9600 |
| C20-C21 | 1.505 (4) | C25B-H25B | 0.9300 | C14-H14 | 0.9300 |
| | | | | C30A-C31A | 1.392 (5) |
| | | | | C25B-C26B | 1.3900 |
| | | | | C26B-H26B | 0.9300 |
| | | | | C26B-C27B | 1.3900 |
| | | | | C27B-H27B | 0.9300 |
| | | | | C27B-C28B | 1.3900 |
| | | | | C28B-H28B | 0.9300 |
| | | | | C28B-C29B | 1.3900 |
| | | | | C29B-H29B | 0.9300 |
| | | | | O1B-C1B | 1.35 (3) |
| | | | | O1B-C2B | 1.373 (14) |
| | | | | C1B-H1BA | 0.9600 |
| | | | | C1B-H1BB | 0.9600 |
| | | | | C1B-H1BC | 0.9600 |
| | | | | C5B-C6B | 1.3900 |
| | | | | C5B-C4B | 1.3900 |
| | | | | C6B-H6B | 0.9300 |
| | | | | C6B-C7B | 1.3900 |
| | | | | C7B-H7B | 0.9300 |
| | | | | C7B-C2B | 1.3900 |
| | | | | C2B-C3B | 1.3900 |
| | | | | C3B-H3B | 0.9300 |
| | | | | C3B-C4B | 1.3900 |
| | | | | C4B-H4B | 0.9300 |
| | | | | C30B-C35B | 1.3900 |
| | | | | C30B-C31B | 1.3900 |
| | | | | C35B-H35B | 0.9300 |
| | | | | C35B-C34B | 1.3900 |
| | | | | C34B-H34B | 0.9300 |

-continued

| | | | |
|---|---|---|---|
| C30A-C35A | 1.385 (5) | C34B-C33B | 1.3900 |
| C31A-H31A | 0.9300 | C33B-H33B | 0.9300 |
| C31A-C32A | 1.388 (5) | C33B-C32B | 1.3900 |
| C24A-C25A | 1.3900 | C32B-H32B | 0.9300 |
| C24A-C29A | 1.3900 | C32B-C31B | 1.3900 |
| C25A-H25A | 0.9300 | C31B-H31B | 0.9300 |
| C11-O5-C16 | 117.3 (2) | C26A-C25A-C24A | 120.0 |
| C18-O4-H4 | 109.5 | C26A-C25A-H25A | 120.0 |
| C15-O2-C8 | 108.21 (19) | C25A-C26A-H26A | 120.0 |
| C19-O3-C9 | 106.49 (19) | C27A-C26A-C25A | 120.0 |
| C13-O6-C17 | 117.3 (2) | C27A-C26A-H26A | 120.0 |
| C19-N1-C18 | 107.2 (2) | C26A-C27A-H27A | 120.0 |
| C21-O8-C22 | 114.5 (3) | C28A-C27A-C26A | 120.0 |
| C2A-O1A-C1A | 117.8 (4) | C28A-C27A-H27A | 120.0 |
| O4-C18-N1 | 110.52 (19) | C27A-C28A-H28A | 120.0 |
| O4-C18-C9 | 114.0 (2) | C27A-C28A-C29A | 120.0 |
| O4-C18-C20 | 109.1 (2) | C29A-C28A-H28A | 120.0 |
| N1-C18-C9 | 105.33 (19) | C24A-C29A-H29A | 120.0 |
| N1-C18-C20 | 112.8 (2) | C28A-C29A-C24A | 120.0 |
| C20-C18-C9 | 105.12 (19) | C28A-C29A-H29A | 120.0 |
| O5-C11-C10 | 115.6 (2) | C30A-C35A-H35A | 119.7 |
| O5-C11-C12 | 125.1 (2) | C30A-C35A-C34A | 120.6 (4) |
| C12-C11-C10 | 119.3 (2) | C34A-C35A-H35A | 119.7 |
| C11-C10-C9 | 130.6 (2) | O6-C17-H17A | 109.5 |
| C15-C10-C11 | 119.2 (2) | O6-C17-H17B | 109.5 |
| C15-C10-C9 | 110.2 (2) | O6-C17-H17C | 109.5 |
| O3-C9-C18 | 102.65 (19) | H17A-C17-H17B | 109.5 |
| O3-C9-C10 | 111.5 (2) | H17A-C17-H17C | 109.5 |
| O3-C9-C8 | 115.8 (2) | H17B-C17-H17C | 109.5 |
| C18-C9-C8 | 106.96 (19) | C31A-C32A-H32A | 119.7 |
| C10-C9-C18 | 119.3 (2) | C33A-C32A-C31A | 120.5 (4) |
| C10-C9-C8 | 101.2 (2) | C33A-C32A-H32A | 119.7 |
| C18-C20-H20 | 107.7 | O1A-C1A-H1AA | 109.5 |
| C23-C20-C18 | 103.55 (19) | O1A-C1A-H1AB | 109.5 |
| C23-C20-H20 | 107.7 | O1A-C1A-H1AC | 109.5 |
| C21-C20-C18 | 111.3 (2) | H1AA-C1A-H1AB | 109.5 |
| C21-C20-H20 | 107.7 | H1AA-C1A-H1AC | 109.5 |
| C21-C20-C23 | 118.3 (2) | H1AB-C1A-H1AC | 109.5 |
| C11-C12-H12 | 120.4 | O8-C22-H22A | 109.5 |
| C11-C12-C13 | 119.3 (2) | O8-C22-H22B | 109.5 |
| C13-C12-H12 | 120.4 | O8-C22-H22C | 109.5 |
| C6A-C5A-C4A | 120.0 | H22A-C22-H22B | 109.5 |
| C6A-C5A-C8 | 118.72 (18) | H22A-C22-H22C | 109.5 |
| C4A-C5A-C8 | 121.26 (18) | H22B-C22-H22C | 109.5 |
| C5A-C6A-H6A | 120.0 | C35A-C34A-H34A | 119.9 |
| C7A-C6A-O5A | 120.0 | C33A-C34A-C35A | 120.1 (4) |
| C7A-C6A-H6A | 120.0 | C33A-C34A-H34A | 119.9 |
| C6A-C7A-H7A | 120.0 | C32A-C33A-C34A | 119.6 (4) |
| C6A-C7A-C2A | 120.0 | C32A-C33A-H33A | 120.2 |
| C2A-C7A-H7A | 120.0 | C34A-C33A-H33A | 120.2 |
| O1A-C2A-C7A | 124.9 (2) | C25B-C24B-C19 | 127.6 (4) |
| O1A-C2A-C3A | 115.1 (2) | C25B-C24B-C29B | 120.0 |
| C3A-C2A-C7A | 120.0 | C29B-C24B-C19 | 112.4 (4) |
| C2A-C3A-H3A | 120.0 | C24B-C25B-H25B | 120.0 |
| C2A-C3A-C4A | 120.0 | C26B-C25B-C24B | 120.0 |
| C4A-C3A-H3A | 120.0 | C26B-C25B-H25B | 120.0 |
| C5A-C4A-H4A | 120.0 | C25B-C26B-H26B | 120.0 |
| C3A-C4A-C5A | 120.0 | C25B-C26B-C27B | 120.0 |
| C3A-C4A-H4A | 120.0 | C27B-C26B-H26B | 120.0 |
| O2-C15-C10 | 113.3 (2) | C26B-C27B-H27B | 120.0 |
| O2-C15-C14 | 122.8 (2) | C28B-C27B-C26B | 120.0 |
| C10-C15-C14 | 123.9 (2) | C28B-C27B-H27B | 120.0 |
| C20-C23-H23 | 106.1 | C27B-C28B-H28B | 120.0 |
| C20-C23-H23A | 110.5 | C27B-C28B-C29B | 120.0 |
| C20-C23-C8 | 103.3 (2) | C29B-C28B-H28B | 120.0 |
| C20-C23-C30B | 117.5 (6) | C24B-C29B-H29B | 120.0 |
| C8-C23-H23 | 106.1 | C28B-C29B-C24B | 120.0 |
| C8-C23-H23A | 110.5 | C28B-C29B-H29B | 120.0 |
| C30A-C23-C20 | 118.0 (3) | C1B-O1B-C2B | 116.0 (15) |
| C30A-C23-H23 | 106.1 | O1B-C1B-H1BA | 109.5 |
| C30A-C23-C8 | 116.3 (3) | O1B-C1B-H1BB | 109.5 |
| C30B-C23-H23A | 110.5 | O1B-C1B-H1BC | 109.5 |
| C30B-C23-C8 | 104.1 (8) | H1BA-C1B-H1BB | 109.5 |
| O3-C19-C24A | 123.3 (3) | H1BA-C1B-H1BC | 109.5 |
| O3-C19-C24B | 103.1 (3) | H1BB-C1B-H1BC | 109.5 |
| N1-C19-O3 | 118.4 (2) | C6B-C5B-C8 | 123.9 (8) |
| N1-C19-C24A | 118.4 (3) | C6B-C5B-C4B | 120.0 |
| N1-C19-C24B | 138.2 (3) | C4B-C5B-C8 | 115.7 (8) |
| O6-C13-C12 | 113.7 (2) | C5B-C6B-H6B | 120.0 |
| O6-C13-C14 | 123.8 (3) | C5B-C6B-C7B | 120.0 |
| C14-C13-C12 | 122.5 (3) | C7B-C6B-H6B | 120.0 |
| O2-C8-C9 | 106.05 (19) | C6B-C7B-H7B | 120.0 |
| O2-C8-C5A | 109.8 (2) | C2B-C7B-C6B | 120.0 |
| O2-C8-C23 | 107.5 (2) | C2B-C7B-H7B | 120.0 |
| C5A-C8-C9 | 114.4 (2) | O1B-C2B-C7B | 115.3 (10) |
| C5A-C8-C23 | 116.8 (2) | O1B-C2B-C3B | 124.7 (10) |
| C23-C8-C9 | 101.44 (19) | C3B-C2B-C7B | 120.0 |
| C5B-C8-O2 | 99.5 (6) | C2B-C3B-H3B | 120.0 |
| C5B-C8-C9 | 126.7 (6) | C2B-C3B-C4B | 120.0 |
| C5B-C8-C23 | 114.3 (7) | C4B-C3B-H3B | 120.0 |
| O7-C21-O8 | 123.3 (3) | C5B-C4B-H4B | 120.0 |
| O7-C21-C20 | 123.0 (3) | C3B-C4B-O5B | 120.0 |
| O8-C21-C20 | 113.7 (2) | C3B-C4B-H4B | 120.0 |
| O5-C16-H16A | 109.5 | C35B-C30B-C23 | 125.0 (10) |
| O5-C16-H16B | 109.5 | C35B-C30B-C31B | 120.0 |
| O5-C16-H16C | 109.5 | C31B-C30B-C23 | 115.0 (10) |
| H16A-C16-H16B | 109.5 | C30B-C35B-H35B | 120.0 |
| H16A-C16-H16C | 109.5 | C34B-C35B-C30B | 120.0 |
| H16B-C16-H16C | 109.5 | C34B-C35B-H35B | 120.0 |
| C15-C14-H14 | 122.0 | C35B-C34B-H34B | 120.0 |
| C13-C14-C15 | 116.0 (3) | C35B-C34B-C33B | 120.0 |
| C13-C14-H14 | 122.0 | C33B-C34B-H34B | 120.0 |
| C31A-C30A-C23 | 120.1 (4) | C34B-C33B-H33B | 120.0 |
| C35A-C30A-C23 | 121.9 (4) | C34B-C33B-C32B | 120.0 |
| C35A-C30A-C31A | 117.9 (3) | C32B-C33B-H33B | 120.0 |
| C30A-C31A-H31A | 119.4 | C33B-C32B-H32B | 120.0 |
| C32A-C31A-C30A | 121.2 (4) | C33B-C32B-C31B | 120.0 |
| C32A-C31A-H31A | 119.4 | C31B-C32B-H32B | 120.0 |
| C25A-C24A-C19 | 117.1 (3) | C30B-C31B-H31B | 120.0 |
| C25A-C24A-C29A | 120.0 | C32B-C31B-C30B | 120.0 |
| C29A-C24A-C19 | 122.9 (3) | C32B-C31B-H31B | 120.0 |
| C24A-C25A-H25A | 120.0 | | |

Document origin: publCIF [Westrip, S. P. (2010). *J. Apply. Cryst.*, 43, 920-925].

Example 6: Dose Response Curves for Aglaroxin C Analogues

According to our previous studies, the $EC_{50}$ of each analog was found to correlate with the treatment time of cells using the compounds, where a longer treatment time gave rise to a lower $EC_{50}$. To simplify the experiment protocol, 3 h treatment of cells using analogues were used for the comparison; aglaroxin C (6) was also included in each independent experiment as a positive control.

To determine the $EC_{50}$ of each compound, Huh7.5.1 cells were infected with JFH-1 HCVcc-Luc (MOI≈0.5) in the presence of compounds at various concentrations for 3 h in 96-well plates. After removal of virus and compounds, cells were further incubated for 72 h prior to luciferase assay. Data were presented as percent inhibition relative to control infections in which cells were treated with dimethyl sulfoxide (DMSO) (0%). Results are expressed as mean±standard deviation (SD) (n=3).

To determine the $EC_{50}$ of each compound, Huh7.5.1 cells were treated with compounds or DMSO at indicated doses for 3 h in 96-well plates. After removal of compounds, cells were further incubated for 72 h prior to the viability assay. The numbers of viable cells in culture were determined using the CellTiter-Glo Cell Viability Luminescent Assay kit according to the manufacturer's instruction (Promega). Percentages of toxicity were calculated using the formulas: 100-percentage of vial cells relative to that from the dimethyl sulfoxide (DMSO) treated group (100%) (n=3) (FIG. 20-FIG. 57).

Some side products were isolated and subjected to the same inhibition of HCV infection assay (FIG. 58-FIG. 67).

Example 7: Comparison Between MTS and Celltiter-Glo Cell Viability Assays

In this comparison, niclosamide was used as a positive control, which is known as HCV inhibitor (unclear mechanisms). Data from CellTiter-Glo assay was obtained from separate experiments conducted on a different date. MTS (3-(4,5-dimethylthiazol-2-yl)-5-(3-carboxymethoxyphenyl)-2-(4-sulfophenyl)-2H-tetrazolium)) assay is a colorimetric assay used to determine the mitochondrial metabolic rate by quantifying the reduced formazan product of MTS in cells to reflect viable cells. To determine the CC50 of each compound, Huh7.5.1 cells were treated with compounds or DMSO at indicated doses for 3 h in 96-well plates. After removal of compounds, cells were further incubated for 72 h prior to conducting the viability assay. The MTS assay in this study is accordance with a protocol provided by manufacturer (Promega, Madison, Wis. USA). One-fifth volume of MTS reagent was added into the culture supernatant at indicated time points. Plates were incubated at 37° C. for 3 hours with 5% CO2 followed by measuring the absorbance at 490 nanometers (nm) with an ELISA reader (SpectraMax Plus 385, Molecular Devices, USA). Percentages of toxicity were calculated using the formulas: 100-percentage of vial cells relative to that from the dimethyl sulfoxide (DMSO) treated group (100%) (n=3) (FIG. 68-FIG. 71).

Example 8: Fluorescence Emission for Pyrimidinone 12N

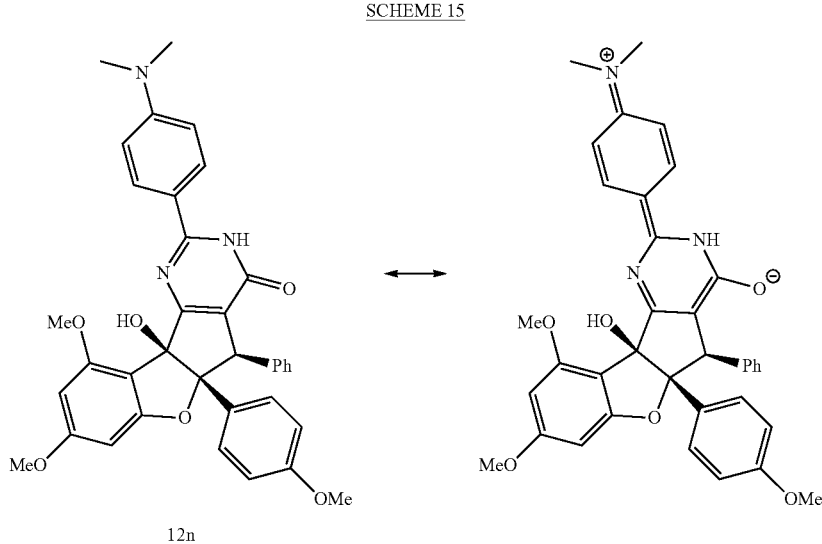 [SMILES: COc1ccc([C@@]23Oc4cc(OC)cc(OC)c4[C@]2(O)c2nc(-c4ccc(N(C)C)cc4)[nH]c(=O)c2[C@H]3c2ccccc2)cc1 ; COc1ccc([C@@]23Oc4cc(OC)cc(OC)c4[C@]2(O)C2=NC(=C4C=CC(=[N+](C)C)C=C4)NC([O-])=C2[C@H]3c2ccccc2)cc1]

SCHEME 15

12n

A strong fluorescence for compound 12n was observed under visible light, which suggests potential future applications as an imaging probe for target identification (Scheme 15). Therefore, the UV absorbance and emission of 12n were obtained using an Infinite 200 PRO plate reader at a concentration of 1 mg/mL. This compound shows maximum absorbance between 345-382 nm. The maximum emission using 356 nm excitation is 428 nm, whereas no emission was observed using 405 nm excitation (FIG. 72A-FIG. 72C).

References For Examples 3-8

Zhong, J.; Gastaminza, P.; Cheng, G.; Kapadia, S.; Kato, T.; Burton, D. R.; Wieland, S. F.; Uprichard, S. L.; Wakita, T.; Chisari, F. V. *PNAS* 2005, 102, 9294.

Scholle, F.; Li, K.; Bodola, F.; Ikeda, M.; Luxon, B. A.; Lemon, S. M. *J Virol.* 2004, 78, 1513.

Liu, S.; McCormick, K. D.; Zhao, W.; Zhao, T.; Fan, D.; Wang, T. *Hepatol.* 2012, 56, 484.

Liu, S.; Wang, W.; Brown, L. E.; Qiu, C.; Lajkiewicz, N.; Zhao, T.; Zhou, J.; Porco, J. A., Jr.; Wang, T. T. *EBioMedicine* 2015, 2, 1600.

Liu, S.; Yang, W.; Shen, L.; Turner, J. R.; Coyne, C. B.; Wang, T. *J. Virol.* 2009, 83, 2011.

Kondratowicz, A. S.; Lennemann, N. J.; Sinn, P. L.; Davey, R. A.; Hunt, C. L.; Moller-Tank, S.; Meyerholz, D. K.; Rennert, P.; Mullins, R. F.; Brindley, M.; Sandersfeld, L. M.; Quinn, K.; Weller, M.; McCray, P. B.; Chiorini, J.; Maury, W. *PNAS* 2011, 108, 8426.

Novac, O; Guenier, A.-S; Pelletier, J. *NAR* 2004, 32, 902.

Yueh, H.; Gao, Q.; Porco, J. A.; Beeler, A. B. *Bioorg. Med. Chem.* 2017, 25, 6197.

Malona, J. A.; Cariou, K.; Spencer, W. T.; Frontier, A. J. *The J. Org. Chem.* 2012, 77, 1891.

Stone, S. D.; Lajkiewicz, N. J.; Whitesell, L.; Hilmy, A.; Porco, J. A. *J. Am. Chem. Soc.* 2015, 137, 525.

Jurgeit, A.; McDowell, R.; Moese, S.; Meldrum E.; Schwendener, R. Greber, U. F. *PLOS Pathogens* 2012, 8, e1002976.

Example 9: Additional Antiviral Activity of IE and IF

FIG. 73A shows a lentiviral reporter construct (pTrip-luciferase), lentiviral packaging construct (HIV-gag-pol) and an expression plasmid of desired viral envelope protein (e.g., CHIKV E1-E3) were co-transfected into 293T cells to produce lentiviral reporter virus particles whose entry depend on the specific viral Envelope protein. FIG. 73B shows a WNV replication-competent construct expressing the luciferase report gene is co-transfected with a flaviviral prM-Env expression plasmid to generate flaviviral Env-specific RVPs. FIG. 73C demonstrates treatment of Huh7.5 cells with 4 µM If and Ie for 3 h nearly abolished OHFV, JEV, WNV, Denv, and Zika viral envelope protein-mediated entry. Notably, the bars representing compound 5 treated groups are hardly visible in the graph because the % infections of this group were inhibited to under 1%.

Example 10: Supplemental Reaction Schemes and Compound Structures

FIG. 74 is an additional figure showing possible reaction pathways for preparation of aglaroxin C analogues. FIG. 75 shows some structures of aglaroxin C analogues according to some embodiments.

---

SEQUENCE LISTING

Gene sequence can be found for PHB prohibitin [Homo sapiens (human)] at:
SEQ ID NO: 1
NCBI Gene ID: 5245; NG_023046.1 RefSeqGene Amino acid sequence for prohibitin isoform 1 [Homo sapiens]:
SEQ ID NO: 2

```
  1    maakvfesig kfglalavag gvvnsalynv daghravifd rfrgvqdivv gegthflipw 61    vqkpiifdcr srprnvpvit gskdlqnvni tlrilfrpva sqlpriftsi gedydervlp 121    sitteilksv varfdageli tgrelvsrqv sddlteraat fglilddvsl thltfgkeft 181    eaveakqvaq qeaerarfvv ekaeqqkkaa iisaegdska aelianslat agdglielrk 241    leaaediayq lsrsrnityl pagqsvllql pq
```

Primer sequences described herein are:
Dengue 16681:
(SEQ ID NO: 3)
F: 5'-CCTGGGAAGAGTGATGGTTATG-3';

(SEQ ID NO: 4)
R: 5'-GCTGCTAGTAGGGCAAGATAAG-3'.

GAPDH:
(SEQ ID NO: 5)
F: 5'-TGCACCACCAACTGCTTA-3';

(SEQ ID NO: 6)
R: 5'-GGATGCAGGGATGATGTTC-3'.

---

What is claimed is:

1. A compound having the structure of Formula (I) or (III)

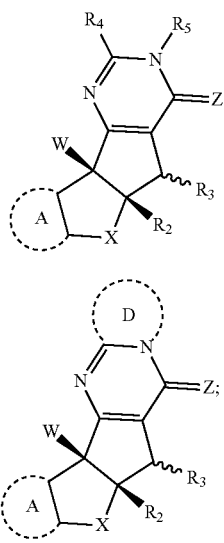

or stereoisomers, tautomers, or pharmaceutically acceptable salts thereof,
wherein:
X is O;
W is —$YR^A$, wherein Y is O or NH, and $R^A$ is H, or ($C_1$-$C_8$)alkyl optionally substituted with a OH, O($C_1$-$C_8$)alkyl, ($C_2$-$C_8$)alkenyl, or ($C_2$-$C_8$)alkynyl;
A has the structure of formula (IV);
wherein formula (IV) is

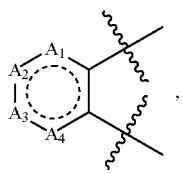

wherein;
$A_1$ is N or $CR_{10}$, wherein $R_{10}$ is H, halogen, or $OR^O$, and wherein $R^O$ is H or ($C_1$-$C_8$)alkyl;
$A_2$ is N or $CR_{11}$, wherein $R_{11}$ H, halogen, ($C_1$-$C_8$) haloalkyl, or $OR^O$, and wherein $R^O$ is H or ($C_1$-$C_8$) alkyl;
$A_3$ is N or $CR_{12}$, wherein $R_{12}$ is H, halogen, or $OR^O$, and wherein $R^O$ is H or ($C_1$-$C_8$)alkyl; or $A_2$ is $CR_{11}$ and $A_3$ is $CR_{12}$, and wherein $R_{11}$ and $R_{12}$ form the ring structure:

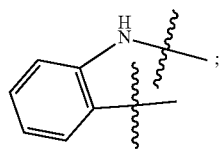 [SMILES: *Nc1ccccc1* ; ";"]

$A_4$ is N or $CR_{13}$, wherein $R_{13}$ is H, halogen, or $OR^O$, and wherein $R^O$ is H or ($C_1$-$C_8$)alkyl;

$R_2$ is phenyl or a 6-membered heteroaryl having a N atom, and where the phenyl can be optionally substituted with a halogen, OH, O($C_1$-$C_8$)alkyl, $NH_2$, NH($C_1$-$C_4$)alkyl, N[($C_1$-$C_4$)alkyl]$_2$, CN, or SMe;

$R_3$ is H, phenyl, ($C_1$-$C_8$)alkyl, 5-6 membered heteroaryl comprising a heteroatom selected from N, O and S, ($C_2$-$C_8$)alkenyl, ($C_1$-$C_8$)haloalkyl, —C(O)$NH_2$, —C(O)$NMe_2$ or —$CO_2$H, where the phenyl can be optionally substituted with a halogen, OH, O($C_1$-$C_8$) alkyl, $NH_2$, NH($C_1$-$C_4$)alkyl or N[($C_1$-$C_4$)alkyl]$_2$, and the ($C_1$-$C_8$)alkyl can be optionally substituted with a OH, O($C_1$-$C_8$)alkyl, ($C_2$-$C_8$)alkenyl, or ($C_2$-$C_8$)alkynyl; and wherein when $R_3$ is not H; $R_3$ is syn to $R_2$ or $R_3$ is trans to $R_2$;

$R_4$ is H, ($C_1$-$C_8$)alkyl, phenyl, benzyl, 5- or 6-membered heteroaryl comprising 1 or 2 heteroatoms selected from the group consisting of N, O and S, ($C_1$-$C_8$)haloalkyl, $C_3$-$C_8$cycloalkyl, NH(aryl), NH(CN), $CO_2$(alkyl), or NH($C_1$-$C_8$alkyl), where the phenyl can be optionally substituted with a halogen, OH, ($C_1$-$C_8$)alkyl, O($C_1$-$C_8$)alkyl, ($C_1$-$C_8$)haloalkyl, $NH_2$, NH($C_1$-$C_4$)alkyl or N[($C_1$-$C_4$)alkyl]$_2$, and the ($C_1$-$C_8$)alkyl can be optionally substituted with halogen, O($C_1$-$C_8$)alkyl, C(O)-lower alkyl, ($C_2$-$C_8$)alkenyl, or ($C_2$-$C_8$)alkynyl;

Z is O, NH, Se, N(alkyl), N(CN), CN or $CR^CR^F$; wherein $R^C$ and $R^F$ independently are H, ($C_1$-$C_8$)alkyl or CN;

$R_5$ is H, ($C_1$-$C_8$)alkyl or phenyl, where the ($C_1$-$C_8$)alkyl can be optionally substituted with 1 or 2 halogen, OH or O($C_1$-$C_8$)alkyl;

D is a 5-6 membered heteroaryl comprising 1 or 2 heteroatoms selected from N, O and S;
or D is a 5-6 membered heterocyclyl comprising 1 or 2 heteroatoms selected from N, O and S; and provided that the compound is not (−)-6, (+)-6, (−)-6-OH, racemates of (−)-6 or (+)-6, structural isomers of (−)-6-OH or enantiomers of (−)-6-OH,

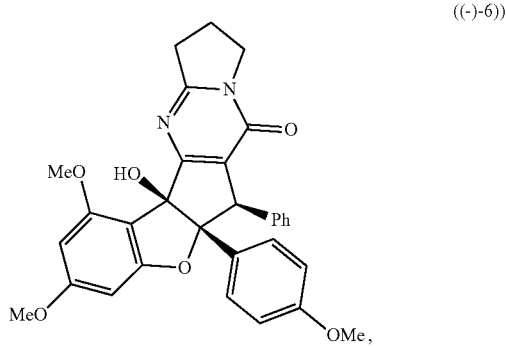

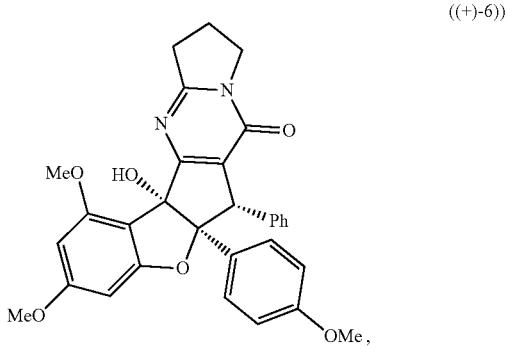

((-)-6)-OH)

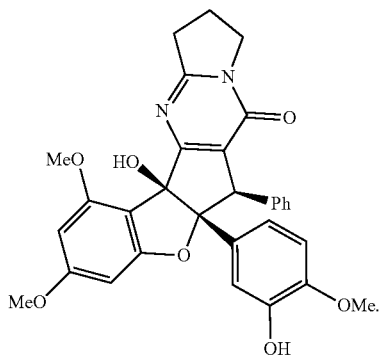

2. The compound according to claim 1, wherein at least one of $R_{10}$, $R_{11}$, $R_{12}$ or $R_{13}$ is a $(C_1$-$C_8)$alkoxy.

3. The compound according to claim 1, wherein:
the compound has the structure of formula (I);
W is OH;
X is O;
Z is O;
$R_2$ is a phenyl optionally substituted with a halogen, $O(C_1$-$C_8)$alkyl, $NH_2$, $N[(C_1$-$C_4)$alkyl$]_2$, or CN;
$R_3$ is a phenyl;
$R_2$ is syn relative to $R_3$;
$R_5$ is H or $(C_1$-$C_8)$alkyl; and
$R_4$ is $(C_1$-$C_8)$alkyl or phenyl, where the phenyl can be optionally substituted with a halogen, OH, $(C_1$-$C_8)$alkyl, $O(C_1$-$C_8)$alkyl, $(C_1$-$C_8)$haloalkyl, $NH_2$, $NH(C_1$-$C_4)$alkyl or $N[(C_1$-$C_4)$alkyl$]_2$, and the $(C_1$-$C_8)$alkyl can be optionally substituted with halogen, $O(C_1$-$C_8)$alkyl, C(O)-lower alkyl or $(C_2$-$C_8)$alkenyl.

4. The compound according to claim 1, wherein the compound is of Formula (I).

5. The compound according to claim 1, wherein;
the compound has the structure of formula (I);
W is OH;
X is O;
Z is O;
$R_2$ is

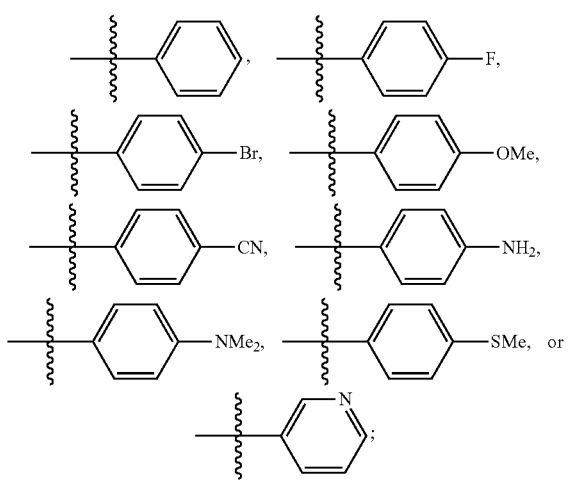

$R_3$ is a phenyl;
$R_2$ is syn relative to $R_3$;
$R_5$ is H or $(C_1$-$C_8)$alkyl; and
$R_4$ is $(C_1$-$C_8)$alkyl,

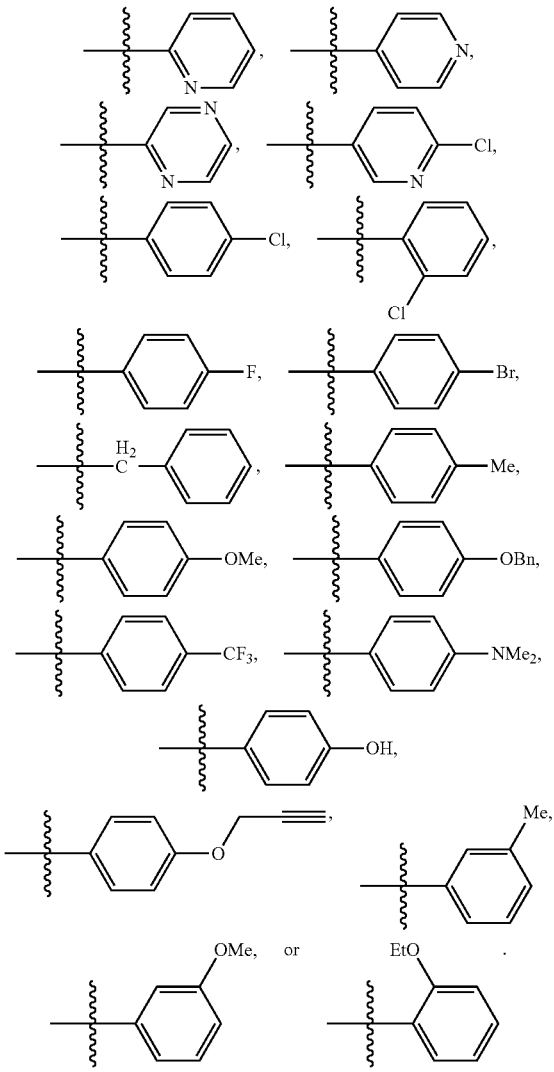

6. The compound according to claim 1, wherein $R_3$ is syn to $R_2$.

7. A compound selected from the following compounds;

(12af)

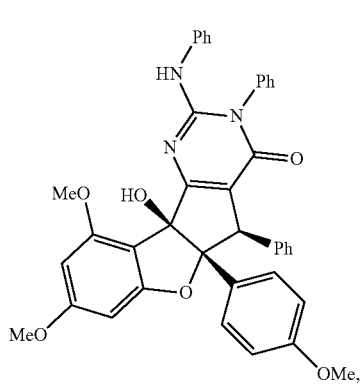

177
-continued
(CMLD012046)
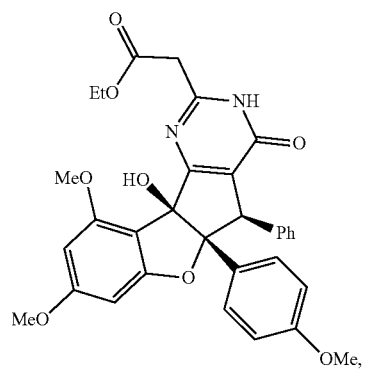
(12g)
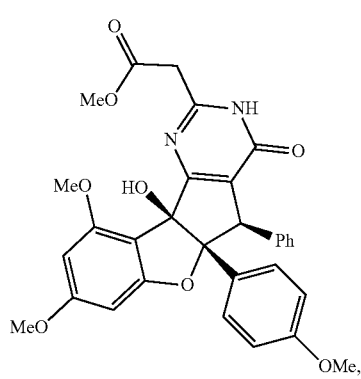
(12aa)
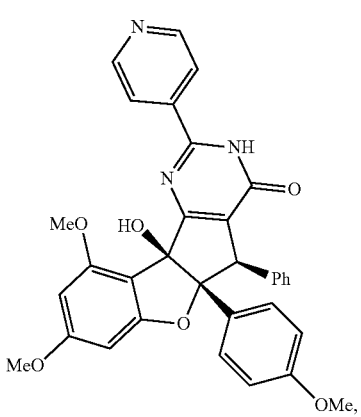
(12ac)
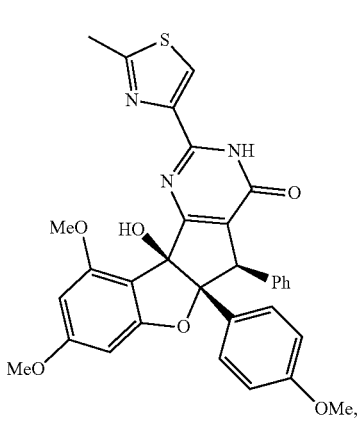
178
-continued
(12ah)
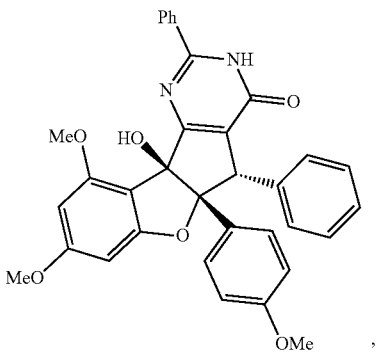
(12z)
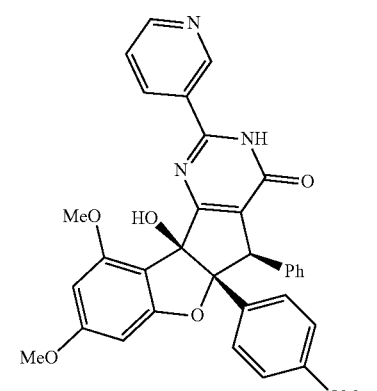
(12j)
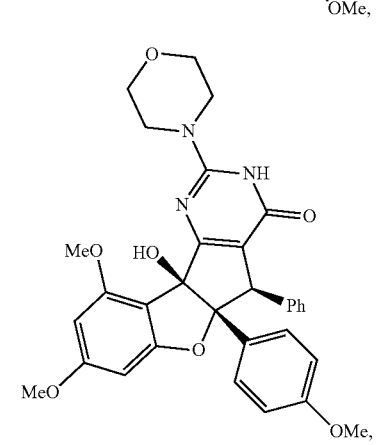
(12d)
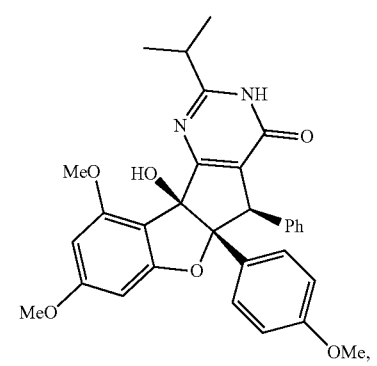

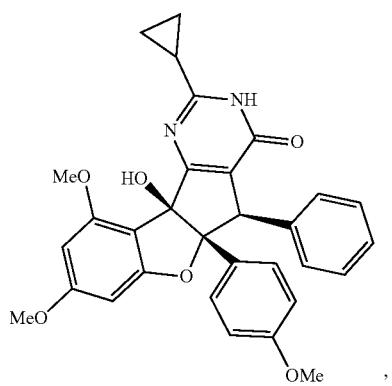
(12h)
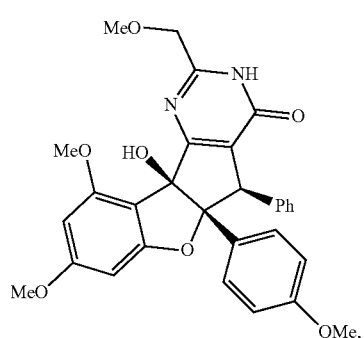
(12i)
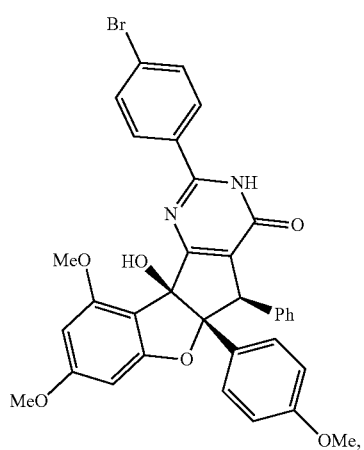
(12r)
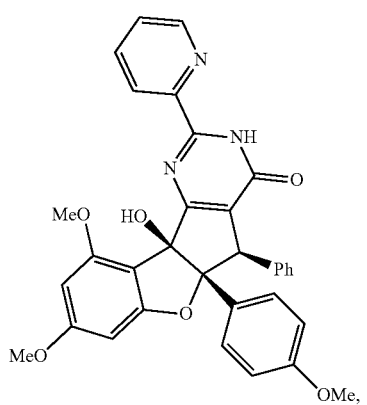
(12ab)
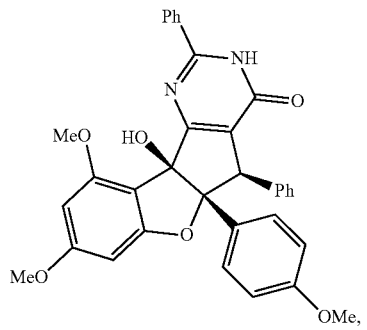
(12a)
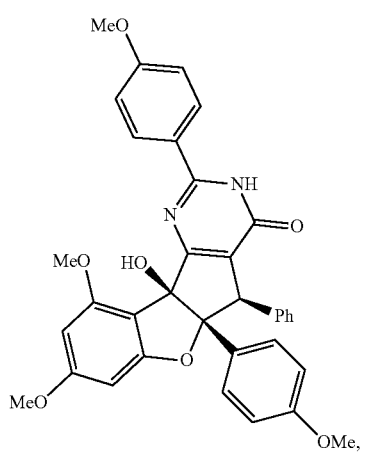
(12k)
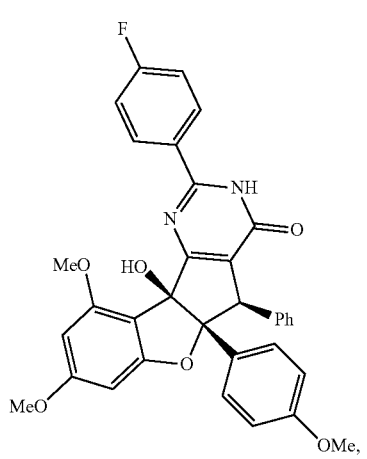
(12p)
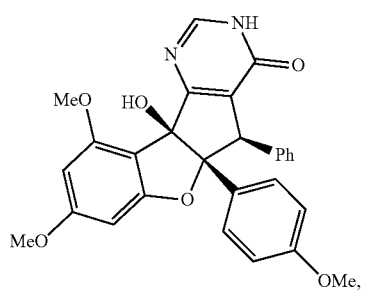
(12f)

-continued
(12b)
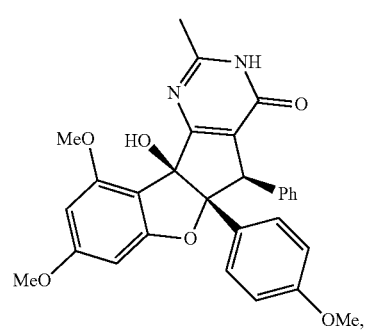
(12q)
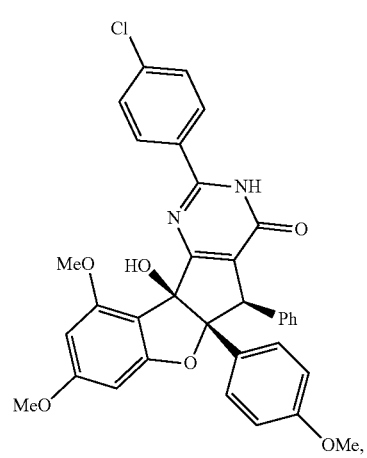
(12x)
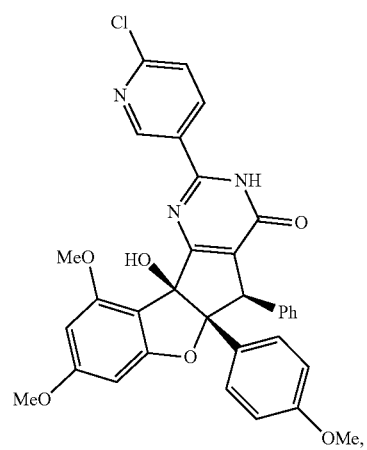
(12w)
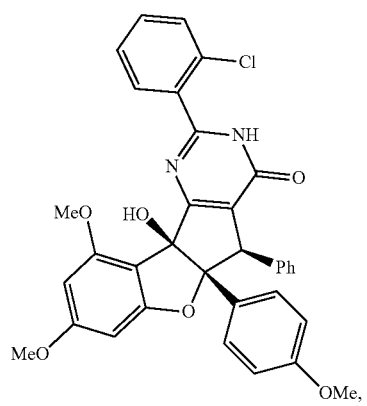
-continued
(12t)
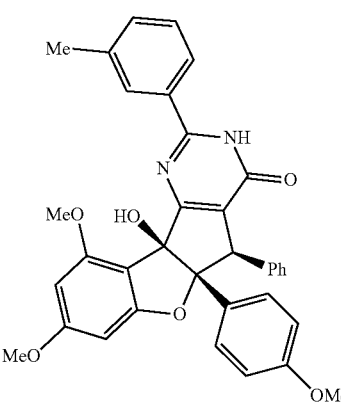
(12c)
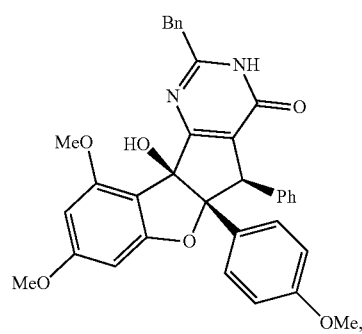
(12m)
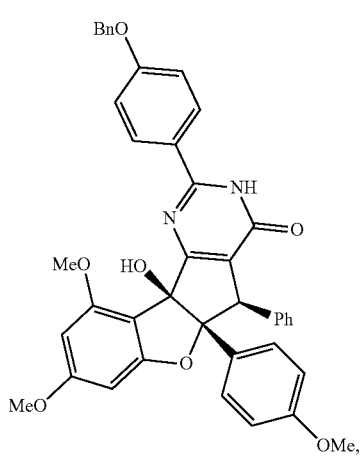
(12ae)
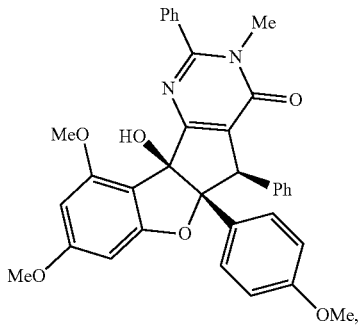

(12o)
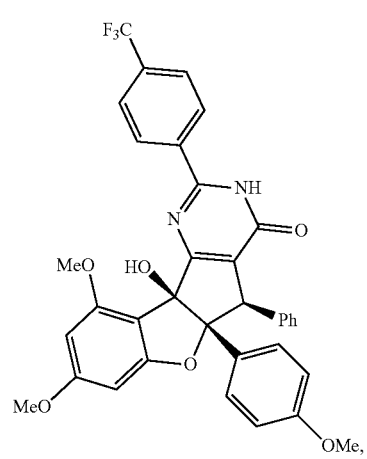
(12y)
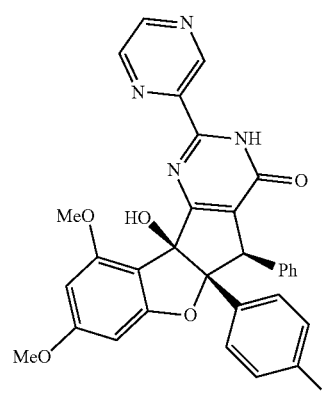
(CMLD012332)
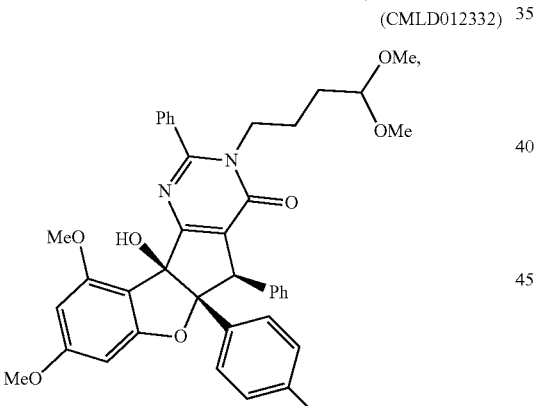
((−)-12s)
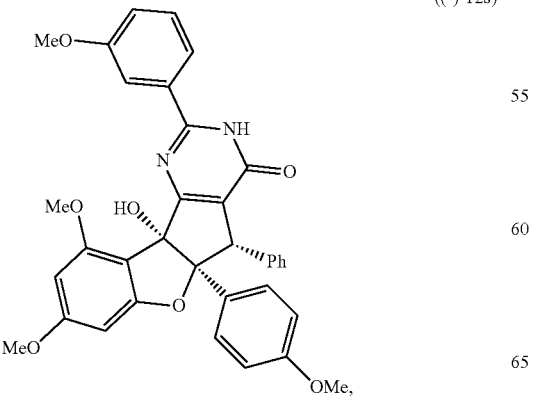
((+)-12s)
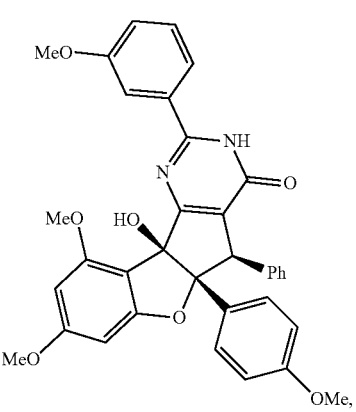
((−)-12l)
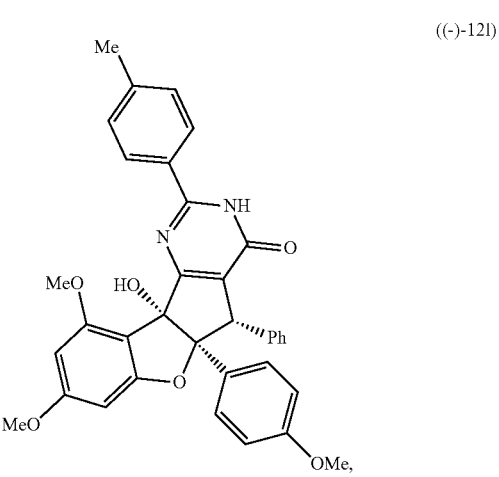
((+)-12l)
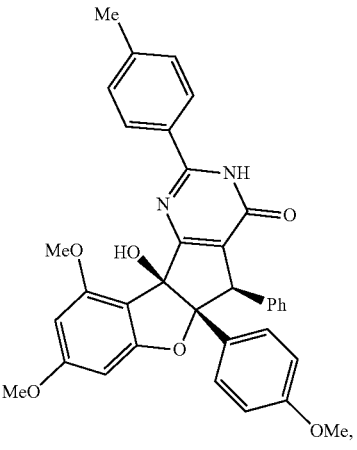

-continued
(12v)
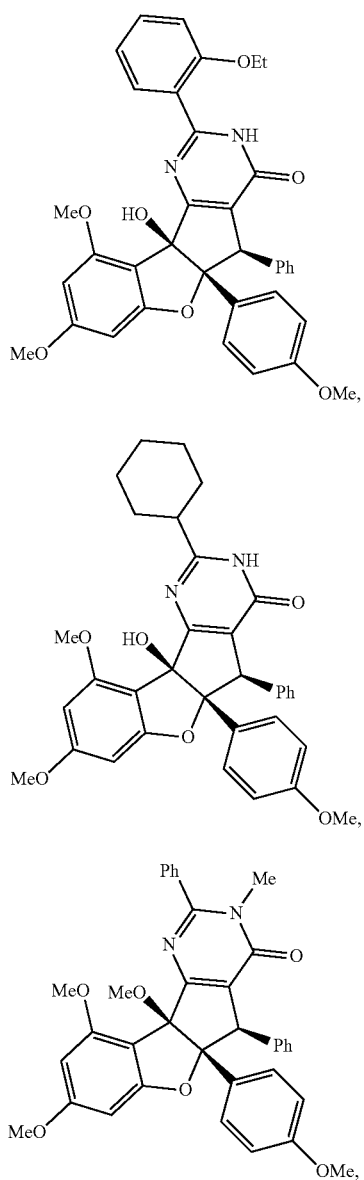
(12e)
(12aj)
(12ak)
-continued
(CMLD012982)
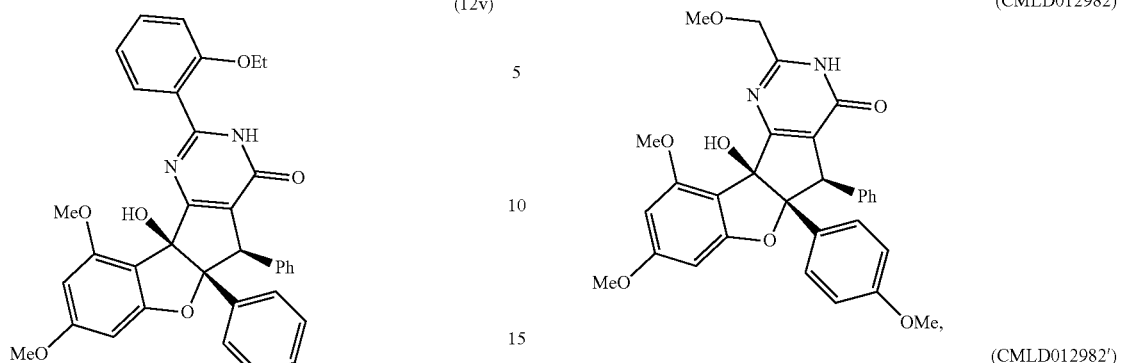
(CMLD012982′)
(12ap)
(12ao)

(12n)
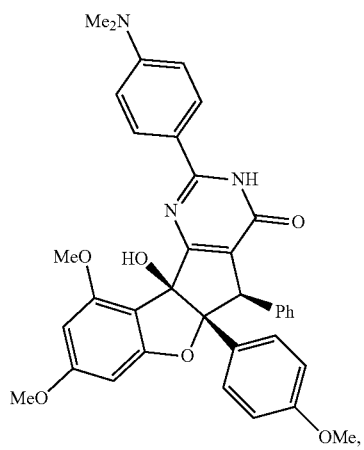
(Ia)
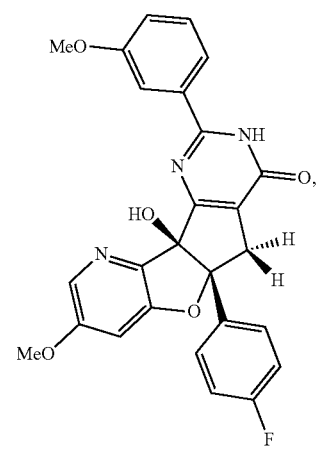
(Ic)
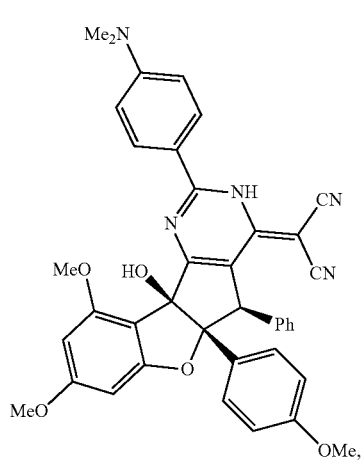
(Id)
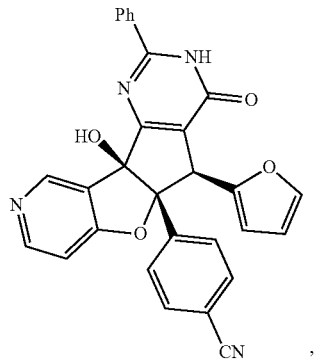
(Ie)
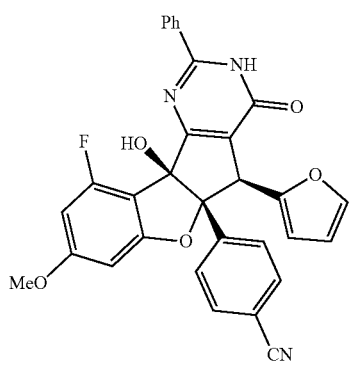
(If)
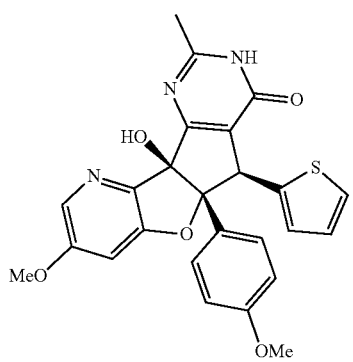
(Ig)
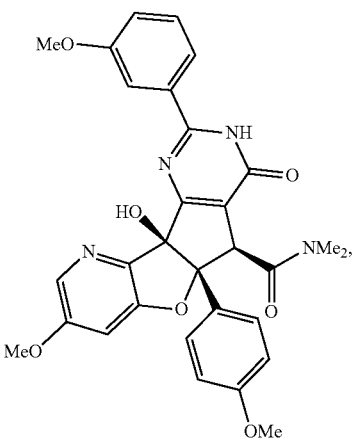

189
-continued
(Ih)
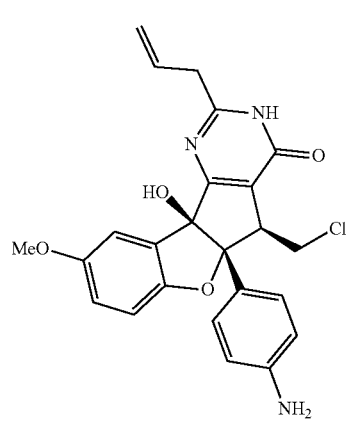
(Ii)
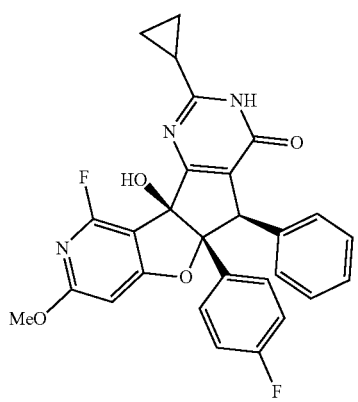
(Ij)
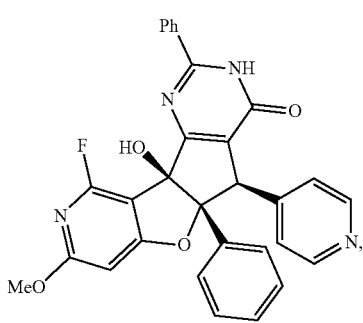
(Ik)
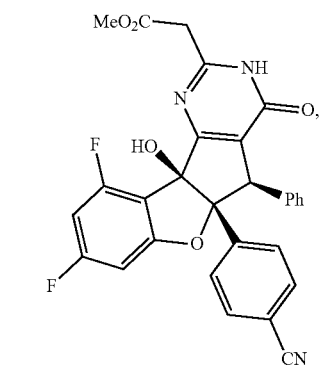
190
-continued
(Il)
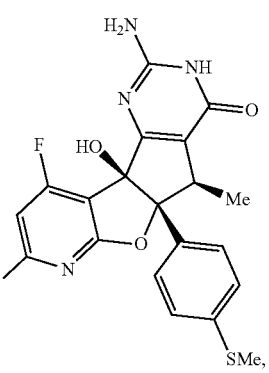
(Im)
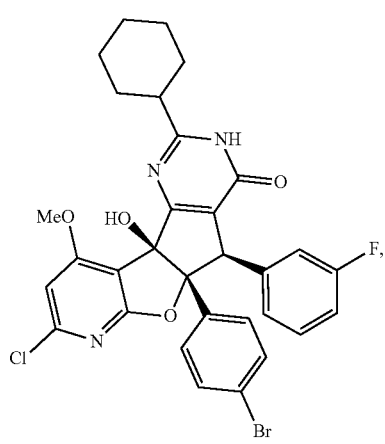
(In)
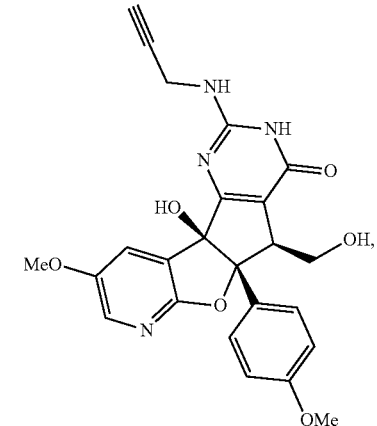
(Io)
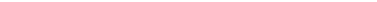

-continued
(Ip)
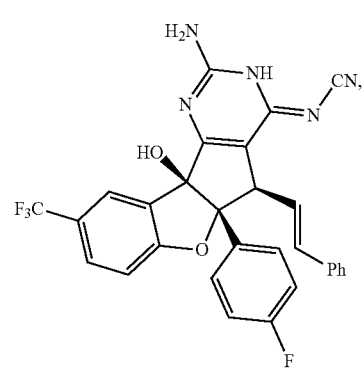
(Iq)
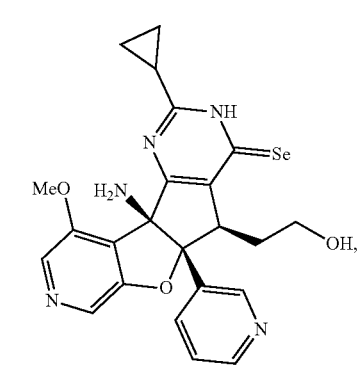
(Ir)
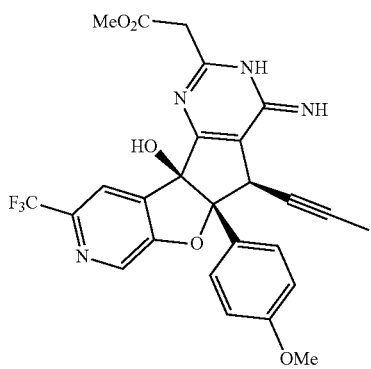
(Is)
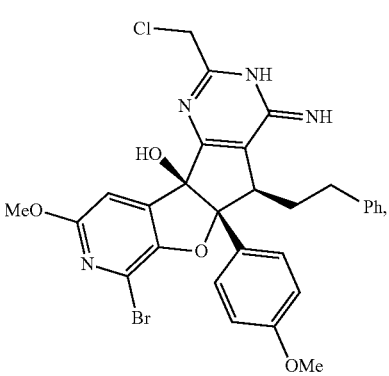
-continued
(It)
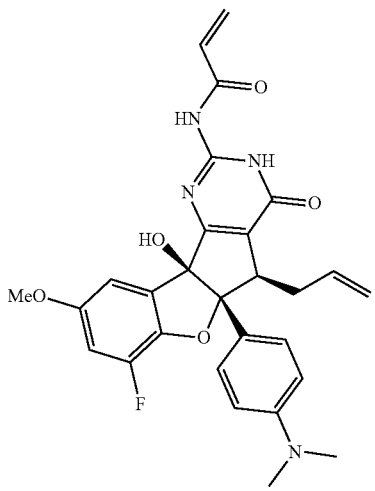
(12am)
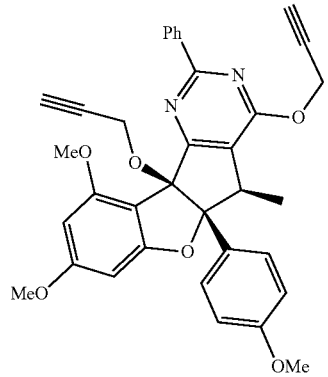
(12an)
(12ai)
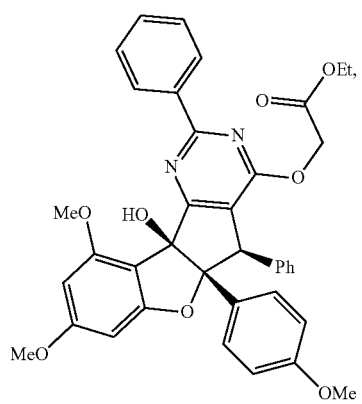

193
-continued

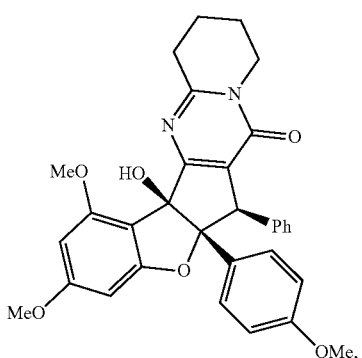
(12ad)

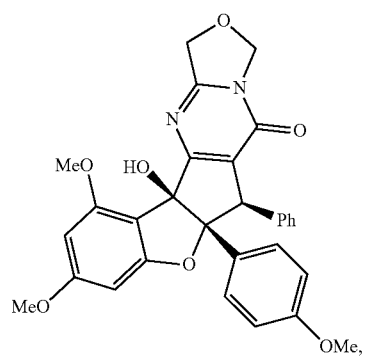
(IIIa)

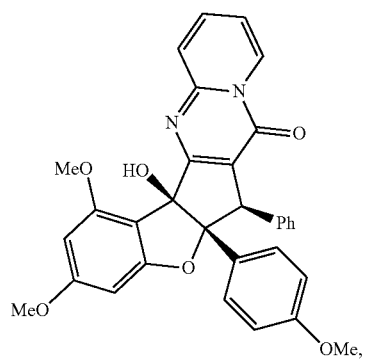
(IIIb)

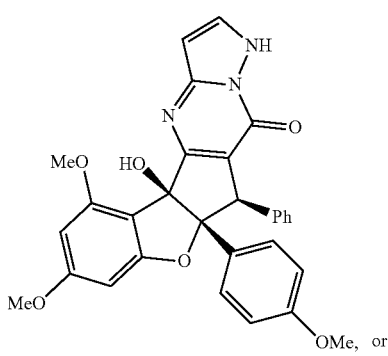
(IIIc)
OMe, or

194
-continued

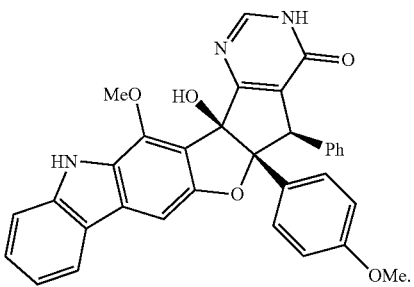
(IIId)

8. A composition comprising the compound of claim 1, and a pharmaceutically acceptable carrier or excipient.

9. The compound of claim 1, wherein ring A is

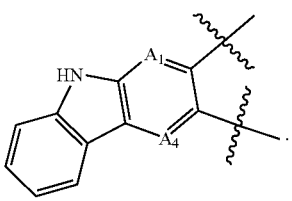

10. The compound of claim 1, wherein

W is OH;

X is O;

Z is O;

$R_2$ is a phenyl optionally substituted with a halogen, $O(C_1$-$C_8)$alkyl, $NH_2$, $N[(C_1$-$C_4)$alkyl$]_2$, or CN; and $R_3$ is phenyl or 5-6 membered heteroaryl comprising a heteroatom selected from N, O and S, where the phenyl can be optionally substituted with a halogen, OH, $O(C_1$-$C_8)$alkyl, $NH_2$, $NH(C_1$-$C_4)$alkyl or $N[(C_1$-$C_4)$alkyl$]_2$.

11. The compound of claim 1, where the compound has the structure of Formula (I);

A has the structure of formula (IV) and, $A_1$ is N or $CR_{10}$, wherein $R_{10}$ is H, OMe or F;

$A_2$ is N, or $CR_{11}$, wherein $CR_{11}$ is H, F, OMe or $CF_3$, and $A_3$ is N or $CR_{12}$, wherein $CR_{12}$ is H, F, Cl, Br or OMe, or $A_2$ is $CR_{11}$ and $A_3$ is $CR_{12}$, wherein $R_{11}$ and $R_{12}$ form the ring structure

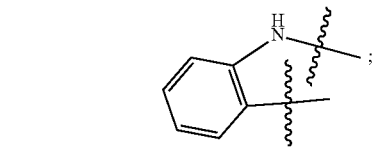 [SMILES: *Nc1ccccc1* ; ";"]

and $A_4$ is N or $CR_{13}$, wherein $CR_{13}$ is H, F, or Br;

W is OH, —$NH_2$, OMe, —$NH(CH_2CH_2)$OMe, or —O—$CH_2C≡CH$;

X is O;

Z is O, Se, =NH, =N(CN), or =C(CN)$_2$;

R$_2$ is

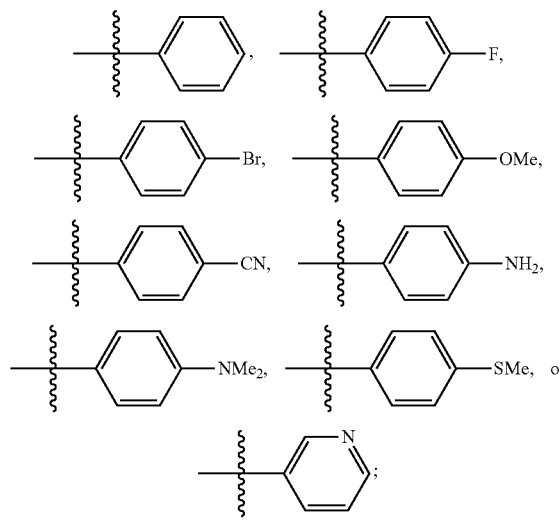

R$_3$ is an H, phenyl, methyl, —CH$_2$CH=CH$_2$, —CH$_2$Cl, —CH$_2$OH, —CH$_2$CH$_2$OH, —C≡CCH$_3$, C(O)NMe$_2$,

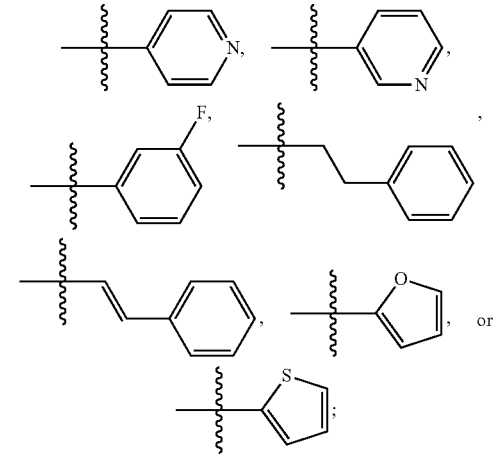

R$_5$ is H, phenyl, methyl or —CH$_2$CH$_2$CH$_2$C(OMe)$_2$;

and R$_4$ is H, Me, —NH$_2$, —CH$_2$Cl, —CH$_2$CH=CH2, —CH$_2$OMe, —CH$_2$C(O)OEt, —CH$_2$C(O)OMe, —CH(CH$_3$)$_2$, -cyclopropyl, -cyclohexyl, phenyl, benzyl, —NHC(O)CH=CH$_2$, —NHCH$_2$C≡CH,

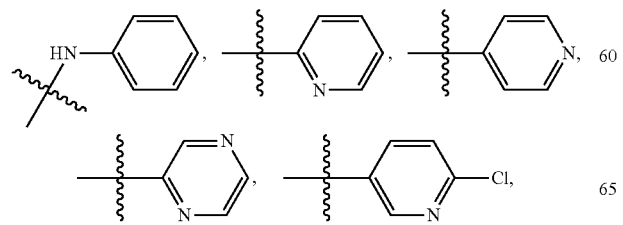

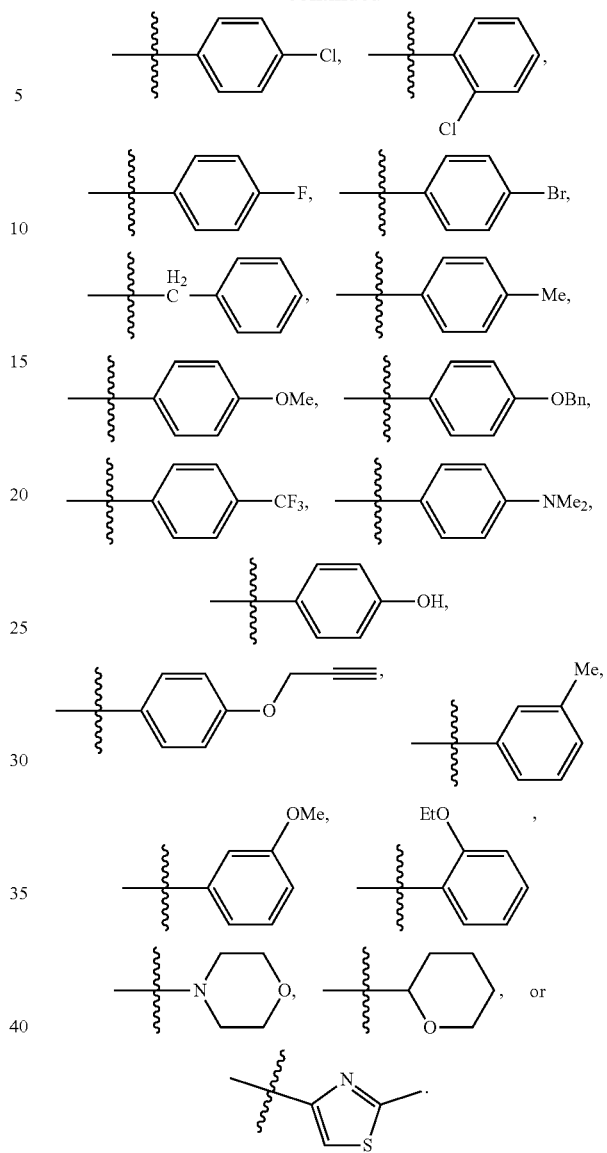

12. The compound of claim 1, wherein the compound has the structure of Formula (III);

A$_1$ is CR$_{10}$, wherein R$_{10}$ is H or OMe;

A$_2$ is CR$_{11}$, wherein CR$_{11}$ is H;

A$_3$ is CR$_{12}$, wherein CR$_{12}$ is H or OMe;

A$_4$ is CR$_{13}$, wherein CR$_{13}$ is H;

W is OH;

X is O;

Z is O;

R$_2$ is

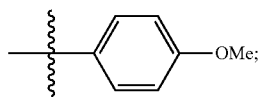 [SMILES: *c1ccc(OC)cc1]

R₃ is phenyl;
D is

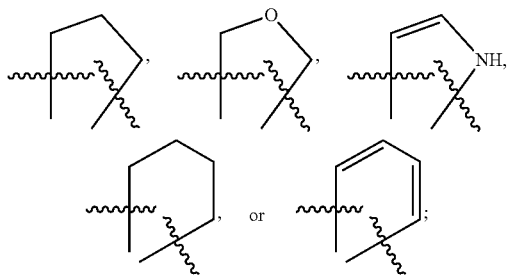

and
wherein the compound is not (−)-6, (+)-6, (−)-6-OH, racemates of (−)-6 or (+)-6, or structural isomers or enantiomers of (−)-6-OH and (+)-6-OH.

13. A method for preparing a compound having formula (I) or (II), wherein:

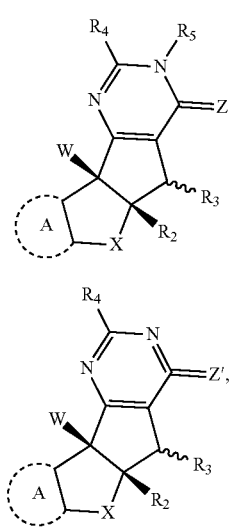

or stereoisomers, tautomers, or pharmaceutically acceptable salts thereof,
wherein:
A has the structure of formula (IV) and,
A₁ is N or CR₁₀, wherein R₁₀ is H, OMe or F;
A₂ is N, or CR₁₁, wherein CR₁₁ is H, F, OMe or CF₃;
A₃ is N or CR₁₂, wherein CR₁₂ is H, F, Cl, Br or OMe; or
A₂ is CR₁₁ and A₃ is CR₁₂, wherein R₁₁ and R₁₂ form the ring structure

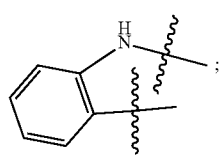

A₄ is N or CR₁₃, wherein CR₁₃ is H, F, or Br;
W is OH, —NH₂, OMe, —NH(CH₂CH₂)OMe, or —O—CH₂C≡CH;

X is O;
Z is O;
Z' is a OH;
R₂ is

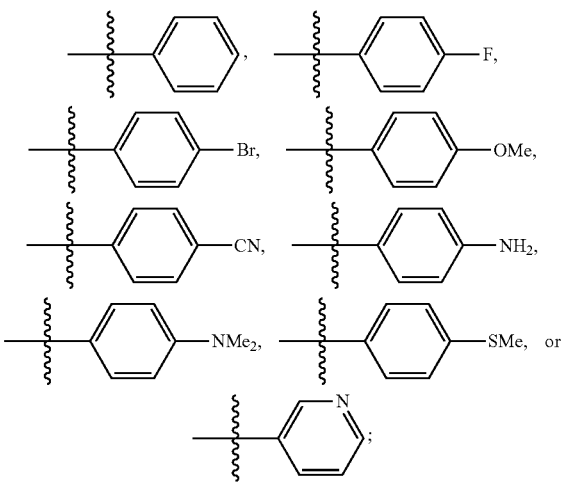

R₃ is an H, phenyl, methyl, —CH₂CH=CH₂, —CH₂Cl, —CH₂OH, —CH₂CH₂OH, —C≡CCH₃, C(O)NMe₂,

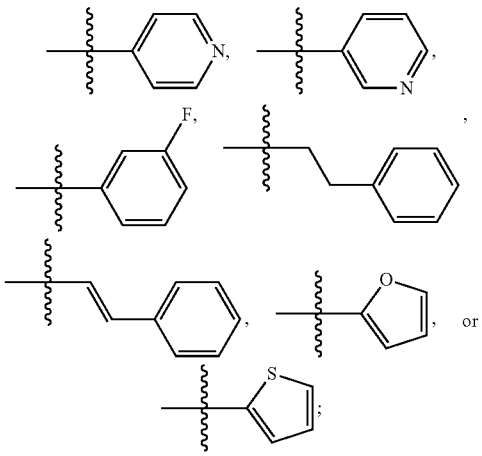

and
wherein the second compound has the structure of (VIII) wherein R₅ is H, phenyl, methyl or —CH₂CH₂CH₂C(OMe)₂, and R₄ is H, Me, —NH₂, —CH₂Cl, —CH₂CH=CH₂, —CH₂OMe, —CH₂C(O)OEt, —CH₂C(O)OMe, —CH(CH₃)₂,-cyclopropyl,-cyclohexyl, phenyl, benzyl, —NHC(O)CH=CH₂, —NHCH₂C≡CH,

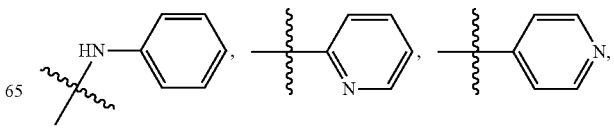

-continued
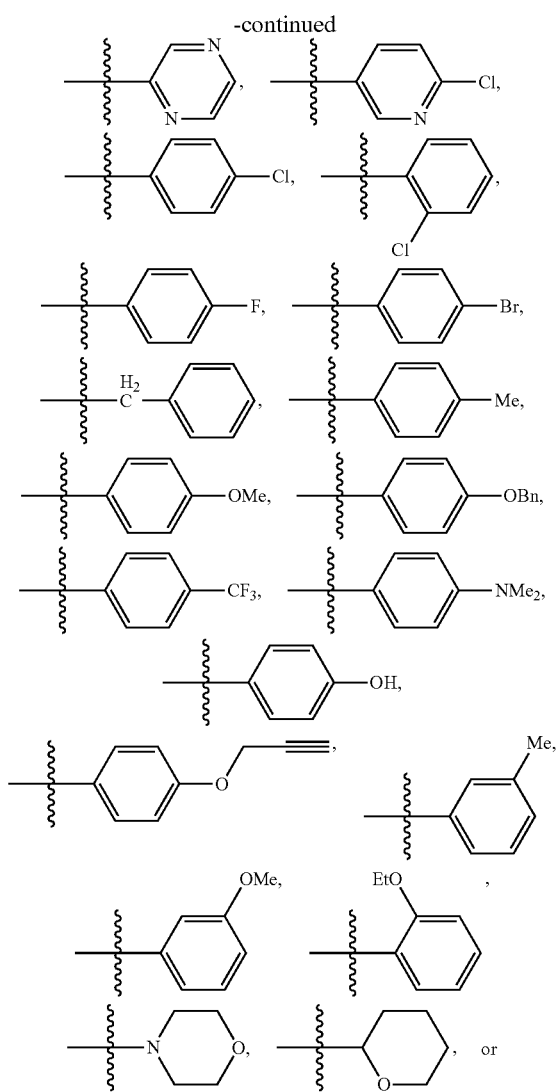
-continued
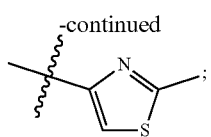
the method comprising:
reacting a compound of structure (VI) or (VII) or a salt thereof with a compound of structure (VIII) or a salt thereof, wherein the structures of (VI), (VII) and (VIII) are
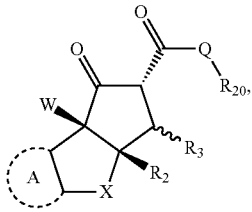
(VI)
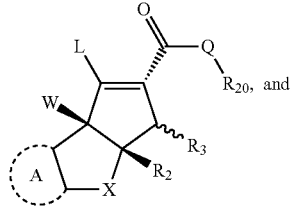
(VII)
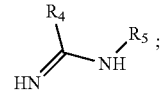
(VIII)
wherein Q is $OR^G$ or $NR^HR^I$, wherein $R^G$, $R^H$ and $R^I$ are independently H or an alkyl, and wherein L is a leaving group.
* * * * *

SEQUENCE LISTING

<160> NUMBER OF SEQ ID NOS: 6

<210> SEQ ID NO 1
<211> LENGTH: 17823
<212> TYPE: DNA
<213> ORGANISM: Homo sapiens

<400> SEQUENCE: 1

```
gggaagtgag gagagcctct gcccggccgc cccatctggg atgtgaggag cgcctctgcc     60
cggccgccac cccatctggg aagtggggag cgcctctgcc cggccgcccc gtctgggatg    120
tgaggagtgc ctctgcccgg ccgcaacccc atctgggaag tggggagcgc ctctgcccag    180
ccgccccatc tgggaggtga ggagcgcctc tgcccggccg ccccatctgg gatgtgagga    240
gcgcctctgc ccgccacca ccccatctgg gaagtgggga gcgcctctgc ctggccaccc    300
catctgggat gtgaggagca cctctgcccg gccacccttc gtctgggaag tgaggagcgc    360
ctctgcccgg ccaccccatc tgggaagtga ggagcgcctc tgcccggccg ccccatctgg    420
gaaatgagga gcgcctctgc ccggctgccc tgtctgggaa gtgagaagcg cctctgcctg    480
gccgctgtgc aatcttccaa gtgtgaagtg acagcctttc tgcaggtgta cccaacagct    540
ccgaatagac agcgaccatc gagaacgggc catgatgacg atggcagttt tgtcaaaaag    600 aaaggggga aatgtgggga aagaaagag agataagatt gttactgtgt ctgtgtagaa    660
agaagtagac atagactcca ttttgttctg tactaagaaa aattcttctg ccttgggatg    720
```

```
ctgttaatct ataaccttac ccccaacccc gtgctctctg aaacatgtgc tgtgtcaact    780
cagggttaaa tggattaagg gcagtgcaag atgtgctttg ttaaacagat gcttgaaggc    840
agcatgctcg ttaagagtca tcaccactgc ctaatctcaa gtacccaggg acacaaacac    900
tgcggaaggc cggaaggcca cggggacttc tgcctaggaa accagagac ctttgttcac     960 gtgtttatct gctgaccttc tctccactat tatcctatga ccccaccaca tccccctctc   1020
cgagaaacac ccaagaatga tcaataaata ctaaaaaaaa aaaaaaaaaa aaaaaaaaa    1080 agaaagaaaa gaatcattat tgggtaaaac atcaaaaaaa aaatttattg aaacaaatga   1140
aaatggaaac acaggccggg tgctgtggct catgcctgta atctcagtac tttgggaggc   1200
tgaagtgggc ggatcacctg agactggag tttgagacca gcctgaccaa catggaggaa    1260
ccctgtctct actaaaaata caaaattagc caggcatggt ggtgcatgcc tgtaatcaca   1320
gctactcagg aggctgaggc aggagaatgg cttgaacccg ggaggcggag gttgcggtga   1380
gccaagatca cgccattgta ctcaagcctg ggcagcaaga gcaaaactcc atctcaaaaa   1440
aaaaaagaaa aagaaaaga aagaaaatg gaaacacaac ataccaaaat atataggata    1500
caacagaagc agtgctaaga cagacattga tagcaataag cacctacatc aaaaaactag   1560
aaagttttca ataaacaac ctaacaatgc tccgcaagga actagaaaag caagaacaaa    1620
ccaaacccaa aattaggaga aggaaaagaa taataacgat tacagcatag caaaacaaaa   1680
cagagagtga aaaaaattta atcaatgaaa ttagacattg tttgtttcaa tggataaaca   1740
aaatcaataa actgctagtt agactcaaca agaagaaaag agaggagacc caaataaata   1800
aaatcagaaa taaaaaatga gacattacaa ctgtttccag agacatacaa taattcatca   1860
gagactatta tgaacaacta cacatgaaaa aattggaaaa cctagagaaa atggataact   1920
ggacacatac aacctacaaa tattgaacca ggaagaaaca gaaaacttga aaagacccat   1980
gacgagtgat gaaattgaat tagtgataaa aagtctccca aaacagaaaa gcccaggaac   2040
agatggcttc actgctaaat tctaccaaac ttataaagaa gaaataatac caatttctc    2100 aaactattcc aaaaaactg aagaggaaga aattcttcct aactcattct ataaggccag    2160
aattaccctg acaccaaaat cagacaaaaa cacaacaaaa aagaaaaaca gcaggccaat   2220
atccttgatg aacatcgatg caaaaatcct caactaaata ctagtaaaca aaatccaaca   2280
gcacatcaaa aggataatac accatgatca agtgggattt attccagaaa tgcaaagacg   2340
gttcaacata cataaatcaa taaccgcgga tacatcacat cagcagaatg aaggacaaaa   2400
accatatgat catctcaata gatgcagaaa aagcacttga taaaattaaa catccttcgt   2460
gataaatatt ctcaacaaat taggcataga agaaacatat ctcaacataa taaactccat   2520 aaaatgacaaa cccacagcta tcatcatatt gaatggggga atagaggaat gcctttcttc   2580
taagaactag aagaaggcaa agatgcccac tttcattact tatttattta tttatttatt   2640
tatttgagat ggagttgtgc tcttgttgcc caggctgggg tgcaatggcg tgatctcggc   2700
tcacggtaac ttctgcctct cggattcaag catttctcct atctcagcct cccgagtaga   2760
tgggattaca ggcatgcgcc accatgcccg gctaattttt tttgtacttt tagtagaaac   2820
ggggtttctc catgttggtc aggctggtct tgaactcccg acctcaggag atccgcccac   2880
cttggcctca agtgctggg attacaggcg tgagccaccg cgcccggccc actttcatca   2940
ctcttaatcc acatagtact gaagtcttag ccagagcaac caggcaagag aaagaaataa   3000
aaggcatcca aattggaaaa aaggaagtca ggccagtgcg aatgtagtga gttatctcaa   3060
```

```
tctcacagta agttacagat tgaactcctt gttctactct ttccccactt ctcactactg    3120
cacttgagta gtcttaaaaa aaaaaaaaat caaattgccc cctttgaaga tgacatgata    3180
cctagtatat agaaaaatct aaagatttca ccaaaaatct cttataactg atacattcag    3240
taaagttgca ggataaaaaa tcattataca aaaactagca tttctgtaca ccaataagga    3300
attagctgaa agagaaatca agaaagcaac cctactacct aggaaaaaat ttaatcaagg    3360
aggaaaaaga cctctacaat aaaaactaca aaacactgat gaaagaaact gaagaggaca    3420
caaacaaatg gaaagacatc tcgtgttcat ggattggtgg attggaagaa ttaatattgt    3480
taaaaatgac catactttt tttttttttt ttttttttt gagacaaggt ctcgctctgt    3540
cacccaggct gcagtgcagt ggcacagtca cagctcactg caaccttgac ctcccaggct    3600
caagcaatcc tcccaccttg gctcccgaat aggtggaact acaggtacat gccaccacat    3660
ccaggtactt tttatttta tttttgtaga gacagggttt caatttgttg cccaggctag    3720
tctcaaactc ctaggctaaa gcaatcctct gtccttggcc tcccgaagtg ctgggattac    3780
aggcgtgacc accacgccca gccctcacgt tcttattcct atgtgggggc taaaagagtt    3840
gatcttatag aggtaaaaac tagaatgaga gctgagcgcg gtggctcatg cctgtaatcc    3900
cacccacttg ggaggccgag gcgggtggat cacctaggtc gggagttcga gaccagcctg    3960
accaacatgg agaaaccccg tctctacaaa aataaaaaat tagccgggtg tggtggtgca    4020
tgcctgtaat ctcagctatt ctgggagggt gaggcaggag aatcgcttga acccgggagg    4080
cggaggttgc ggtgagccga gatcgcgcca ctgcactcca gcctgggcaa caaaagcgaa    4140
actccatctc aaaacaaac aacaaaacaa aacaaaaca agaaaataaa cacacacgca    4200
cacggaggtg gggcggcgga gtggcggcag ggaggaggag gggagaggta agaaacaaat    4260
gataaaacaa atgaagcaaa ttgttaacaa taggtgaatc tgagccaaag tttaacgtgc    4320
gttcttttgc cctattcttg caacttttcc aaataaaacg tttctctaaa atcatgtcta    4380
ggggacctga attccaagcc gagccccttt tctcactcgg tgcatgaccc tgaatgaatt    4440
ccttcctctc ggttggtctc agttttcag cacagatggt tctctctggg tctggtaatc    4500
aacgtctcac aactctgagg acgtttgcag acagggcttt ggaaggaaga cggcccttcg    4560 tttccccaa agggtctcag cctgccggtg atttccaccac gacttcctcc agagttccac    4620
ctgtcctctt catcagccat gaacttgccc ctactaattt ttgccaccag ctggacgccc    4680
acctcctctt tcccggagcc ctaaggctct ccttgcggca gtcttagcct ctgtacagga    4740
taggcacgtg catttagccc cagaaaacta cagcccccaa aaggctttgc ggcaacatcc    4800
tcgcgttgat caccaaagag aaaacgcttt tctccgcggg cccgccgctg catagccttt    4860
tgggagttgt agttcatctg ctaagagccg cagaaccagg gtgaggttct aagccaccct    4920
tcccagaact cacagcgctc ttccacacca ataggaagcg tggatcttgg aaagcgggcg    4980
gggcagagga gctcatgcgc agtatgtgtg gttggggaat tcatgtggag gtcagagtgg    5040
aagcaggtga gaatgagggg ggcggcaaag gctcgtttct gggcatctct gcagtcctcc    5100
tctgctccat gatgtgcact ttgggcgagg agagtgcgtg cgtgagtccg acttgtgagg    5160 gagggggagaa ggggctgagc ccgggacgag ccaggggttg ctcagagtaa gggaggtgtc    5220
catggaggca gggtgaggaa taatccagaa gctattacaa atgtaaaggg ccgggtgtcc    5280
cagcctcaga gaaggaagat ttaaatgcac tggacgagat cagggtagtc tcaggagttg    5340
aggtctggga agtagggagg gaggatttga gactggagcg ggcaacgacg gtggggcgga    5400
gcgttagaaa gttacatgct ggcgtgattt ctagttaggt caactgtgct tatgcccacc    5460
```

| | |
|---|---|
| ccgcctcagc cccaccctcc cagttattcc agagctcact gtccctgtgc agctagttag | 5520 |
| agcctttctc ccaaatgggt tcttcagtta tcttggcccc aggatgtcat ccagctcctg | 5580 |
| cttccataag aagcatgtcg ttcttaatac acgatgttga caagcagtat ggtgaggagg | 5640 |
| taagctgtgt ctgctagcat tagacctctg ggttctaatt ctggttctac cacttaataa | 5700 |
| ctgcaatctc ggcttctcat gtaacctctc tgtgtgcctc tgtttcctct gtagtaatat | 5760 |
| gcttcatagg gtaattgtga gaagtaaata aattgctttt attaggctac ctgatataag | 5820 |
| tgttagctgt tacggttact ttttttgttg gcatcaacat gtagcacatt ttttaagtta | 5880 |
| ttttttttcaa accataattg caccaatcta acctcacagc ctcttttttgg gggcctactt | 5940 |
| gtccaggaaa tgagagggtg gtttagtgtg gtgctaagtt ctctgtggat ttcaagccca | 6000 |
| tgcattgttt tcattattga accaagtgtc ccagacacct tactttaaat ggttgagaaa | 6060 |
| aaaagagaaa tcagccaggc atgatggctc atgcctgtaa tcccaacact tgggaggccg | 6120 |
| aggcaggggg atcacttgag cccaggagtt tgagaccacc tggggcaacg tagcaagacc | 6180 |
| ccatctctgc aaaaaatgaa caaaattagc cgggcatggt ggcacacttc tgtggtccca | 6240 |
| gctacttggg aggttgaggt gagaagatcg cttgagcctg ggaggtcgag gcttcagtga | 6300 |
| gctgagattg caccactgca ctccagcctg ggtgacagag caagaccctg tctccaaaaa | 6360 |
| aaaaaaaagg aaagaaaaga aactgaaaaa aaaaaaaagc agaagaattg atagtacact | 6420 |
| ttccaagcta taaagcatta tttattaggt atccttcaat ggatgattta gcactttcag | 6480 |
| gaatggggaa ataaatagcc aggttgaaaa gtgactgttg tgtgtcagag agggccttct | 6540 |
| ctgaggattt ggcatcaagt ttgattgtat tttgttttta tcccttaagg tgtgagaggg | 6600 |
| tccagcagaa ggaaacatgg ctgccaaagt gtttgagtcc attggcaagt ttggcctggc | 6660 |
| cttagctgtt gcaggaggcg tggtgaactc tgccttatat aatggtgagg catggaggga | 6720 |
| cagtgggtca ctgcactttc ctaggagttt tctgttggtc tgcatagccc atgtgacact | 6780 |
| cttgatggta gctgccgtca gtgaatgtgt ttgtggccaa gagggctcac ctcctgccat | 6840 |
| ttcataccac aggactgcat tgttatcaga gcccctgacc tttcagtcat aggttctctc | 6900 |
| agagcctgta ttcaaaaaga gcttcccagc ccacttccta gttggatgtg tccagtggct | 6960 |
| tctgtcaagg tgaagtgaag ccgcaccacc caaatgctgc cgcacagtgt ctggatttcc | 7020 |
| ctggctatct gaaatggaga tctcatttgt tctcctctgc ttgcatgtgg aataacagca | 7080 |
| aaggctgcag atctgtttgg gtgaccttgt cctgaacagg aacttttgct gtgctgaatt | 7140 |
| cgggtagttt cagagaaagt atctttgaga tgcattgccc agcttttaac agtgtaggag | 7200 |
| ggaggttaag ctggctttttc ttccacttta ctgtggaagc ttcctcattg gtcaagcaat | 7260 |
| ggatttgacc tgactttatc tgtaggacct cctttaattc tgacattctg acactttcac | 7320 |
| atgctgcaaa gcagcaatag attgacccat ccggtgtgtg gctggctgac aagaggagct | 7380 |
| ttactttcag agtgaagata tttgaccaa tgataaagtt cagagaggca gctgattaga | 7440 |
| aaagcctgct tggcttatat gacacatctt agcagtactg tgatccttttt ggccacatct | 7500 |
| gcaactagac agaaattgcc atcataaatt tctctctgtg ccaagacagc tctataaccc | 7560 |
| cttaaaactt tagcgaaaca gagctattag gaagaaagag taggctcttc gaaatgtagg | 7620 |
| attcccataa tgagggtgct acttctggga gcactaggtt aaattggagc ccgatggata | 7680 |
| tgtggtaact gggaagacct cactgagttt tagaagtttt ggtagatgat tcctggaaat | 7740 |
| atgttggtgg gagttcaggg atagaatggt cattcagaaa atcaacagcc agttccctca | 7800 |

```
aggagaaagg atgctaagga acaggtccta ttaccaatcc ttggggacat gtggaacagg    7860
aagtgactgc ttagttttgc agctagttag aagtctctag agaccaggag ttggggaaga    7920
cagagagaag aggggagact taataagtga acagaaagca ccagggctct ttcaaagaca    7980
tgatccttt gttt aaagga tgagaggatt tttatgacat gtcattgtcc tttcttccta    8040
gtggatgctg ggcacagagc tgtcatcttt gaccgattcc gtggagtgca ggacattgtg    8100
gtaggggaag ggactcattt tctcatcccg tgggtacaga aaccaattat ctttgactgc    8160
cgttctcgac cacgtaatgt gccagtcatc actggtagca aaggtgagtc ttgcctatgg    8220
ttcaggtaaa gtagggagtg tggaagaggt gctctgttct tctgtgtcac aggagcatct    8280
gtgggatacc aggatccaaa agagtttgaa ctgtacatca taggaatgac tagactactt    8340
gccctggaga gcttgatatg gaatcttaga aatacccact tatggctggg tgcggtggtt    8400
catgcctgta atcccagcac tttgggaggc tgaggcaggt ggatcacctg aggtcaggag    8460
ttcaagacca gcctggccaa tgtggtgaaa ccccatctct cctaaaaata caaaaattag    8520
ccggtggtgg ggggtgcctg taatcccagc tacttgagag gctgaggcag gagaattgct    8580
tgagcctggg gggcggaggt tgcagtgagc taagattgtg ccacttcact gcagcctggg    8640
caacagagtg agactctgtc tcaaaaaaaa aaaaaaaaa agcctgcttc taatcttccc     8700
atctctttgg aatttctttc cgtactgttt tgcagttgtt ttcaggatac attatgtacc    8760
tatttctaaa actattgata ggagcttcca gagatcaggg agttgtaggt attaatacat    8820
tgcccacctc tcttggtgcc cagttcaggg ctgtctcatg ggcgcttggt ccatattgtt    8880
gacatctgta agcaagccgt gacagtgctt tggctccagg caggcctgaa ttgtccaggg    8940
gaaagtataa ttctctccct ggatccttta aatggtccaa gtaatgagaa gcagaacata    9000
ggatcagtct gttaacccct tatatgtgtt acacatttga cagagtgctt ttacgtctgt    9060
tttctccttc aattttcccc aacatttccg caaggcccag aaagcaaatg aaattgtccc    9120
cattctcata gacagggaaa taagctcagg ttggctaagg cttagagagg ccacatcatt    9180
agtaaatagc ccagatcttt ggactgatag tctaacaccg tttccaccag acccgaacta    9240
acctctccaa ggctgactcc tgacttggcc acaatcacca gagcatgtaa aggcctcacc    9300
ctacaattct tagcattgcc ctgtctattg tcttaaaatg ttcagtgttg caaactttgc    9360
atggcacctg ttagacatat aatctgaatt atgtatatct gagggcattc aggggatacc    9420
aaaaagctgc tatcactgaa gcctcttaag aaattataaa ctctttatga tgctctattg    9480
ggttctctgc caaggaaacc aggcatacct gcaccttgcc ctctgggatc ttataatcag    9540
cagatttgct tataaattgt agcaaatttg gagccaggca cagtggtgcg tgtcagctac    9600
tcaagaggct gaggcaggag aaatgcttaa gctcaggagc ttgagtctag cctgggccac    9660
atagcaagac cttgtctcta aaataaaaa ataaaaattg ccaggcgtaa tggctcacac     9720
ctgtaattct agcattttgg gaggctgagg cagttggatc acttgagccc aggagtttga    9780
gaccagcctg ggaaatatgg cgaaacccca gctctacaaa aagtacagag attagctggg    9840
cgtggtggtc tgtgcctgtg tagtcccagc tacttggaag gtgtaggtgg gaggatcaac    9900
tgagcccagg aggtcaaagc ggctacagtg agctgtgatc ttaccactgc acttcagcct    9960
gggcaacatg tgaccctgtc tcaaaataca taaataaaaa ttgtagcaaa ttggagtagg   10020
agaggtcata taaagacca cttgtggcca ggtgcggtgg ctcacacctg taatcccagc    10080
actttgggag gctgaggcag gtagatcacc tgaggtcagg agtttgagac cagcctaaca   10140
tggtgacacc ctgtctctac taaaaataca aaacagctgg gtgtggcggc gcgtgcctgt   10200
```

```
aatcccagct actcaggagg ctgaggcagg agaattgctt gaatctggga ggcagaggtt   10260
gtagtgagcc gagattgtcc cattgtactc cagcctaggc aacaagagca aaaacctgtc   10320
tcaaaaaaaa aaaaaaacaa aaaaaaaaca cttgttttcc tacagtggtt tttatttta    10380 actccagtgt ttgtcccta  ccctaagatt tacagaatgt caacatcaca ctgcgcatcc   10440
tcttccggcc tgtcgccagc cagcttcctc gcatcttcac cagcatcgga gaggactatg   10500
atgagcgtgt gctgccgtcc atcacaactg agatcctcaa gtcagtggtg gtgagtgaac   10560
aggggccttt agcctcgagc ccagagcacc accctgggag ggtgccaggt ggcaggaagc   10620
gcttggcagt gggttggttg ggatgtggct gctagtttcc tggttccttt tctgcttcct   10680
cattaacctg acctgccctt ctgctcctcc ctttgaaacc aggctcgctt tgatgctgga   10740
gaactaatca cccagagaga gctggtctcc aggcaggtga gcgacgacct tacagagcga   10800
gccgccacct ttgggctcat cctggatgac gtgtccttgg taagatcctt cgggagaccg   10860
aggaggggaa ggggctgcag ttctcgttta ggtgcctggc tccatttctg ggtagacgct   10920
attaggtcct cccttctgct ttgctagatg tgagacttga aaacacggaa acatgctgag   10980
gtgaggcagt ctccgtgggt ttttcagttg agggttcttt taccttcccc ctgccacaca   11040
cattttcctt atgacctctg gttgtatcca gatagtctct aaccactaaa tgttttacct   11100
tctccaaact gttacccaga gagtgatgcc ttgttaaccc tgtttgacac aggcagaaac   11160
tgcctggtag agaccagaga acagctcggg tagtccttct ccctagcaca gacctcccag   11220
cctgactcct gggagcttcc taacacttta cagtccgaag ctcagtgaag taagctctgg   11280 gaacccagt gaaaggtgat agagtgtaaa cgaacggttg gattccccca ggcctggtat    11340 aggggggcaag ggacatctct gaggcgtaag ctatcctctt gagacactat agcttgtgtg  11400
tttatatgac attggatgtc ataactcaga aagcaatgca ggcaggatag cgtttcaggt   11460
tgaggagggt gaggggaagg ggtcgtgttt ctagattctc tgggaaaaac catttggagt   11520
gatttgttcg ggcagtgagg taaagtgttt cctgttcagt tctcccgtgc attgctaggg   11580
aaaggcactg cctcccccgg catctgtgca gctgtttaaa cagccacttg acaacaccca   11640
gtgctaaccc ctgggcactg ctccaccttg ctccgcctgc tggaagtcct gggggcttgg   11700
ggctccctct gctggcaaga ggccaggctg cagccattct gtgggcccctt ccctcgtaat   11760 taccgttaac ctgaacacct tggctgtgag aaaacgctga gtaaaaacct aagggaaaag   11820
ttggcatttt actagacttt aaccacatac tccattctgg ggaaatgtgg gctgaccaca   11880 agaaaccta  tctaaggtgt gagaagaaaa ttaggtttca tggggaattt gctgccctca   11940 gctggcccctt gtagaaataa attttattcc ttaattatac atttcatttt tcatgtctca   12000
ggatcagatt ttcttaccca aactttgact aagaaactag aaatggatca ggcgaagtac   12060
aacagctgca gttagagtta ggaggttaaa aattctggaa gagaatgaga ccaggattta   12120
ctcttcagga gaagtttgga gctgcttttt taaaaagcag aggttgggag agtggaggaa   12180
atgaaacaac tagaatttga tggcaaaacc aatgctcttc tcttgattct ttttcaataa   12240
aaattaggat gaataagtaa attgctctag gctgggcatt aggaattctg aggtcccttc   12300
ccattgtttg tgctatcttt agggacagtc ccgtcagacc tgacatgatt agggaaggtc   12360
tatggatcat cagacttcta aaccctcatg ccgaccaatg actttacctg ctttctcttt   12420
cttttaaacc gttaacagaa accattcaca ttgggaatac catgatttgc gttccaccgt   12480
ccctcgtcct cttcctgttc agtggtggag ctgctgtggg aagacgcgga ctggttaatc   12540
```

```
cataaacaga gagcatcagg ctcttggatc cctgggaacc agctgcctcc ctcactctca   12600
gggaccctgt tttccatctg gccttccttg ggctttgaac aaggcatcaa aggcccttgg   12660
aagagcacta gtcagtggcg ggggtcttag aacccacagt tctcctcctc tggggaggtg   12720
gtcgattgag tagataccct ctggtgcctg tgggccccat caaaagcccc cggtgccatt   12780
tgctacatga ggtcactgta ctgagagtga cagagtaata tacaggagca gtttgggcag   12840
ccagagagtc tgggtgtaaa ctcagtttgg atacagatac ggaggtggaa gagtgttctg   12900
gcctcacgga tgcctccagc tgctagagcc attgctggcc tcttcttcca gcggccatgg   12960
agccctccca gcagtgctgt cgaagcaatc acactgcctc atcttgtgct cactctctcc   13020
ccttagacac atctgacctt cgggaaggag ttcacagaag cggtggaagc caaacaggtg   13080
gctcagcagg aagcagagag ggccagattt gtggtggaaa aggtgagcct tcgaccagat   13140
ggcaggagcc tctctctccc ctttctccgg cactcagctt ccccatttgc tgggtggcct   13200
ggaaattcat catctgtcat cccttcttcc gggataatca aaggggcttt gaaggaattg   13260
tacttctgca attggttcca gagtcttcag ggctagtaca aggatatgtg gagttatgtt   13320
cctaaatcac tgaagggtaa ttttttcttcc acttctctga gatcaaaaac actctcttac   13380
aaataaaaat gtttctcctg gagtattttc agcttcactg agaagtcatt tttaaccata   13440
gttacatagt gaaagctgac agcaaaaaag atcaaacgtt gcaccagatg tgctttcgtc   13500
actagatttt tttctagtgc taaatccatc cagatgtgtc aaagaatgtg atgggacaca   13560
gtgtatttgc gtagcagcct ggtctttctg gtatttgcaa agacatgttc atttattgtt   13620
gtccccttct tcccaccacc agtatcccta attggtgggg agatgggac agcaagaaat   13680 aaaatgggaa aagagggata gatttaattt tggagaatga aaacactgtg tgggcagaga   13740
cttgtgttgc tttgtatctg ccataacttc agagattata ataagtctag tacagtgcct   13800
ggtgatagta ggtatacagt aaatgtttgt tgagcaaata gacgcagggc ccagtcattt   13860
caaaattgta tgtaatttca gggaggctta atactgtctt cttcctcaca ctcctgaagg   13920
tcacacgttg cagagagctg tcttcctatt gatattggta gggcaagcct aggagatctc   13980
actctgggtg cctggattct ggtcaggaac cagcctaact cacaggcagc tctaggaaca   14040
gtcaaaagtg catgctgctc ttccttagcc atcccgaggt ttttttgttt gtttgtttgtt   14100 tgtttgtttt tttgtgacag ctctgtggcc caggctggag tgcaatggca tgatcatagc   14160
tcactgcagc cttggcctcc tgggctcaag tgatcctcct gcctccgcct cccaaagtgc   14220
caggattaca ggcatgagcc accacacccg gccctgtcct ggctttgatg aagtccttta   14280
gacttaaggc tggaggaaaa gatgagcctt gaggattgat tccacctttc ttttgcttct   14340
gttttccttg gccttggctt ctcctggctc agagtagggt tgttaaacta gattgcaatt   14400
aatattaatg aggactttga aataagacaa atattcctgc agccaacaga gatgtatccc   14460
tcccgtgaca aggagtgagc atgaaaggat aggggaggac tggtgggcaa tgtgctctgc   14520
ttccccccgc ttcccccgct agccatcagg aggaagtaaa ctccccgagt tccttcagga   14580
gcctgggaag gtggctttct ggtgaagggc ctttggttgt agcctgacat gcggtgccct   14640
gaggtttgat ctttgtctcc acctccattc ttttaggctg agcaacagaa aaaggcggcc   14700
atcatctctg ctgagggcga ctccaaggca gctgagctga ttgccaactc actggccact   14760 gcagggggatg gcctgatcga gctgcgcaag ctggaagctg cagaggacat cgcgtaccag   14820
ctctcacgct ctcggaacat cacctacctg ccagcggggc agtccgtgct cctccagctg   14880
ccccagtgag ggcccacccct gcctgcacct ccgcgggctg actgggccac agccccgatg   14940
```

```
attcttaaca cagccttcct tctgctccca ccccagaaat cactgtgaaa tttcatgatt   15000
ggcttaaagt gaaggaaata aaggtaaaat cacttcagat ctctaattag tctatcaaat   15060
gaaactcttt cattcttctc acatccatct acttttttat ccacctccct accaaaaatt   15120
gccaagtgcc tatgcaaacc agctttaggt cccaattcgg ggcctgctgg agttccggcc   15180
tgggcaccag catttggcag cacgcaggcg gggcagtatg tgatggactg gggagcacag   15240
gtgtctgcct agatccacgt gtggcctccg tcctgtcact gatggaaggt ttgcggatga   15300
gggcatgtgc ggctgaactg agaaggcagg cctccgtctt cccagcggtt cctgtgcaga   15360
tgctgctgaa gagaggtgcc ggggaggggc agagaggaag tggtctgtct gttaccataa   15420
gtctgattct ctttaactgt gtgaccagcg gaaacaggtg tgtgtgaact gggcacagat   15480
tgaagaatct gccctgttg aggtgggtgg gcctgactgt tgcccccag ggtcctaaaa    15540
cttggatgga cttgtatagt gagagaggag gcctggaccg agatgtgagt cctgttgaag   15600
acttcctctc tacccccac cttggtccct ctcagatacc cagtgaatt ccaacttgaa    15660
ggattgcatc ctgctggggc tgaacatgcc tgccaaagac gtgtccgacc tacgttcctg   15720
gccccctcgt tcagagactg cccttctcac gggctctatg cctgcactgg gaaggaaaca   15780
aatgtgtata aactgctgtc aataaatgac acccagacct tccggctcag ccatgggttg   15840
gttttttgtt tgtgggagcc gtgggatcag aacagagtgt tctagcagtt tttgtgtgta   15900
catgtttgca ttgccagctg gacagagtc tccagtaagg cagaaaatgc tttgttttca    15960
gaaaacactt tgtgttgtgt tccagatcca tccccaaccc gaagggaatc tctgtggtag   16020
caggtgaggt ttgtcatggg ataggcagtg aaggtaggtg gagggcagtt aacttgttct   16080
gtgtgttttg gtgccactac tcactgggag ttacaggcct gcccgccaac tgccagcaac   16140
accttccccc aatgctaggg aagtggttga cgtaaataat gtgtccggta gccctcagtt   16200
agatggcttg gggcactctg cagtaggttt ttttttttct cttgttttct tttcctttct   16260
ttctttttttt cttttctttt tttttttttt tttttttttt ttttgaggca gggtcacact   16320
ttgttgccca ggctagagtg cagtggcatg aacatggctc actgcagcct tgacctcctg   16380
ggctcaagtg atcctcctgc cctagcttcc tgagtatctg ggactacatg tgtgtgccac   16440
tatgcttggc taattttgta ttttttataa gagaccaggt ctcaccatgt tacccaggct   16500
gattttgaac tcctgggctc aagtgatcca gccttggcct cccaaagtgc tgggattaca   16560
ggcgtgagcc actgcgccca gccagtgggt ttgtattgct tattctgctt tgctttgaca   16620
atagggaaat tggaaatgcc ttggcatttg aggggagctg agtttgtgca ttttggatga   16680
tggggaggga aagcccaccg caggttgaga aatgaactgt gtcaatcacc cacccccaaat   16740
ccttctagga acagagtgga aacagcatgc agtgagtgga cagcactgac tgtgctttaa   16800
atctgctctt catttaatcc ccaggctcac cacctggcca cagagagggg tctttaagaa   16860
gactccacag gctgctctct gacctggatt ccacatttcc tcccccagag tgatcgggcc   16920
accacctgtc agctggggaa gagggagacc cgatgcacag atttgggatg gagccaggga   16980
ttgagttctc ccaatccctg catcctgcac ccctcccagg gcctcccagc agccatcccg   17040
ggagcagacc acagtgtgtg gtgggctcct gaccctcagc tgcacctcaa acctccctcc   17100
cgtgagcctc cccgcatcca gcccatctcc ctgccgcctc cccagcatca tttatctcag   17160
gcctcaggat atctcttccc actttggctc ttttgctgta agaataggct ttcgaatgat   17220
gaggtgcctg aactcaaagc gcattaaaga ttggagcaga aagagcctaa ttcctaaata   17280
```

-continued

```
agttccagac cagcttccac tctgcgccct tcctccttt  cctgctgttt attgctttgg    17340 acacccttt  gggggtggga ggacaggagg ctcctctctc tttcccaggc tctttttaaa    17400
agagcagttg tgtttcctgc atttggcggg agattgggtt tcatcctcca ggtgtctgta    17460
ggggagccct gagctgcaaa gctgccttgc actgctttga ggttgctagt gccttcaggt    17520 cagcccttc  agtggcagga gggccaggtt tcctgctggc tttgccatta gcctccctgc    17580
cagggatggc aaaggcatat cccagtggca gccagggc   ctcatttgc  cttgacttcc    17640 gccaagtaat tcttttcaca aatgttcaag ggctgttaac cagcttctta gccctgatg    17700 gcctctgggt ttctccagaa actgccacaa tgggccttta tcagctcggg attctctggg    17760
ccttggatca aaaccatgt  cctgtcctgg ccagggaagg gagagcagga agtgtcttcc    17820
tcc                                                                 17823
```

<210> SEQ ID NO 2
<211> LENGTH: 272
<212> TYPE: PRT
<213> ORGANISM: Homo sapiens

<400> SEQUENCE: 2

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
    130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
cctgggaaga gtgatggtta tg                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gctgctagta gggcaagata ag                                              22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tgcaccacca actgctta                                                   18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ggatgcaggg atgatgttc                                                  19